(12) United States Patent
Hitchcock et al.

(10) Patent No.: US 10,076,627 B2
(45) Date of Patent: Sep. 18, 2018

(54) FOREHEAD SUPPORTS FOR FACIAL MASKS

(71) Applicant: ResMed Limited, Bella Vista, New South Wales (AU)

(72) Inventors: Robin Garth Hitchcock, Carlington (AU); Eva Ng, Double Bay (AU); Vincent Chu, Little Bay (AU); George Giles Campbell, Adelaide (AU); Errol Savvio Alex D'Souza, Hornsby (AU); Scott Alexander Howard, Frenchs Forest (AU); Murray William Lee, Quakers Hill (AU); Paul Stewart Huxtable, Trinity Gardens (AU); Geoffrey Crumblin, Baulkham Hills (AU); Nicholas John Roseby, Mill End (AU)

(73) Assignee: RESMED LIMITED, Bella Vista (AU)

( * ) Notice: Subject to any disclaimer, the term of this patent is extended or adjusted under 35 U.S.C. 154(b) by 840 days.

(21) Appl. No.: 13/920,834

(22) Filed: Jun. 18, 2013

(65) Prior Publication Data
US 2013/0319421 A1    Dec. 5, 2013

Related U.S. Application Data

(63) Continuation of application No. 11/793,055, filed as application No. PCT/AU2006/000037 on Jan. 12, 2006.
(Continued)

(51) Int. Cl.
*A61M 16/06* (2006.01)
(52) U.S. Cl.
CPC ........ *A61M 16/0683* (2013.01); *A61M 16/06* (2013.01); *A61M 16/0611* (2014.02);
(Continued)

(58) Field of Classification Search
CPC .............. A61M 16/06; A61M 16/0605; A61M 16/0633; A61M 16/0638; A61M 16/0644; A61M 16/065; A61M 16/0655
(Continued)

(56) References Cited

U.S. PATENT DOCUMENTS

| | | | |
|---|---|---|---|
| 2,747,464 | A | 5/1956 | Bowerman |
| 4,034,426 | A | 7/1977 | Hardwick et al. |

(Continued)

FOREIGN PATENT DOCUMENTS

| | | |
|---|---|---|
| EP | 1 205 205 | 5/2002 |
| EP | 1 555 039 | 7/2005 |

(Continued)

OTHER PUBLICATIONS

U.S. Appl. No. 13/782,102—Lang et al., filed Mar. 1, 2013.
(Continued)

*Primary Examiner* — LaToya M Louis
(74) *Attorney, Agent, or Firm* — Nixon & Vanderhye, P.C.

(57) ABSTRACT

A face mask assembly (FMA) for supplying breathable gas to a wearer. The face mask assembly (FMA) includes a mask frame including a support, a facial cushion attached to the mask frame, and a forehead support. The forehead support includes a forehead cushion assembly and an adjustment knob operatively coupled to the forehead cushion assembly. The adjustment knob is threadably engaged with the forehead cushion assembly such that turning movement of the adjustment knob causes the mask frame to be moved between retracted and extended positions with respect to the forehead cushion assembly.

30 Claims, 173 Drawing Sheets

Related U.S. Application Data

(60) Provisional application No. 60/643,113, filed on Jan. 12, 2005, provisional application No. 60/696,502, filed on Jul. 6, 2005, provisional application No. 60/715,173, filed on Sep. 9, 2005, provisional application No. 60/735,823, filed on Nov. 14, 2005.

(52) U.S. Cl.
CPC .... *A61M 16/0633* (2014.02); *A61M 16/0638* (2014.02); *A61M 16/0655* (2014.02)

(58) Field of Classification Search
USPC ............ 128/205.25, 206.21, 206.23, 206.24, 128/206.27, 206.28, 207.11, 207.13
See application file for complete search history.

(56) References Cited

U.S. PATENT DOCUMENTS

| | | | |
|---|---|---|---|
| 4,944,210 | A | 7/1990 | Flock et al. |
| 5,906,199 | A | 5/1999 | Budzinski |
| 6,062,148 | A | 5/2000 | Hodge et al. |
| 6,119,693 | A | 9/2000 | Kwok et al. |
| 6,374,826 | B1 | 4/2002 | Gunaratnam et al. |
| 6,463,931 | B1 | 10/2002 | Kwok et al. |
| 6,532,961 | B1 | 3/2003 | Kwok et al. |
| 6,557,556 | B2 | 5/2003 | Kwok et al. |
| 6,691,708 | B2 | 2/2004 | Kwok et al. |
| 7,000,614 | B2 | 2/2006 | Lang et al. |
| 7,047,971 | B2 * | 5/2006 | Ho et al. ................. 128/207.11 |
| 7,059,326 | B2 | 6/2006 | Heidmann et al. |
| 7,100,610 | B2 | 9/2006 | Biener |
| 7,234,773 | B2 | 6/2007 | Raftery et al. |
| 7,320,323 | B2 | 1/2008 | Lang et al. |
| 7,610,916 | B2 | 11/2009 | Kwok et al. |
| 7,654,263 | B2 | 2/2010 | Lang et al. |
| 7,775,209 | B2 | 8/2010 | Biener |
| 7,967,014 | B2 | 6/2011 | Heidmann et al. |
| 7,992,559 | B2 | 8/2011 | Lang et al. |
| 8,277,403 | B2 * | 10/2012 | Ceriani et al. ................. 602/26 |
| 8,402,972 | B2 | 3/2013 | Lang et al. |
| 8,479,738 | B2 | 7/2013 | Lang et al. |
| 2002/0148473 | A1 | 10/2002 | Kwok et al. |
| 2003/0062048 | A1 | 4/2003 | Gradon et al. |
| 2003/0075180 | A1 | 4/2003 | Raje et al. |
| 2003/0075182 | A1 | 4/2003 | Heidmann et al. |
| 2003/0089373 | A1 | 5/2003 | Gradon et al. |
| 2004/0045551 | A1 | 3/2004 | Eaton et al. |
| 2004/0112387 | A1 | 6/2004 | Lang et al. |
| 2004/0182398 | A1 | 9/2004 | Sprinkle et al. |
| 2004/0255949 | A1 | 12/2004 | Lang et al. |
| 2005/0039753 | A1 | 2/2005 | Schumacher |
| 2005/0197605 | A1 | 9/2005 | Bonutti et al. |
| 2006/0191538 | A1 | 8/2006 | Heidmann et al. |
| 2006/0191539 | A1 * | 8/2006 | Ho et al. ................. 128/207.11 |
| 2010/0071700 | A2 | 3/2010 | Hitchcock et al. |
| 2011/0220111 | A1 | 9/2011 | Heidmann et al. |

FOREIGN PATENT DOCUMENTS

| | | |
|---|---|---|
| JP | 2005-506156 | 3/2005 |
| WO | 00/78384 | 12/2000 |
| WO | WO 2003/035156 | 5/2003 |
| WO | WO/2004/012803 | 2/2004 |
| WO | 2004/021960 | 3/2004 |
| WO | 2004/022145 | 3/2004 |
| WO | 2005/068002 | 7/2005 |
| WO | WO 2005/123166 A1 | 12/2005 |

OTHER PUBLICATIONS

U.S. Appl. No. 13/923,671—Lang et al., filed Jun. 21, 2013.
U.S. Appl. No. 13/751,479—Biener et al., filed Jan. 28, 2013.
Office Action issued in Japanese Appln. No. 2007-550640 (dated Mar. 29, 2011).
International Search Report for PCT/AU2006/000037 dated Mar. 17, 2006.
Examination Report issued in related New Zealand Appln. 556041 (dated May 6, 2011).
Office Action issued in related Chinese Appin. No. 201010508994.X (dated Jun. 15, 2011) with English translation.
Examination Report issued in related New Zealand Appln. 592219 (dated Apr. 11, 2011).
Examiner's First Report issued in related Australian Appln. 2006206044 (dated Dec. 1, 2010).
Japanese Office Action issued in related Application No. 2007-550640 (dated Mar. 27, 2012).
Supplementary European Search Report issued in EP Appln. No. EP 06704773 (dated Mar. 29, 2011).
Photo of "Weinmann Mask" 1998, 1 page.
4 additional photographs of "Weinmann Mask".
Notification of First Office Action issued in Chinese Application No. 201210377725.3 dated Oct. 11, 2014, (26 pages).
Communication w/Search Report issued in European Application No. 14175770.8-1651/2789361 dated Nov. 11, 2014 (9 pages).
Communication w/Search Report issued in European Application No. 14175770.8-1651/2789360 dated Nov. 11, 2014 (9 pages).
Communication w/Search Report issued in European Application No. 14175770.8-1651/2786775 dated Nov. 13, 2014 (9 pages).
Communication w/Search Report issued in European Application No. 14175770.8-1651/2786776 dated Nov. 14, 2014 (9 pages).
First Communication pursuant to Article 94(3) EPC issued in related European Application No. 14 175 774.0 dated Jan. 24, 2018, 6 pages.
First Communication pursuant to Article 94(3) EPC issued in related European Application No. 14 175 778.1 dated Jan. 23, 2018, 9 pages.
Examiner's Answer issued in related U.S. Appl. No. 11/793,055, dated Oct. 7, 2016, (19 pages).
Office Action issued in related U.S. Appl. No. 11/793,055, dated Aug. 3, 2015, (45 pages).
Notification of the Second Office Action issued in related Japanese Application No. 201210377725.3 dated Aug. 11, 2015 with English translation, (21 pages).
Third Office Action issued in related Japanese Application No. 201210377725.3 dated Jan. 21, 2016 w/English translation (18 pages).
Final Rejection issued in related U.S. Appl. No. 11/793,055, dated Mar. 11, 2016, including PTO-892 citing Lang et al., U.S. Patent Application Publication No. 2004/0112387, published Jun. 17, 2004 (36 pages).
Office Action issued in related European Application No. 14 175 770.8 dated Jan. 17, 2018, 6 pages.

* cited by examiner

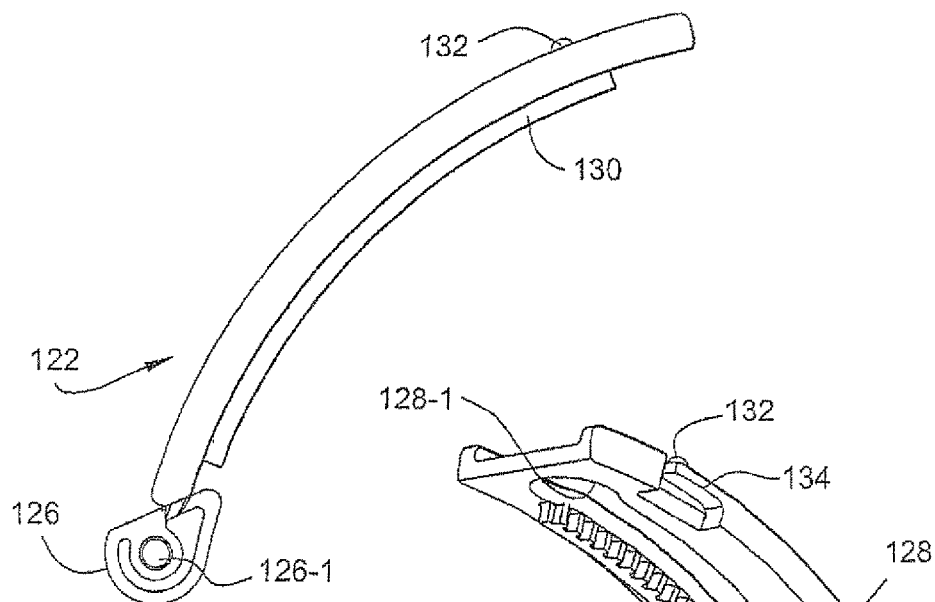
Fig. 9-4
Fig. 9-5
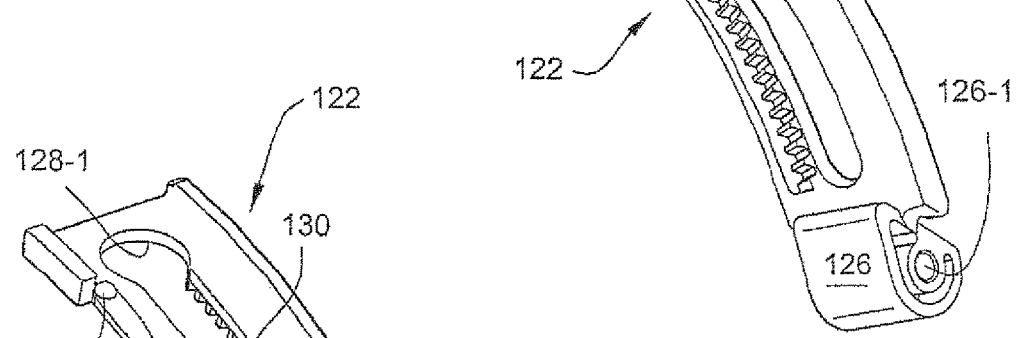
Fig. 9-6

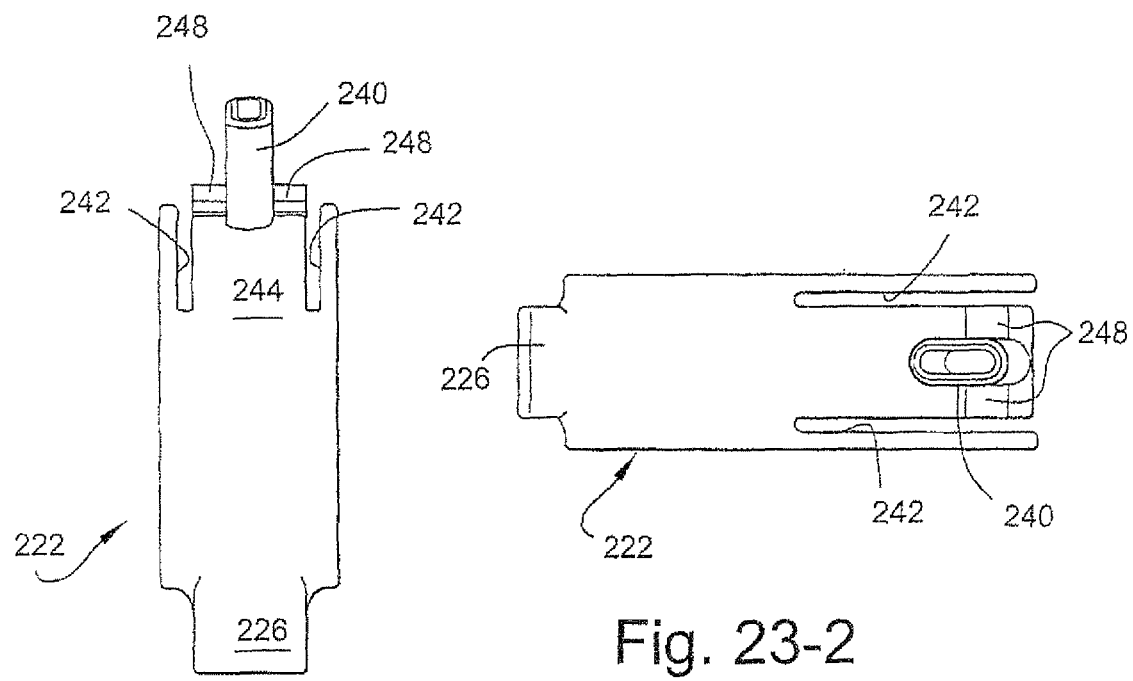
Fig. 23-1
Fig. 23-2
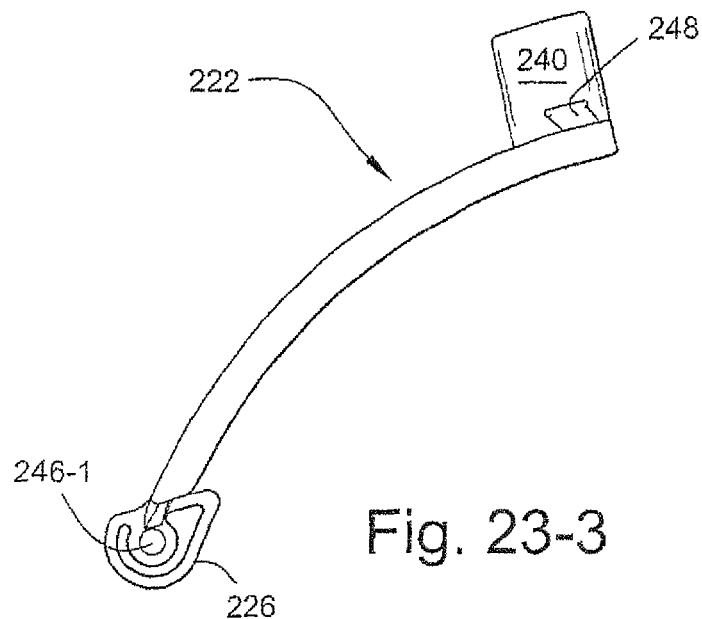
Fig. 23-3

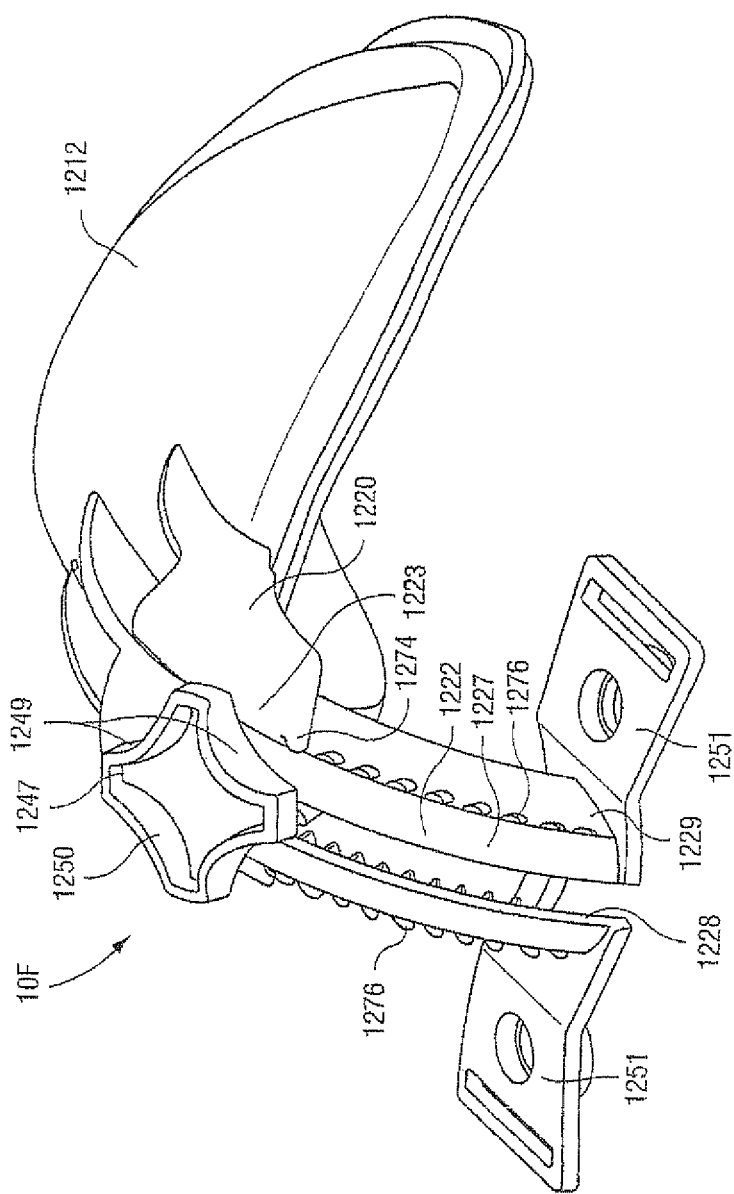

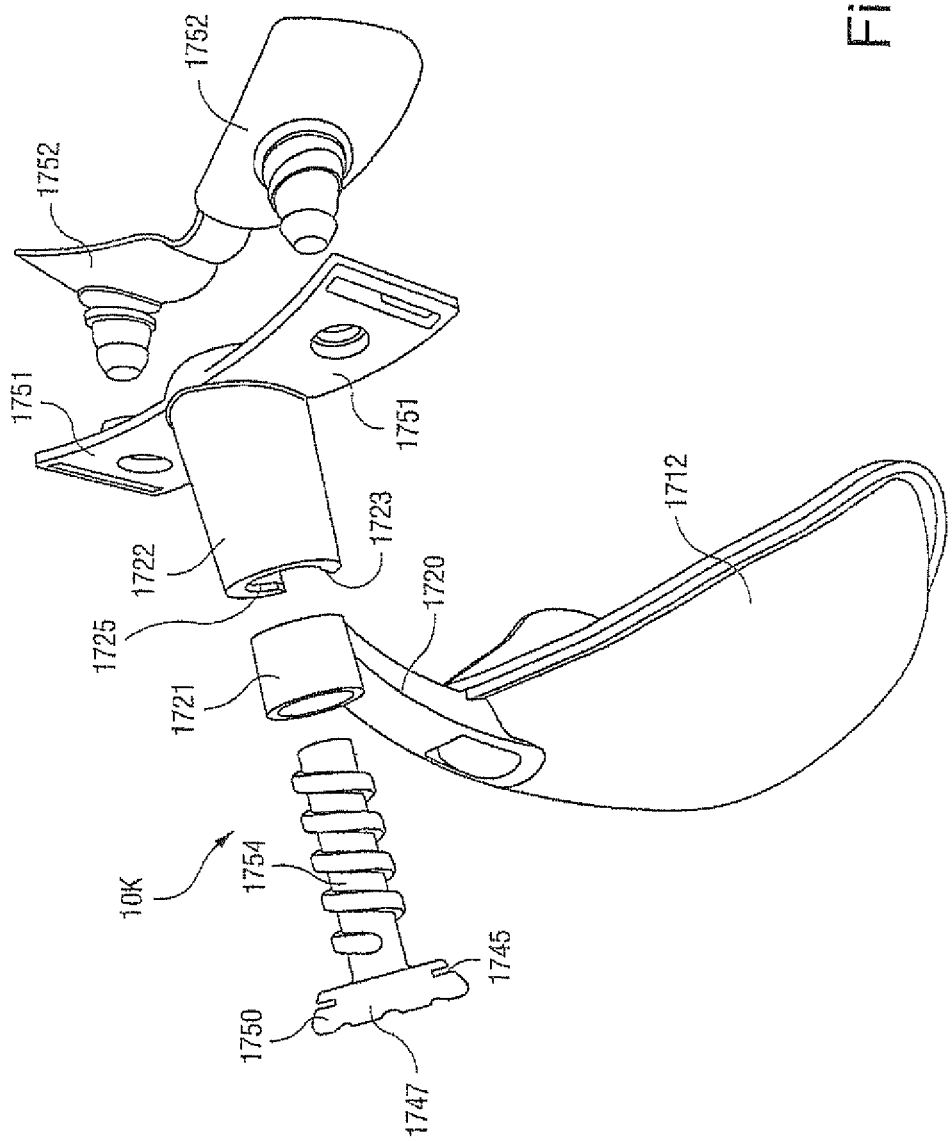

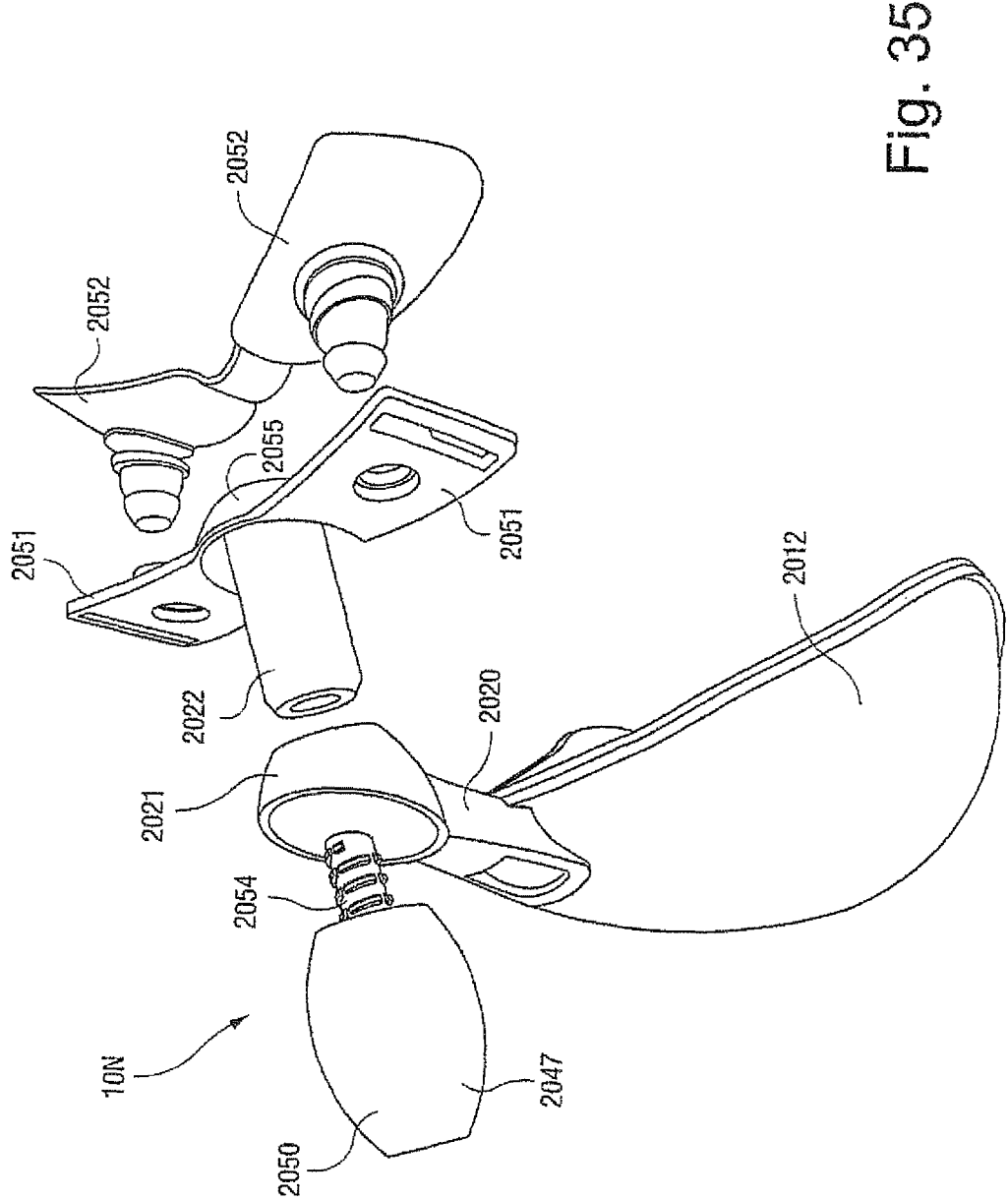

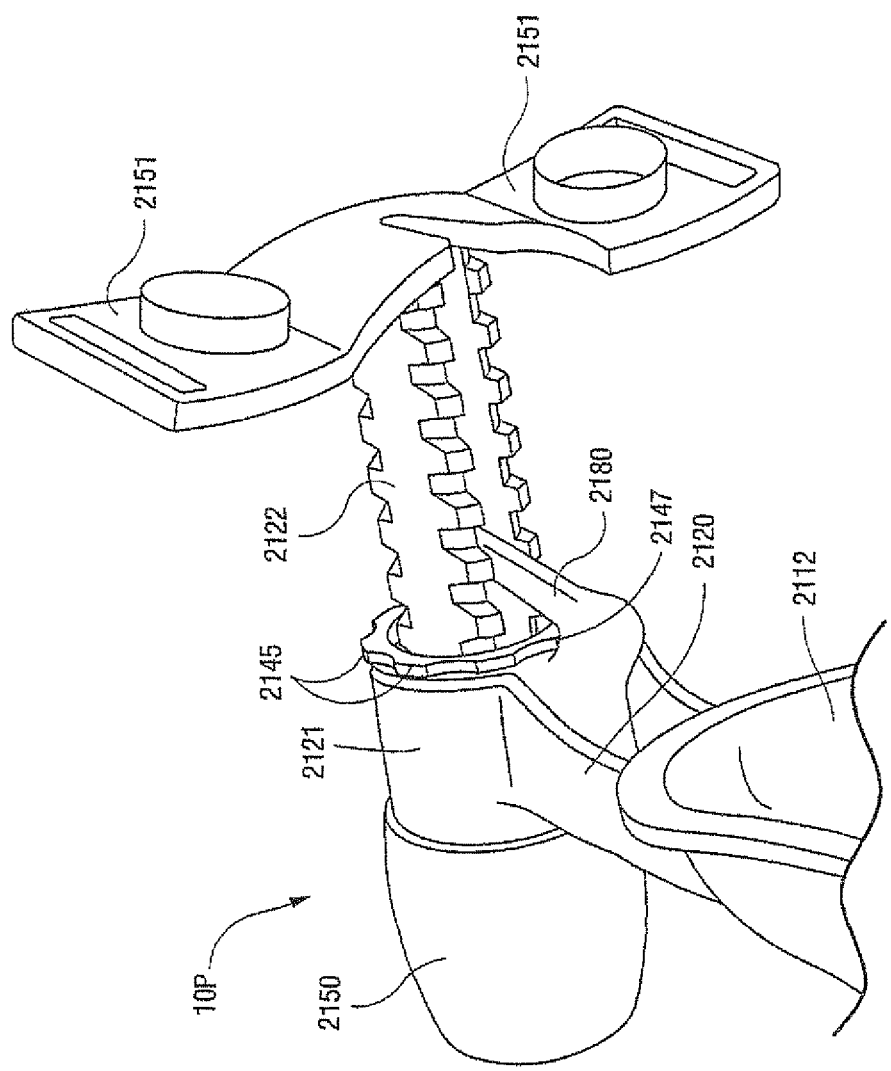

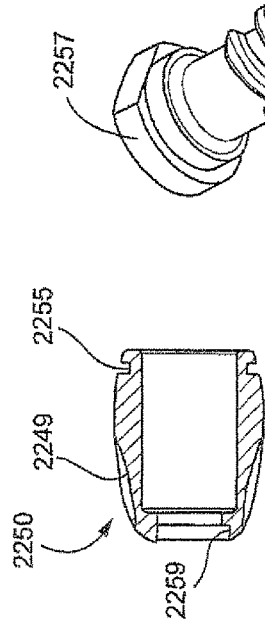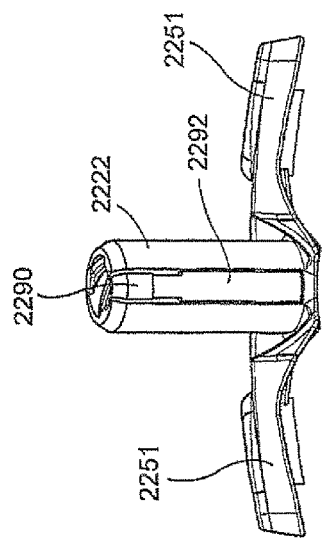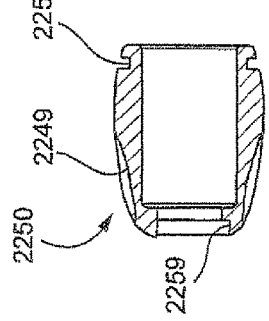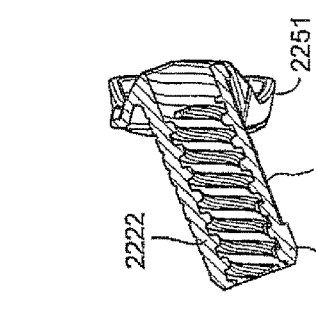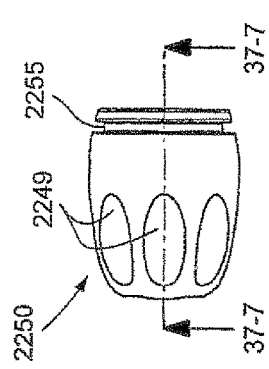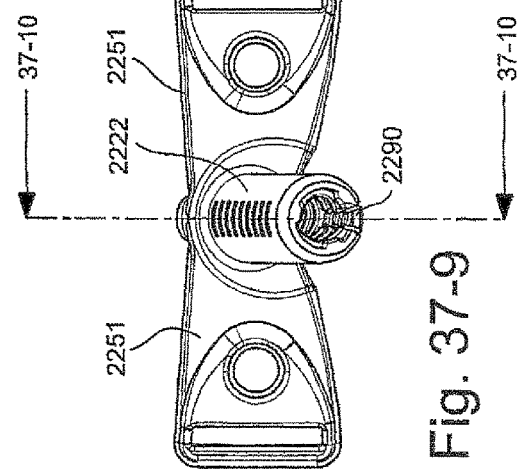

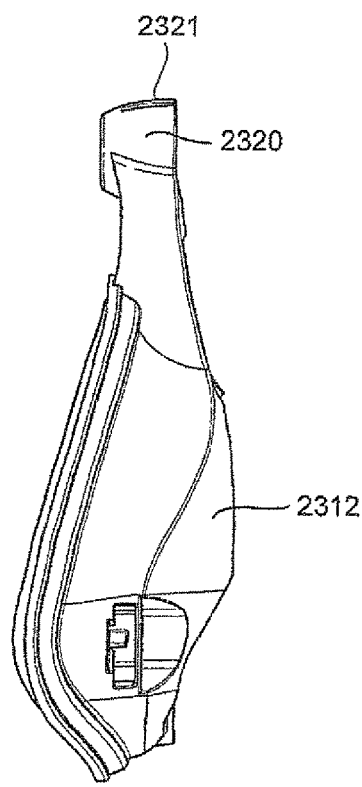 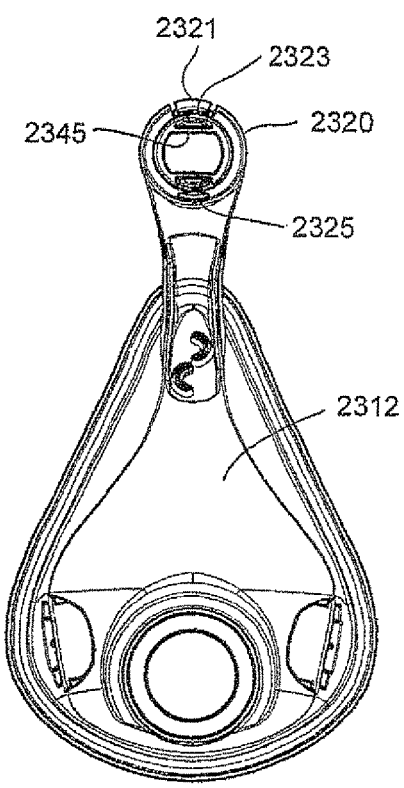
Fig. 38-8　　　　　Fig. 38-9

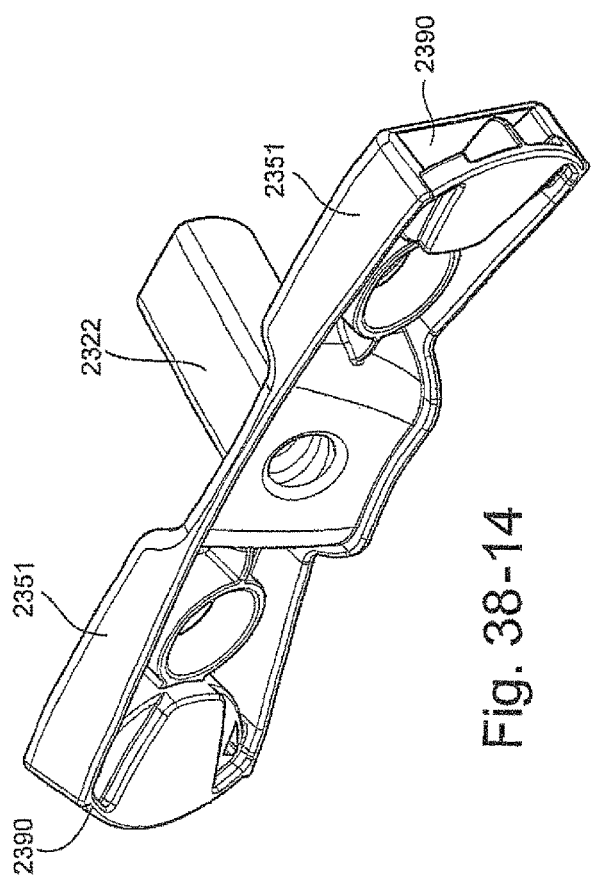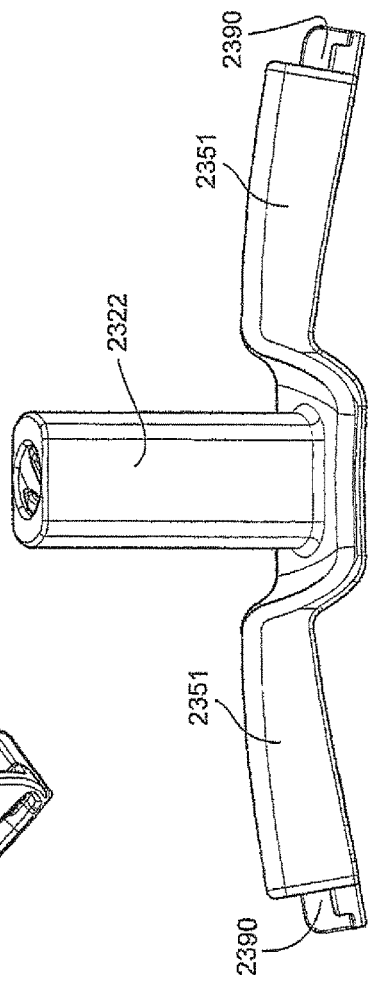

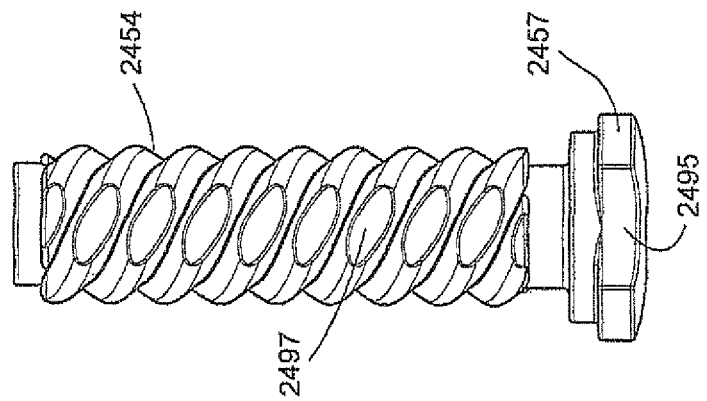
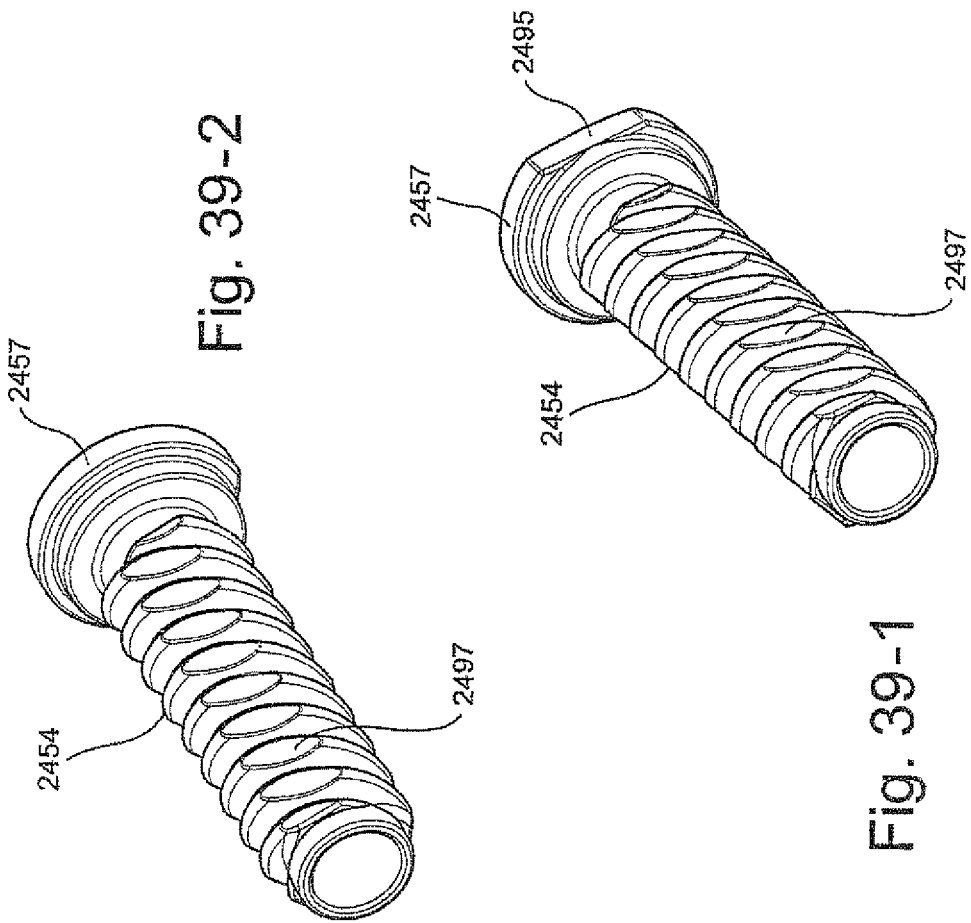

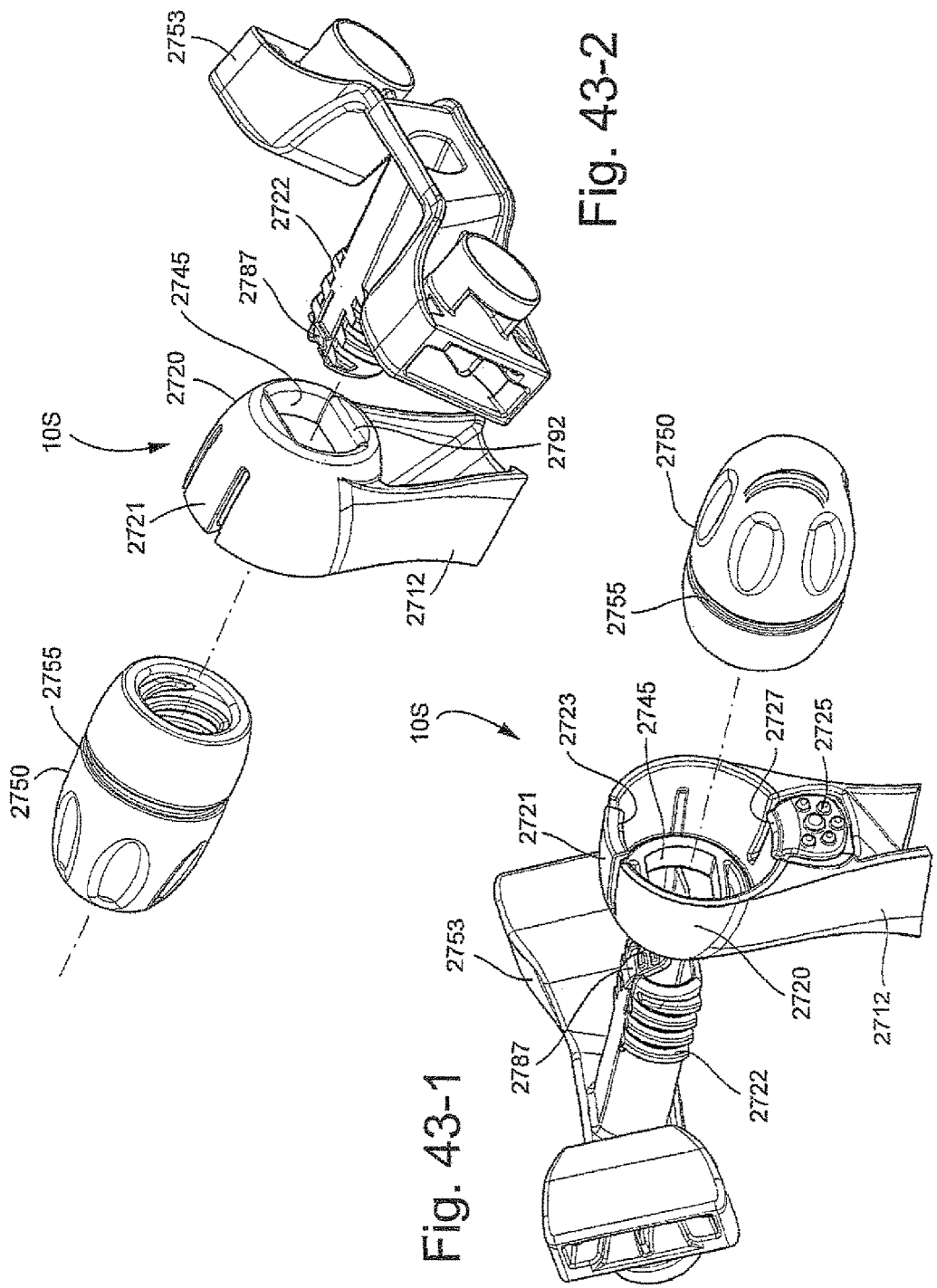

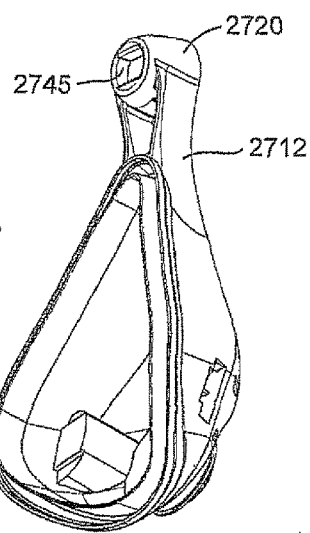
Fig. 43-17
Fig. 43-18
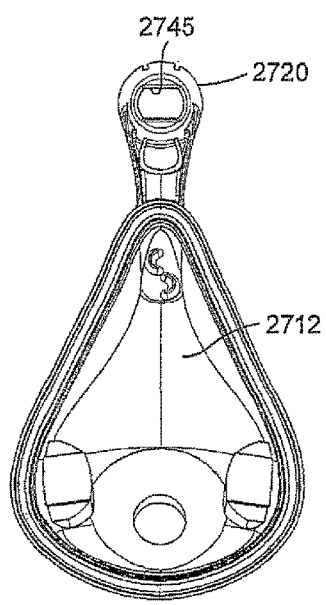 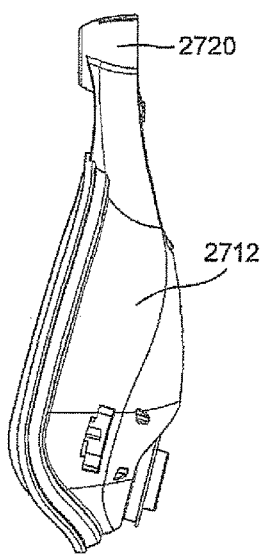 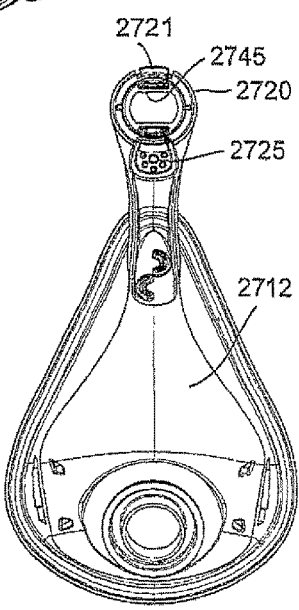
Fig. 43-19    Fig. 43-20
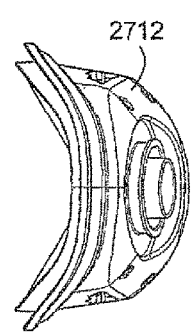
Fig. 43-21

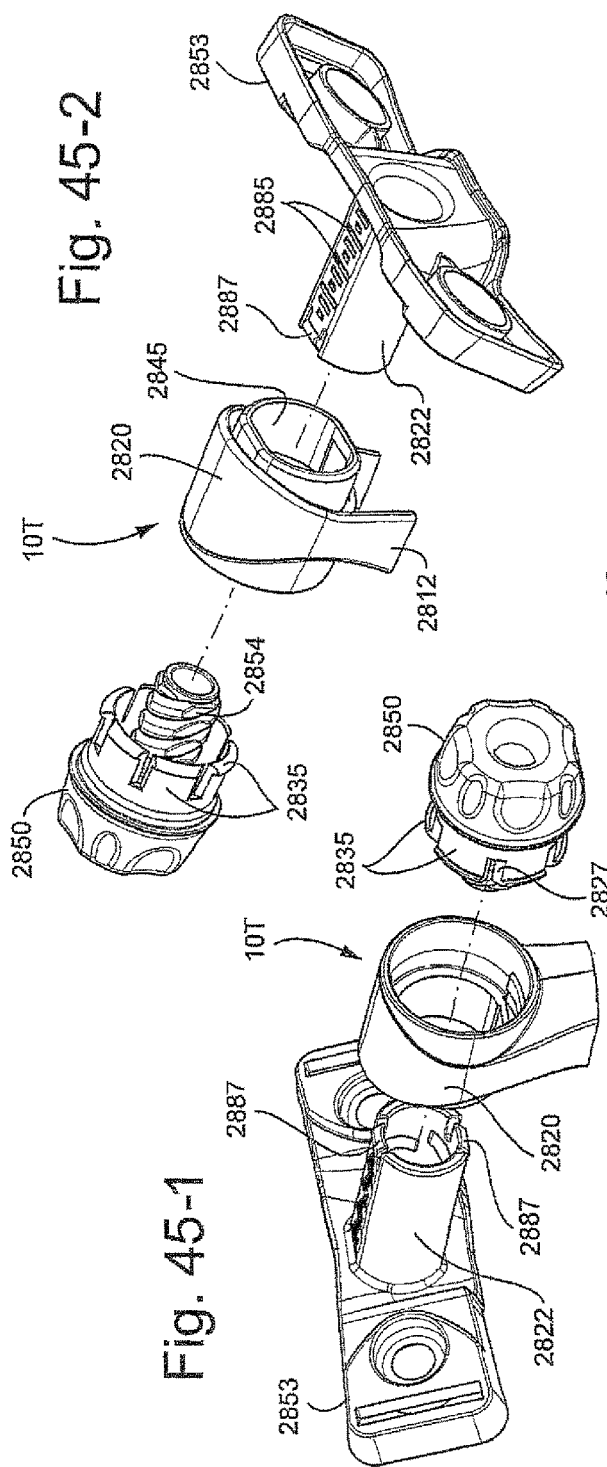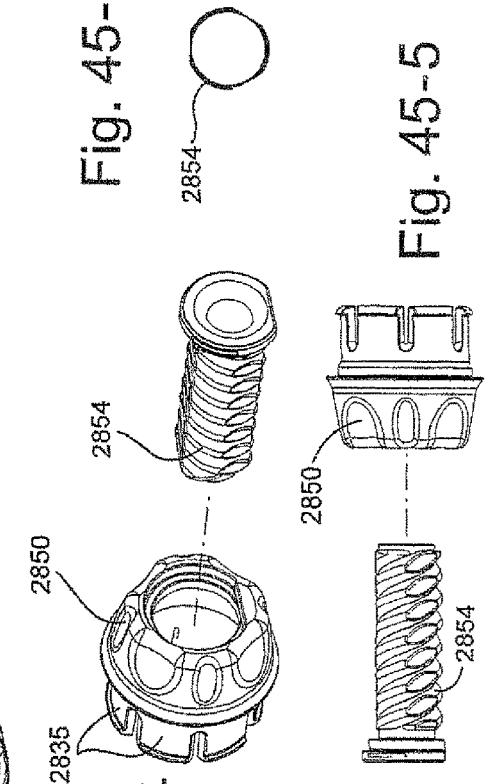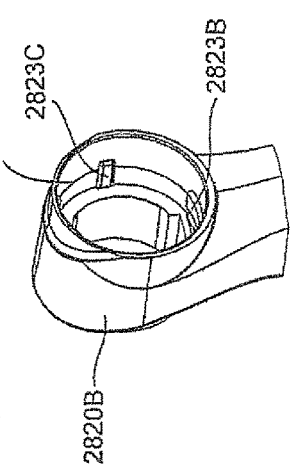

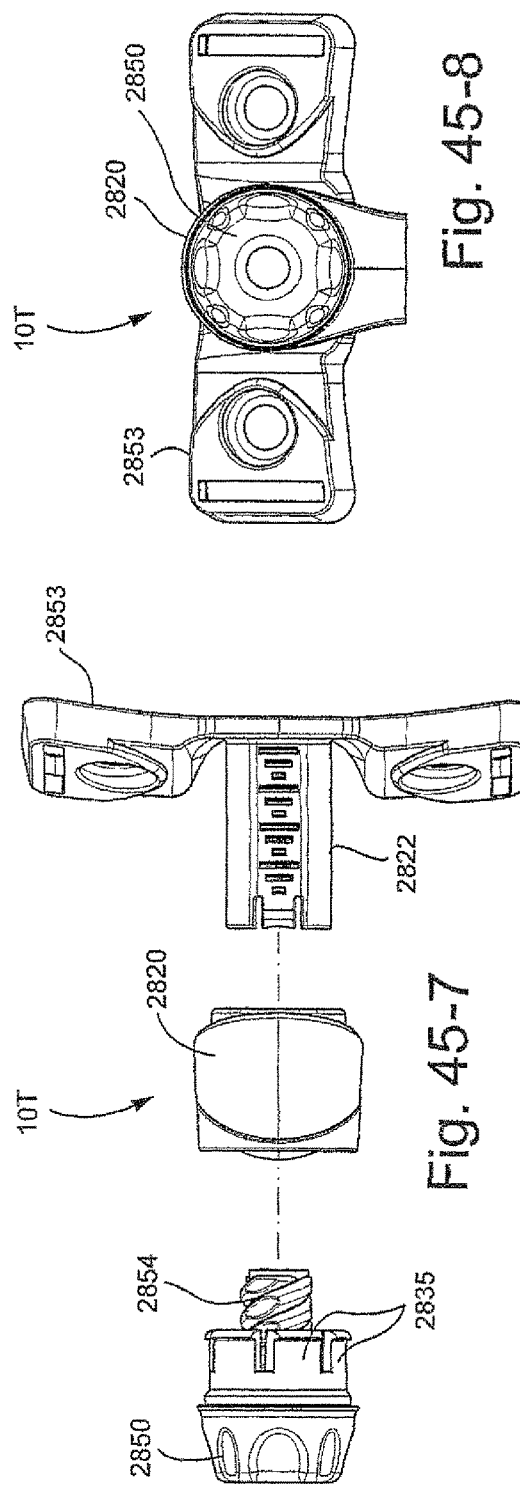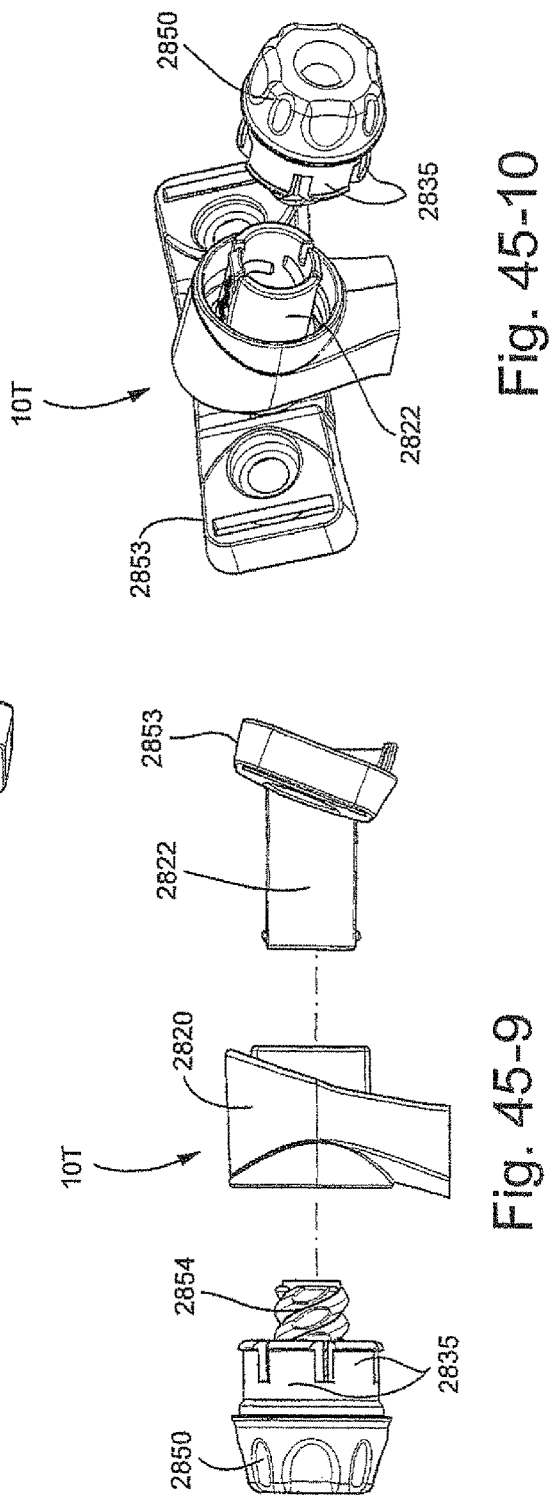

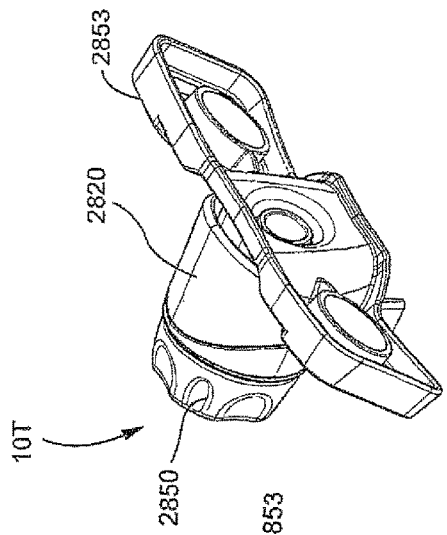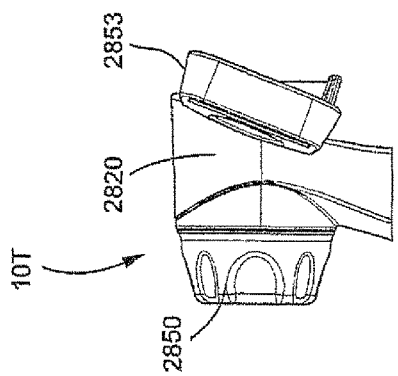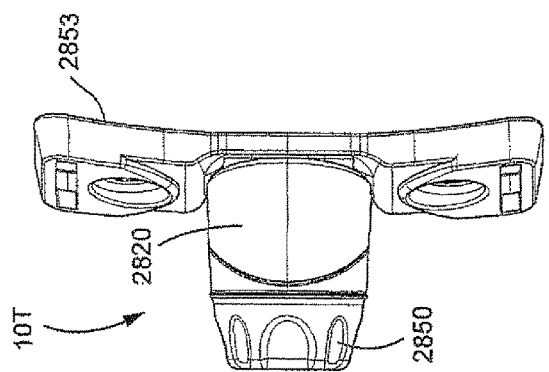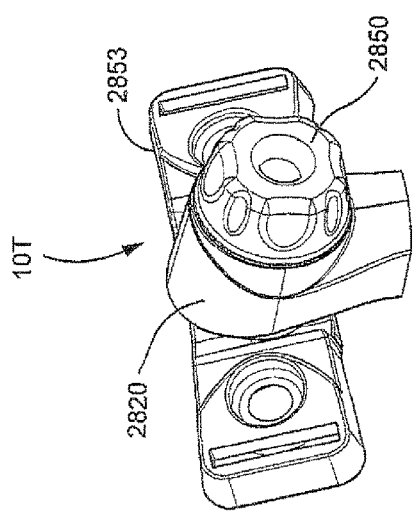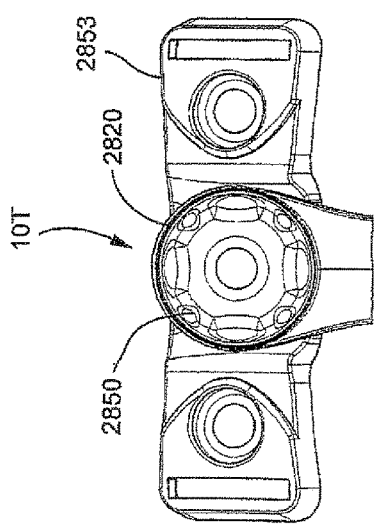
Fig. 45-16
Fig. 45-19
Fig. 45-17
Fig. 45-15
Fig. 45-18

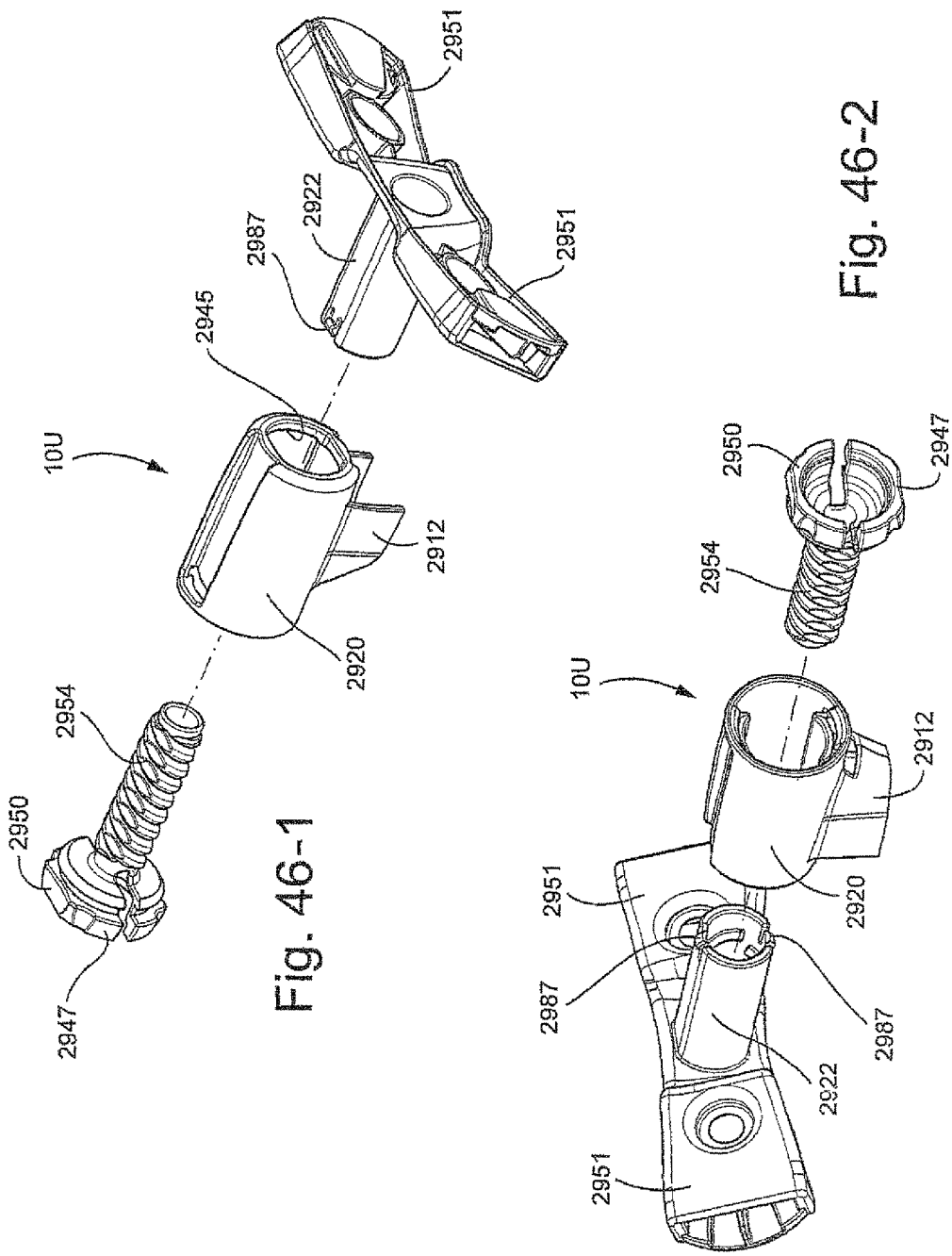

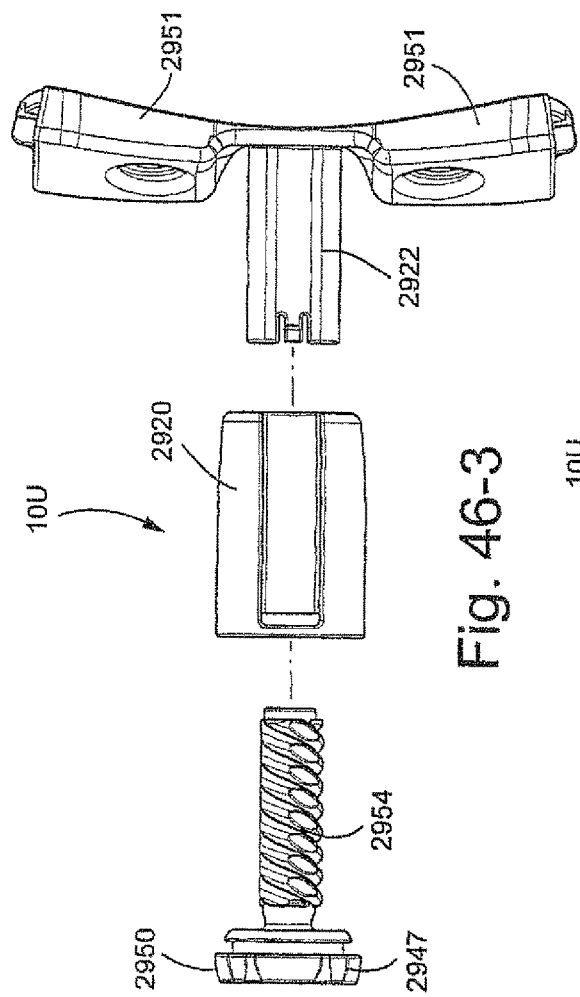
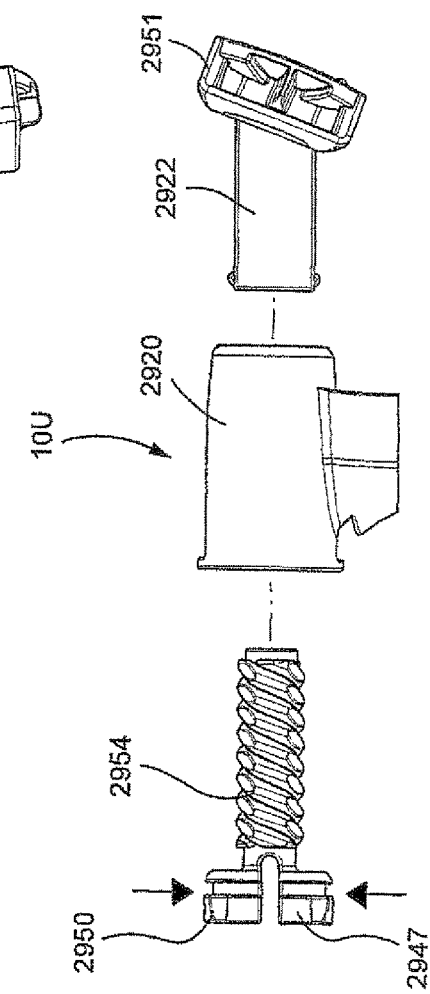
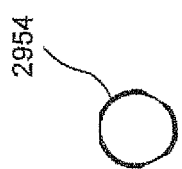
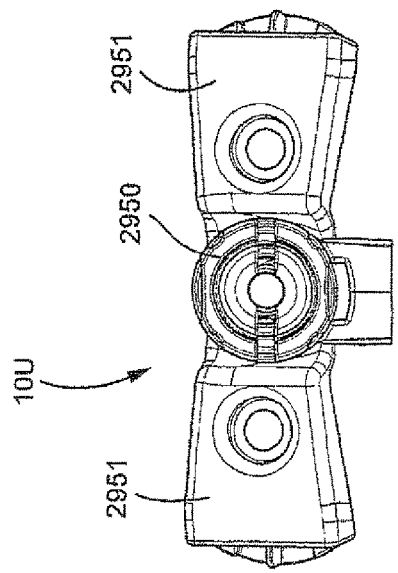

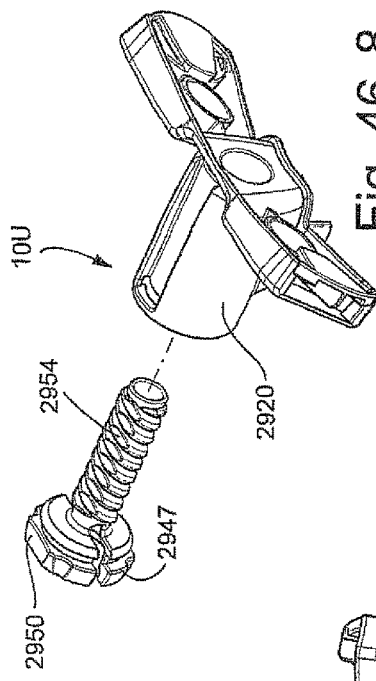
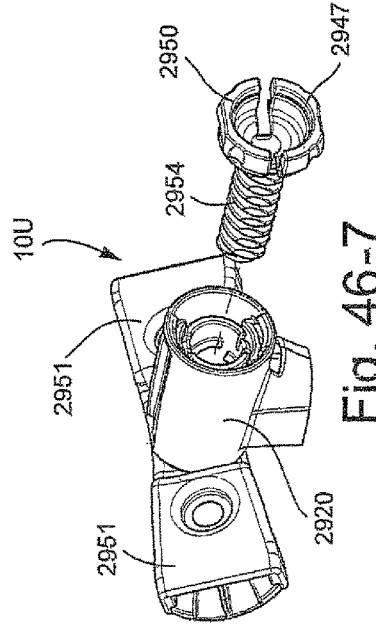
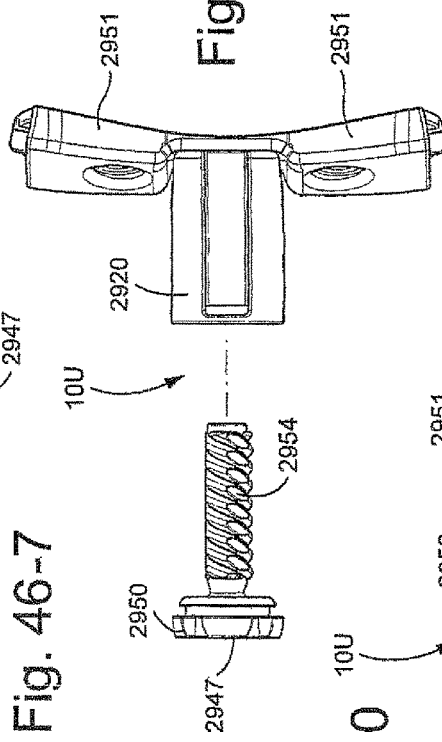
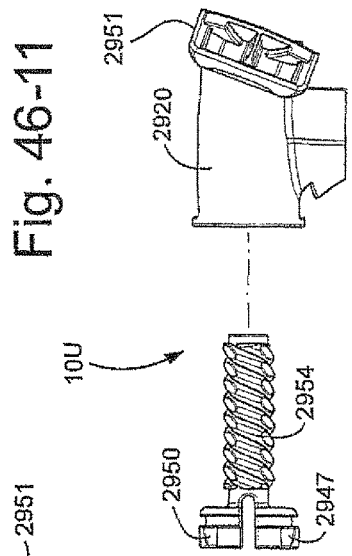
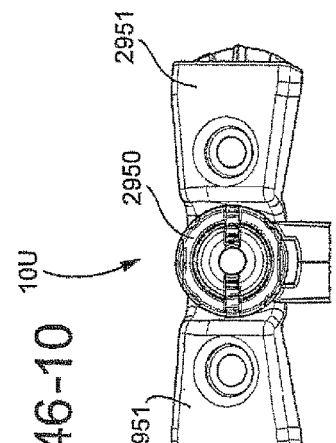

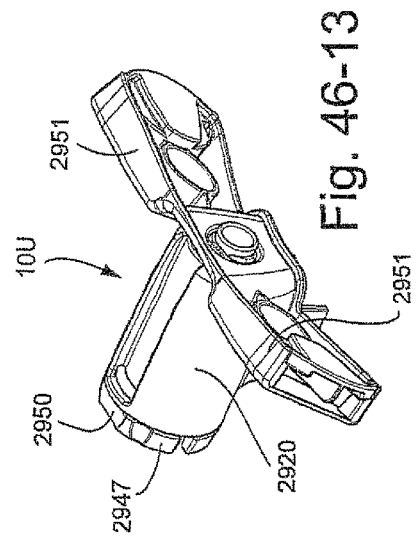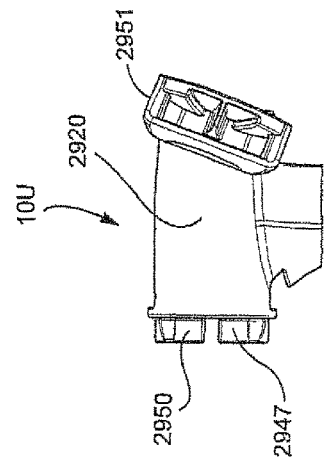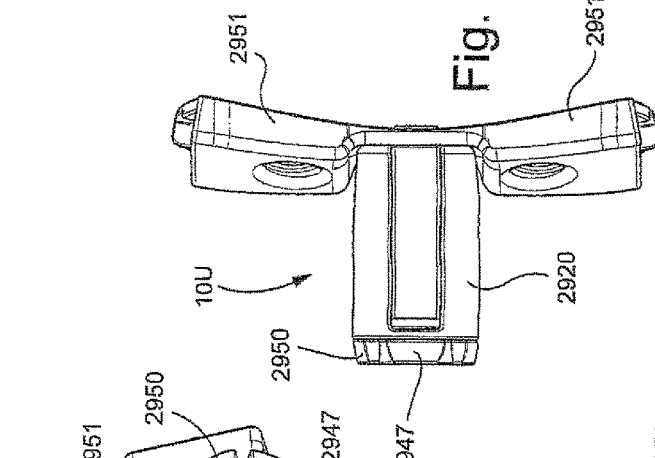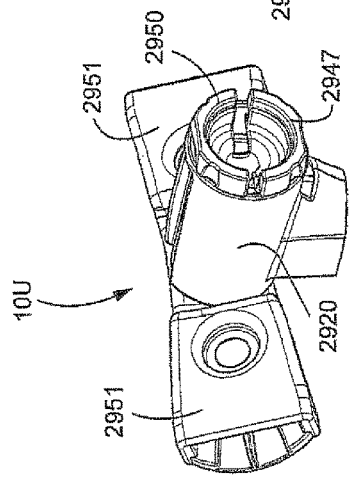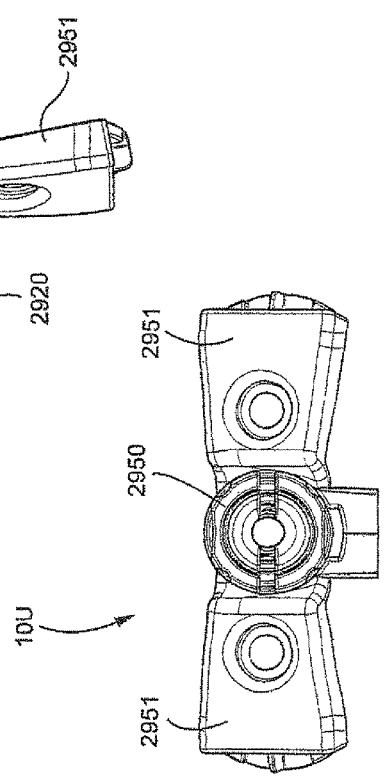

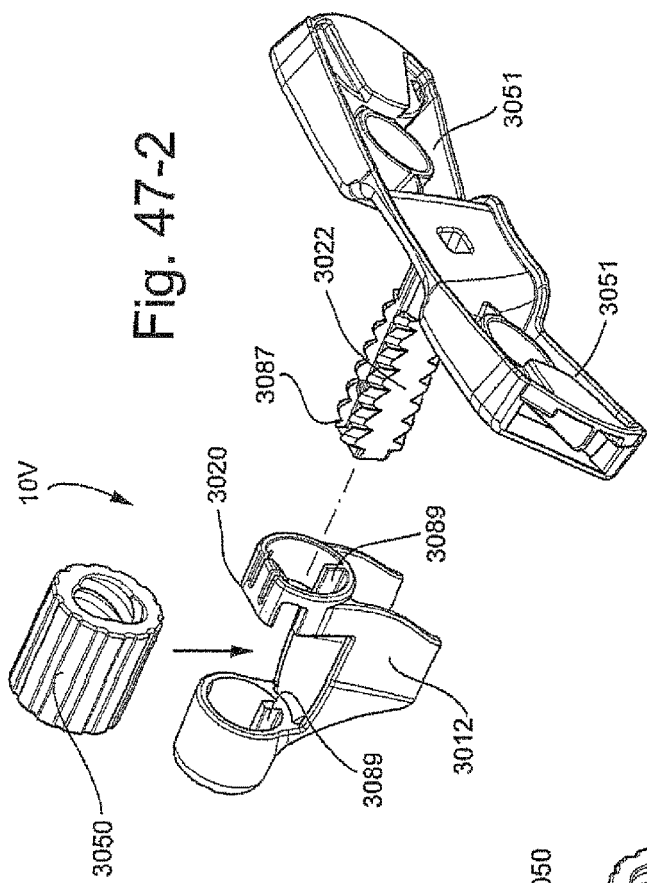
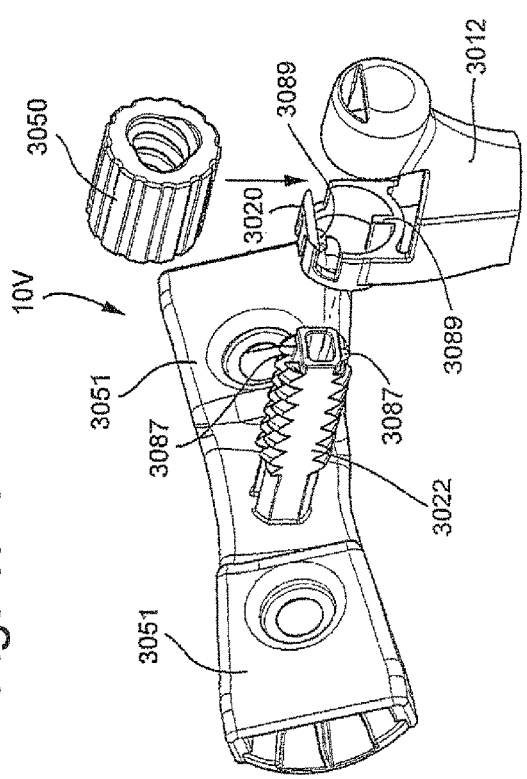
Fig. 47-1
Fig. 47-2
Fig. 47-3

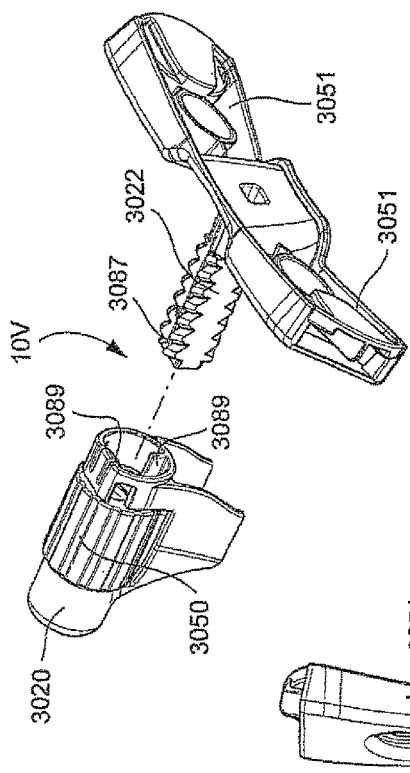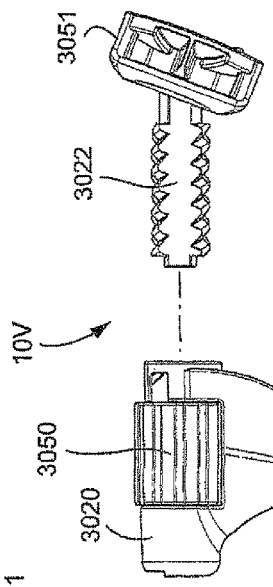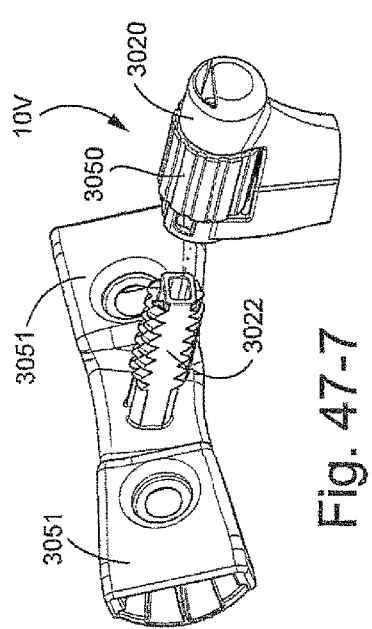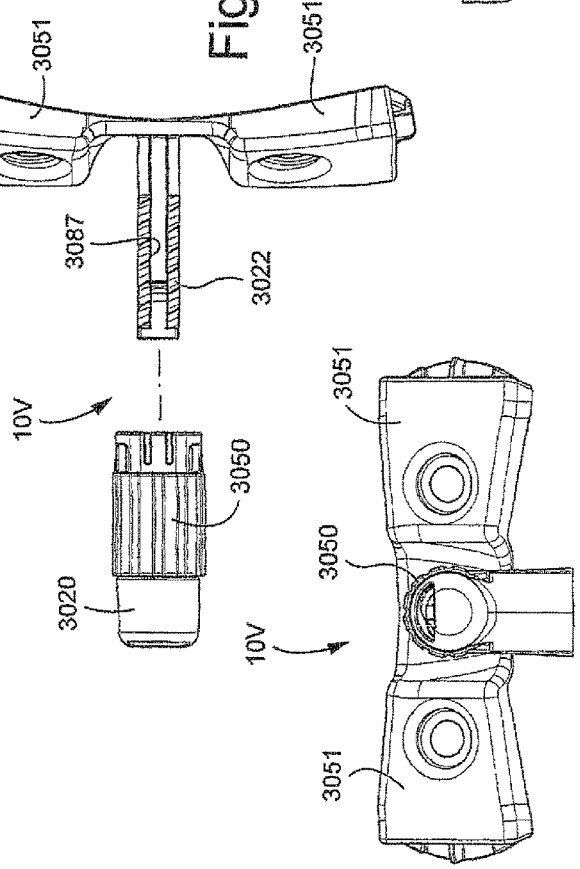
Fig. 47-7  Fig. 47-8  Fig. 47-9  Fig. 47-10  Fig. 47-11

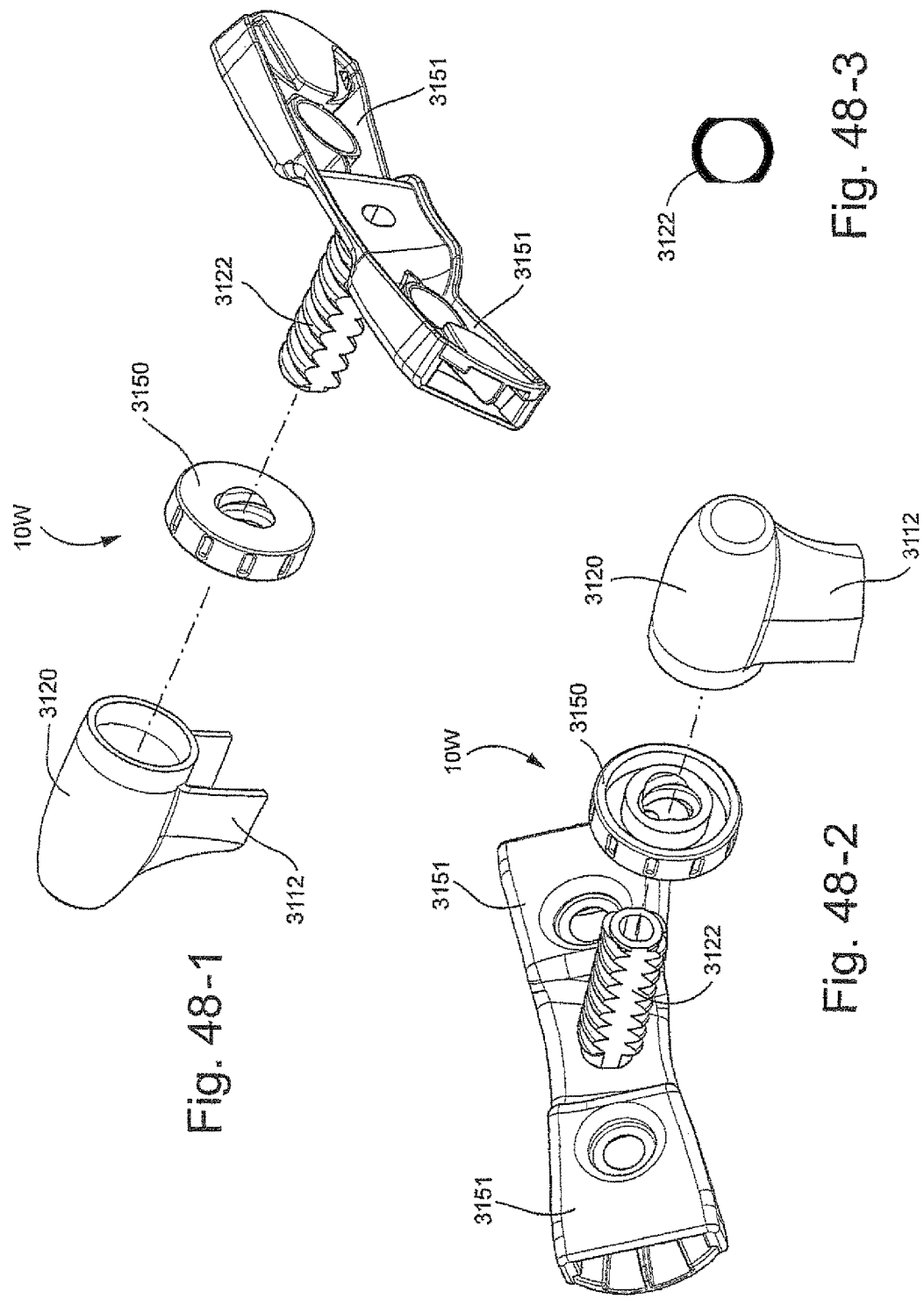

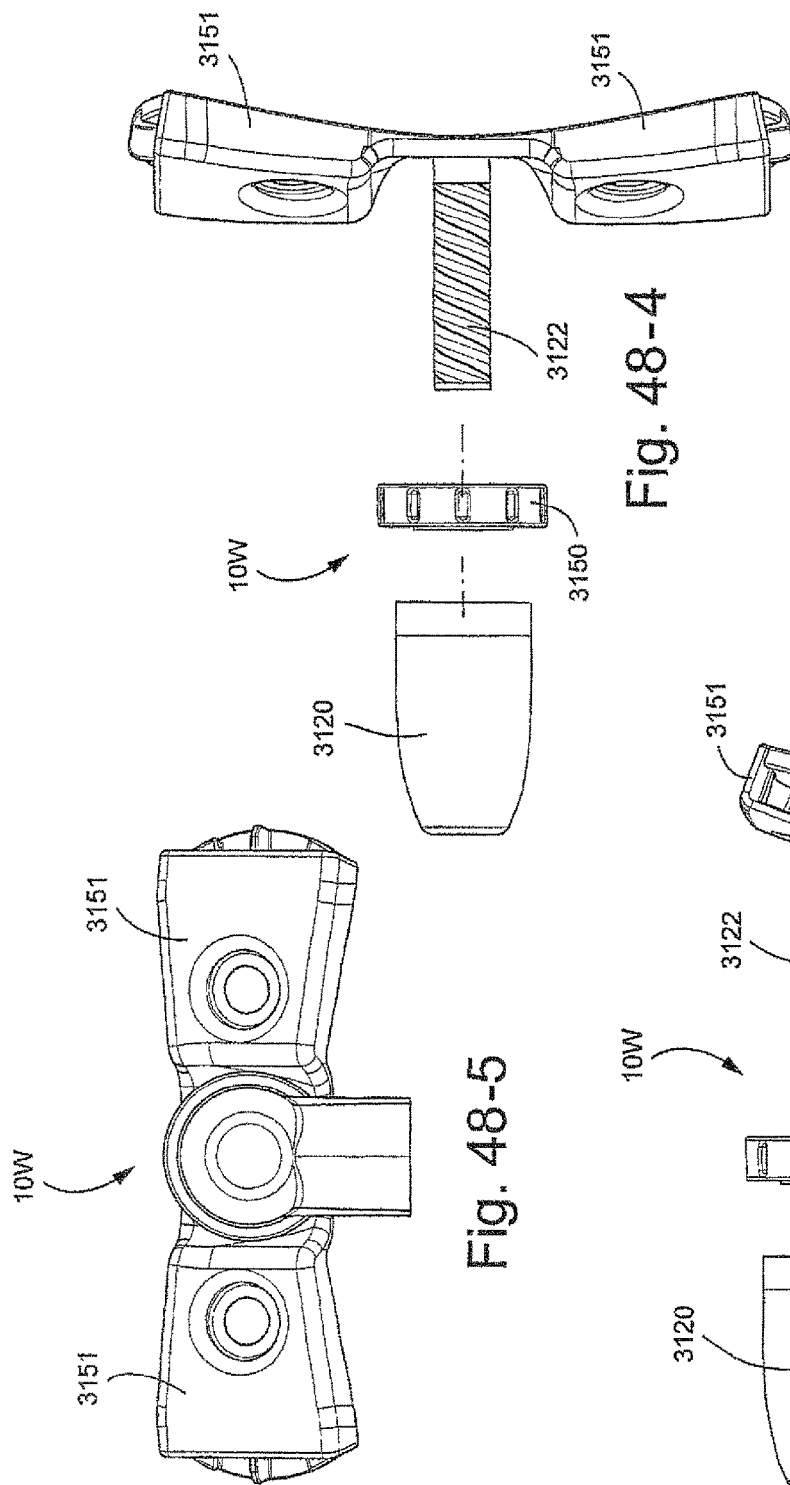

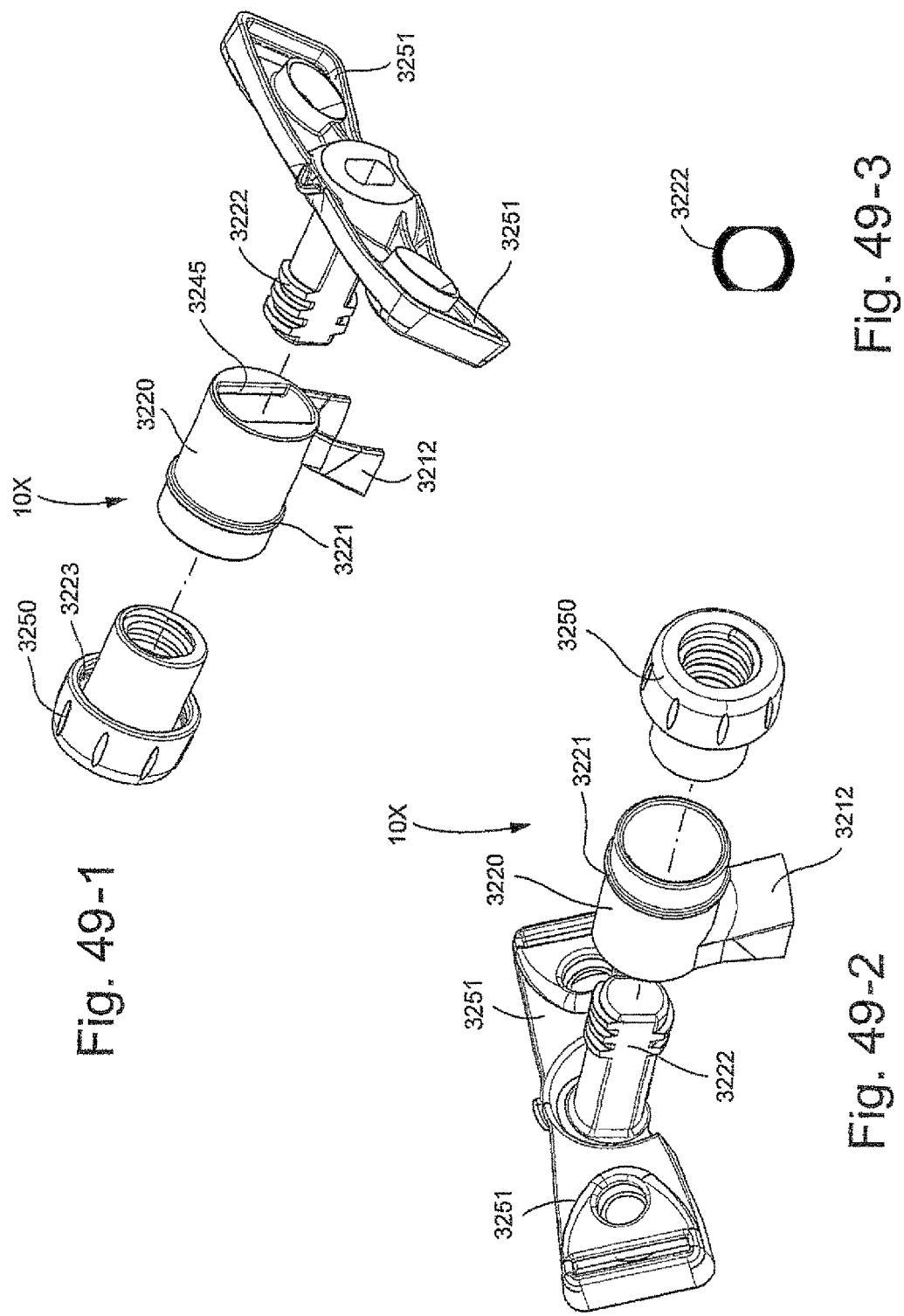

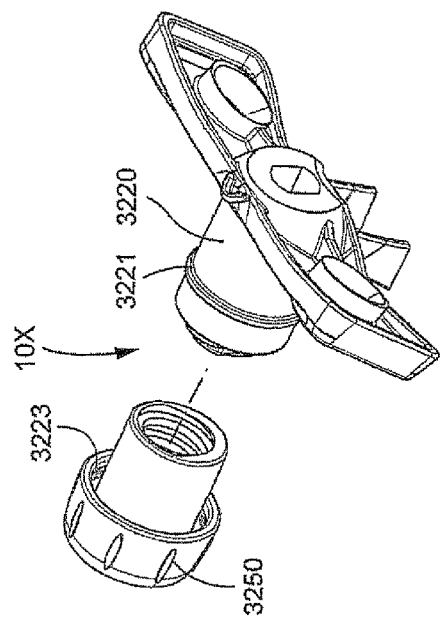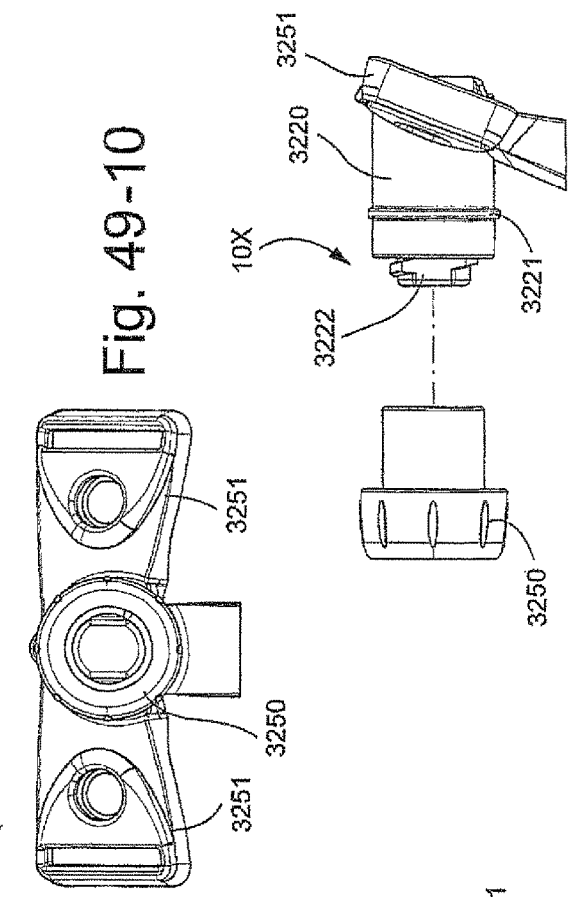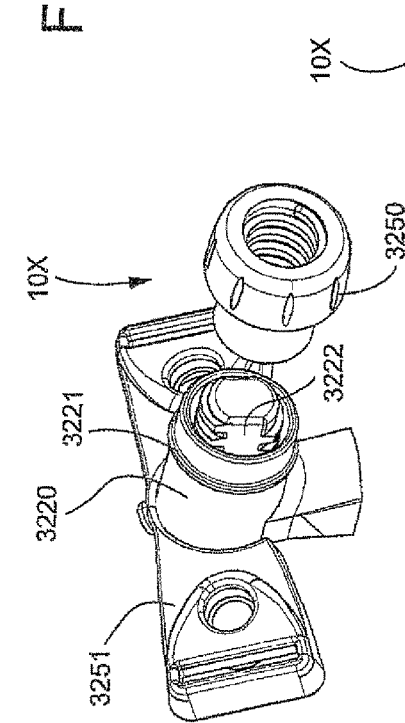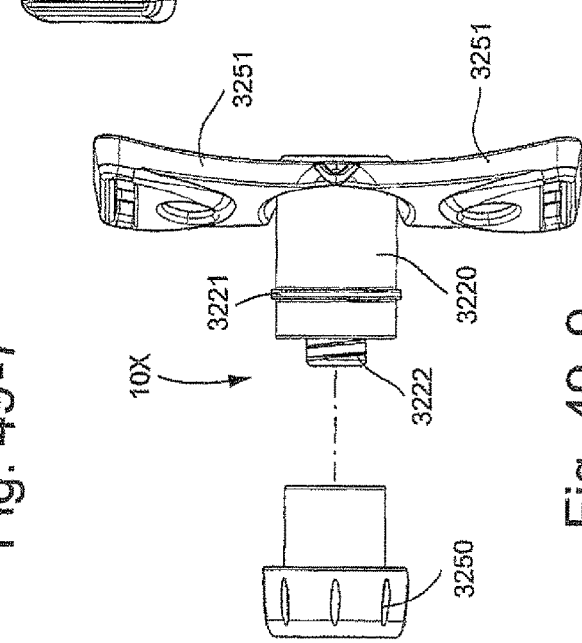

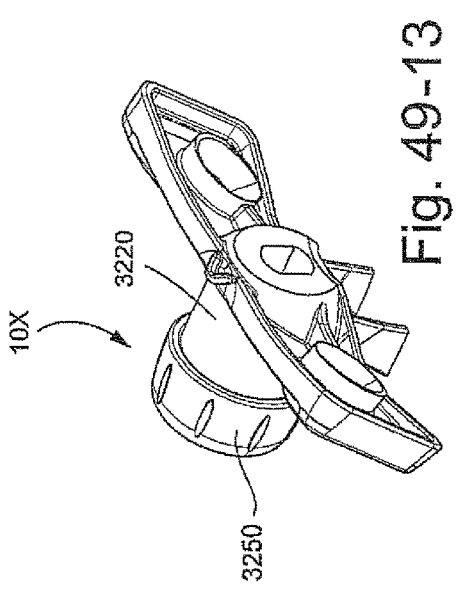
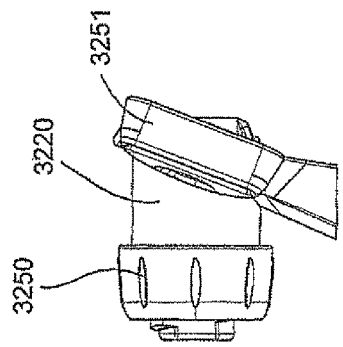
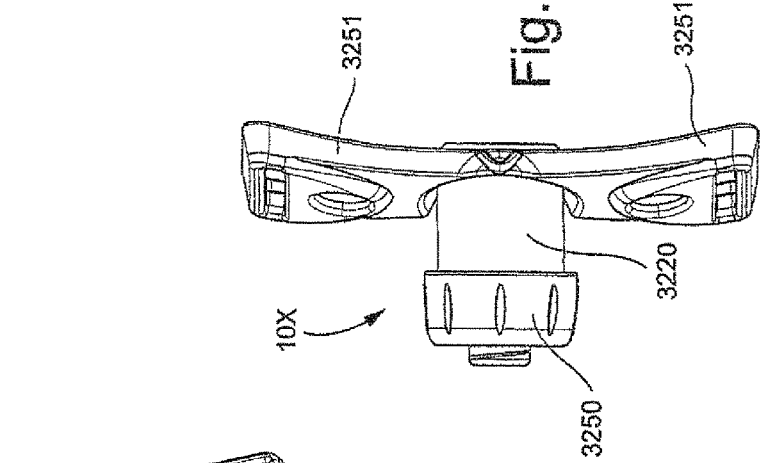
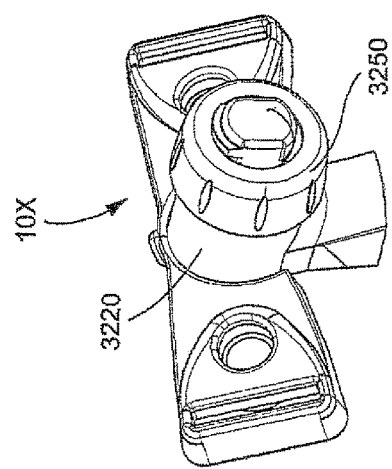

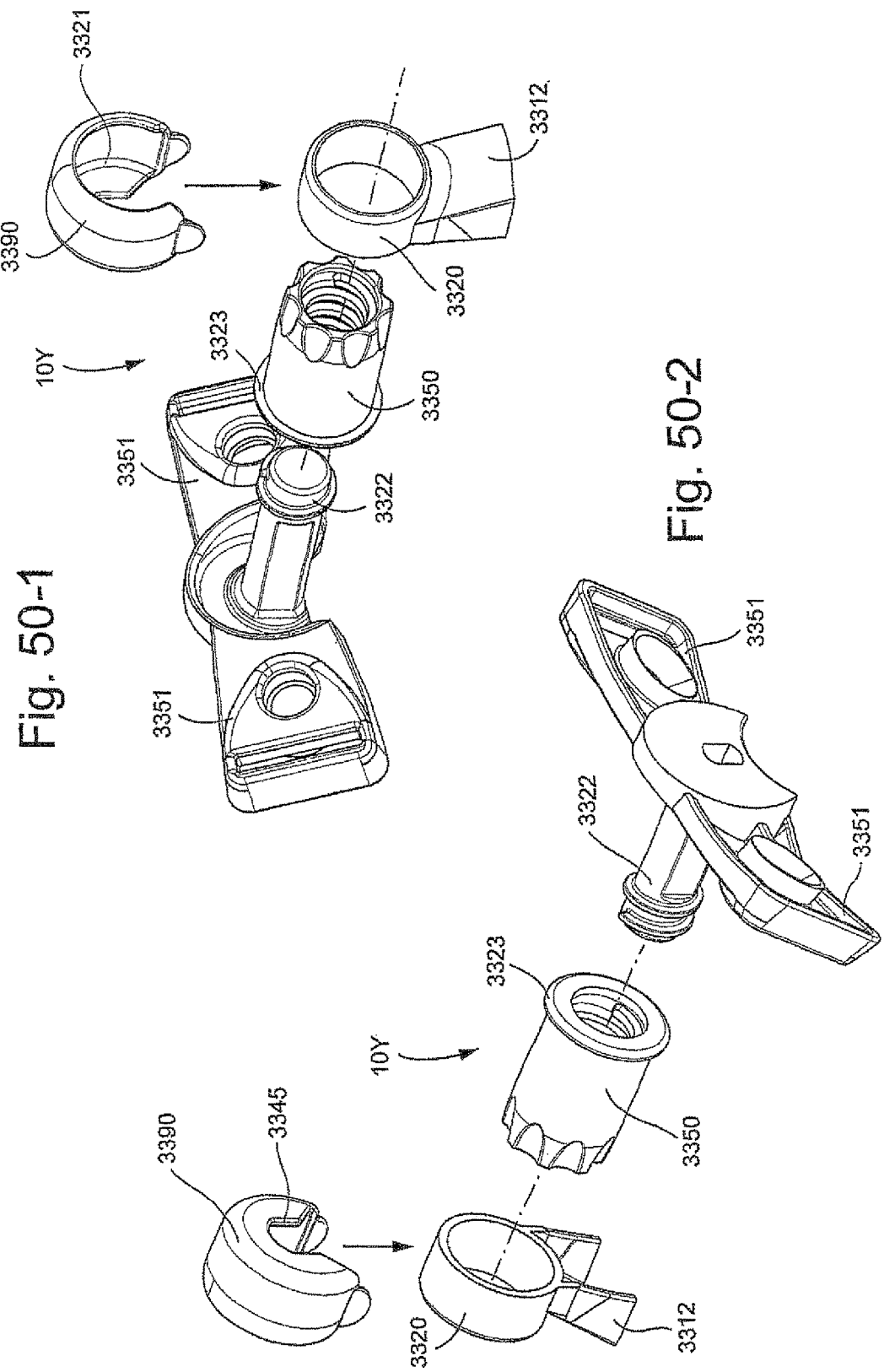

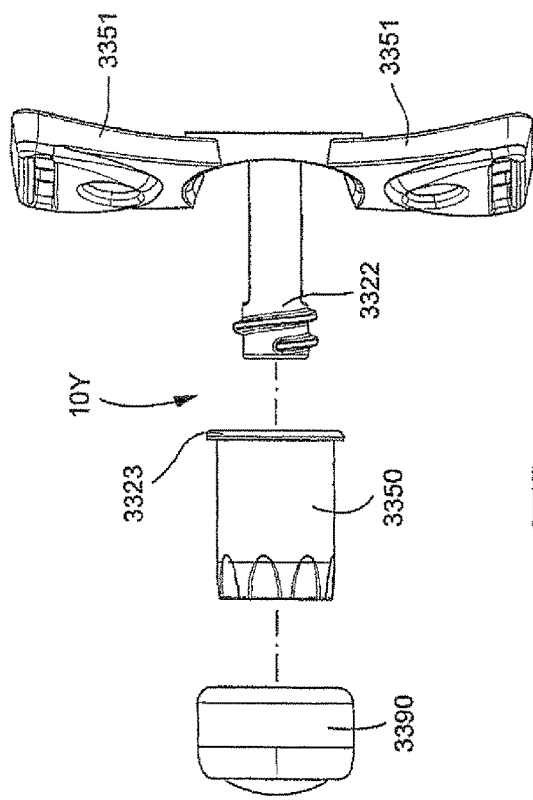
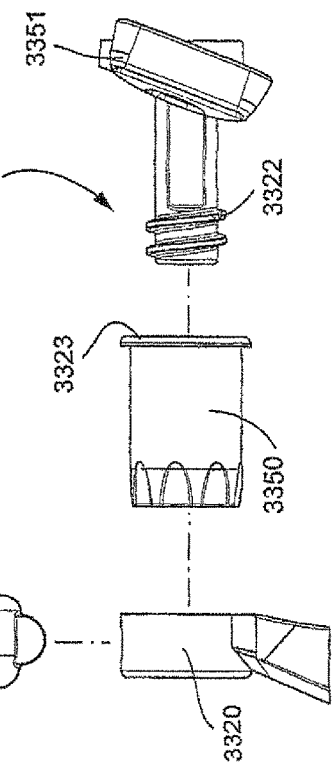
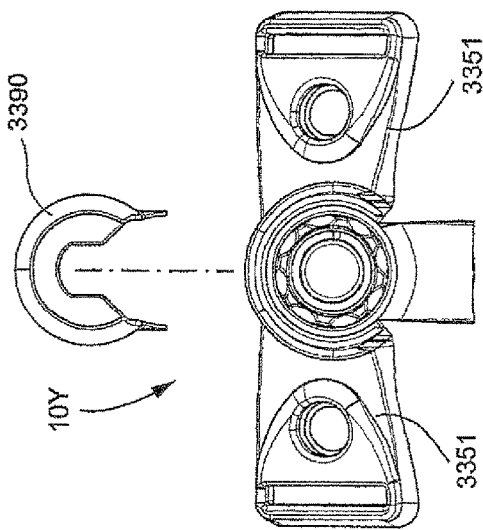
Fig. 50-3
Fig. 50-4
Fig. 50-5

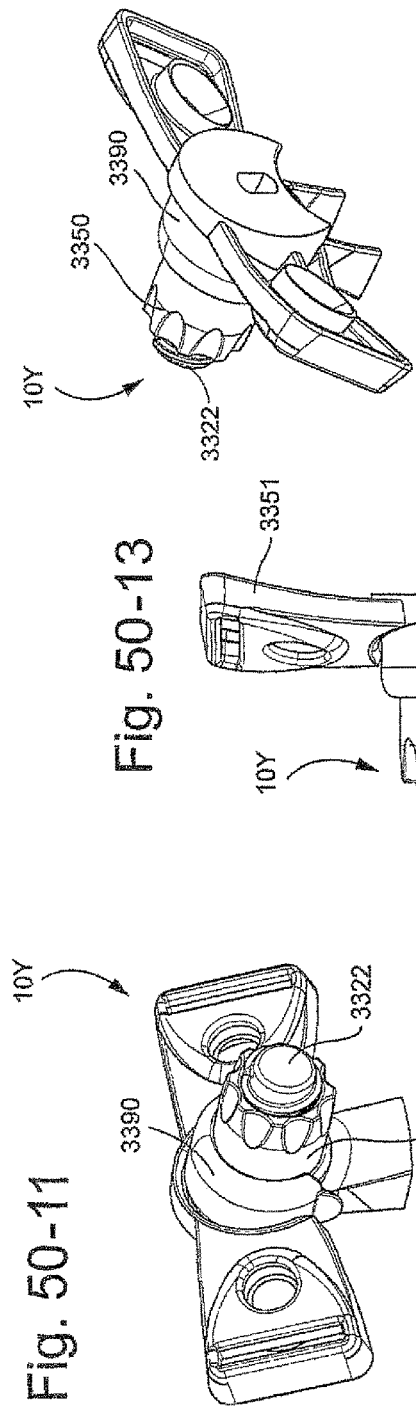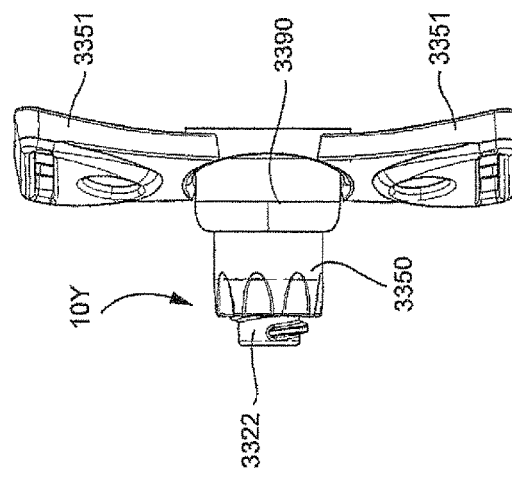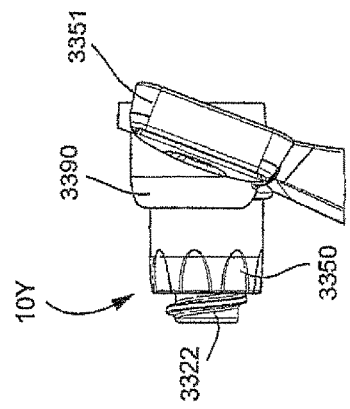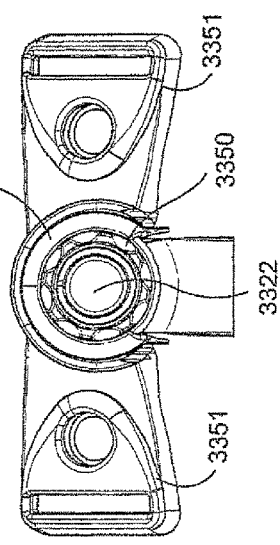

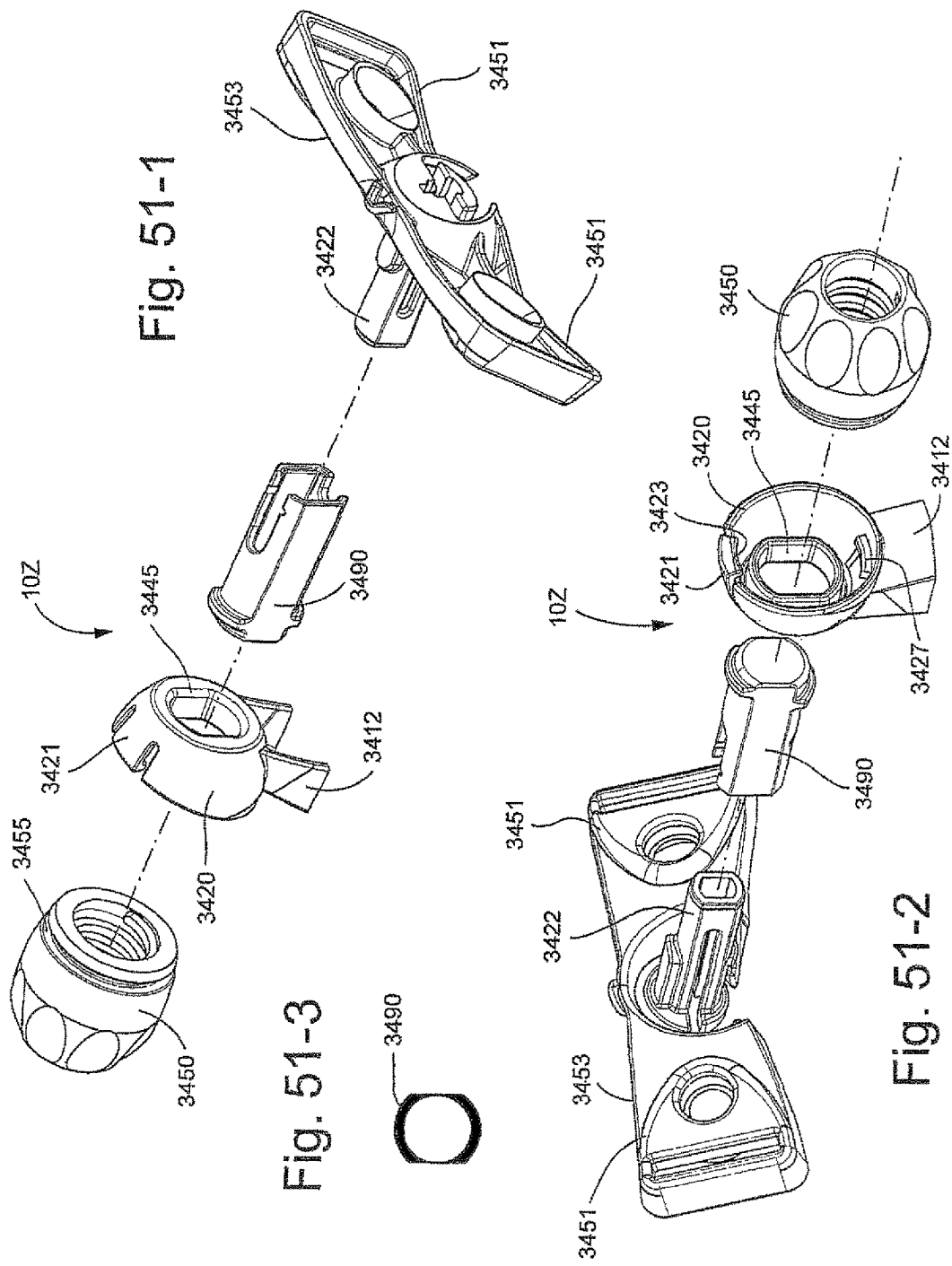

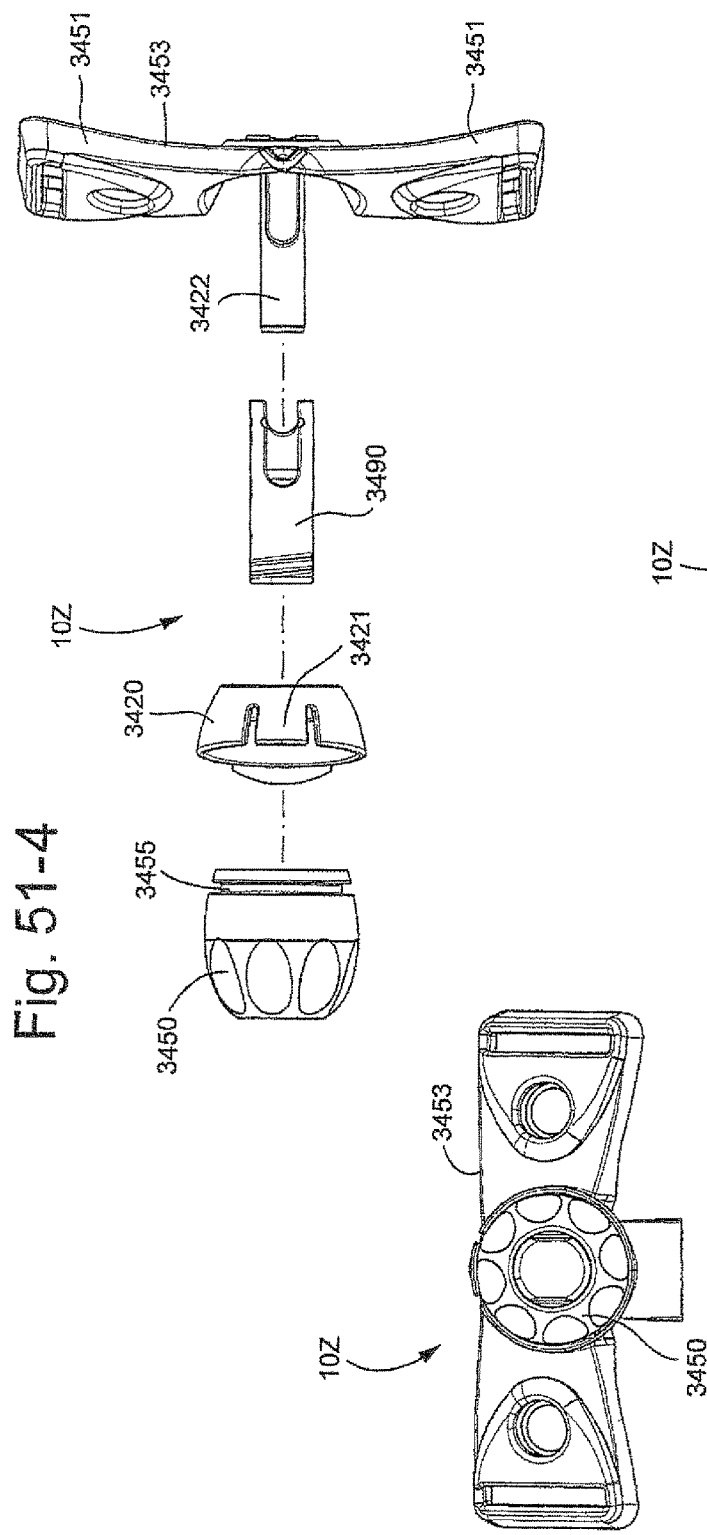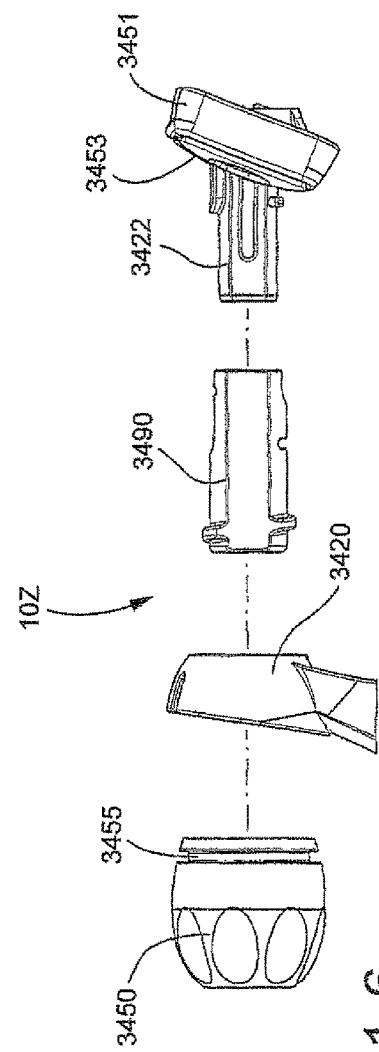
Fig. 51-4
Fig. 51-5
Fig. 51-6

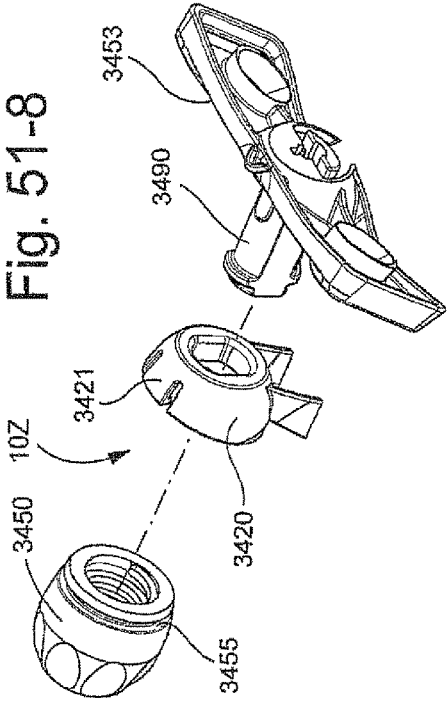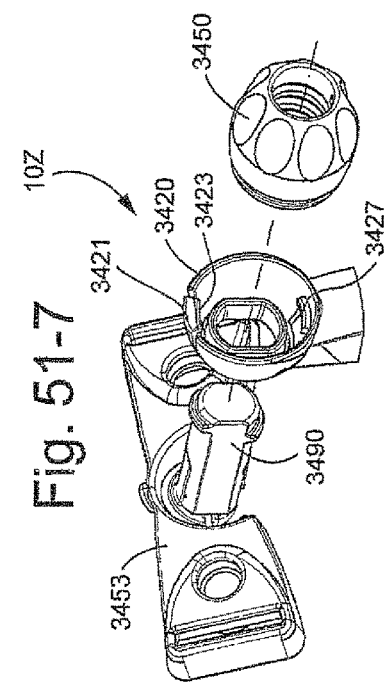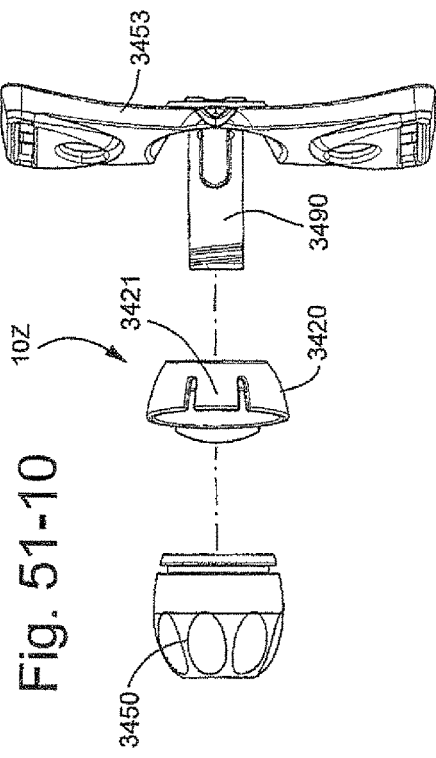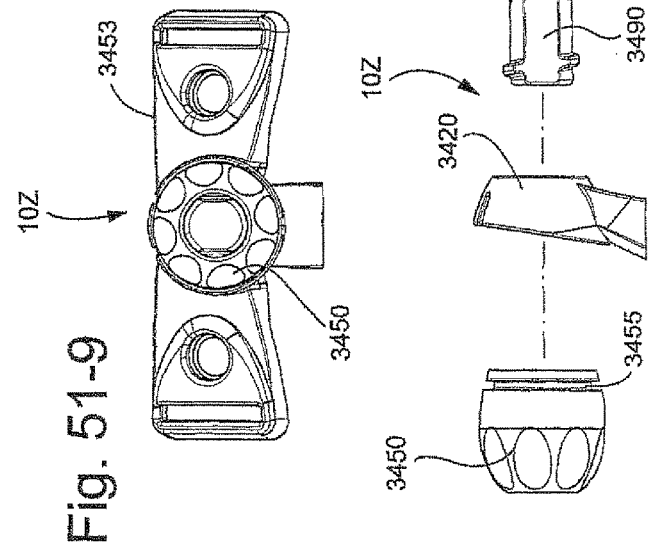
Fig. 51-7  Fig. 51-8  Fig. 51-9  Fig. 51-10  Fig. 51-11

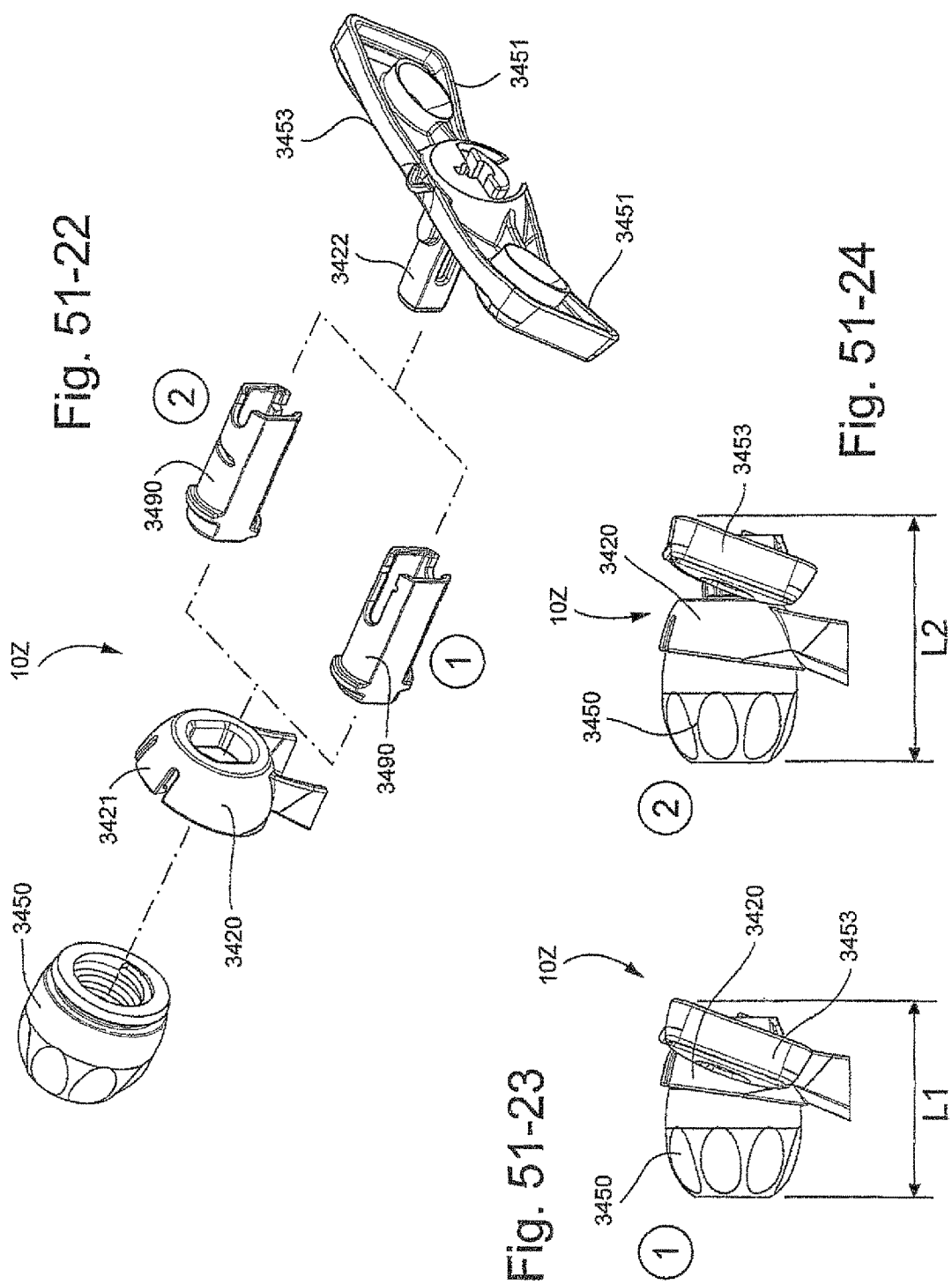

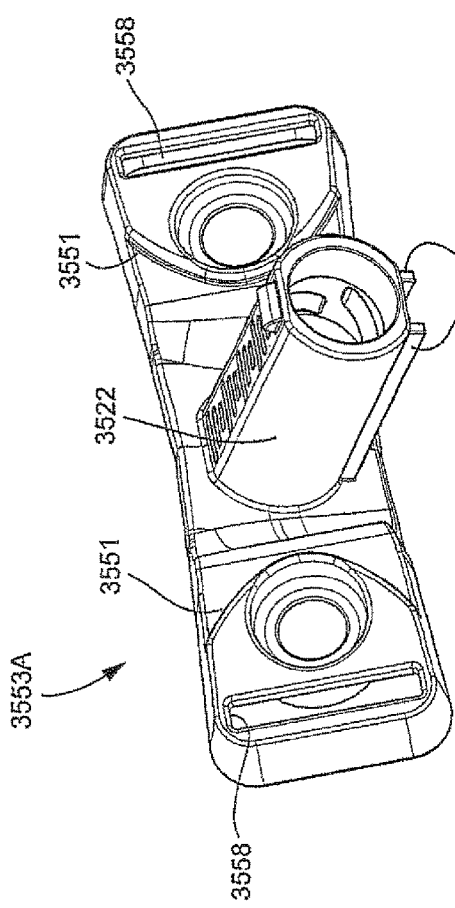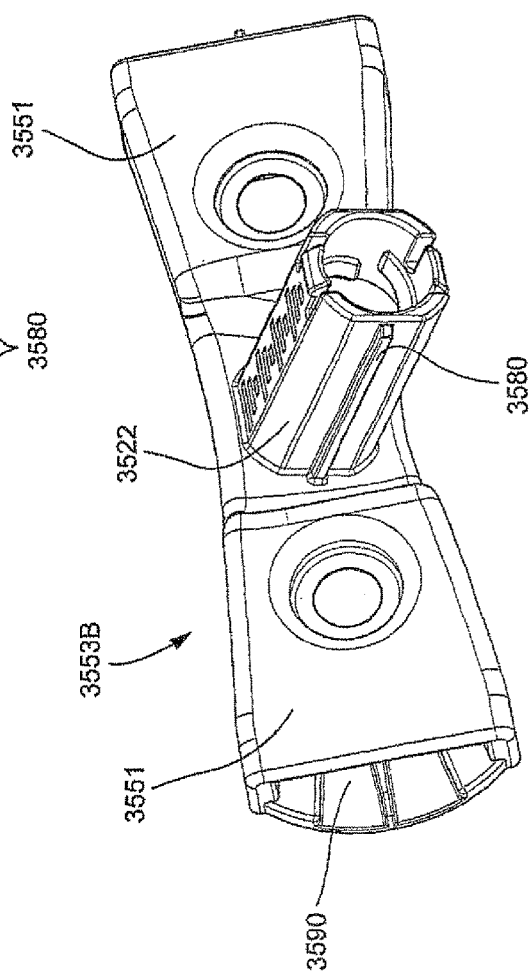

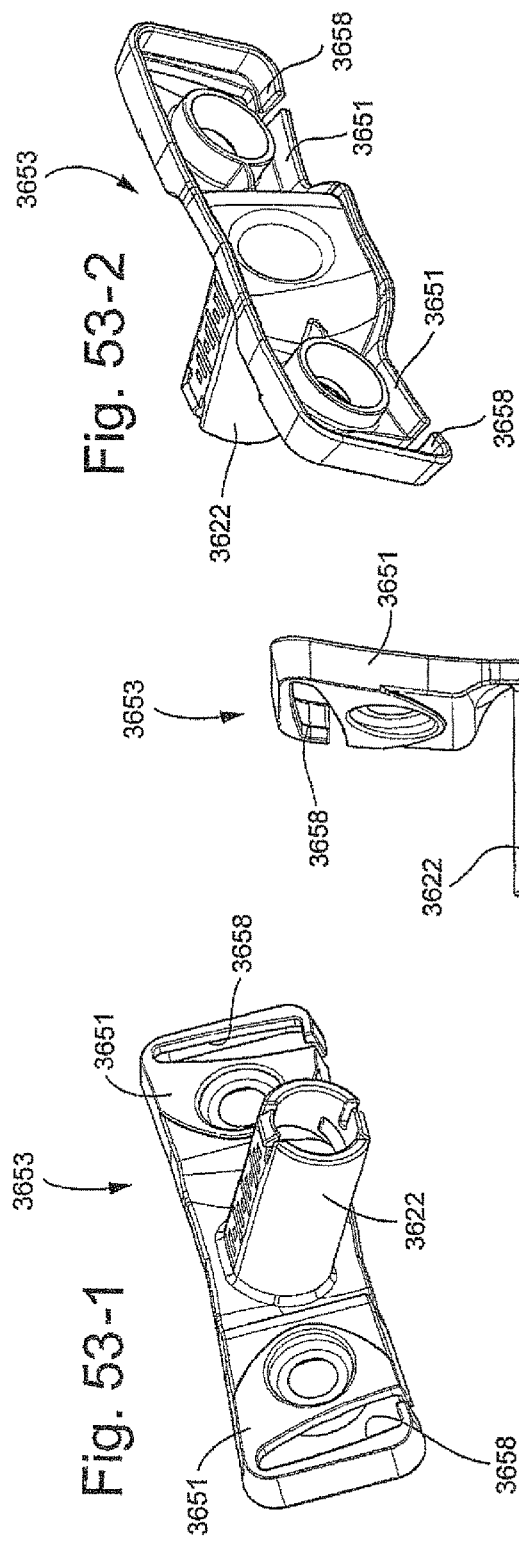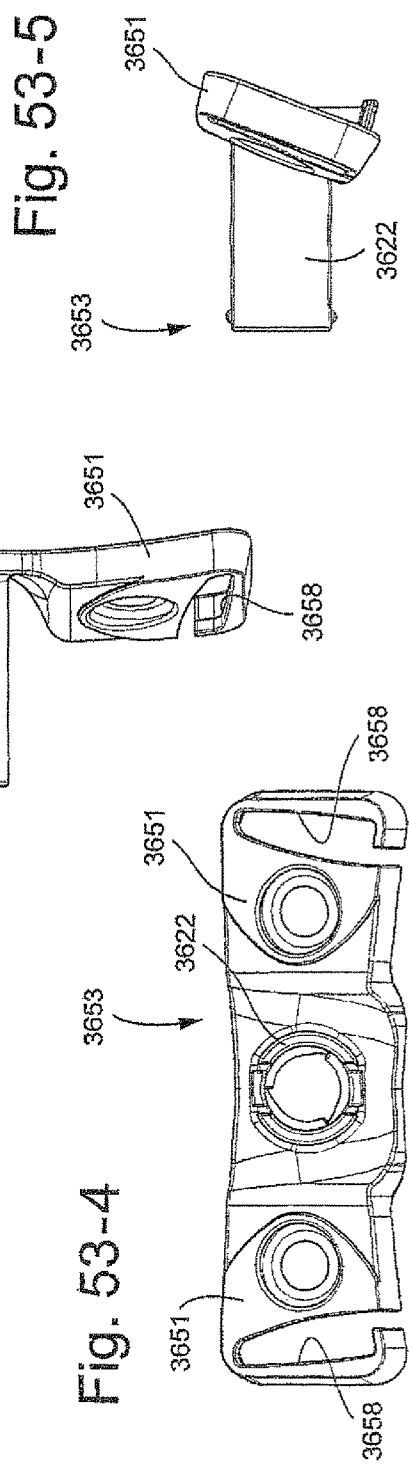

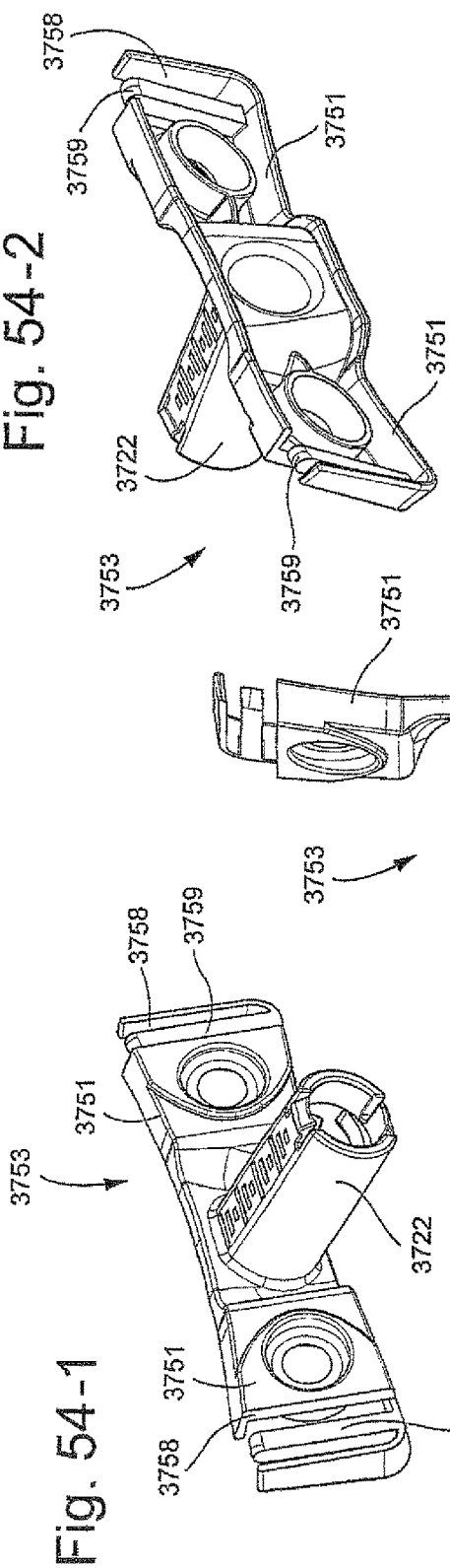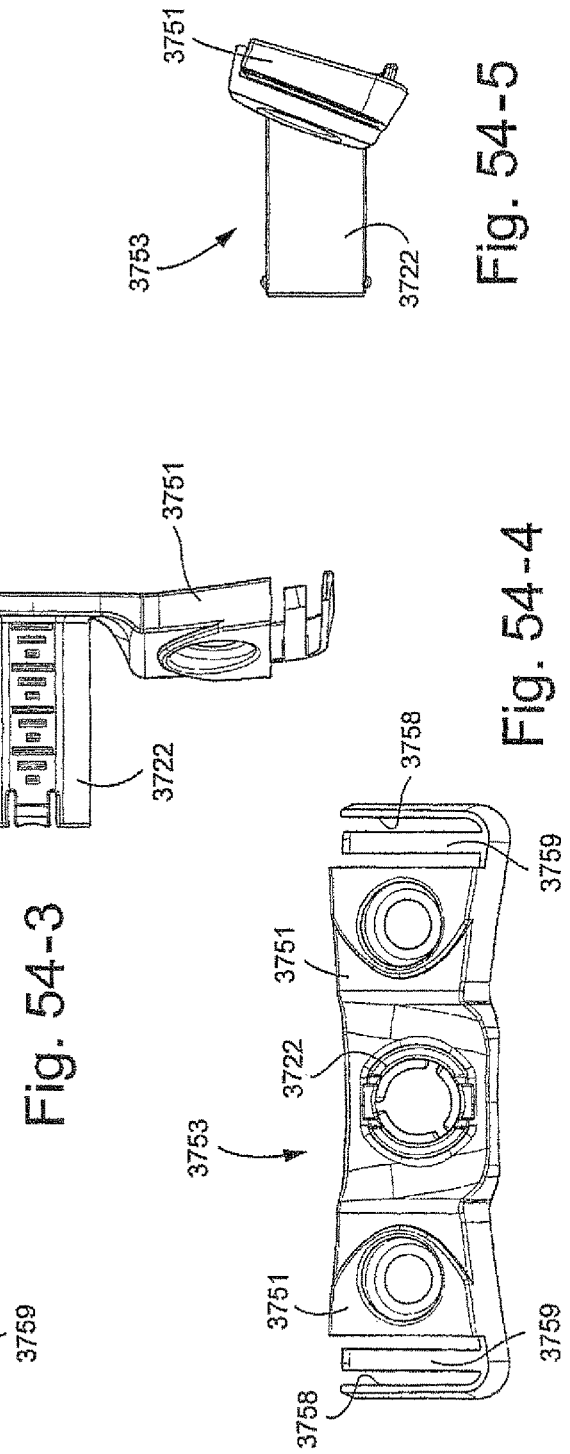

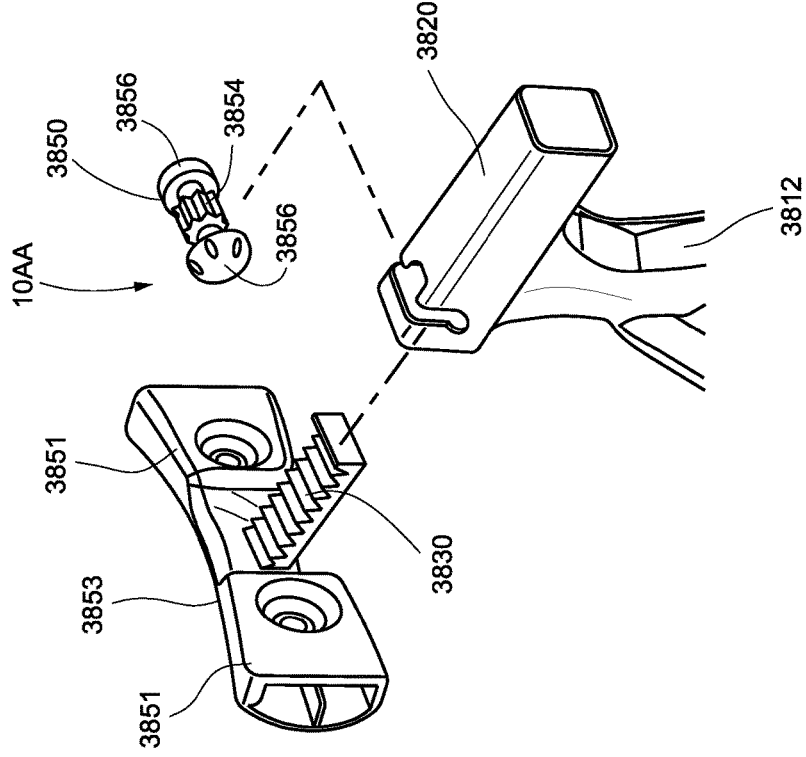
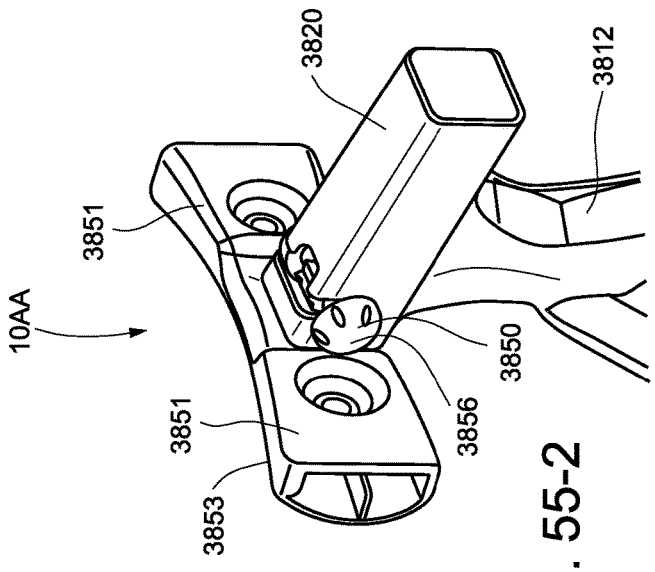
Fig. 55-1
Fig. 55-2

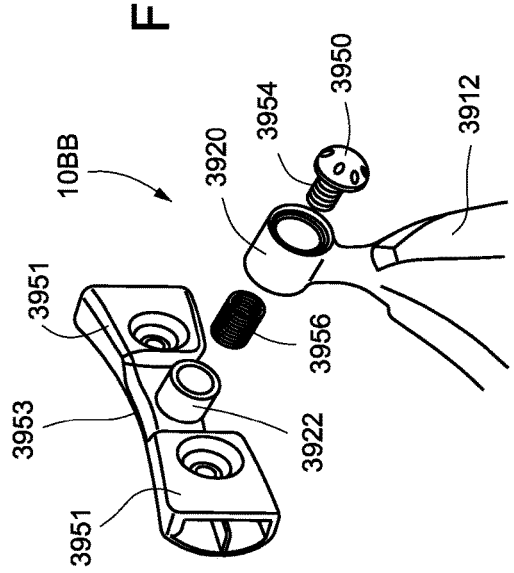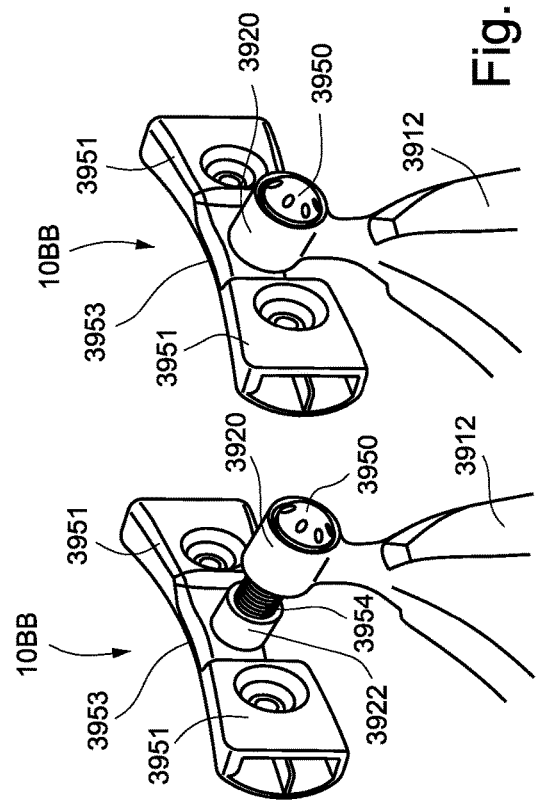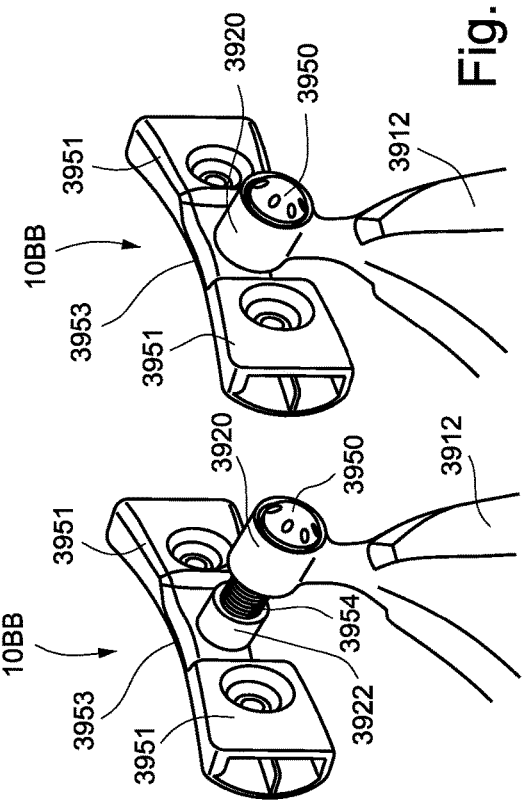

FOREHEAD SUPPORTS FOR FACIAL MASKS

CROSS-REFERENCE TO APPLICATIONS

This application is a continuation of U.S. application Ser. No. 11/793,055, filed Jun. 15, 2007, which application is the US national phase of international application PCT/AU2006/000037, filed 12 Jan. 2006, which designated the U.S. and claims the benefit of U.S. Provisional Application Nos. 60/643,113, filed Jan. 12, 2005, 60/696,502, filed Jul. 6, 2005, 60/715,173, filed Sep. 9, 2005, and 60/735,823, filed Nov. 14, 2005, each of which is incorporated herein by reference in its entirety.

FIELD OF THE INVENTION

The present invention relates generally to the field of forehead supports for facial masks used to supply breathable gas to a wearer's airways.

BACKGROUND OF THE INVENTION

Facial masks are well known for use in continuous positive airway pressure (CPAP) treatment of various respiratory ailments and sleep disordered breathing (SDB), such as, for example, obstructive sleep apnea (OSA) and/or other ventilatory assistance treatments such as noninvasive positive pressure ventilation (NPPV). See, for example, U.S. Pat. No. 4,944,210, the entire content of which is expressly incorporated hereinto by reference. While the present invention will be described below with reference to a full facial mask for use in CPAP treatment, it will be understood that such a reference is non-limiting and is directed toward a particularly preferred embodiment of the present invention. Thus, the various characteristics and advantages of the present invention could equivalently be embodied in another type of mask, such as a nasal mask, or in another type of noninvasive ventilation treatment.

Apparatus for the treatment of SDB generally involves a blower which delivers a supply of air at positive pressure to a patient interface via a conduit. The patient interface may take several forms, such as a nasal mask assembly and a nasal and mouth mask assembly (i.e., a full face mask). Patients typically wear a mask assembly while sleeping to receive the NPPV therapy.

Mask assemblies typically include a rigid shell or frame and a soft face-contacting cushion. The cushion cushions the rigid frame from the patient's face, and provides a seal with the patient's face. The frame and cushion define a cavity which receives the nose or nose and mouth. The frame and cushion are held in position on the patient's face by a headgear assembly. The headgear assembly typically comprises an arrangement of straps which pass along both sides of the patient's face to the back or crown of the patient's head.

One problem that arises with existing masks used for CPAP treatments is that tightening of the mask straps results in compression of the mask against the wearer's face which may therefore apply undue force against certain of the wearer's facial features, such as the wearer's nose. A poorly fitting mask can leak when pressurized which encourages a patient to tighten the headgear straps excessively which, in turn leads to discomfort, marks on the face and in some cases facial sores.

Thus, conventional masks have been provided with a forehead support, which provides a support and stability mechanism between the mask and the forehead. The forehead support prevents both the mask from pushing too strongly against the wearer's facial region as well as minimizing movement of the mask with the addition of a contact point between the mask and the wearer's head thereby reducing uncomfortable pressure points. Furthermore, in facial masks having a gusseted facial cushion such as described in U.S. Provisional Patent Application Ser. No. 60/643,113, filed Jan. 12, 2005, the entire content of which is expressly incorporated hereinto by reference, a forehead support may be employed to control the amount of gusset opening and/or closing thereby assisting in the applied force to the wearer's face, for example, the patient's nasal region.

Typically, a mask forehead support is adjustable so that a standard mask may be capable of adjustment suitable for a number of patients with different anthropometric features. Conventional masks having adjustable forehead supports are evidenced by U.S. Pat. Nos. 6,119,693; 6,463,931; 6,557,556; and 6,691,708, the entire content of each such prior-issued patent being incorporated expressly hereinto by reference. To facilitate adjustability, conventional forehead supports may also be capable of displacement relative to the mask as shown, for example, in U.S. Pat. No. 6,532,961 (the entire content of which is expressly incorporated hereinto by reference), so as to provide a means by which the relative angle between the mask and the forehead support can be varied to accommodate the facial features of a particular wearer.

A problem with conventional forehead supports for masks, however, is that the range of adjustment is relatively limited which therefore does not in fact provide a universal fit for a relatively large number of wearers. That is, due to the anthropometric features of a particular user's head, the adjustability of conventional forehead supports may not be sufficient to allow for a comfortable fit. Thus, while the forehead supports described above perform in a satisfactory manner, improvements to forehead supports for masks are needed.

SUMMARY OF THE INVENTION

In one embodiment, a mask forehead support provides for greater universality of fit as compared to conventional forehead support structures. More specifically, according to embodiments of the present invention, forehead supports are provided which are capable of a more useful and beneficial range of adjustment as compared to conventional forehead support structures thereby allowing the forehead supports of the present invention to more universally fit a much larger number of patients.

According to a particularly preferred aspect of the present invention, there is provided a face mask assembly for supplying breathable gas to a wearer, said face mask assembly comprising a mask frame; a facial cushion attached to the mask frame; and a forehead support. Advantageously, the forehead support includes a receiver attached to the mask frame and defining an arcuately shaped channel, an arcuately shaped elongate bar which is received within said channel of the receiver and configurable between retracted and extended positions, and a forehead cushion assembly adjustably (e.g., pivotally) attached to a distal end of the bar.

Preferably, the forehead cushion assembly comprises a pair of cushion support plates.

In another aspect of the invention, the forehead support assembly comprises a central support adjustably (e.g., pivotally) connected to a distal end of the slider bar, and wherein said support plates extend outwardly from said central support.

A further aspect of the invention is embodied in the central support plates being connected to the central support so as to be substantially V-shaped or substantially T-shaped relative to the slider bar.

The cushion support assembly most preferably comprises a convex or concave forehead cushion. Specifically, in accordance with an aspect of the present invention, the cushion support plates comprise apertures, and the forehead cushion assembly comprises a pair of cushions having concave interior surfaces, and an attachment head protruding rearwardly therefrom which is inserted into and through a respective one of the apertures in the support plates so as to physically attach the cushions thereto.

According to another aspect of the invention, the receiver comprises a pair of opposed openings, and the slider bar comprises a series of apertures spaced apart from one another in a general lengthwise direction of the slider bar and capable of respective alignment with the opposed openings of the receiver upon sliding movement of the slider bar between said retracted and extended positions thereof. A position pin may be provided which is insertable through said opposed openings and a respective one of said apertures of the slider bar when said at least one aperture is aligned with said openings to positionally maintain the slider bar relative to the receiver.

According to another aspect of the present invention, the slider bar comprises a gear rack, and the receiver comprises an adjustment knob having a pinion gear meshed with said gear rack. As such, turning movement of the adjustment knob causes the slider bar to be moved between the retracted and extended positions thereof.

The slider bar may comprise a resilient detent button, while the receiver comprises a series of longitudinally spaced apart position apertures. The detent button may thus be resiliently engageable with the position apertures as the slider bar is moved between the retracted and extended positions thereof.

In one aspect of the invention, the slider bar comprises an elongate slot, and the adjustment knob comprises a head portion and a cylindrical post which connects the head portion to the pinion gear thereof. The cylindrical post is thus received within the elongate slot to allow for movement of the slider bar between the retracted and extended positions thereof. The receiver may also comprise a circular bearing surface against which the underside of the adjustment knob bears.

According to yet another aspect of the invention, a face mask assembly is provided with a forehead cushion support having a slider bar which includes a resilient central tongue member, a push button and a fixed pawl carried by the tongue member. The receiver comprises an elongate slot through which the push button extends, and a series of ratchet teeth engageable with said pawl. Thus, the pawl is disengaged from a respective one of said ratchet teeth upon pressing the push button so as to allow the slider bar to be moved slidably within the receiver between the retracted and extended positions thereof. Preferably, a fixed pawl is provided on each side of said push button.

One aspect of the invention is embodied in a forehead cushion pad having a generally concave cushion flange, a cushion body portion supporting the cushion flange, and a pair of rearwardly protruding elongate foot pads. According to this aspect of the invention, the cushion body portion comprises an open channel, while cushion support plates have retaining clips which extend into said open channel and thereby retain the cushion pads to said support plates.

Another aspect of the invention relates to a face mask assembly for supplying breathable gas to a wearer. The face mask assembly includes a mask frame, facial cushion attached to the mask frame, and a forehead support. The forehead support includes a receiver attached to the mask frame including spaced-apart arcuately shaped channels that define an elongated central finger and outer guide rails. An arcuately shaped elongate slider bar is slidably received within the channels of the receiver for movements between retracted and extended positions. The slider bar is supported on the central finger and guided by the outer guide rails. A forehead cushion assembly is attached to a distal end of the slider bar.

Yet another aspect of the invention relates to a face mask assembly for supplying breathable gas to a wearer. The face mask assembly includes a mask frame, a facial cushion attached to the mask frame, and a forehead support. The forehead support includes a forehead cushion assembly and an adjustment knob operatively coupled to the forehead cushion assembly such that turning movement of the adjustment knob causes the forehead cushion assembly to be moved between retracted and extended positions.

Still another aspect of the invention relates to a face mask assembly for supplying breathable gas to a wearer. The face mask assembly includes a mask frame including a support, a facial cushion attached to the mask frame, and a forehead support. The forehead support includes a forehead cushion assembly and an adjustment knob operatively coupled to the forehead cushion assembly. The adjustment knob is threadably engaged with the forehead cushion assembly such that turning movement of the adjustment knob causes the mask frame to be moved between retracted and extended positions with respect to the forehead cushion assembly.

Still another aspect of the invention relates to a face mask assembly for supplying breathable gas to a wearer. The face mask assembly includes a mask frame, a facial cushion attached to the mask frame, and a forehead support. The forehead support includes a forehead cushion support movably mounted to the mask frame for movements between retracted and extended positions and a forehead cushion attached to the forehead cushion support. The forehead cushion support includes a first connector that engages a second connector provided by the forehead cushion, and the first and second connectors each include a connector side wall with one or more slots through the connector side wall that allows the first and second connectors to compress in use.

Still another aspect of the invention relates to a forehead cushion support for a forehead support of a mask assembly. The forehead cushion support includes forehead cushion support plates to support forehead cushions and a slider provided to the support plates. The slider includes a resilient tab to provide quick-release assembly to a mask frame.

Still another aspect of the invention relates to a forehead support for a mask assembly. The forehead support includes a support provided to a mask frame, a forehead cushion support movably mounted to the support for generally linear movement between retracted and extended positions with respect to the support, and an adjustment knob threadably engaged with the forehead cushion support such that turning movement of the adjustment knob causes the forehead cushion support to be moved between the retracted and extended positions.

Still another aspect of the invention relates to a face mask assembly for supplying breathable gas to a wearer. The face mask assembly includes a mask frame, a facial cushion attached to the mask frame, and a forehead support. The forehead support includes a receiver attached to the mask frame and defining an arcuately shaped channel, an arcuately shaped elongate slider bar which is slidably received within the channel of the receiver for movement between retracted and extended positions, and a forehead cushion assembly rigidly connected to a distal end of the slider bar.

It will of course be understood that, while the present invention will be described in connection with a full facial mask, those in this art will recognize that such a description represents one preferred embodiment and is thus non-limiting. Thus, the structural and/or functional features of the present invention may, for example, also be usefully employed in nasal masks or nasal prongs, nozzles, nare seals, and/or cannulae.

These and other aspects and advantages will become more apparent after careful consideration is given to the following detailed description of preferred exemplary embodiments thereof.

BRIEF DESCRIPTION OF THE DRAWINGS

Reference will hereinafter be made to the accompanying drawings, wherein like reference numerals throughout the various FIGURES denote like structural elements, and wherein;

FIG. 2 shows a side view of a "standard" facial profile superimposed onto a grid of vertical and horizontal distances centered substantially on the nasion region, together with superimposed circular ranges of movement of forehead supports according to a prior art mask and a facial mask in accordance with an aspect of the invention;

FIGS. 3-1 to 3-8 show various views of an alternative embodiment of a slider bar subassembly that may be employed in the facial mask assembly of the present invention depicted in FIGS. 1-1 to 1-4, including a left and right side elevation views (FIGS. 3-1 and 3-5, respectively), top and bottom elevation views (FIGS. 3-2 and 3-4, respectively), a front elevation view (FIG. 3-3) and front, bottom and rear perspective views (FIGS. 3-6, 3-7 and 3-8, respectively);

FIGS. 4-1 to 4-6 show various views of an embodiment of a facial mask frame that may be employed with the facial mask assembly of the present invention depicted in FIGS. 1-1 to 1-4 including front and side elevation views (FIGS. 4-1 and 4-2, respectively), a bottom elevation view (FIG. 4-6), and front, side and rear perspective views (FIGS. 4-3, 4-4 and 4-5, respectively);

FIG. 5 shows a detailed plan view of the forehead cushion subassembly that may be employed in accordance with the forehead support shown in FIGS. 1-1 to 1-4 according to the present invention;

FIGS. 6-1 to 6-3 are various views of an alternative forehead cushion that may be employed in combination with the cushion support plate shown in FIG. 5;

FIGS. 7-1 to 7-3 are side views of various alternative slider bars that may be employed in the forehead supports according to the present invention;

FIGS. 8-1 to 8-5 show various views of a full facial mask assembly providing patient interface for respiratory therapy with a forehead support in accordance with another embodiment of the invention, including front and side elevation views (FIGS. 8-1 and 8-2, respectively), a top view (FIG. 8-3) and rear and top perspective views (FIGS. 8-4 and 8-5, respectively);

FIGS. 9-1 to 9-6 show various views of an embodiment of a slider bar subassembly that may be employed in the facial mask assembly depicted in FIGS. 8-1 to 8-4, including a front elevation view (FIG. 9-1), a top view (FIG. 9-2), right and left side elevation views (FIGS. 9-3 and 9-4, respectively), and bottom and top perspective views (FIGS. 9-5 and 9-6, respectively);

FIGS. 10-1 to 10-5 show various views of an embodiment of a facial mask frame that may be employed with the slider bar subassembly depicted in FIGS. 9-1 to 9-6 including front and side elevation views (FIGS. 10-1 and 10-2, respectively), a top view (FIG. 10-3), and top and rear perspective views (FIGS. 10-4 and 10-5, respectively);

FIGS. 11-1 to 11-3 show various views of a position adjustment knob that may be employed operatively with the slider bar subassembly depicted in FIGS. 9-1 to 9-6, including a side perspective view (FIG. 11-1), a front elevation view (FIG. 11-2), and a bottom plan view (FIG. 11-3);

FIGS. 12-1 TO 12-6 show various views of a full facial mask assembly providing patient interface for respiratory therapy with a forehead support in accordance with another embodiment of the invention, including a front elevation view (FIG. 12-1), side elevation views (FIGS. 12-2 and 12-3), a top view (FIG. 12-4) and rear and top perspective views (FIGS. 12-5 and 12-6, respectively);

FIGS. 13-1 to 13-7 show various views of an embodiment of a slider bar subassembly that may be employed in the facial mask assembly depicted in FIGS. 12-1 to 12-6, including a top elevation view (FIG. 13-1), a front view (FIG. 13-2), a bottom view (FIG. 13-3), a right side elevation view (FIG. 13-4), bottom perspective views (FIGS. 13-5 and 13-6), and a top perspective view (FIG. 13-7);

FIGS. 14-1 to 14-3 show various views of a position adjustment knob that may be employed operatively with the slider bar subassembly depicted in FIGS. 13-1 to 13-7, including a side perspective view (FIG. 14-1), a front elevation view (FIG. 14-2), and a bottom plan view (FIG. 14-3);

FIGS. 15-1 TO 15-8 show various views of a full facial mask assembly providing patient interface for respiratory therapy with a forehead support in accordance with another embodiment of the invention, including a front elevation view (FIG. 15-1), a side elevation view (FIG. 15-2), a top view (FIG. 15-3), rear perspective views (FIGS. 15-4 and 15-5), top perspective views (FIGS. 15-6 and 15-7), and an exploded view (FIG. 15-8);

FIGS. 16-1 to 16-7 show various views of an embodiment of a slider bar subassembly that may be employed in the facial mask assembly depicted in FIGS. 15-1 to 15-8, including a top elevation view (FIG. 16-1), a front view (FIG. 16-2), right and left side elevation views (FIGS. 16-3 and 16-4, respectively), top perspective views (FIGS. 16-5 and 16-6), and a bottom perspective view (FIG. 16-7);

FIGS. 17-1 to 17-7 show various views of an embodiment of a facial mask frame that may be employed with the slider bar subassembly depicted in FIGS. 16-1 to 16-7 including front and side elevation views (FIGS. 17-1 and 17-2, respectively), a top view (FIG. 17-3), top perspective views (FIGS. 17-4 and 17-5), and bottom perspective views (FIGS. 17-6 and 17-7);

FIGS. 18-1 to 18-5 show various views of a position adjustment knob that may be employed operatively with the slider bar subassembly depicted in FIGS. 16-1 to 16-7, including a side perspective view (FIG. 18-1), a bottom perspective view (FIG. 18-2), a front elevation view (FIG. 18-3), a top plan view (FIG. 18-4), and a bottom plan view (FIG. 18-5);

FIGS. 19-1 to 19-2 show various views of position markings that may be employed on an adjustment knob (FIG. 19-1) and/or a slider bar subassembly (FIG. 19-2);

FIGS. 20-1 to 20-2 show various views of employing a variable rate of motion in a slider bar subassembly;

FIGS. 22-1 to 22-5 show various views of a full facial mask assembly providing patient interface for respiratory therapy with a forehead support in accordance with yet another embodiment of the invention, including front and side elevation views (FIGS. 22-1 and 22-2, respectively), a top view (FIG. 22-3) and rear and top perspective views (FIGS. 22-4 and 22-5, respectively);

FIGS. 23-1 to 23-5 show various views of an embodiment of a slider bar subassembly that may be employed in the facial mask assembly depicted in FIGS. 22-1 to 22-5, including a front elevation view (FIG. 23-1), a top view (FIG. 23-2), a left side elevation views (FIG. 23-3), and top and bottom perspective views (FIGS. 23-4 and 23-5, respectively);

FIGS. 24-1 to 24-5 show various views of an embodiment of a facial mask frame that may be employed with the slider bar subassembly depicted in FIGS. 23-1 to 23-5 including front and side elevation views (FIGS. 24-1 and 24-2, respectively), a top view (FIG. 24-3), and top and rear perspective views (FIGS. 24-4 and 24-5, respectively);

FIGS. 26-1 to 26-4 show various views of a full facial mask assembly providing patient interface for respiratory therapy with a forehead support in accordance with yet another embodiment of the invention;

FIGS. 27-1 to 27-6 show various views of a full facial mask assembly providing patient interface for respiratory therapy with a forehead support in accordance with yet another embodiment of the invention;

FIGS. 28-1 to 28-3 show various views of a full facial mask assembly providing patient interface for respiratory therapy with a forehead support in accordance with yet another embodiment of the invention;

FIGS. 29-1 to 29-3 show various views of a full facial mask assembly providing patient interface for respiratory therapy with a forehead support in accordance with yet another embodiment of the invention;

FIGS. 30-1 to 30-3 show various views of a full facial mask assembly providing patient interface for respiratory therapy with a forehead support in accordance with yet another embodiment of the invention;

FIGS. 31-1 to 31-8 show various views of a full facial mask assembly providing patient interface for respiratory therapy with a forehead support in accordance with yet another embodiment of the invention;

FIGS. 32-1 to 32-6 show various views of a full facial mask assembly providing patient interface for respiratory therapy with a forehead support in accordance with yet another embodiment of the invention;

FIGS. 33-1 to 33-6 show various views of a full facial mask assembly providing patient interface for respiratory therapy with a forehead support in accordance with yet another embodiment of the invention;

FIGS. 34-1 to 34-5 show various views of a full facial mask assembly providing patient interface for respiratory therapy with a forehead support in accordance with yet another embodiment of the invention;

FIG. 35 is an exploded view of a full facial mask assembly providing patient interface for respiratory therapy with a forehead support in accordance with yet another embodiment of the invention;

FIGS. 36-1 to 36-5 show various views of a full facial mask assembly providing patient interface for respiratory therapy with a forehead support in accordance with still another embodiment of the invention;

FIGS. 37-1 to 37-11 show various views of a full facial mask assembly providing patient interface for respiratory therapy with a forehead support in accordance with still another embodiment of the invention;

FIGS. 37-12 to 37-15 show various sizes of a frame for the mask assembly shown in FIGS. 37-1 to 37-11;

FIGS. 38-1 to 38-18 show various views of a full facial mask assembly providing patient interface for respiratory therapy with a forehead support in accordance with still another embodiment of the invention;

FIGS. 39-1 to 39-9 show various views of a thread form for a forehead support in accordance with an embodiment of the present invention and showing exemplary dimensions of an embodiment;

FIGS. 40-1 to 40-3 show various views of a forehead cushion for a forehead support in accordance with an embodiment of the present invention and showing exemplary dimensions of an embodiment;

FIGS. 41-1 to 41-2 show various views of a forehead cushion support for a forehead support in accordance with an embodiment of the present invention and showing exemplary dimensions of an embodiment;

FIG. 41-3 is a perspective view illustrating the forehead cushion shown in FIGS. 40-1 to 40-3 assembled to the forehead cushion support shown in FIGS. 41-1 to 41-2;

FIGS. 42-1 to 42-8 show various views of a forehead cushion support for a forehead support in accordance with an embodiment of the present invention;

FIGS. 43-1 to 43-21 show various views of a full facial mask assembly providing patient interface for respiratory therapy with a forehead support in accordance with still another embodiment of the invention;

FIGS. 44-1 to 44-8 show various views of a forehead cushion support for a forehead support in accordance with an embodiment of the present invention;

FIGS. 45-1 to 45-19 show various views of a forehead support in accordance with still another embodiment of the invention;

FIGS. 46-1 to 46-16 show various views of a forehead support in accordance with still another embodiment of the invention;

FIGS. 47-1 to 47-16 show various views of a forehead support in accordance with still another embodiment of the invention;

FIGS. 48-1 to 48-16 show various views of a forehead support in accordance with still another embodiment of the invention;

FIGS. 49-1 to 49-16 show various views of a forehead support in accordance with still another embodiment of the invention;

FIGS. 50-1 to 50-15 show various views of a forehead support in accordance with still another embodiment of the invention;

FIGS. 51-1 to 51-24 show various views of a forehead support in accordance with still another embodiment of the invention;

FIGS. 52-1 and 52-2 show forehead cushion supports for a forehead support in accordance with alternative embodiments of the present invention;

FIGS. 53-1 to 53-5 show various views of a forehead cushion support for a forehead support in accordance with another embodiment of the present invention;

FIGS. 54-1 to 54-5 show various views of a forehead cushion support for a forehead support in accordance with another embodiment of the present invention;

FIGS. 55-1 to 55-2 show various views of a forehead support in accordance with still another embodiment of the invention;

FIGS. 56-1 to 56-3 show various views of a forehead support in accordance with still another embodiment of the invention; and FIGS. 57-1 to 57-15 show various views of a forehead support in accordance with still another embodiment of the invention.

DETAILED DESCRIPTION OF ILLUSTRATED EMBODIMENTS

Figure 1:
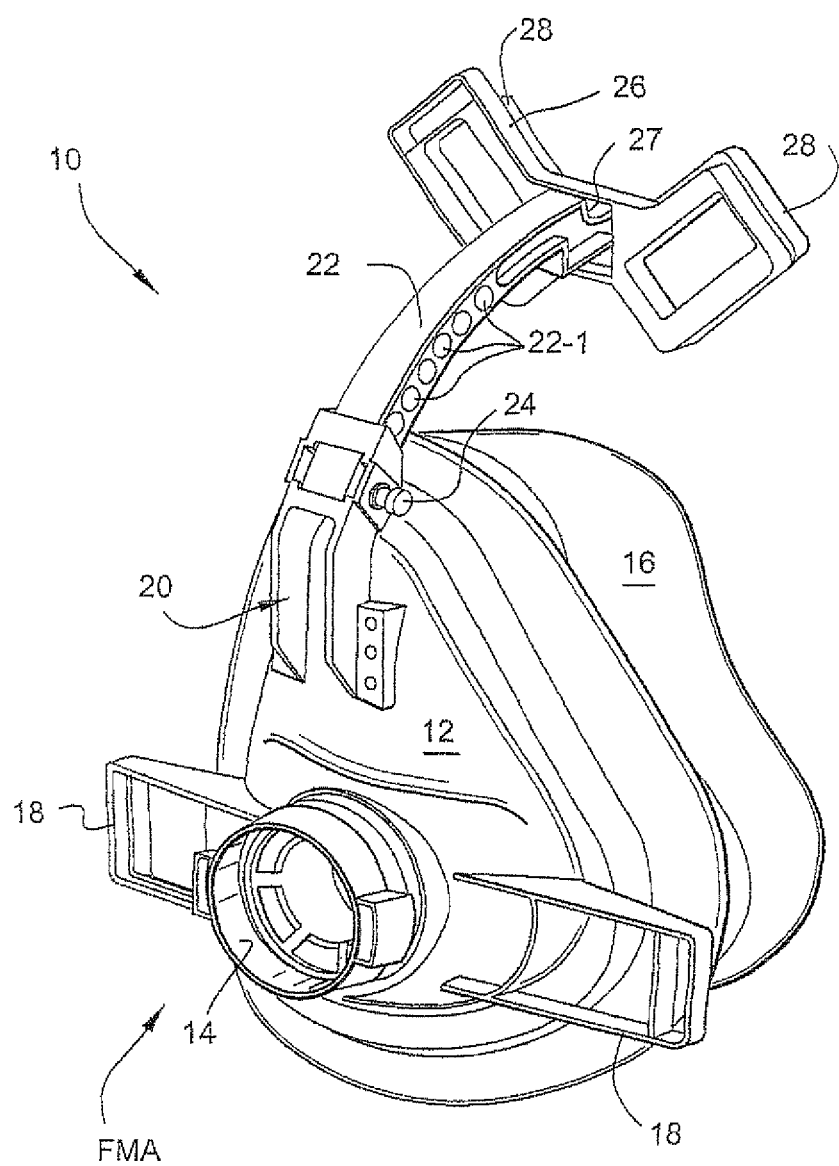
FIGS. 1-1 to 1-4 show various views of a full facial mask assembly providing patient interface for respiratory therapy with a forehead support in accordance with an embodiment of the invention, including front and rear perspective views (FIGS. 1-1 and 1-2, respectively), a front plan view (FIGS. 1-3) and a cross-sectional left side elevational view (FIGS. 1-4) as taken along line A-A in FIGS. 1-3 but shown without the face cushion for ease of depiction.

I. First Illustrated Embodiment of Forehead Support

An exemplary embodiment of a full facial mask assembly ("FMA") which includes a forehead support 10 according to one embodiment of the present invention is depicted in accompanying FIGS. 1-1 to 1-4. The FMA includes a mask frame 12 provided with a connection port 14 to which an elbow connector (not shown) associated with a gas supply conduit may be coupled to allow gas under pressure to be supplied to the FMA. A facial cushion 16 is attached to a rear portion of the mask frame 12 so as to cushion the FMA against the face of the wearer. Strap connectors 18 extend laterally from the mask frame 12 so as to allow attachment of straps associated with a conventional headgear assembly (not shown) and thereby permit the FMA to be secured to a wearer's head when in use.

A. Slider Bar

According to the present invention, the mask frame 12 includes a receiver 20 defining a channel 20-1 (see FIGS. 1-4) which is sized and configured to slidably receive therein an arcuate slider bar 22. The slider bar 22 includes a series of transverse apertures (a representative few of which are identified by reference number 22-1) which are spaced apart from one another in the general lengthwise direction of the slider bar 22. Slider bar 22 includes 2-9 transverse apertures 22-1, and preferably about 7-8 transverse apertures 22-1. The apertures 22-1 are adapted to receive a position pin 24 associated with the receiver 20 and thereby establish a respective position of the slider bar 22 relative to the mask frame 12.

B. Forehead Cushion Support Plate

The distal end of the slider bar 22 is connected pivotally to a generally V-shaped forehead cushion support plate 26 which carries a pair of forehead cushions 28 for placement against a wearer's forehead region. The cushions 28 depicted in FIGS. 1-1 to 1-4 are hollow structures which present an essentially convexly curved cushion surface to the patient's forehead. The cushions are removably attached by the support plates 26 by means of retaining clips 26-1 (FIGS. 1-3, 1-4, and 5) thereof which extend into the hollow of the cushions 28 and thereby positionally retain the cushions 28 against their respective support plate 26.

As is perhaps best depicted in FIGS. 1-4, the support plate 26 is coupled to the distal end of the slider bar 22 by means of a pivot pin 30 or another arrangement (e.g., slider, ball joint, etc.) which allows movement to occur therebetween as shown by arrows A1. Also, since the slider bar 22 is itself arcuately shaped, its arcuate sliding movement between a retracted position (shown generally in solid line in FIGS. 1-4) and an extended position (shown generally in dashed line in FIGS. 1-4) as shown by arrows A2 allows the cushion support plate 26 to be positioned at various angular orientations relative to the mask frame 12. Pivotal movement of the cushion support frame 26 thereby allows the forehead cushions 28 to be positioned flat against a wearer's forehead. In such a manner, therefore, the forehead support 10 may be adjustable over a wide range of dimensions and angular orientations to fit various facial profiles of a wearer. The amount of pivotal movement in a clockwise direction as viewed in FIGS. 1-4 is limited by means of the stop surface 27 formed at the distal end of the slider bar 22. In the example of FIGS. 1-4, plate 26 may pivot in about a 90° range (and preferably about 10°-50° or more or less) relative to slider bar 22.

C. Range of Adjustments

Figures 1, 2:
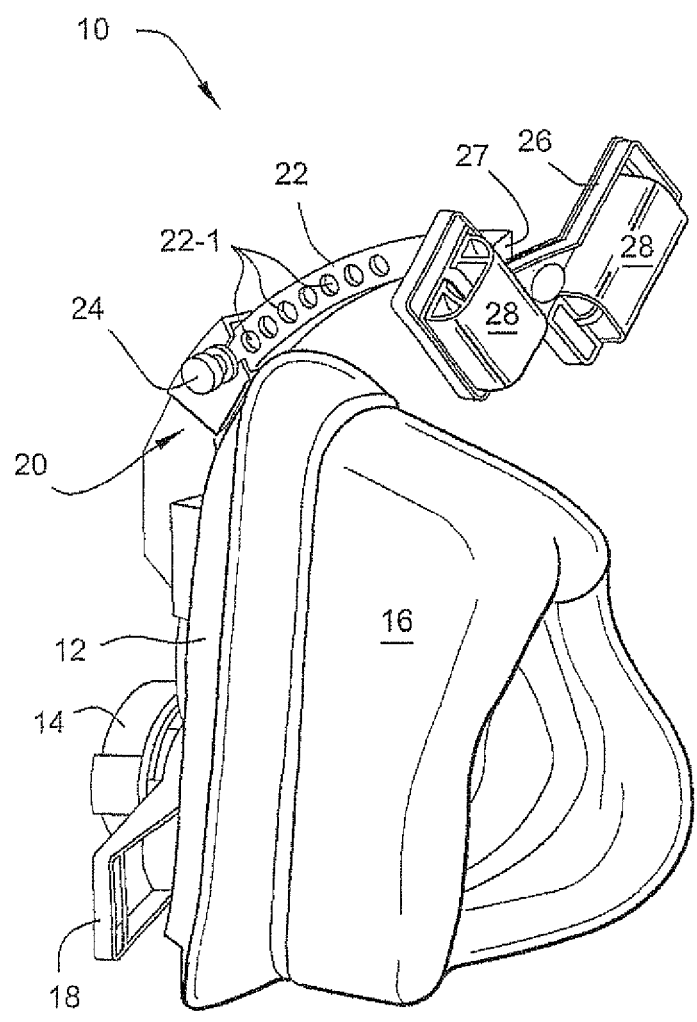

The universality and wide range of adjustments achieved by the forehead support 10 according to the present invention is graphically represented in accompanying FIG. 2. In order for the advantages of the present invention to be better understood, a co-ordinate system is defined with respect to the facial profile of a patient. When a patient is sitting upright, the x-axis is horizontal, the y-axis is vertical and the z-axis is into the plane of the face (i.e., leftward as viewed from FIGS. 1-4). The travel path $CR_P$ for a prior art forehead support is depicted graphically in FIG. 2. With this support, some patients may end up with forehead pads positioned at or above their hair-line. In contrast, the forehead support 10 of an embodiment of the present invention provides a generally more appropriate range of relative movement in the z-direction as depicted graphically by the circular range of travel designated $CR_I$ shown in FIG. 2.

According to an embodiment of the present invention, a target window TW is defined for the forehead pads 28 in the z- and y-directions. The target window TW has upper and lower (y-axis) limits, as well as inner and outer (z-axis) limits. The window has been determined on the basis of anthropometric data from a range of sources including Anthropometry of the Head and Face, Leslie Farkas, Raven Press NY, N.Y. 1994. From this data, average and standard deviations for hairline, glabella (the smooth prominence on the forehead between the eyebrows and just above the nose) and forehead position were determined. The target window TW for the forehead support 10 according to the present invention may therefore be defined as follows:

(i) the upper Y-axis limit ($Y_u$) is average hairline minus two standard deviations minus 15 mm;

(ii) the lower y-axis limit ($Y_l$) is 15 mm above the average glabella (G);

(iii) the inner z-axis limit (Zi) is half the cushion-gusset travel (GT) plus two standard deviations from the mean forehead position;

(iv) the outer z-axis limit ($Z_o$) is the mean forehead position minus two standard deviations, minus half the cushion-gusset travel (GT).

Advantageously, the cushion-gusset travel (GT) ranges between about 20 to about 40 mm, preferably about 30 mm (the gusset has about 16 mm of travel and the cushion membrane has about 15 mm of travel, therefore together the cushion-gusset travel is about 30 mm). With a coordinate system with the zero point superimposed substantially on a patient's nasion (N), the average hairline is between about 60 to about 70 mm, the average glabella is about 10 mm, and the mean forehead position varies between about −2 to about +2 in the z-direction within the target window.

In accordance with especially preferred embodiments of the invention, the target window TW, also referred to as a target plane, which the forehead pads may assume by virtue of their pivotal connection with the distal end of the slider bar 22 and the range or arcuate movement provided by the adjustable positioning of the slider bar 22 within the receiver 20 is preferably an area bounded by the following approximate y,z points (+/−) of a coordinate system depicted in FIG. 2 (i.e., with the zero point being located substantially coincident with a patient's nasion region): 37,28; 30,20; 30,−22 and 37,−22.

In order for the forehead support 10 to achieve the required movement, the arc of the slider bar 22 (and corresponding channel 20-1 of the receiver 20) establish the generatrices of a circle having a radius of about 35-70 mm, and most preferably in the range of about 50-60 mm. In this example, the radius is about 54 mm (+/−2 mm).

D. Alternative Embodiment of Slider Bar Subassembly

Accompanying FIGS. 3-1 to 3-8 show various views of an alternative embodiment of a slider bar subassembly that may be employed in the facial mask assembly of the present invention depicted in FIGS. 1-1 to 1-4. In this regard, the embodiment of the slider bar subassembly depicted in FIGS. 3-1 to 3-8 differs principally from the slider bar subassembly embodiment discussed previously in the structural features of the forehead cushion support plates 50 and the forehead cushions 52 carried thereby. Thus, as compared to the general V-shaped support plates 26, the support plates 50 depicted in FIGS. 3-1 to 3-8 extend generally transversely relative to the slider bar 22 and thus are more generally T-shaped.

More specifically, the support plates 50 include a relatively narrow width medial end 50-1 and a relatively larger width lateral end 50-2. The medial ends 50-1 are joined to a central support 54 which is in turn joined pivotally to the slider bar 22 by means of pivot pin 56. Thus, the support plates 50 and the cushions 52 carried thereby are capable of pivotal movements relative to the slider bar 22 about a pivot axis defined by the pivot pin 56 so that the cushions 52 can assume a range of angular positions relative to the patient's forehead. As is perhaps best shown in FIGS. 3-2 and 3-4, the support plates 50 are gently curved so as to conform more closely to the contour of a patient's forehead. If desired, the forehead cushion supports 50 may be attached to straps associated with a headgear assembly (not shown) by inserting such straps through slots 58 defined in the lateral ends 50-2 thereof.

The cushions 52 are generally conformably shaped to the support plates 50. The interior surfaces 52-1 of the cushions 52 have a general "concave" contour and thus be adapted for conformable shaping relative to a patient's forehead profile. Each cushion 52 has an attachment head 52-2 protruding rearwardly therefrom which is inserted into and through a respective aperture (not shown) formed in the support plates 50 so as to physically attach the cushions 52 to the support plates 50. The attachment head 52-2 is joined to the back of the cushion by a flexible accordion-style connector 52-3 which serves to allow compliant movement of the cushions 50 so they may be comfortably positioned in contact with the patient's forehead. The cushions 52 are most preferably joined to one another with a one-piece bridge 52-4.

In another variant, the forehead pads can take the form of a single member that extends over the upper "T" of the forehead support. In still another variant, the forehead support may have the shape of a lower case "l", instead of being T-shaped. In this variant, the upper portion of the slider bar would include slots 58 to directly receive headgear straps, in which case folded-over portions of the headgear straps could engage the forehead of the patient, thereby rendering forehead pads unnecessary.

E. Mask Frame

As noted previously, the slider bar 22 is sized and configured so as to be slidably received within a conformably shaped channel 20-1 formed in receiver 20 associated with the mask frame 12. Accompanying FIGS. 4-1 to 4-6 depict in greater detail an embodiment of the mask frame 12 that may be employed with the FMA shown in FIGS. 1-1 to 1-4 discussed previously. In this regard, the mask frame 12 includes a receiver 20 which as discussed previously is a component part of the forehead support 10 in accordance with the present invention as it receives the slider bar 22. The receiver 20 is mounted toward the upper extent of the mask frame 12 and is preferably formed as a unitary (one piece) molded structure therewith. The channel 20-1 defined by the receiver 20 is itself arcuately shaped in conformance with the arcuate shape of the slider 22 which it receives.

The receiver 20 includes a pair of opposed openings 60 through which the pin 24 may be inserted when aligned with a respective one of the slider apertures 22-1. Thus, when one of the apertures 22-1 is aligned with the openings 60, the pin 24 may be inserted therethrough so as to maintain the slider 22 in the position established by the selected aperture 22-1.

A plurality of vents 64 which penetrate the mask frame 12 to its inside surface (see FIG. 4-5) may be provided to allow venting of the interior of the FMA and prevent build-up of patient-exhaled gas (e.g., carbon dioxide).

Figures 1, 3:
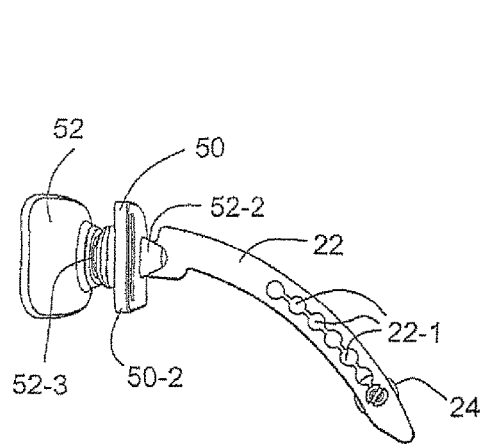
Figures 2, 3:
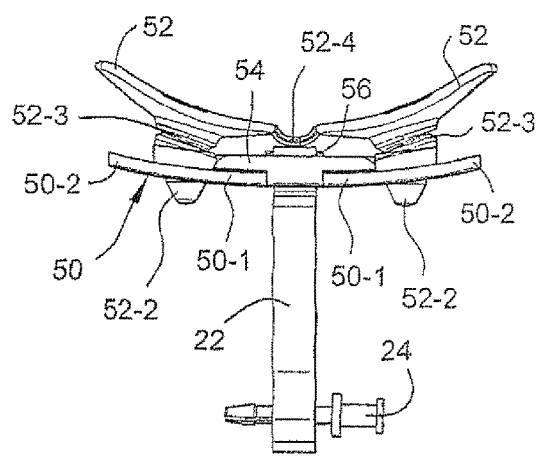
Figure 3:
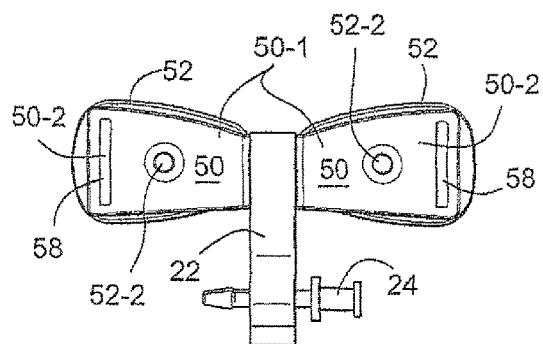
Figures 3, 4:
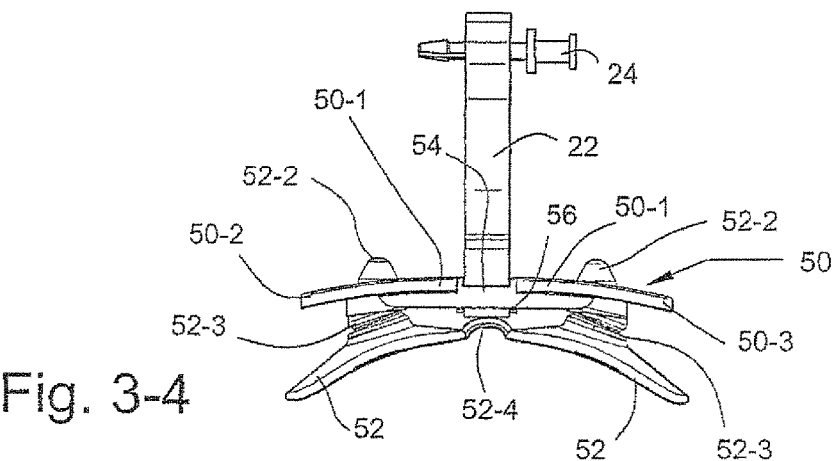
Figures 3, 4, 5:
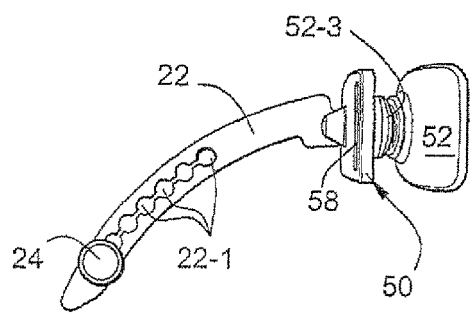

The cushion support plate 26 that may be employed in accordance with the forehead support 10 shown in FIGS. 1-1 to 1-4 according to the present invention is depicted in greater detail in accompanying FIG. 5. In this regard, the support plate 26 includes a pair of retaining clips 26-1 so as to retain the cushions 28 to the plates 26 in the manner described previously. The plates 26 also define at their terminal ends a slot 26-2 for receiving a strap associated with a conventional headgear assembly (not shown) as may be desired. A pair of parallel edge channels 26-3 is provided so as to accept respective side edges of the cushion 28.

F. Alternative Form of a Forehead Cushion

Figures 3, 4, 5, 6:
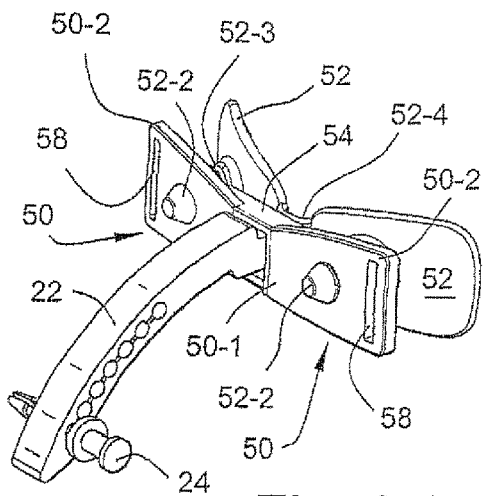

An alternative form of a forehead cushion 70 that may be employed with the support plates 26 for the forehead supports 10 in accordance with the present invention is depicted in FIGS. 6-1 to 6-2. Specifically, the forehead cushion 70 includes a generally concave cushion flange 72 which most preferably defines the generatrices of a cylindrical surface. The cushion flange 72 is supported by a cushion body portion 74 having an open channel 76 therethrough and a pair of rearwardly protruding elongate foot pads 78. The open channel 76 is sized and configured so as to accept therein the retaining clips 26-1 so as to retain the cushion 70 against the support plate 26. On the other hand, the elongate foot pads 78 are sized and configured to be accepted in the channels 26-3.

G. Alternative Forms of Slider Members

Figures 1, 2, 3:
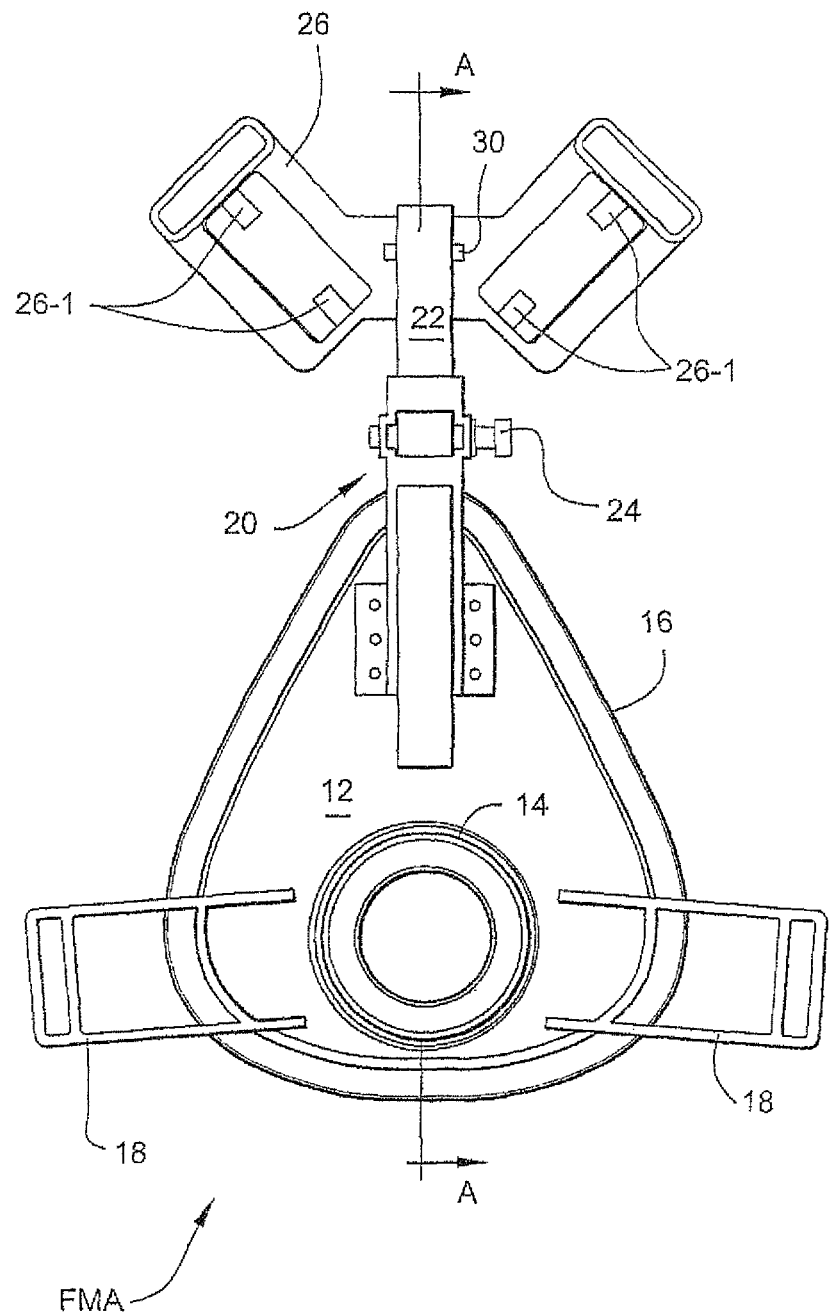
Figures 3, 4, 5, 6, 7:
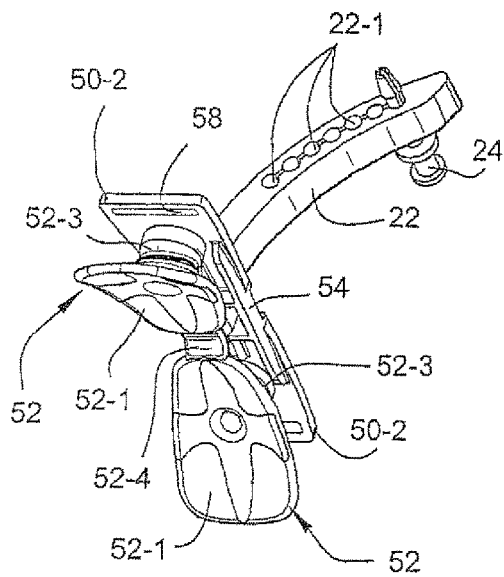

Alternative forms of slider members 22A, 22B and 22C that may be employed in the forehead support 10 of the present invention are depicted in FIGS. 7-1 to 7-3, respectively. In this regard, the slider member 22A shown in FIG. 7-1 is molded such that it has a side wall 22A1 that extends along a centerline of a perimeter wall 22A2. Individual aperture walls 22A3 define each of the individual position apertures 22-1 while an individual aperture wall defines the aperture 22-2 adapted to receive the pivot pin 30. The slider bar 22B shown in FIG. 7-2 includes connecting channels 22-3 which connect adjacent ones of the position apertures 22-1. The connecting channels 22-3 serve to allow a narrowed diameter portion of the pin 24 to be accepted therein so that the slider bar 22B may be moved within the receiver 20 without the need to fully remove the pin 24. In a similar manner, the slider bar 22C includes an entrance channel 22-4 to allow the slider bar 22 to be snap fit onto the pin 24. An entrance channel 22-5 is similarly provided with the aperture 22-2 so as to allow it to be snap fit onto the pivot pin 30. The entrance channels 22-4, 22-5 and connecting channels 22-3 may be formed using a manufacturing method, e.g., laser cutting, in which a continuous path is cut to form the channels and apertures.

II. Second Illustrated Embodiment of Forehead Support

Figures 3, 4, 5, 6, 7, 8:
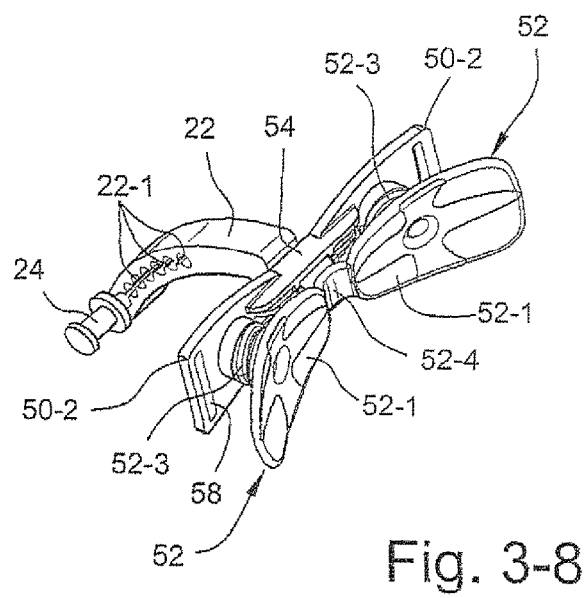
Figures 1, 4:
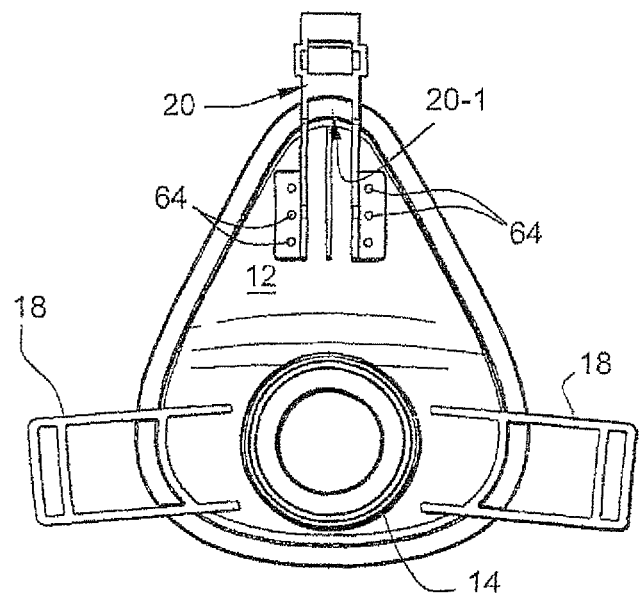
Figures 2, 4:
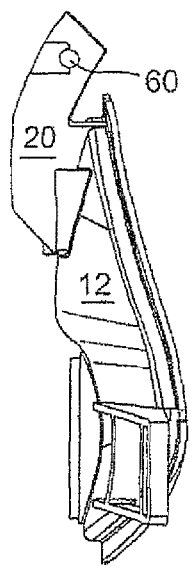
Figures 3, 4:
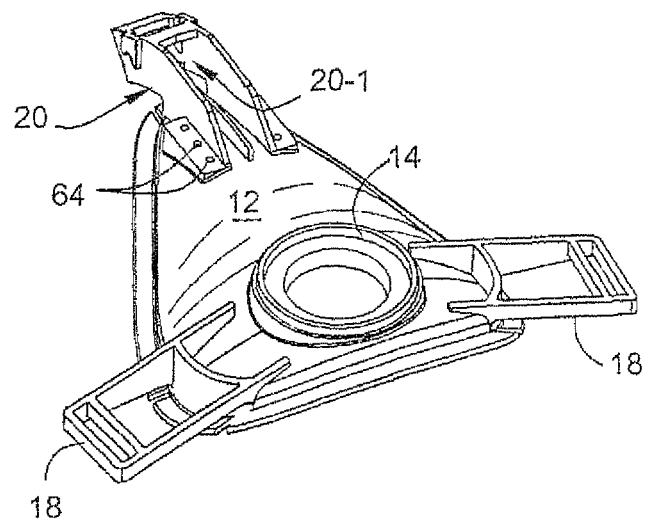
Figure 4:
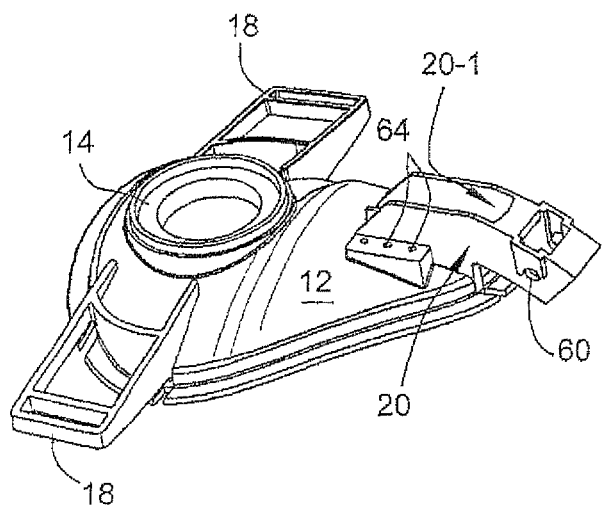
Figures 4, 5:
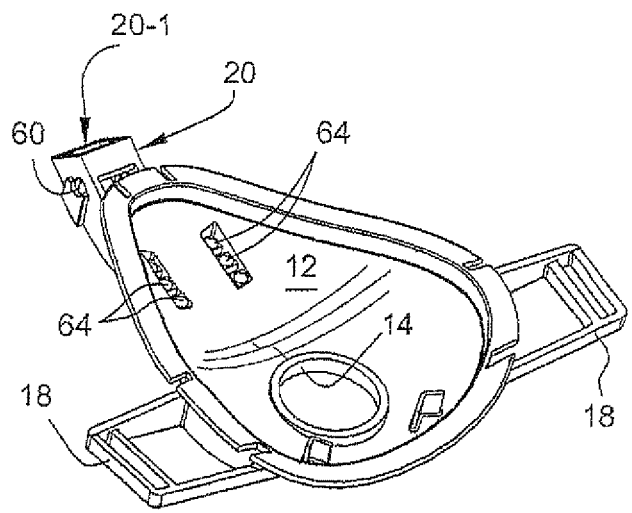
Figures 4, 5, 6:
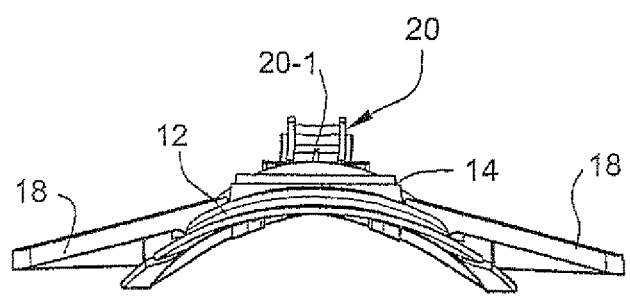
Figure 5:
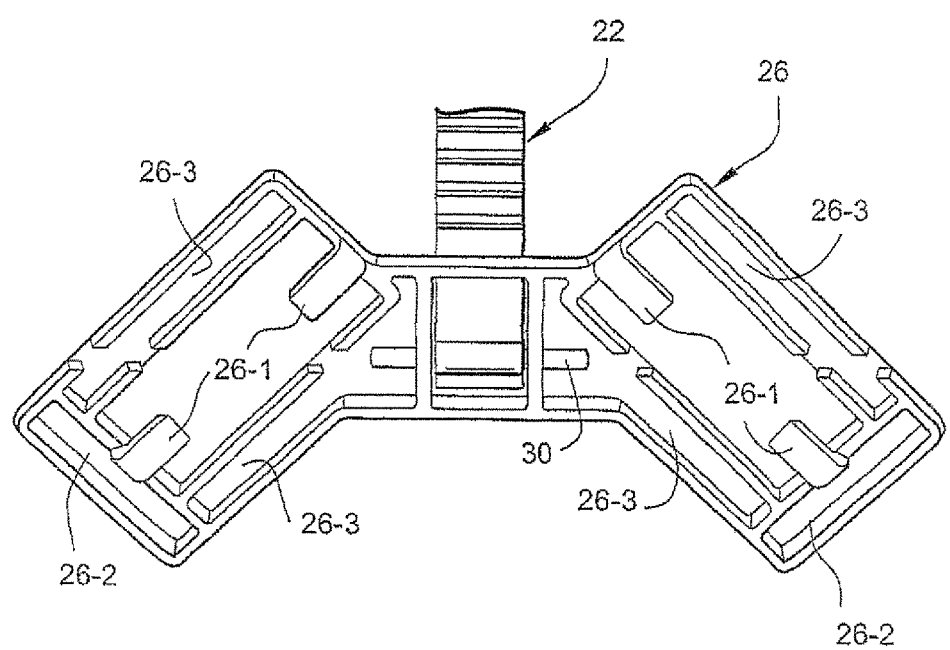
Figures 1, 6:
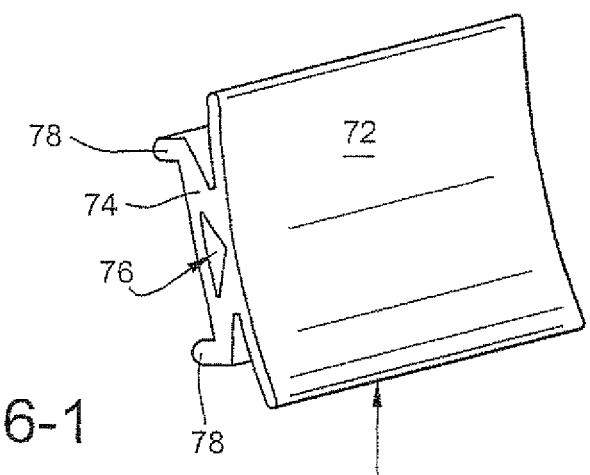
Figures 2, 6:
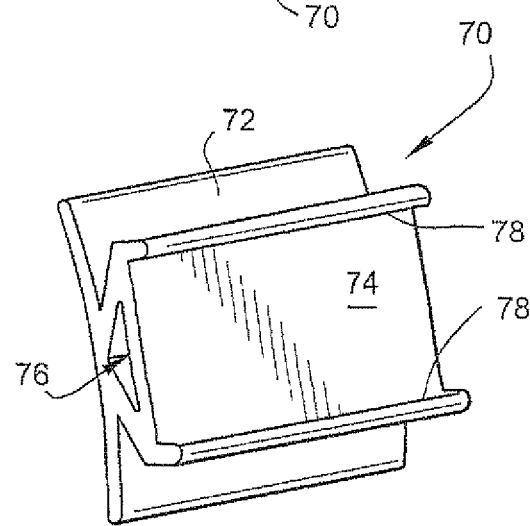
Figures 3, 6:
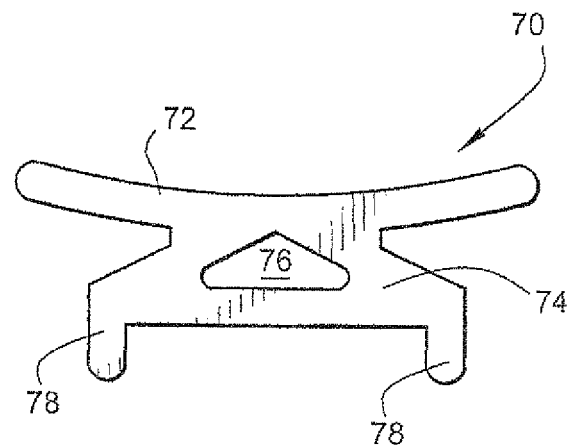
Figures 1, 7:
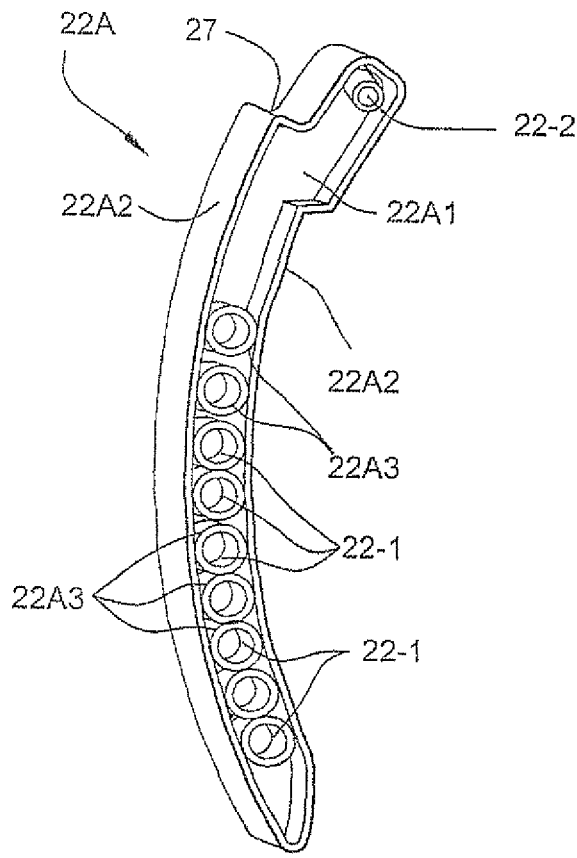
Figures 2, 7:
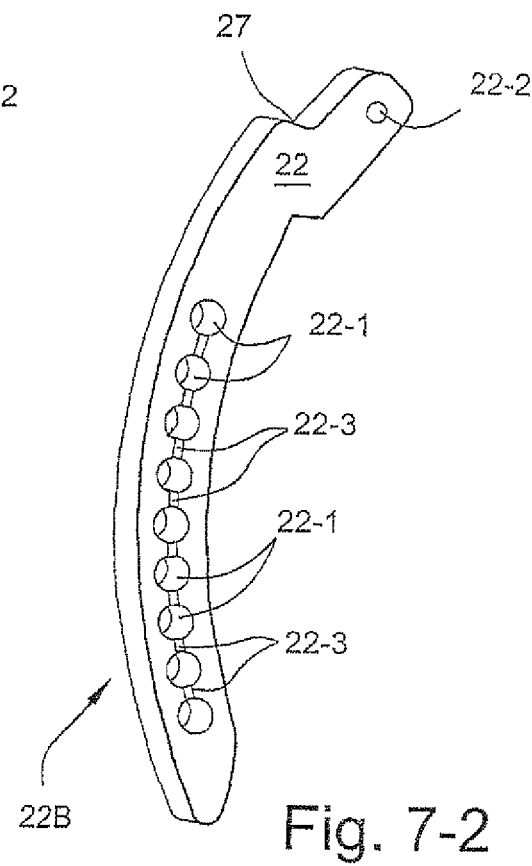
Figures 3, 7:
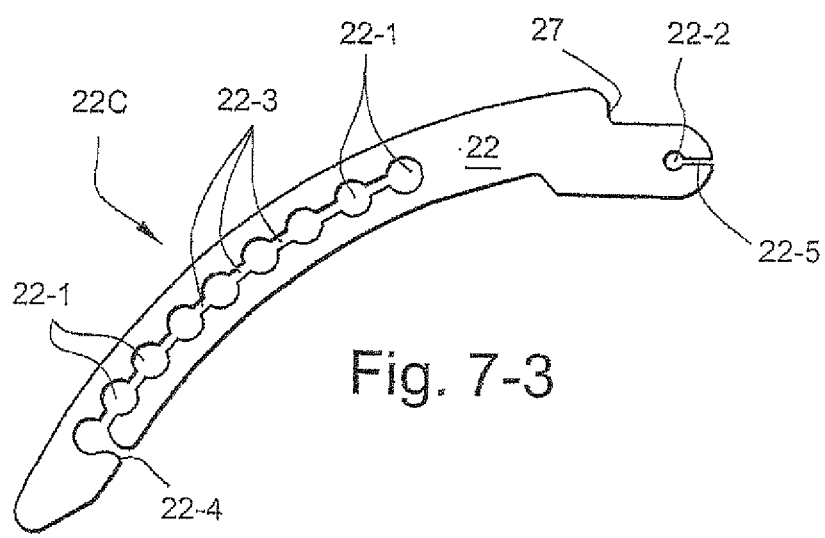
Figures 1, 8:
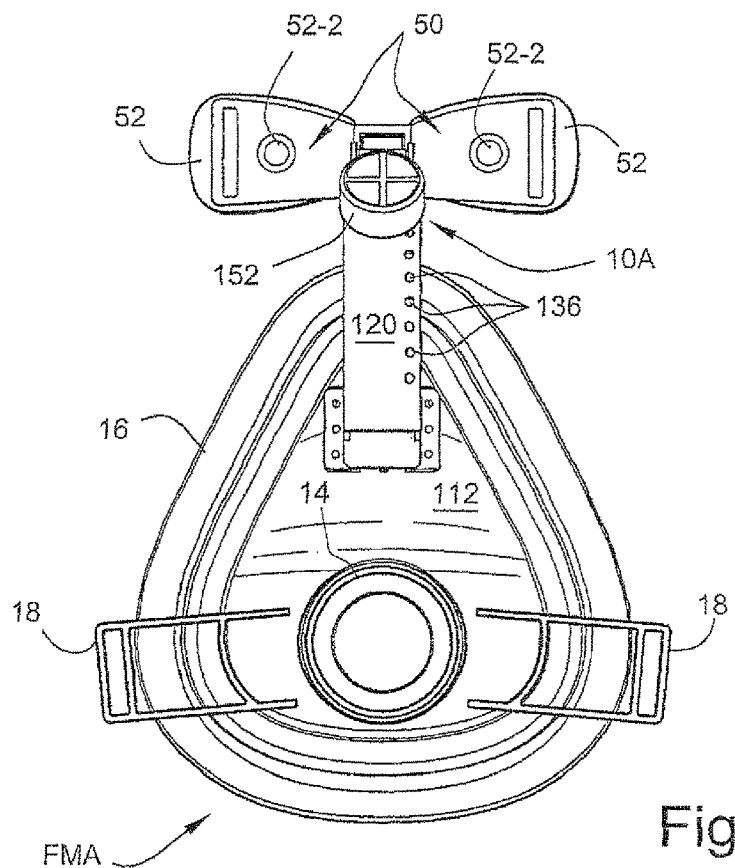
Figures 3, 8:
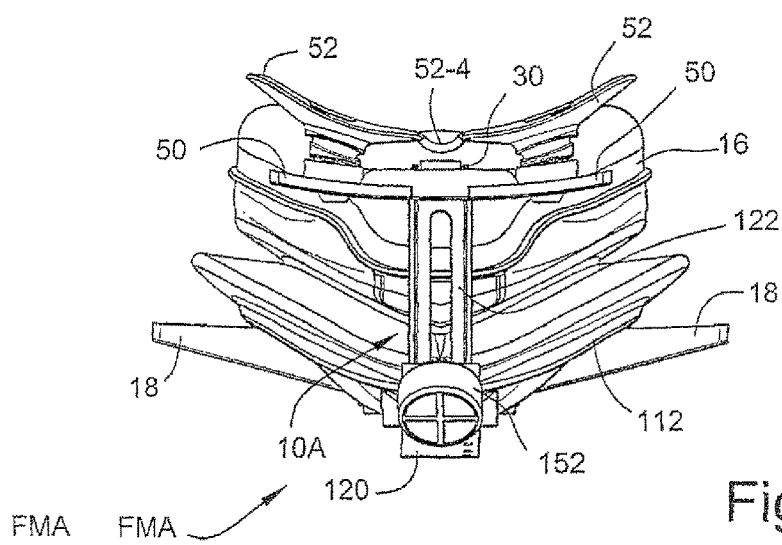
Figures 2, 8:
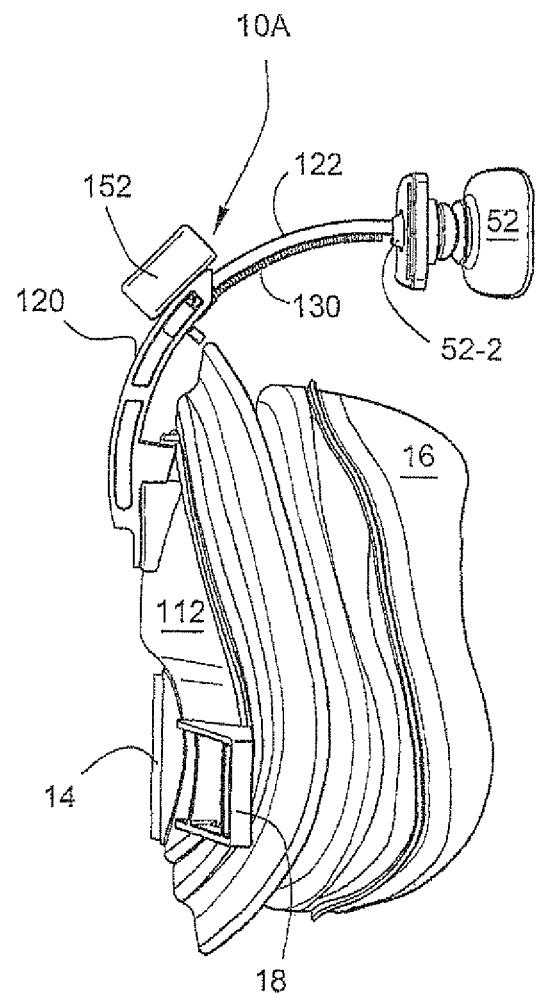
Figures 4, 8:
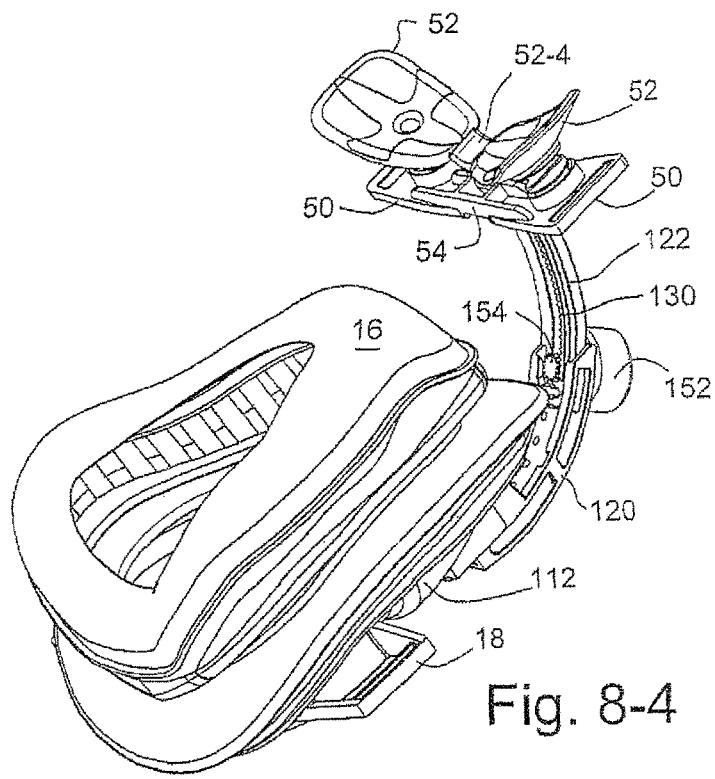
Figures 5, 8:
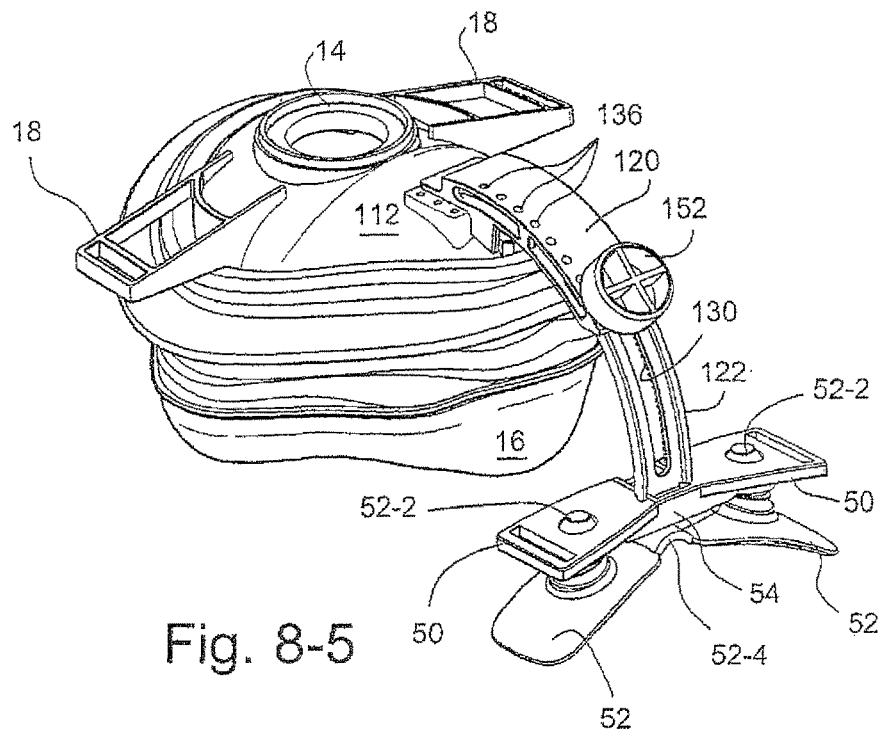

Accompanying FIGS. 8-1 to 8-5 depict a FMA provided with another embodiment of a forehead support 10A according to the present invention. FIGS. 9-1 to 9-6 and FIGS. 10-1 to 10-5 depict in greater detail a slider bar 122 and a mask frame 112 that may be employed in the forehead support 10A. In this regard, structural components that are similar to those discussed previously have been shown with the same reference numerals. Thus, a detailed discussion of such similar structural components will not be repeated.

A. Slider Bar

The forehead support 10A generally comprises a receiver 120 which defines an arcuately shaped channel 120-1 (see FIGS. 10-5) for receiving a corresponding arcuately shaped slider bar 122. As is perhaps best shown in FIGS. 9-1 to 9-6, the slider bar 122 includes at its distal end a connector portion 126 which defines an aperture 126-1 for receiving the pivot pin 30 (see FIG. 8-3). The pivot pin 30 thus serves to pivotally join the central support 54 (see FIG. 8-5) of the forehead cushion support plates 50 to the distal end of the slider bar 122 and thereby permit pivotal movements of the former relative to the latter.

B. Adjustment Knob

An adjustment knob 150 (see FIG. 11-1) operatively carried at a distal end of the receiver 120. As will be discussed in greater detail below, the adjustment knob 150 is capable of being turned manually in both clockwise and counterclockwise directions so as to adjust the position of the slider bar 122 between its retracted and extended positions. As shown more clearly in FIGS. 11-1 to 11-3, the adjustment knob 150 includes an upper head portion 152 and a lower pinion gear 154. The head portion 152 and pinion gear 154 are connected to one another by a cylindrical post member 156. The post member 156 is positioned in opening 157 of the receiver 120 so that the pinion gear 154 can engage operatively the gear rack 130 of the slider bar 122.

Figures 1, 9:
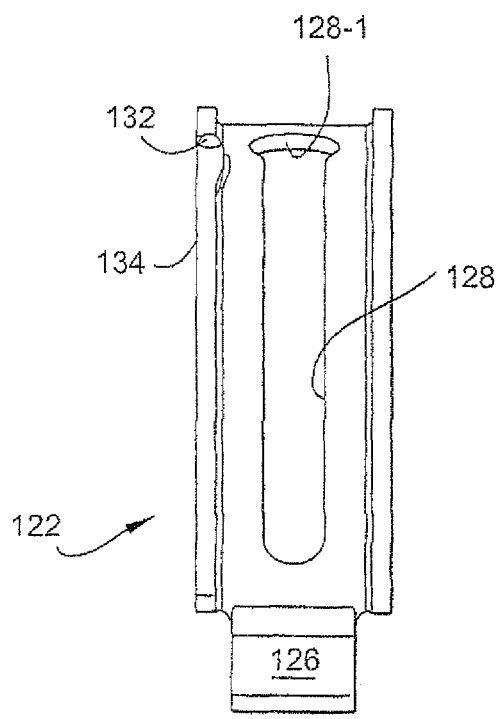
Figures 2, 9:
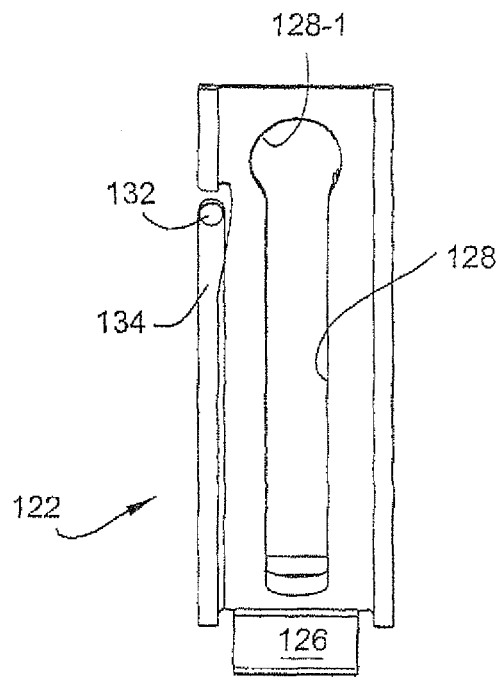
Figures 3, 9:
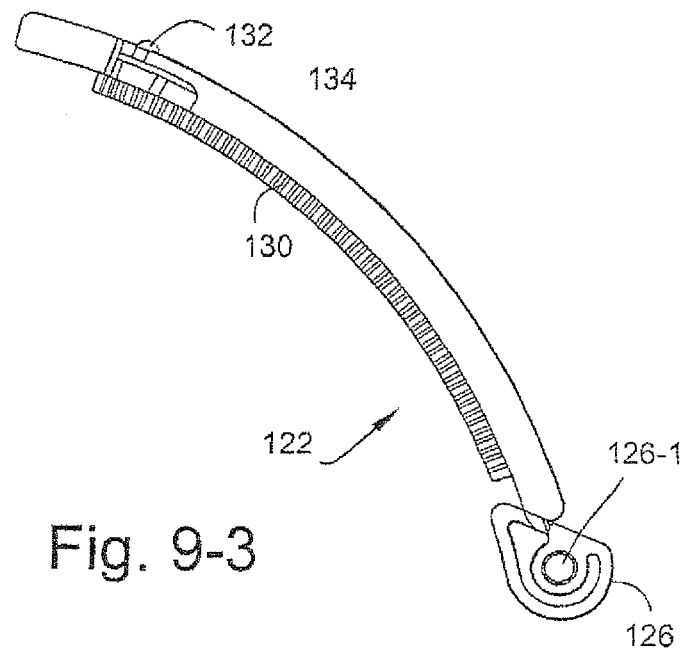

As shown in FIGS. 9-1 to 9-6, the slider bar 122 defines a central elongate slot 128 extending from near its proximal end to near its distal end. The slot 128 is provided with an enlarged diameter portion 128-1 near the proximal end which is sized so as to allow the pinion gear 154 of the adjustment knob 150 to pass therethrough and thus permit the slider bar 122 to be assembled within the receiver 120. A gear rack 130 is provided on an underside of the slider bar 122 extending substantially the entire length of the slot 128 on a lateral side thereof. The gear rack 130 is intermeshed with the pinion gear 154 of the adjustment knob 150. Thus, when the adjustment knob 150 is turned in a clockwise direction as viewed from the front of the FMA, the slider bar 122 will be adjustably moved toward its extended position (i.e., in a direction toward a patient's forehead). Conversely, when the adjustment knob 150 is turned in a counterclockwise direction as viewed from the front of the FMA, the slider bar 122 will be adjustably moved toward its retracted position (i.e., in a direction away from the patient's forehead). The receiver 120 includes a circular raised bearing surface 153 (see FIGS. 10-1, 10-3 and 10-4) which bears against the head portion 152 of the adjustment knob 150. In an alternative embodiment, an adjustment knob is provided that tightens by turning anti-clockwise.

C. Detent Assembly

Figures 1, 10:
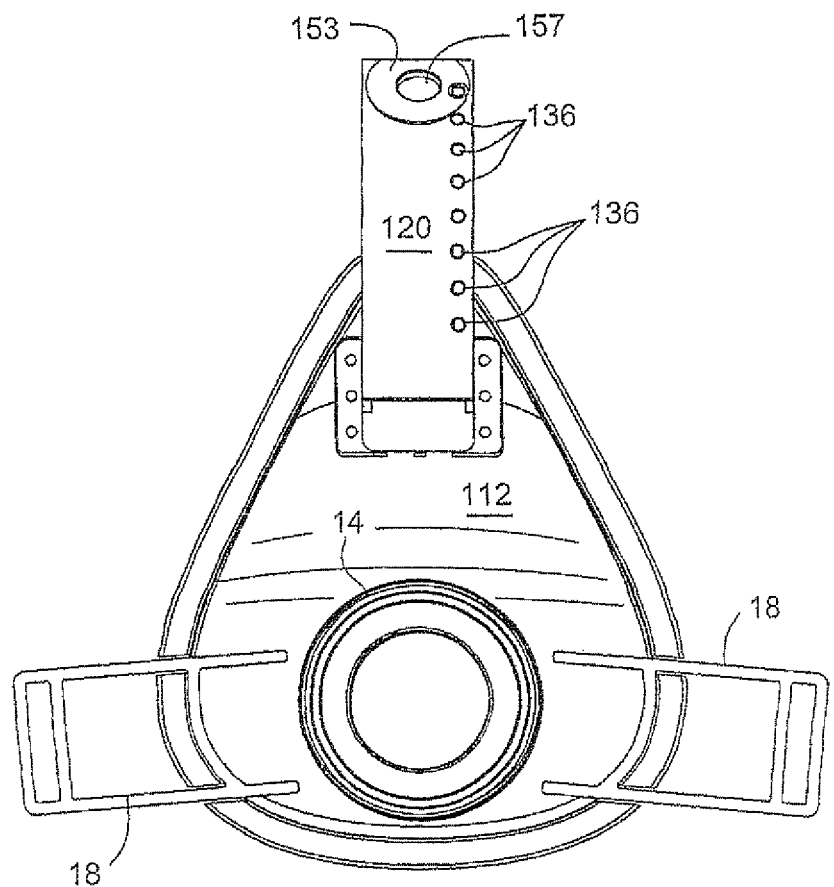
Figures 3, 10:
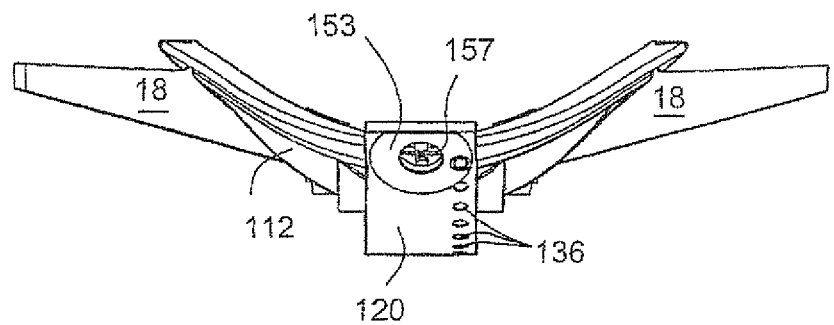
Figures 2, 10:
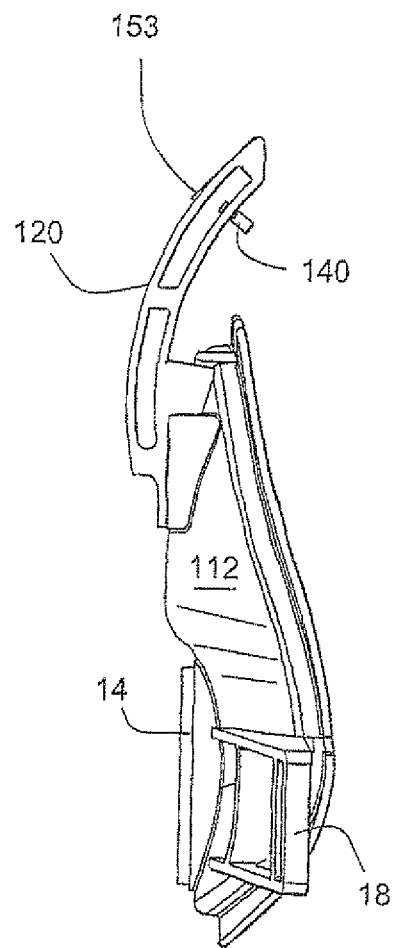
Figures 4, 10:
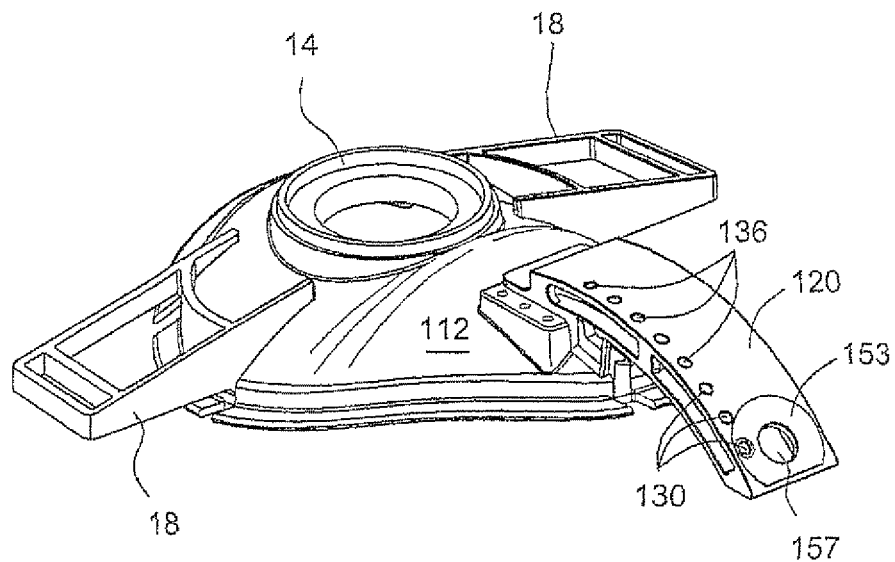
Figures 5, 10:
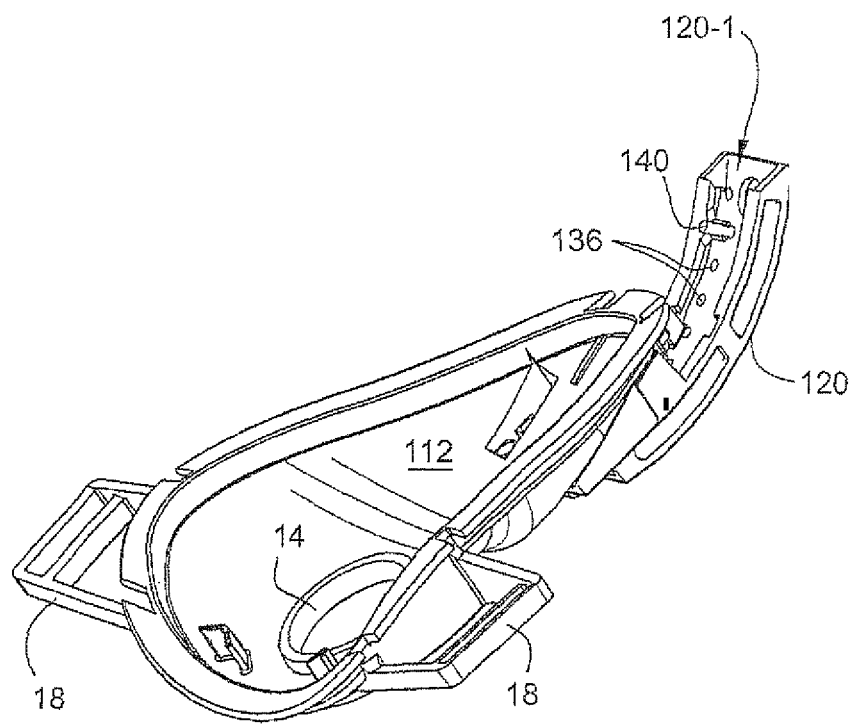

The slider bar 122 includes a resilient detent button 132 carried at the end of a resilient arm 134. The detent button 132 is adapted to be received within respective ones of the position apertures 136 provided along a lateral edge region of the receiver 120 (see FIGS. 10-1 to 10-5). As the slider bar 122 is moved between its extended and retracted positions within the channel 120-1 by turning movements applied to the adjustment knob 150 (FIG. 11-1), the detent button 132 (FIG. 9-5) will be moved resiliently and sequentially into and out of engagement with the position apertures 136 (FIG. 10-1). As such, the detent button 132 will be seated within one of the apertures 136 to assist in restraining the slider bar 122 (FIG. 8-5) at the desired position. However, turning movement applied to the adjustment knob 150 will cause the detent button 132 to be resiliently unseated from the aperture 136 by virtue of the arm 134 to allow sliding movement of the slider bar 122 until the next aperture 136 is aligned with the button, whereby the button is again seated therewithin.

As shown in FIGS. 10-2 and 10-5 the receiver 120 includes a pin 140 which extends into the channel 120-1. The pin 140 acts as an endstop to prevent the slider bar 122 from being wound all the way to the end of the gear rack 130. The pin 140 is cantilevered to provide a detent release to allow full disassembly of the slider bar 122 from the channel 120-1.

III. Third Illustrated Embodiment of Forehead Support

Figures 1, 12:
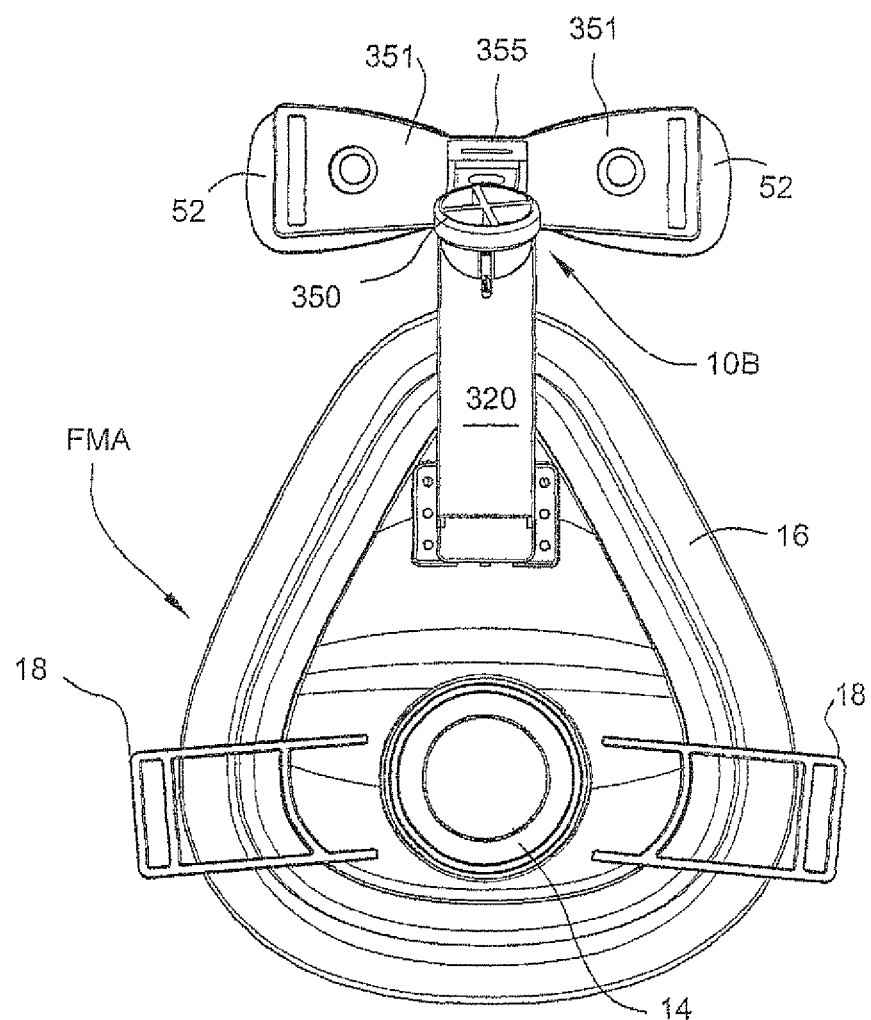
Figures 2, 12:
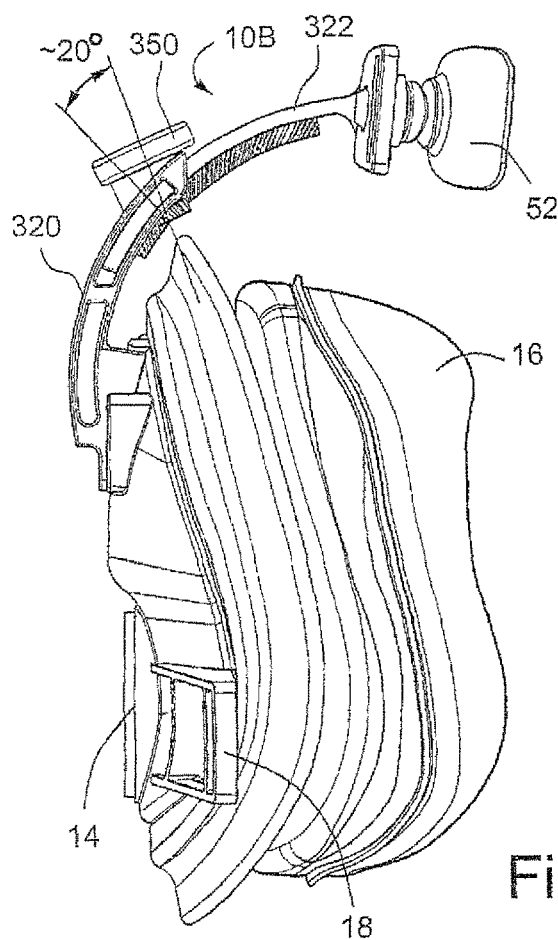
Figures 3, 12:
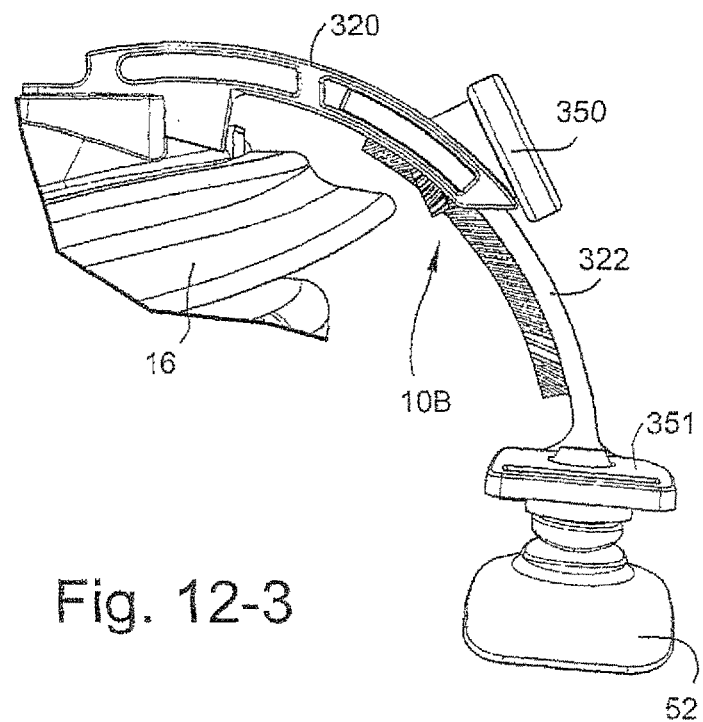
Figures 4, 12:
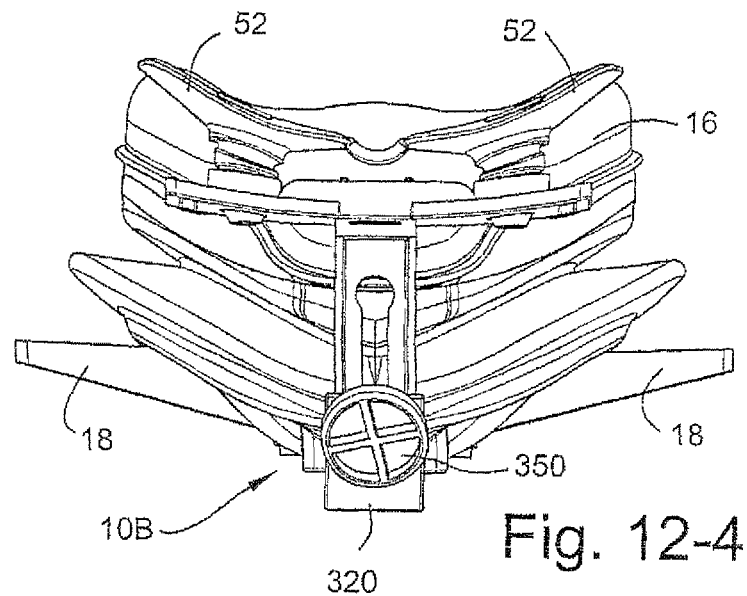
Figures 5, 12:
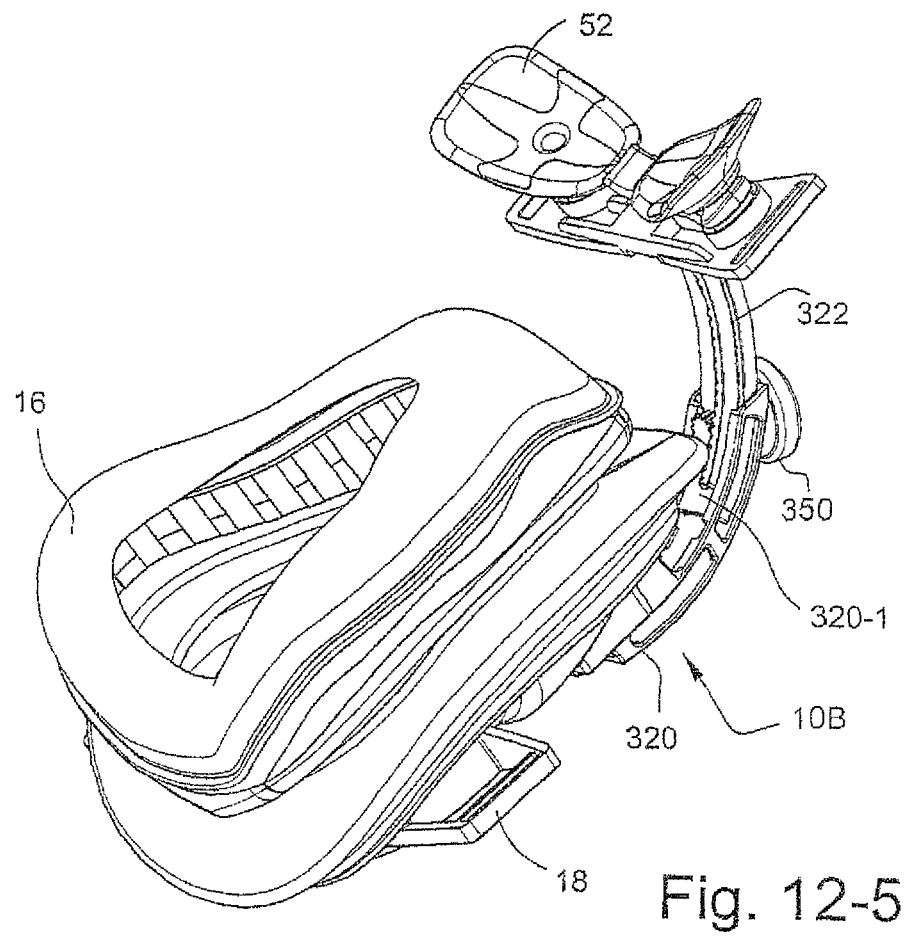
Figures 6, 12:
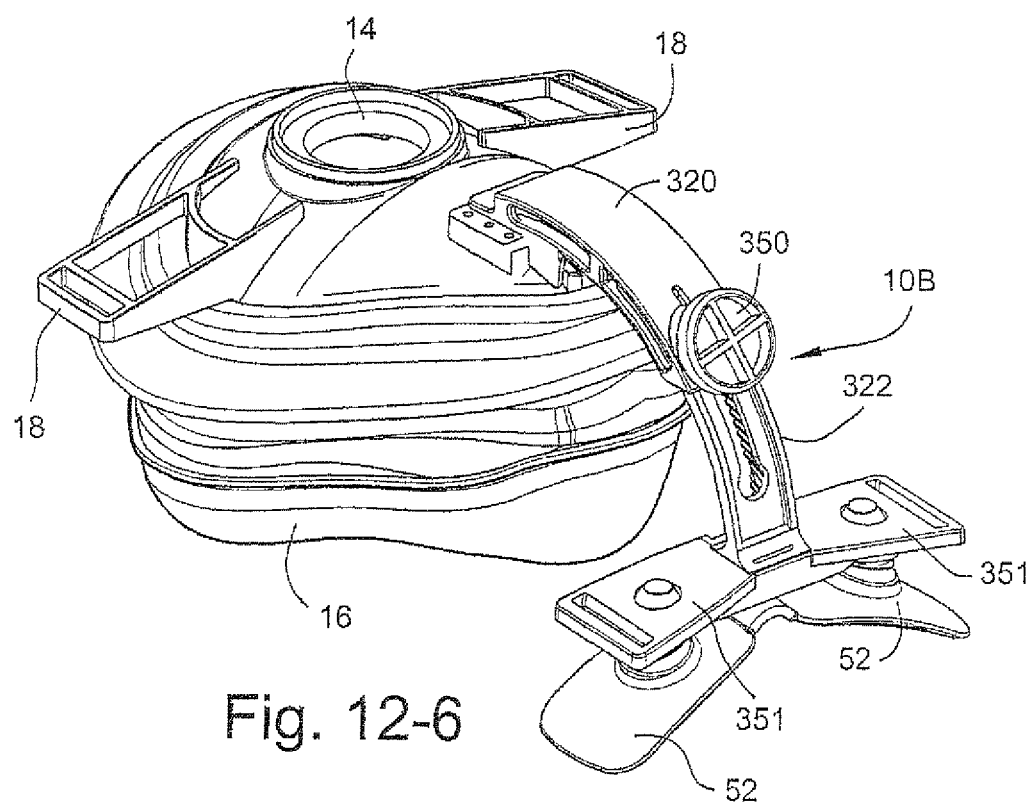

Accompanying FIGS. 12-1 to 12-6 depict a FMA provided with another embodiment of a forehead support 10B according to the present invention. FIGS. 13-1 to 13-7 and FIGS. 14-1 to 14-3 depict in greater detail a slider bar 322 and an adjustment knob 350 that may be employed in the forehead support 10B. In this regard, structural components that are similar to those discussed previously have been shown with the same reference numerals. Thus, a detailed discussion of such similar structural components will not be repeated.

A. Slider Bar

The forehead support 10B generally comprises a receiver 320 which defines an arcuately shaped channel 320-1 (see FIG. 12-5) for receiving a corresponding arcuately shaped slider bar 322. As is perhaps best shown in FIGS. 13-1 to 13-7, the distal end of the slider bar 322 is joined to the central support 355 (FIG. 12-1) of the forehead cushion support plates 351. The distal end may be joined to the central support 355 in any suitable manner, e.g., fixedly.

B. Adjustment Knob

An adjustment knob 350 is operatively carried at a distal end of the receiver 320. The adjustment knob 350 is capable of being turned manually in both clockwise and counter-clockwise directions so as to adjust the position of the slider bar 322 between its retracted and extended positions. As shown more clearly in FIGS. 14-1 to 14-3, the adjustment knob 350 includes an upper head portion 352 and a lower pinion gear 354. The head portion 352 and pinion gear 354 are connected to one another by a cylindrical post member 356. The post member 356 is positioned in an opening of the receiver 320 so that the pinion gear 354 can engage operatively the gear rack 330 of the slider bar 322. Also, the adjustment knob 350 includes a bearing portion 353 that is adapted to engage the receiver 320 with a snap fit. The bearing portion 353 provides a sturdy connection between the mask frame and the adjustment knob 350 thereby reducing potential play which will affect the smooth running of the rack 330.

Figures 1, 13:
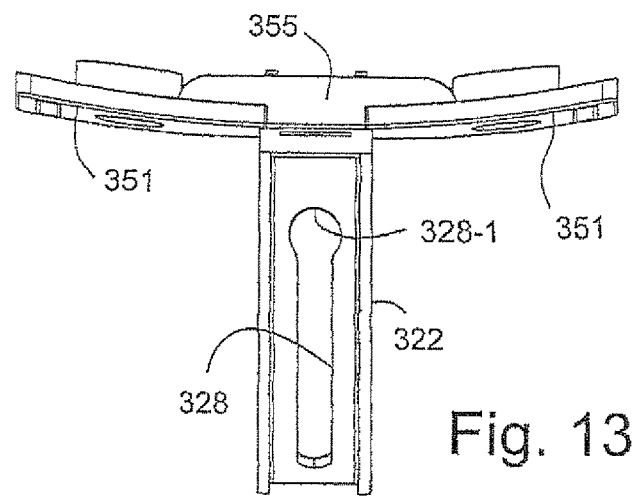
Figures 2, 13:
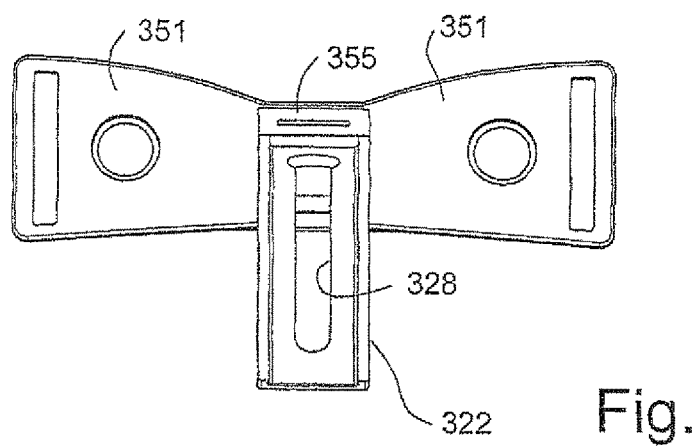
Figures 3, 13:
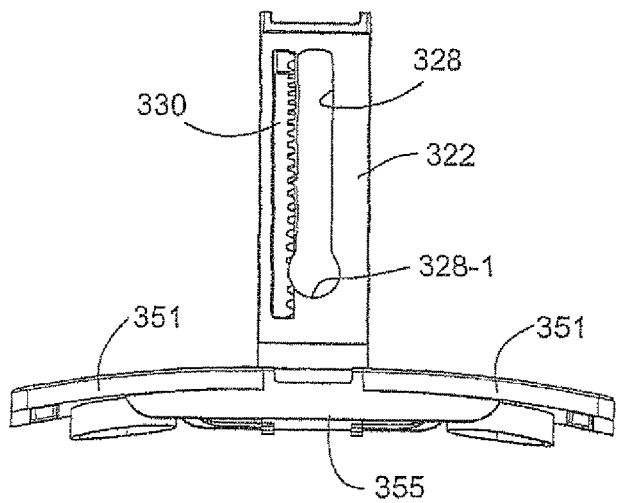
Figures 4, 13:
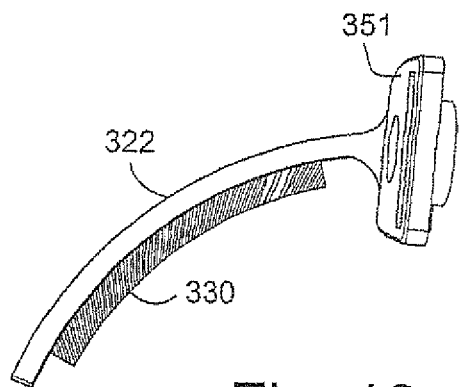
Figures 5, 13:
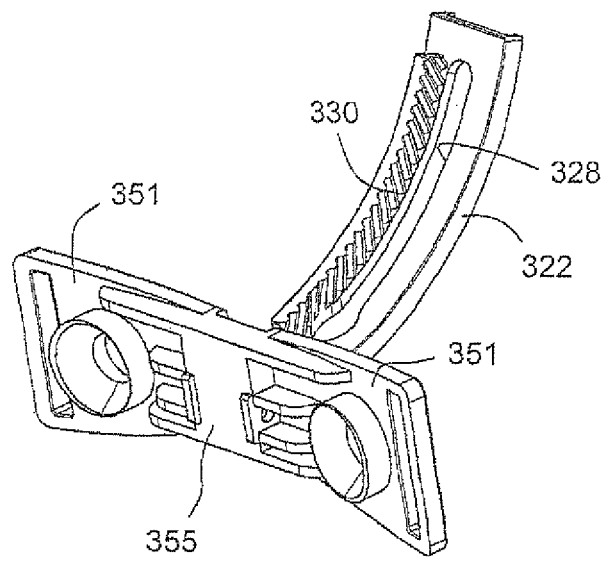
Figures 6, 13:
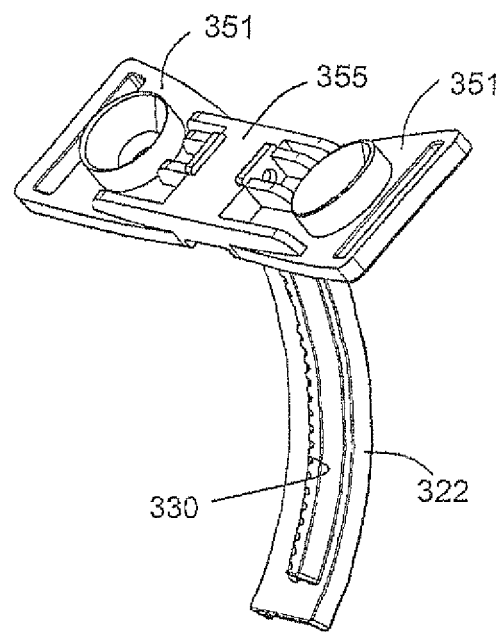
Figures 7, 13:
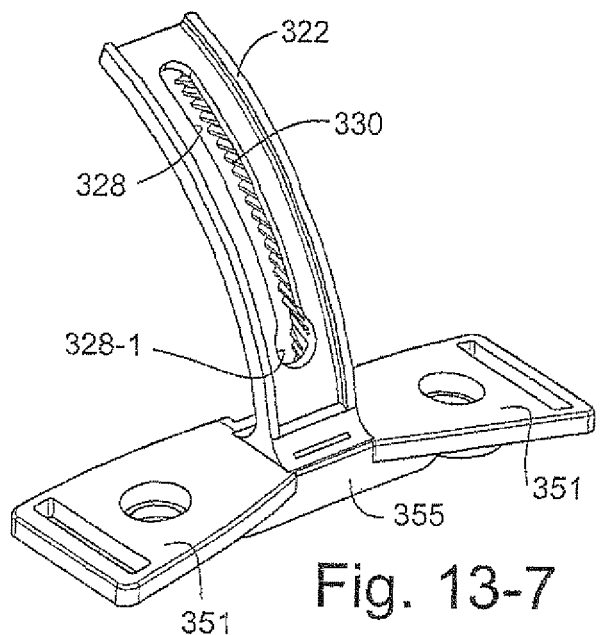

As shown in FIGS. 13-1 to 13-7, the slider bar 322 defines a central elongate slot 328 extending from near its proximal end to near its distal end. The slot 328 is provided with an enlarged diameter portion 328-1 near the proximal end which is sized so as to allow the pinion gear 354 of the adjustment knob 350 to pass therethrough and thus permit the slider bar 322 to be assembled within the receiver 320. A gear rack 330 is provided on an underside of the slider bar 322 extending substantially the entire length of the slot 328 on a lateral side thereof. The gear rack 330 is intermeshed with the pinion gear 354 of the adjustment knob 350. Thus, when the adjustment knob 350 is turned in a clockwise direction as viewed from the front of the FMA, the slider bar 322 will be adjustably moved toward its extended position (i.e., in a direction toward a patient's forehead). Conversely, when the adjustment knob 350 is turned in a counterclockwise direction as viewed from the front of the FMA, the slider bar 322 will be adjustably moved toward its retracted position (i.e., in a direction away from the patient's forehead). However, the direction of movement of the slider bar as the adjustment knob is turned clockwise may be designed to extend or retract by moving the gear rack onto the other side of the slider bar. Thus, the direction of rotation of the adjustment knob may be swapped, e.g., clockwise movement could extend or retract the slider bar.

C. Helical Teeth on Gear Rack and/or Pinion Gear

In this embodiment, at least one of the gear rack 330 of the slider bar 322 and the pinion gear 354 of the adjustment knob 350 is a helical gear including helical teeth, i.e., a gear having teeth cut at an angle to the face of the gear. The use of helical teeth on at least one of the gear rack 330 and the pinion gear 354 provides a self-locking feature so that the gear rack 330 and the pinion gear 354 will not move when force is applied from either the forehead support or the mask. That is, helical teeth are configured such that the adjustment knob 350 can easily move the slider bar 322, but the slider bar 322 cannot move the adjustment knob 350. This arrangement prevents inadvertent movement of the forehead support during use. Also, because the gears 330, 354 provide a self-locking feature, a detent button on the slider bar 322 and position apertures on the receiver 320 are not required.

In the illustrated embodiment, the gear rack 330 includes helical teeth having a helix angle at 40 degrees, and the pinion gear 354 includes a helix angle of 20 degrees and the pinion is angled at 20 degrees to the gear rack 330 (see FIG. 12-2). The helix of 20 degrees on the pinion and the 20 degree angle of the pinion to the gear rack results in the gear rack helix angle of 40 degrees. However, the pinion gear 354 may be angled 20 degrees in the other direction (i.e., counter-clockwise) to improve the angle of the adjustment knob 350 relative to the patient and hence ease of adjustment. Also, the teeth of the gears 330, 354 may have any other suitable angle, e.g., 10 to 40 degrees, to provide the self-locking feature.

Further, there are other potential design options to provide the self-locking feature. For example, helical teeth may be provided on the gear rack 330 only, helical teeth may be provided on the gear rack 330 with angled teeth on the pinion gear 354, or straight teeth may be provided on the gear rack 330 with angled teeth on the pinion gear 354. All of these options will help to lock the gear rack 330 and pinion gear 354 when force is applied from either the forehead support or mask.

IV. Friction Locking of Forehead Support

In an alternative embodiment, the gear rack and pinion gear may be designed such that sufficient friction is provided to lock the slider bar into position when in use. This arrangement prevents the gear rack and the gear from moving when force is applied from either the forehead support or the mask. This friction may be achieved through the use of surface texture, particular materials, and/or a reduction in the clearance between gear teeth.

V. Fourth Illustrated Embodiment of Forehead Support

Figures 1, 15:
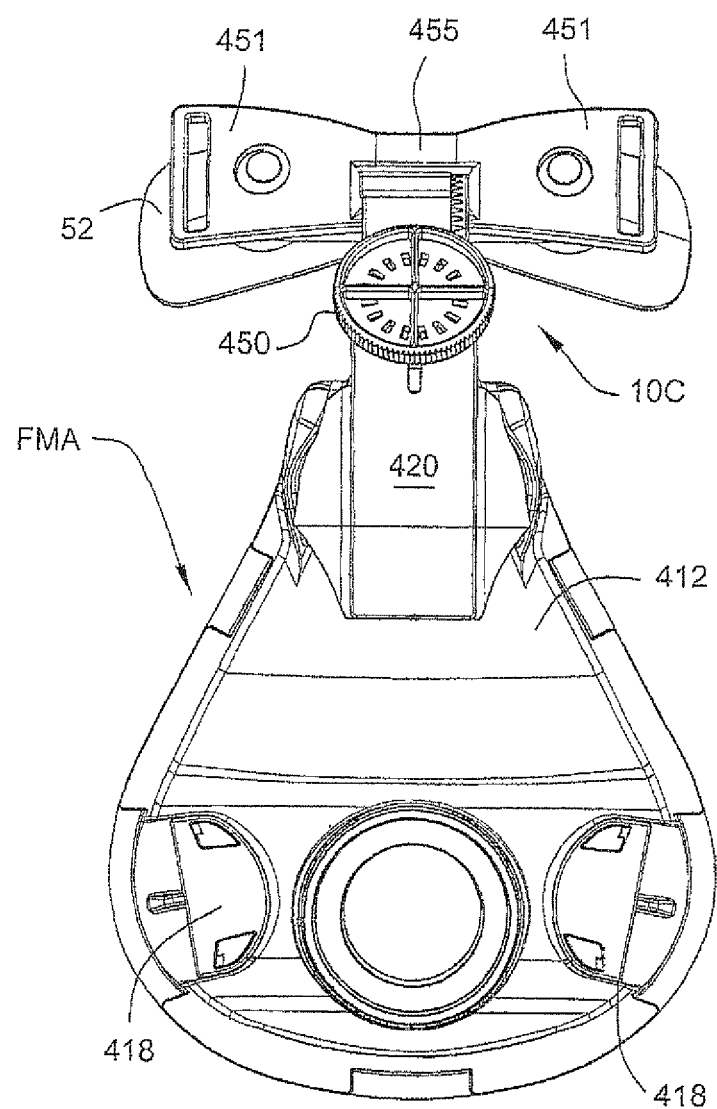
Figures 2, 15:
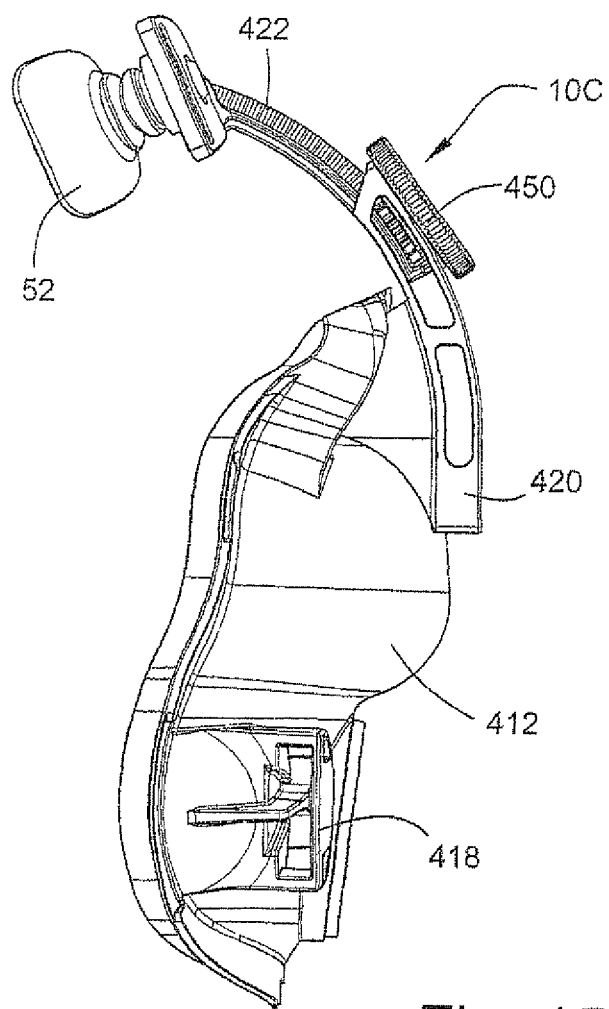
Figures 3, 15:
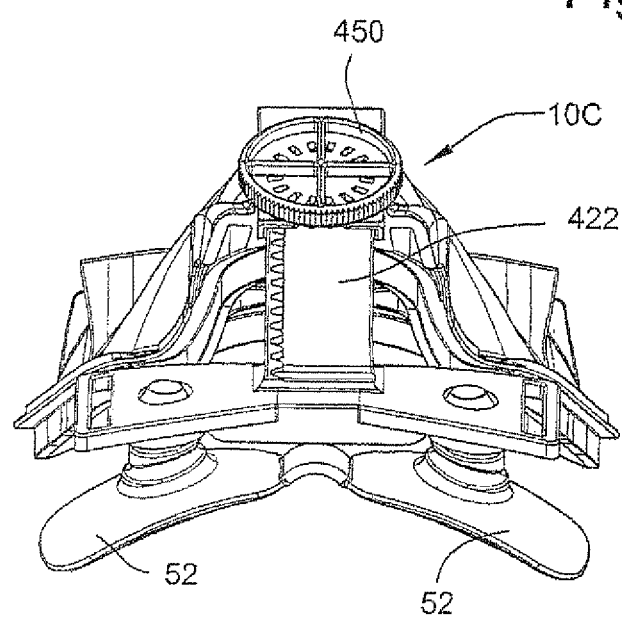
Figures 4, 15:
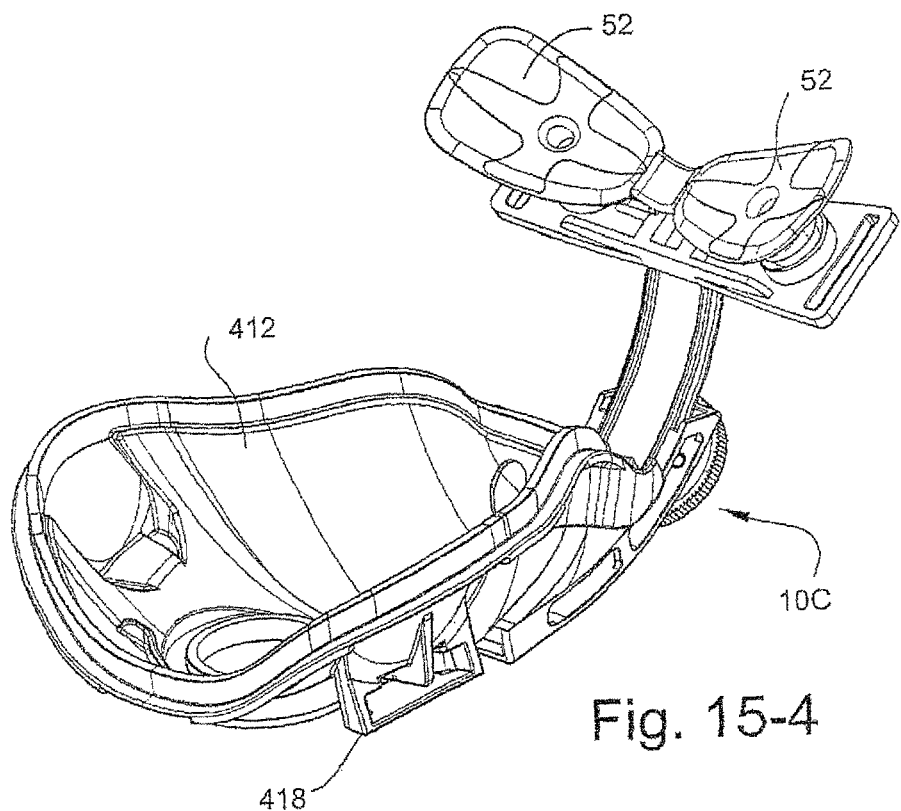
Figures 5, 15:
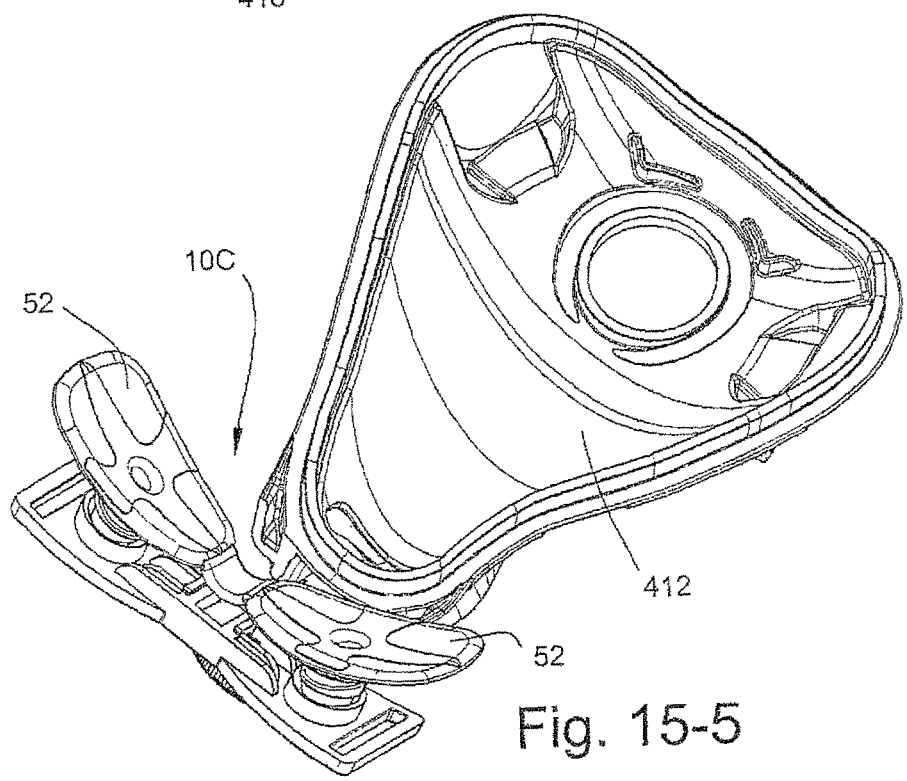
Figures 6, 15:
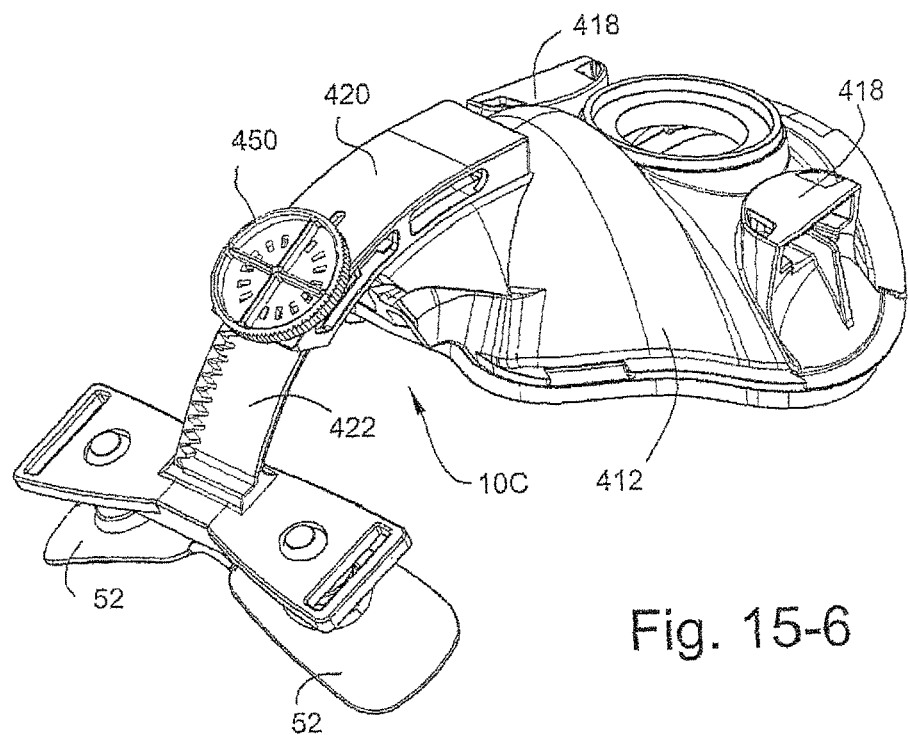
Figures 7, 15:
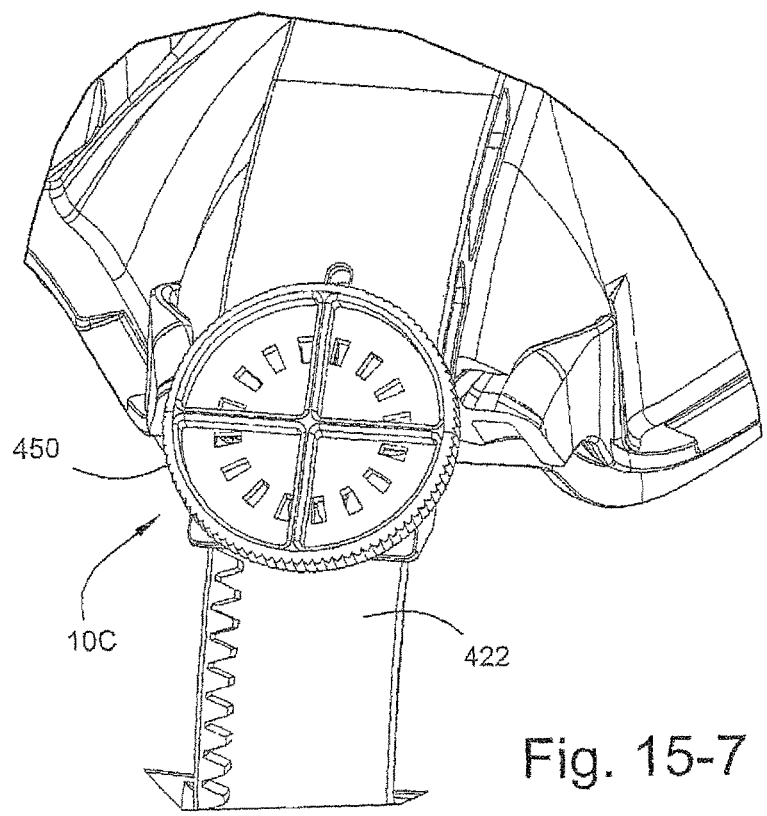
Figures 8, 15:
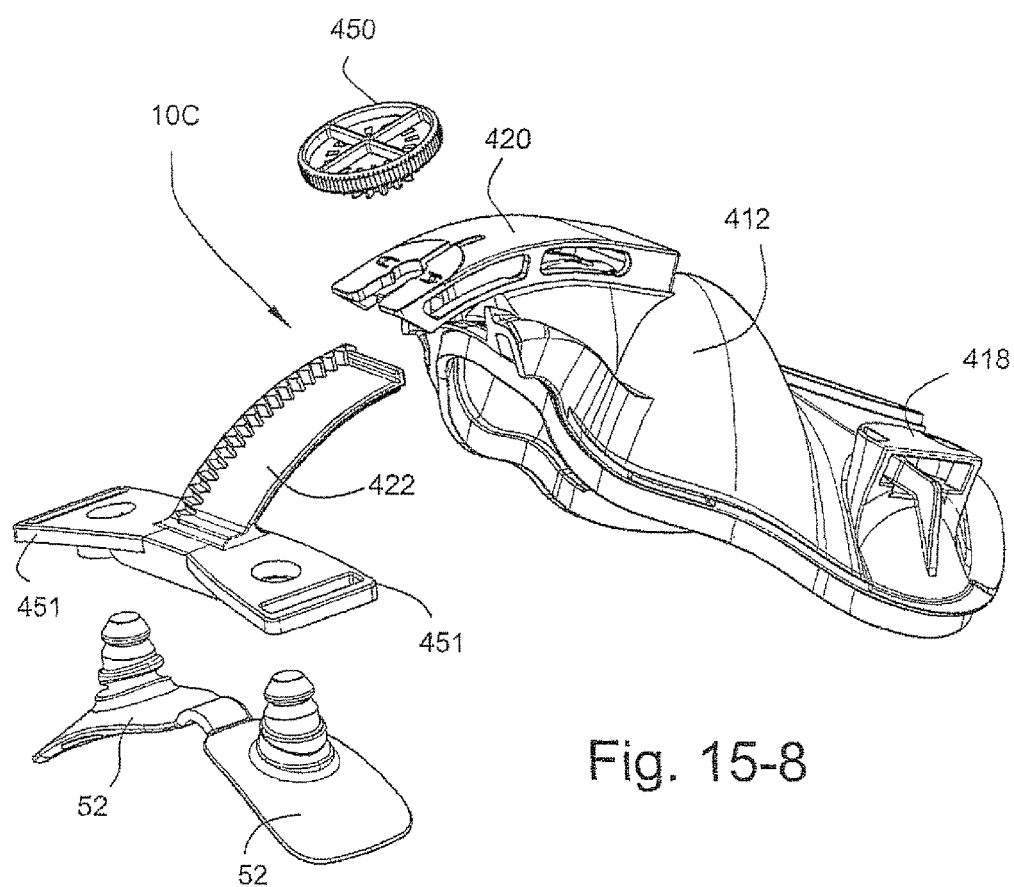

Accompanying FIGS. 15-1 to 15-8 depict a FMA provided with another embodiment of a forehead support 10C according to the present invention. FIGS. 16-1 to 16-7, FIGS. 17-1 to 17-7, and FIGS. 18-1 to 18-5 depict in greater detail a slider bar 422, a mask frame 412, and an adjustment knob 450 that may be employed in the forehead support 10C. In this regard, structural components that are similar to those discussed previously have been shown with the same reference numerals. Thus, a detailed discussion of such similar structural components will not be repeated. It is noted that the mask frame 412 includes connection structures 418 that are adapted to connect to headgear clips associated with a headgear assembly.

A. Slider Bar

The forehead support 10C generally comprises a receiver 420 which defines an arcuately shaped channel 420-1 (see FIG. 17-6) for receiving a corresponding arcuately shaped slider bar 422. As illustrated, the receiver 420 is relatively stronger and wider to provide more support to the forehead support and to prevent any cracking or fracture. As is perhaps best shown in FIGS. 16-1 to 16-7, the distal end of the slider bar 422 is joined to the central support 455 of the forehead cushion support plates 451. In the illustrated embodiment, the forehead support does not have a hinge, which results in the angle of the pad against the forehead changing about 20 degrees with the motion of the slider bar 422. This arrangement helps keep the pad flat against the forehead. However, the slider bar 422 may be joined to the central support 455 in any other suitable manner, e.g., via a pivot pin.

B. Adjustment Knob

An adjustment knob 450 is operatively carried at a distal end of the receiver 420. The adjustment knob 450 is capable of being turned manually in both clockwise and counter-clockwise directions so as to adjust the position of the slider bar 422 between its retracted and extended positions. As shown more clearly in FIGS. 18-1 to 18-5, the adjustment knob 450 includes an upper head portion 452 and a lower pinion gear 454. The head portion 452 and pinion gear 454 are connected to one another by a cylindrical post member 456. The post member 456 extends through opening 457 of the receiver 420 so that the pinion gear 454 can engage operatively the gear rack 430 of the slider bar 422. Specifically, the receiver 420 provides ramped portions 431 adjacent to the opening 457. The ramped portions 431 assist with assembly so that the post member 456 can engage within the opening 457 with a snap fit. The ramped portions 431 also provide shoulders to prevent easy disassembly. Also, the receiver includes an elongated stress relief opening 433 adjacent the opening 457. The opening 433 allows the opposing arms of the receiver 420 to open to accommodate the adjustment knob 450 within the opening 457. As illustrated, the upper head portion 452 has a gear-like configuration around its perimeter to provide a tactile grip.

Figures 1, 16:
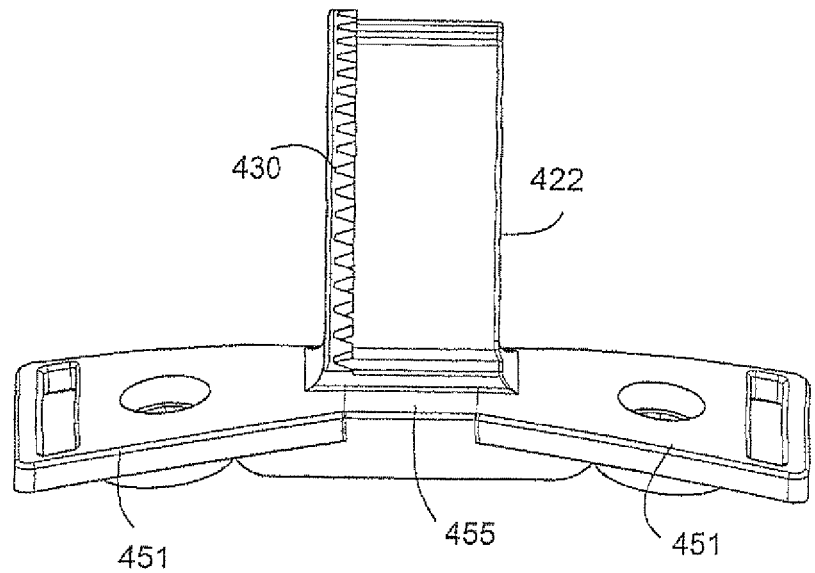
Figures 2, 16:
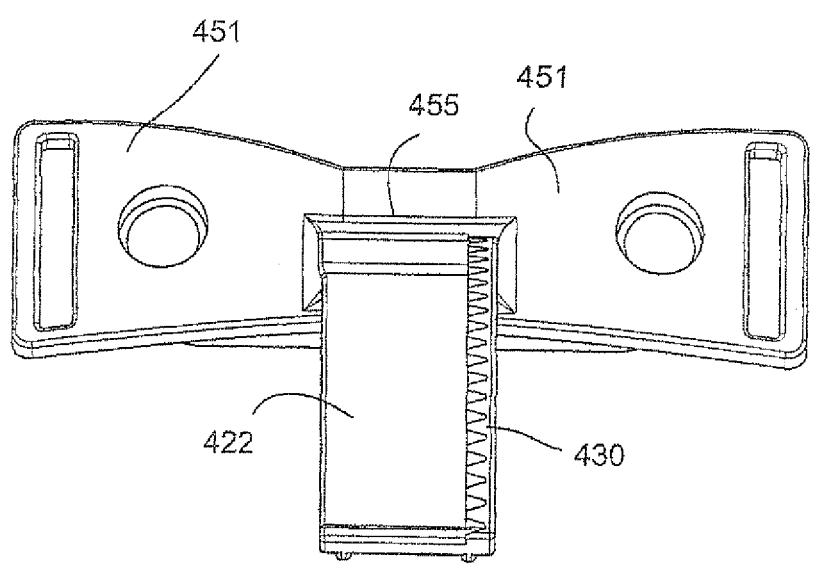
Figures 3, 16:
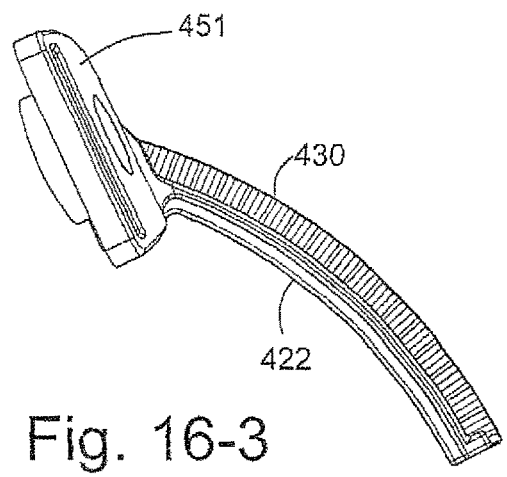
Figures 4, 16:
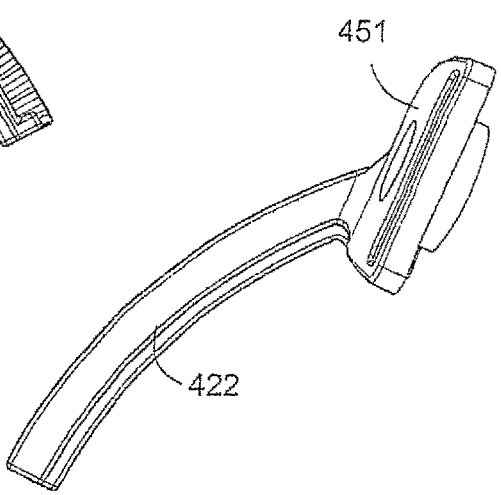
Figures 5, 16:
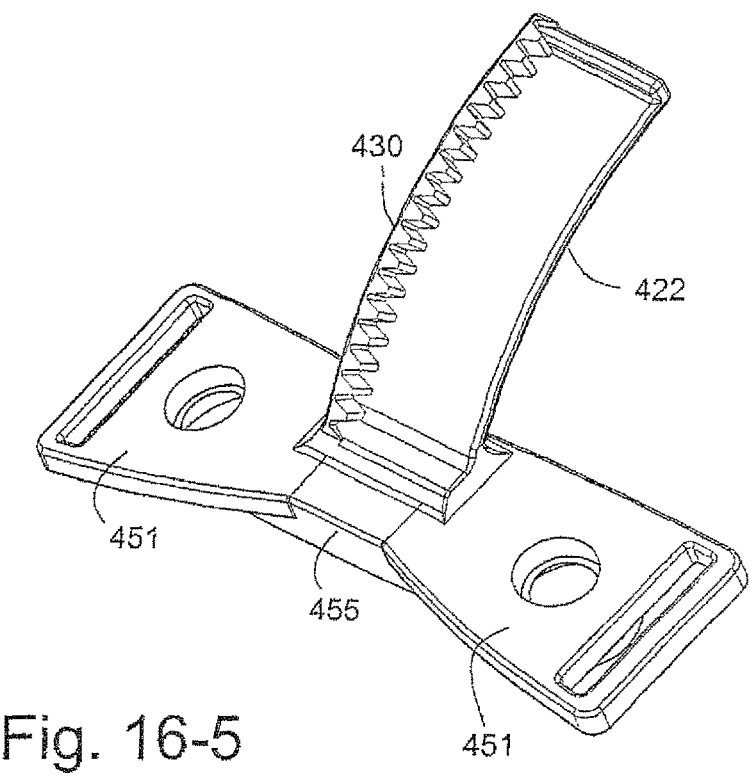
Figures 6, 16:
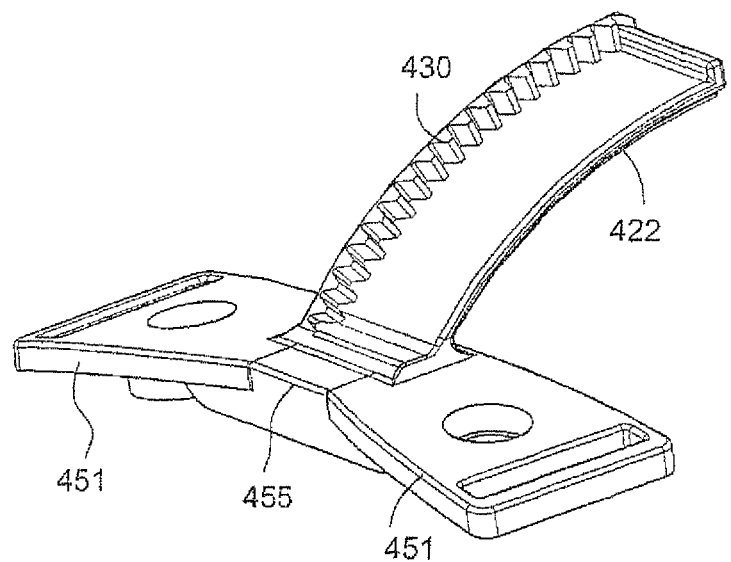
Figures 7, 16:
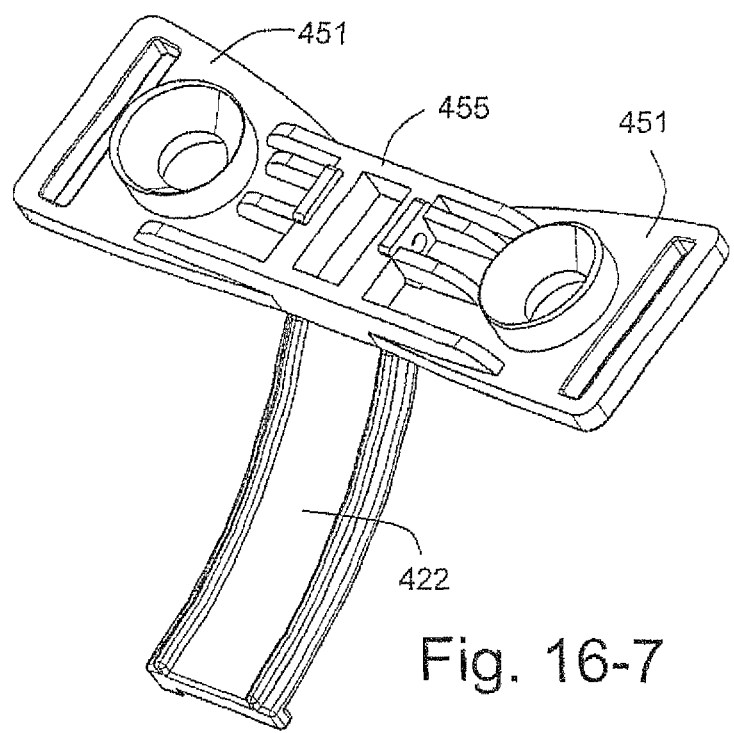

As shown in FIGS. 16-1 to 16-7, a gear rack 430 is provided on an upper surface of the slider bar 422 extending substantially the entire length thereof. The gear rack 430 is intermeshed with the pinion gear 454 of the adjustment knob 450. Thus, when the adjustment knob 450 is turned in a counter-clockwise direction as viewed from the front of the FMA, the slider bar 422 will be adjustably moved toward its extended position (i.e., in a direction toward a patient's forehead). Conversely, when the adjustment knob 450 is turned in a clockwise direction as viewed from the front of the FMA, the slider bar 422 will be adjustably moved toward its retracted position (i.e., in a direction away from the patient's forehead). As illustrated, substantially large teeth are provided on the gears 430, 454 to improve the robustness of the design.

C. Detent Assembly

In this embodiment, a detent assembly is provided in order to provide tactile feedback with the motion of the slider bar 422. In the illustrated embodiment, the detent assembly is provided by raised triangular position markers 432 on the receiver 420 that interact with apertures 436 on the adjustment knob 450. As the adjustment knob 450 is turned to extend or retract the slider bar 422, the raised triangular position markers 432 will move into and out of engagement with apertures 436 provided on adjustment knob 450. As such, the raised triangular position markers 432 will be seated within respective apertures 436 to assist in restraining the slider bar 422 at the desired position. However, turning movement applied to the adjustment knob 450 will cause the raised triangular position markers 432 to be resiliently unseated from respective apertures 436 to allow sliding movement of the slider bar 422 until the next apertures 436 are aligned with respective raised triangular position markers 432, whereby the raised triangular position markers 432 are again seated therewithin. This detent assembly provides the user with a means of measuring the amount of adjustment one makes to the forehead support position.

The spacing of the apertures 436 may or may not align to provide feedback that corresponds to the position of the gear teeth. Also, the detent assembly may be structured to provide a locking feature.

VI. Position Markings on Forehead Support

Figures 1, 19:
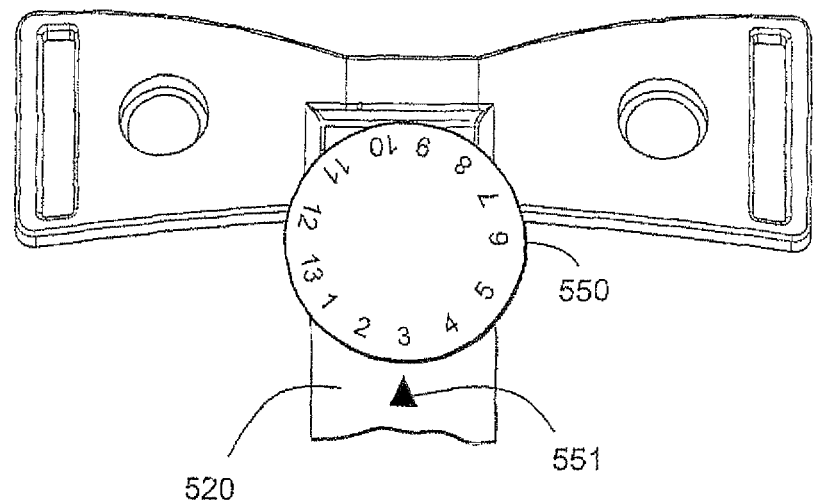
Figures 2, 19:
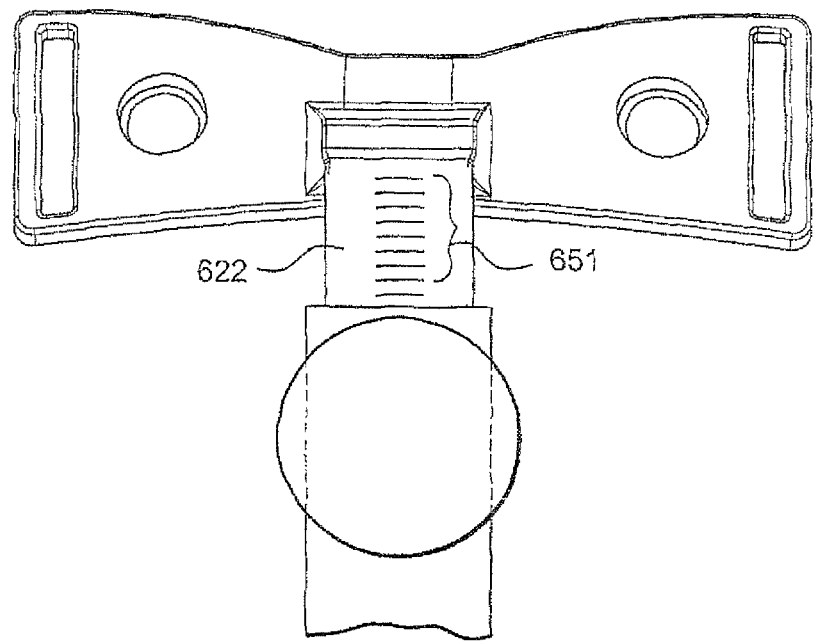

In an embodiment, position markings may be provided on the adjustment knob 150, 350, 450 and/or the slider bar 122, 322, 422 to indicate the forehead support's position. For example, as shown in FIG. 19-1, numbers may be provided on an adjustment knob 550 that align with a position arrow 551 provided on the receiver 520 to indicate the forehead support's position. As illustrated, the numbers range from 1-13. In embodiments, the numbers may range from a minimum of 1-4 and a maximum of 1-30. However, any suitable range and marking may be provided on the adjustment knob. As shown in FIG. 19-2, spaced markings 651, which may be color-coded and/or numbered, may be provided on a slider bar 622 to indicate the forehead support's position as the slider bar 622 is extended and retracted during use. However, any other suitable marking may be provided on the slider bar.

VII. Adjustment Knob Cap

In a further embodiment, the adjustment knob 150, 350, 450 may have a cap which provides a surface that may be used for branding, instructions, and/or labeling of positions, for example.

VIII. Variable Rate of Motion of Forehead Support

Figures 1, 20:
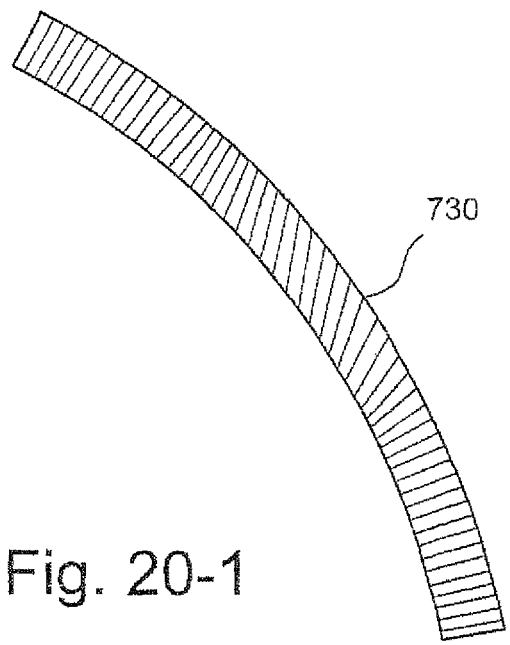
Figures 2, 20:
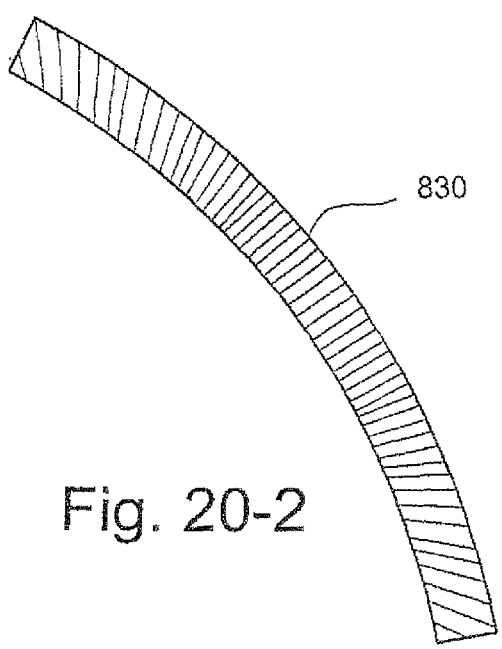

In yet another embodiment, the rack and pinion gearing as described above may be configured to provide a variable rate of motion of the slider bar. That is, the rack and pinion gearing may be configured to provide finer adjustment along portions of the range of motion, and coarser adjustment along other portions of the range of motion. For example, as shown in FIG. 20-1, a gear rack 730 may be configured such that finer adjustment, e.g., slower motion, of the forehead support position per rotation of the adjustment knob may be provided at the ends of the range of motion as an indication that the extremes of motion have been reached. In an alternative embodiment, as shown in FIG. 20-2, a gear rack 830 may be configured such that finer adjustment of the forehead support position per rotation of the adjustment knob may be provided at the middle of the range of motion to provide fine control at the position where the majority of patients will fit the forehead support.

IX. Alternative Design Target

Figure 21:
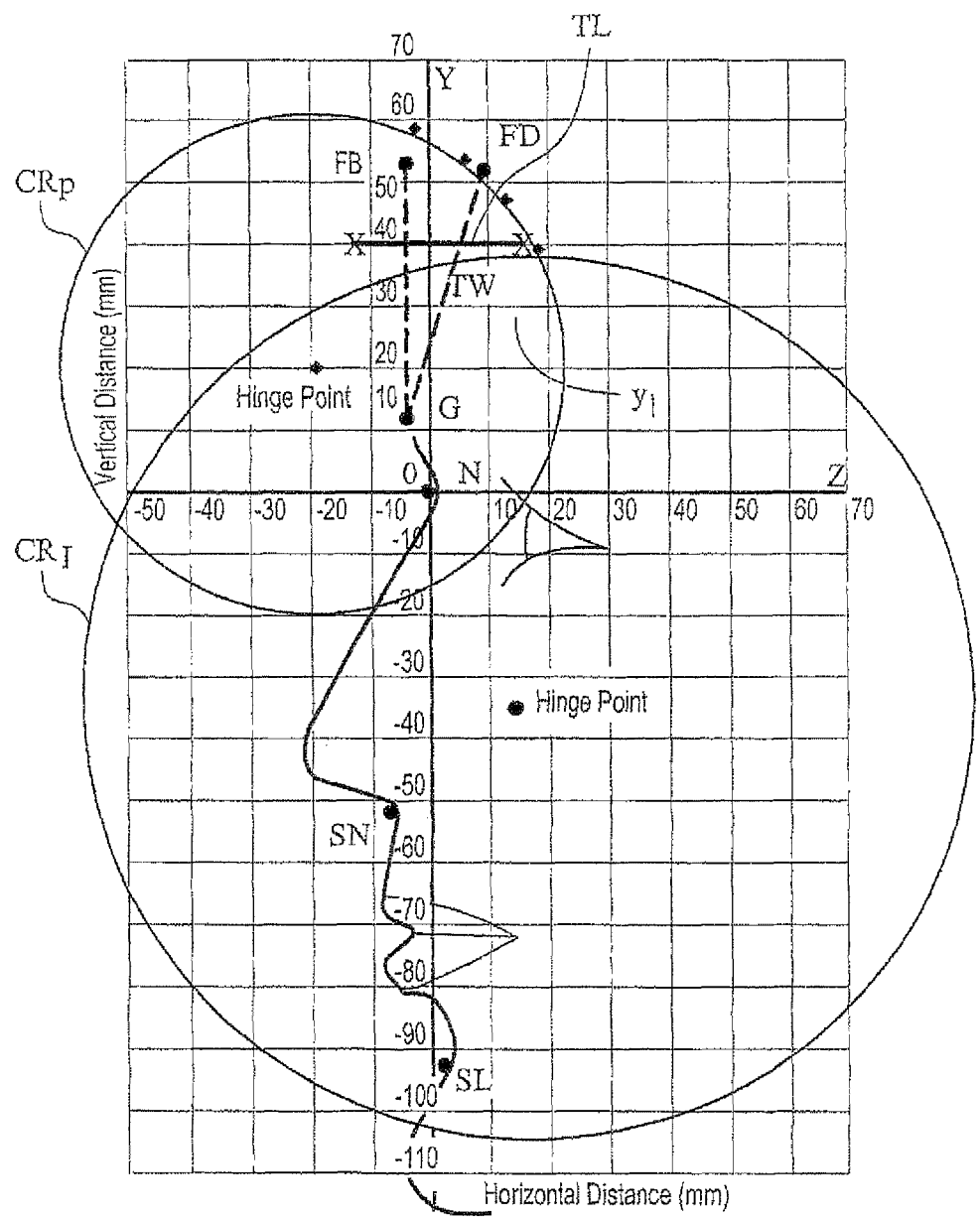
FIG. 21 shows a side view of a "standard" facial profile superimposed onto a grid of vertical and horizontal distances centered substantially on the nasion region, together with superimposed circular ranges of movement of forehead supports according to a prior art mask and a facial mask in accordance with another aspect of the invention.

In the embodiments of forehead supports 10B and 10C, the design target for the center of the forehead pad is a substantially straight line defined by the line TL in FIG. 21. The end points of the line TL have the coordinates (40.3, −13.7; 40.3, 16.9). In general, the line TL may be described as a 30 mm horizontal distance that allows about 15 mm clearance between the bottom of a forehead pad (assuming the pad has a height of about 28 mm) and G (Glabella).

The horizontal coordinates are calculated from the intersection of the 40.3 mm height with a line drawn from G to FB (most forward forehead position at the average hairline measurement minus two standard deviations) and G to FD (most rear forehead position at the average hairline measurement minus two standard deviations) plus 7.5 mm travel either side. While the target in these embodiments is a horizontal line, the movement of the forehead support will be arcuate due to its construction.

X. Fifth Illustrated Embodiment of Forehead Support

Figures 1, 22:
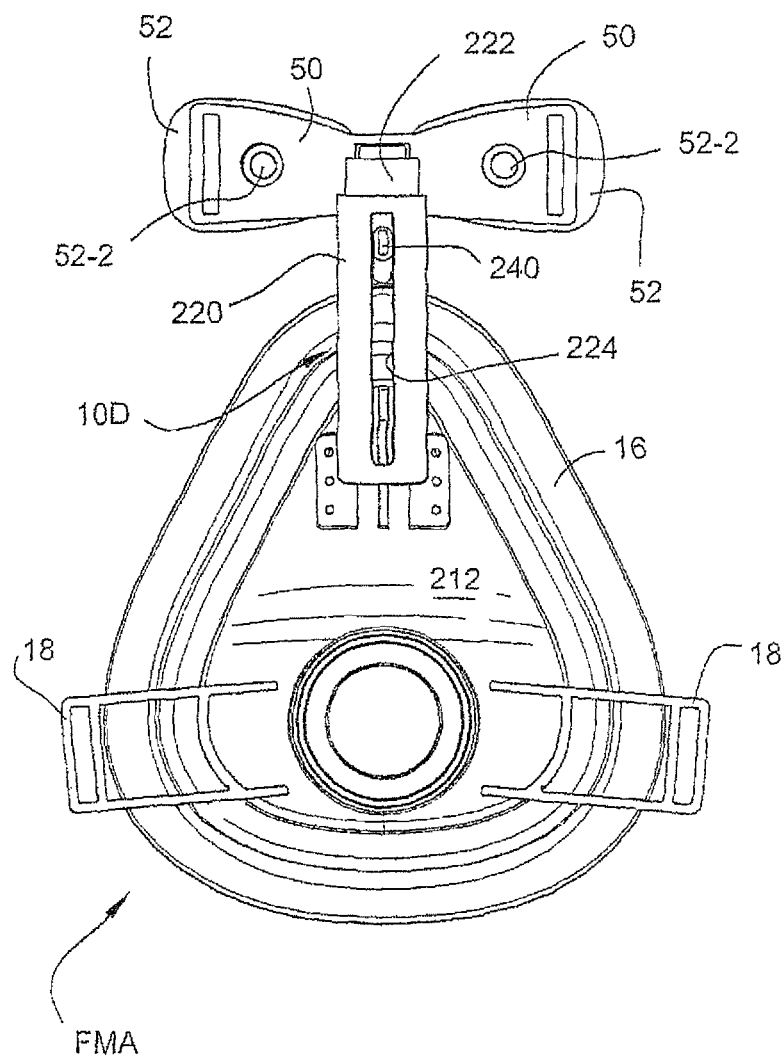
Figures 2, 22:
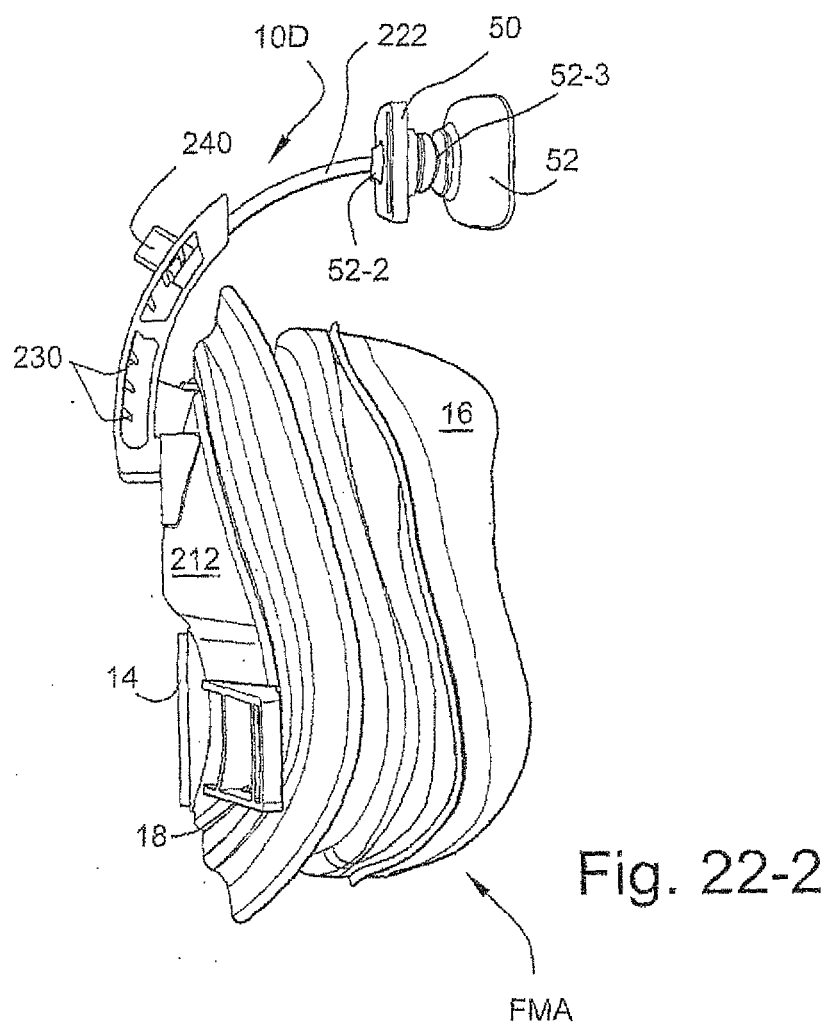
Figures 3, 22:
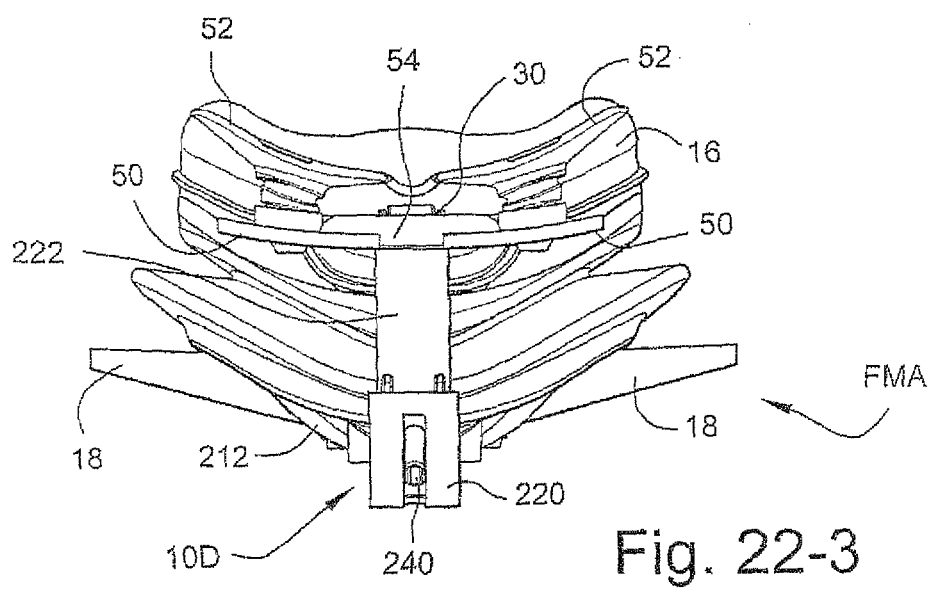
Figures 4, 22:
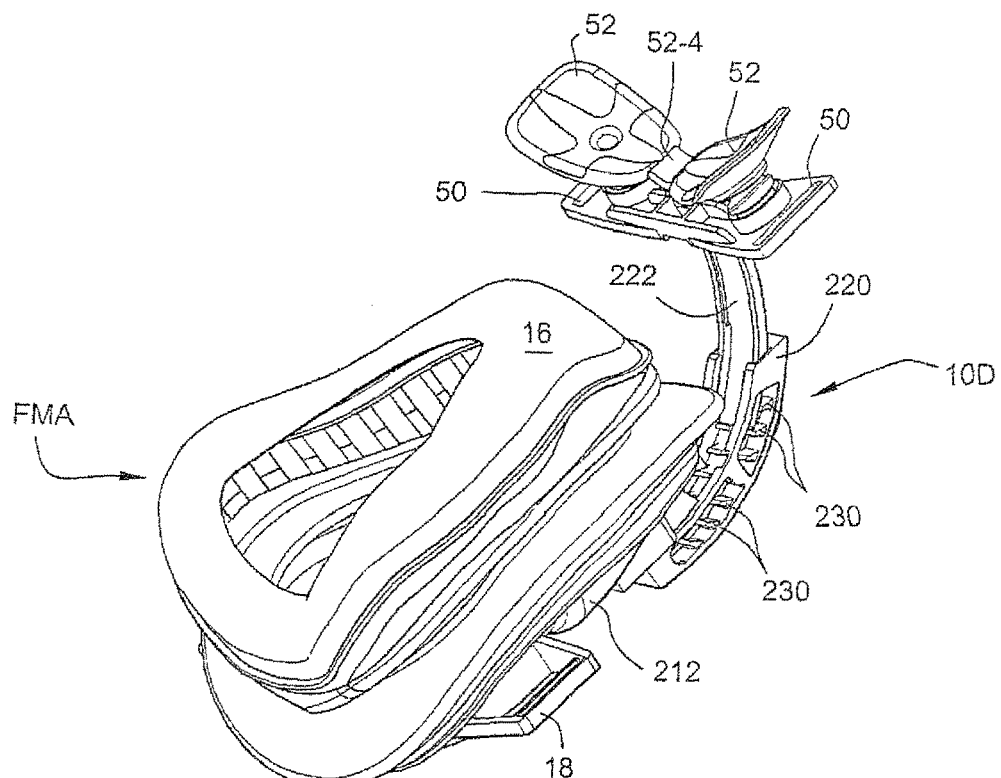
Figures 5, 22:
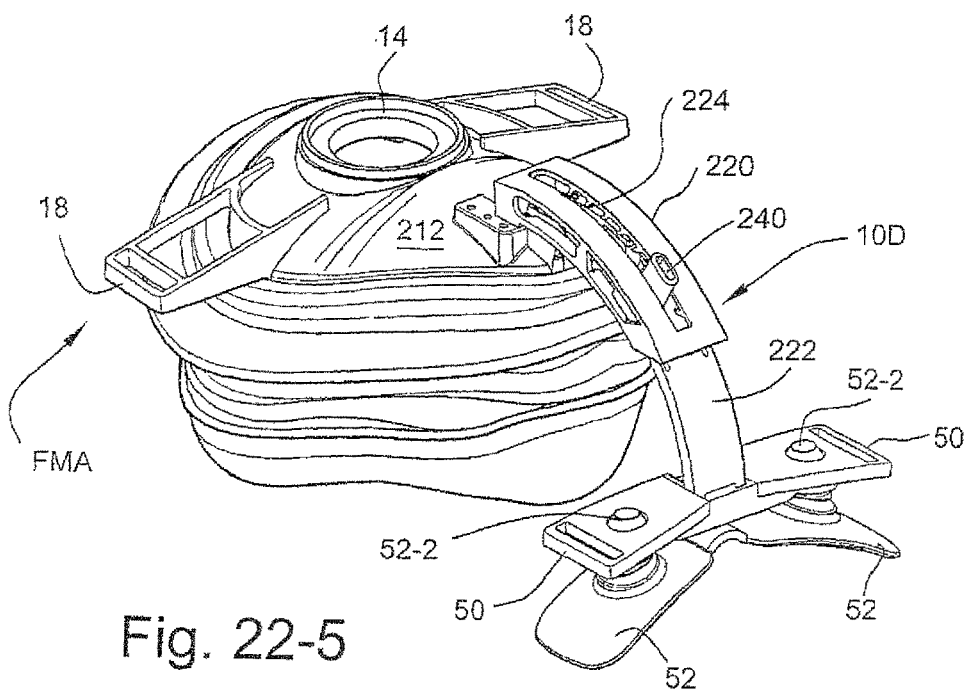

Accompanying FIGS. 22-1 to 22-5 depict a FMA provided with another embodiment of a forehead support 10D according to the present invention. FIGS. 23-1 to 23-5 and FIGS. 24-1 to 24-5 depict in greater detail a slider bar 222 and a mask frame 212 that may be employed in the forehead support 10D. In this regard, structural components that are similar to those discussed previously have been shown with the same reference numerals. Thus, a detailed discussion of such similar structural components will not necessarily be repeated, although some mention thereof may be to ensure clarity of discussion.

A. Slider Bar

The forehead support 10D generally comprises a receiver 220 fixed to the mask frame 212. The receiver 220 defines an arcuately shaped channel 220-1 (see FIGS. 24-5) for receiving a corresponding arcuately shaped slider bar 222. The receiver 220 also defines an elongate central slot 224 through which the raised push button 240 associated with the slider bar 222 protrudes. As is perhaps best shown in FIGS. 23-1 to 23-6, the slider bar 222 includes at its distal end a connector portion 226 which defines an aperture 246-1 for receiving the pivot pin 30 (see FIG. 22-3). The pivot pin 30 thus serves to pivotally join the central support 54 of the forehead cushion support plates 50 to the distal end of the slider bar 222 and thereby permit pivotal movements of the former relative to the latter. In an alternative embodiment, the central support may be rigidly connected to the distal end of the slider bar.

B. Receiver with Ratchet Teeth

The receiver 220 includes a series of paired ratchet teeth 230 protruding into the channel 220-1 (FIG. 24-5) along the lateral sides of the central slot 224 (see FIGS. 24-2 and 24-5) from the proximal end of the receiver 220 to the distal end thereof. As is perhaps best shown in FIG. 24-2, the ratchet teeth 230 are angled in a generally downward direction when the mask frame 212 is in an upright condition.

C. Tongue Member on Slider Bar

Figures 4, 23:
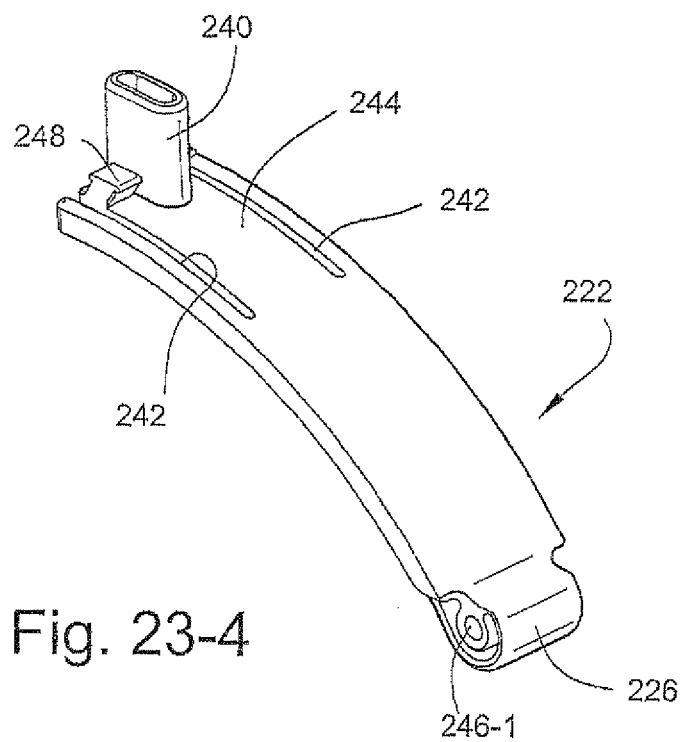
Figures 5, 23:
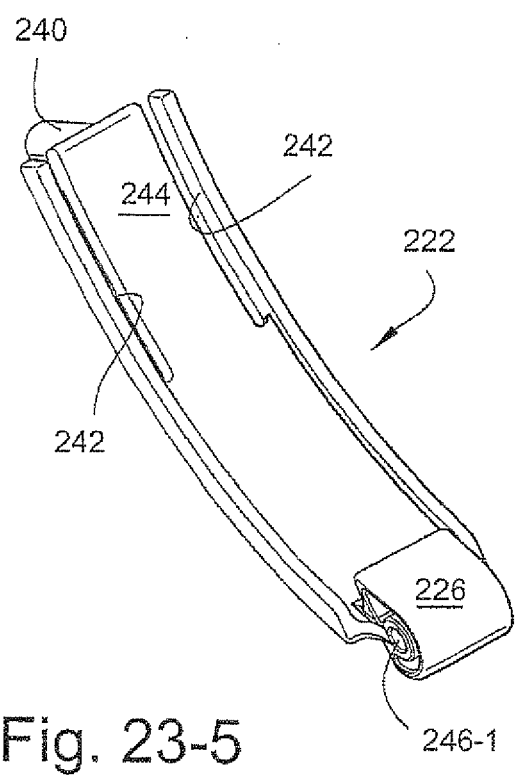

As shown in FIGS. 23-1 to 23-5, a pair of elongate parallel slots 242 is provided near respective lateral sides of the slider bar 222. The slots 242 extend substantial one-fourth to about one-half the circumferential distance of the arcuate slider bar 222 starting at the distal end thereof so as to establish a resilient central tongue member 244. The tongue member 240 also carries a pair of fixed engagement pawls 248 which are sized and configured to be engaged with a respective pair of ratchet teeth 230 of the receiver 220.

In use, the slider bar 222, and hence the forehead cushions 52 carried thereby, may be positionally adjusted so as to assume a desired position by pressing against the push button 240. Pressure against the push button 240 thereby causes the resilient tongue 244 to be flexed downwardly so as to release engagement between the pawls 248 and a pair of the ratchet teeth 230. While the pawls 248 and teeth 230 are disengaged, therefore, the slider bar 222 may be slid along the channel 220-1 of the receiver 220 between its retracted and extended positions so as to assume a desired position. Upon reaching such desired position, the push button 240 may be released which causes the resilient tongue 244 to return to its normal condition thereby bringing the pawls 248 into engagement with another pair of ratchet teeth 230.

It should be understood that other suitable mechanisms may be utilized to secure the slider bar with respect to the receiver. For example, the slider bar may be secured with respect to the receiver by, e.g., a fastener such as a screw, friction, etc. Also, the slider bar may be attached to the receiver by a loose pivoting arrangement, or a spring arrangement.

XI. Spiral Screw Mechanism

Figure 25:
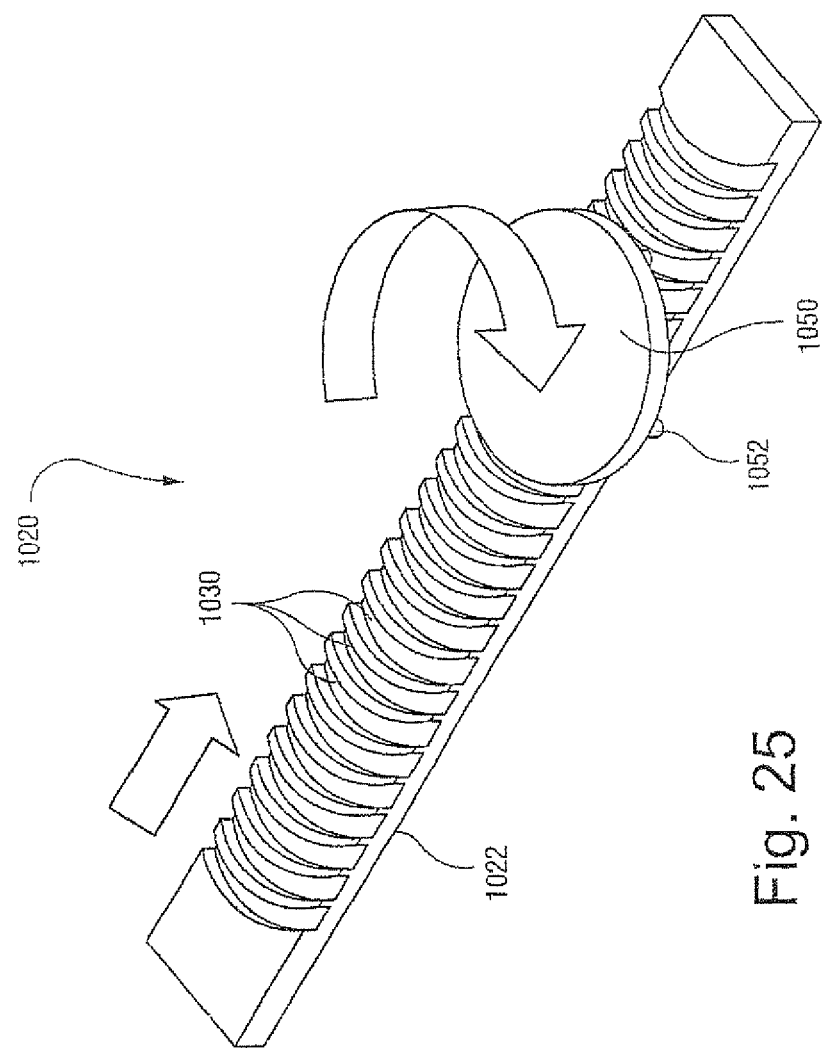
FIG. 25 is a perspective view of a spiral screw mechanism according to an embodiment of the present invention.

FIG. 25 schematically illustrates a spiral screw mechanism 1020 according to an embodiment of the present invention. The spiral screw mechanism 1020 may be employed in a forehead support of a FMA such as those discussed above.

As illustrated, the spiral screw mechanism 1020 includes a knob 1050 with a number of pins 1052 (or spiral ribs) and a strap 1022 with a number of spiral-shaped grooves 1030. The pins 1052 of the knob 1050 are adapted to engage with the spiral-shaped grooves 1030 on the strap 1022. As the knob 1050 is turned, the pins 1052 push or pull the strap 1022 towards or away from the knob axis. In the flat configuration shown, the pins 1052 could potentially interfere with the strap 1022 as they rotate back over it. However, this should not be an issue if the strap 1022 is curved (e.g., provided on a curved receiver of the mask frame) so that the strap 1022 misses the backside trajectory of the pins 1052. Advantages of this concept include simplicity, strength, and the ability to provide a pull/push force that is closely aligned with the axis of the knob 1050 which reduces jamming issues with the slide action.

XII. Sixth Illustrated Embodiment of Forehead Support

Figures 1, 2, 3, 4:
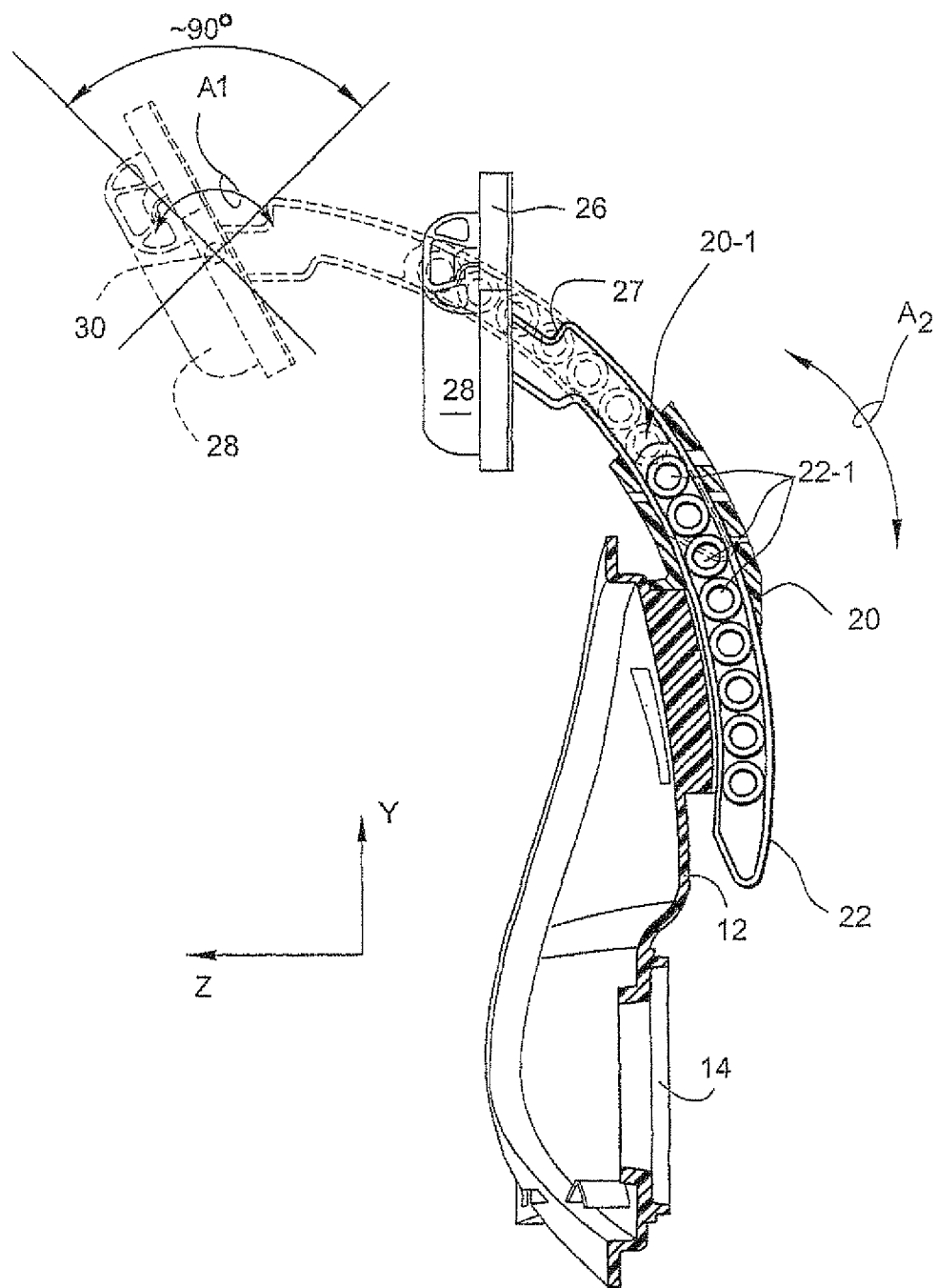
Figure 2:
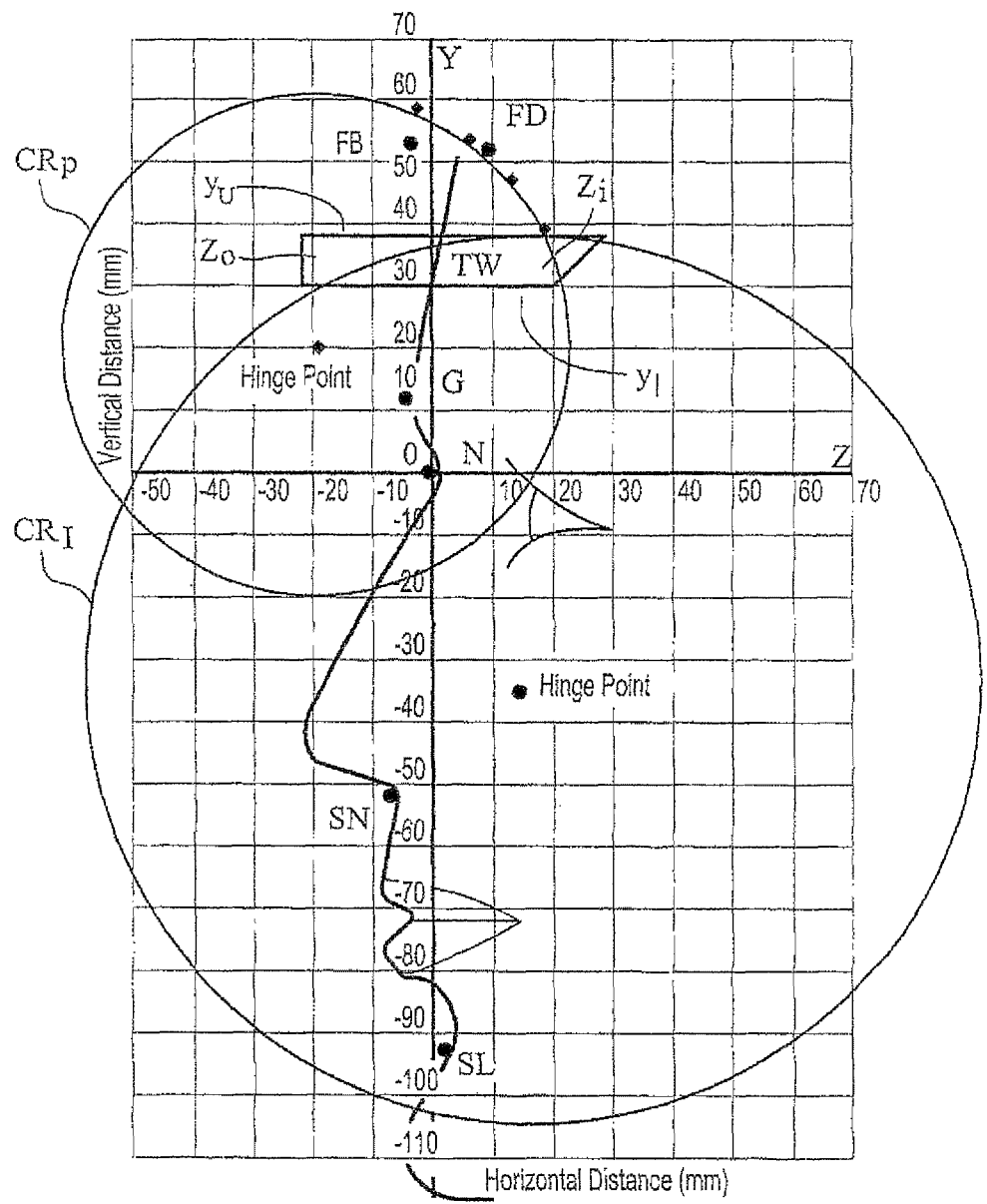
Figures 1, 26:
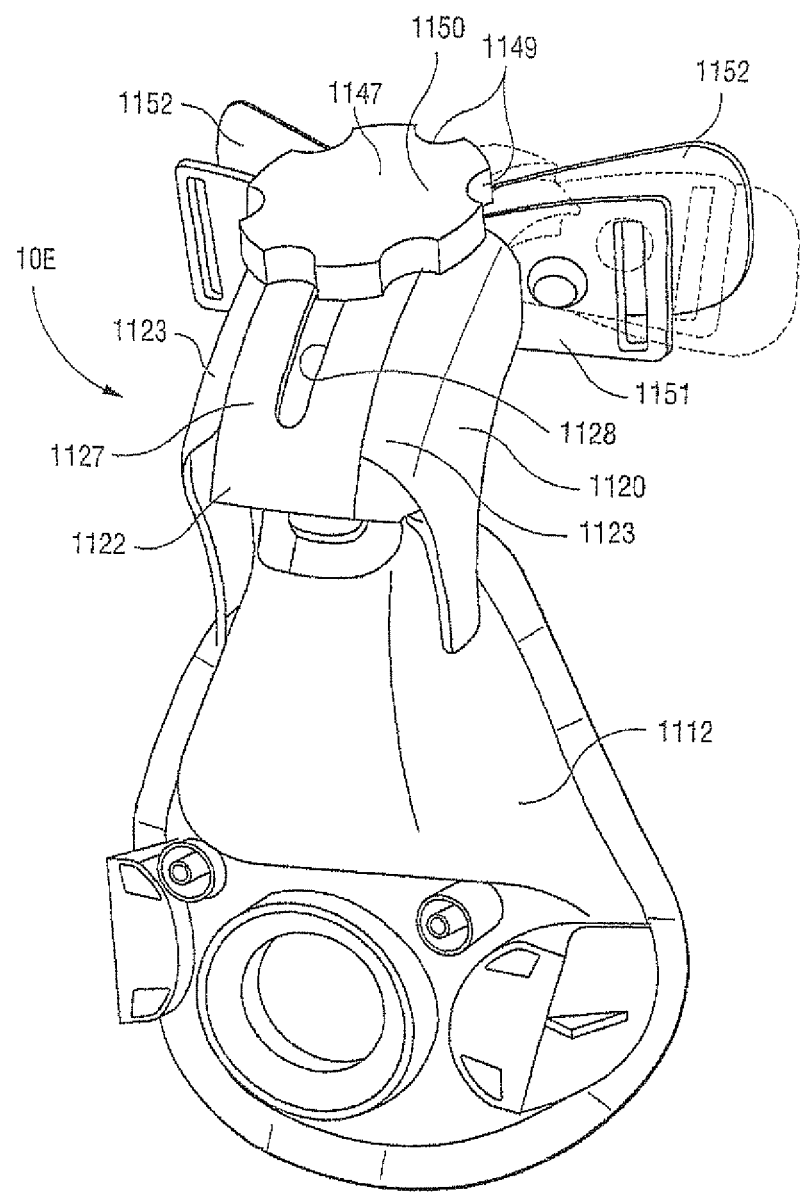
Figures 2, 26:
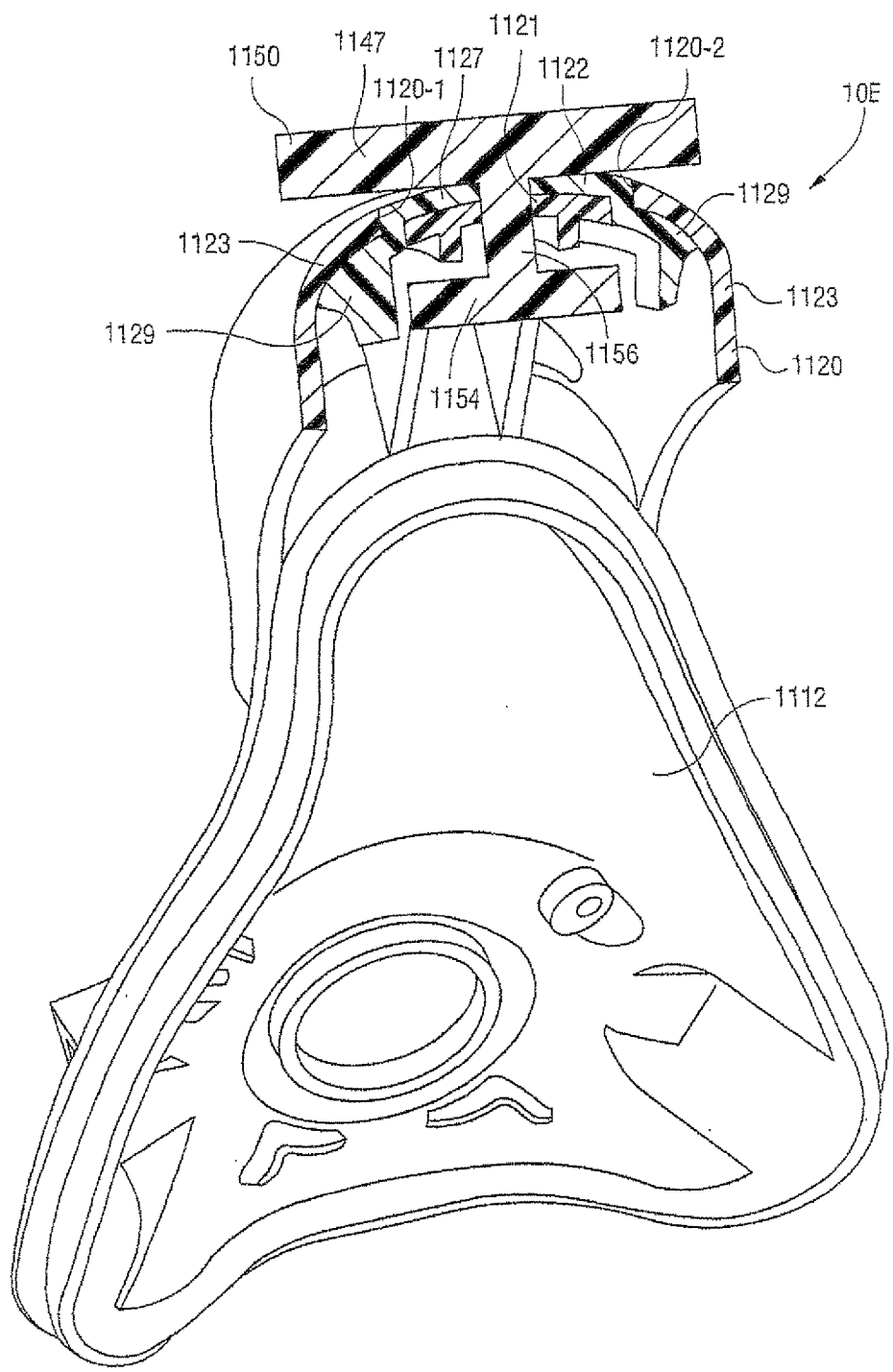
Figures 3, 26:
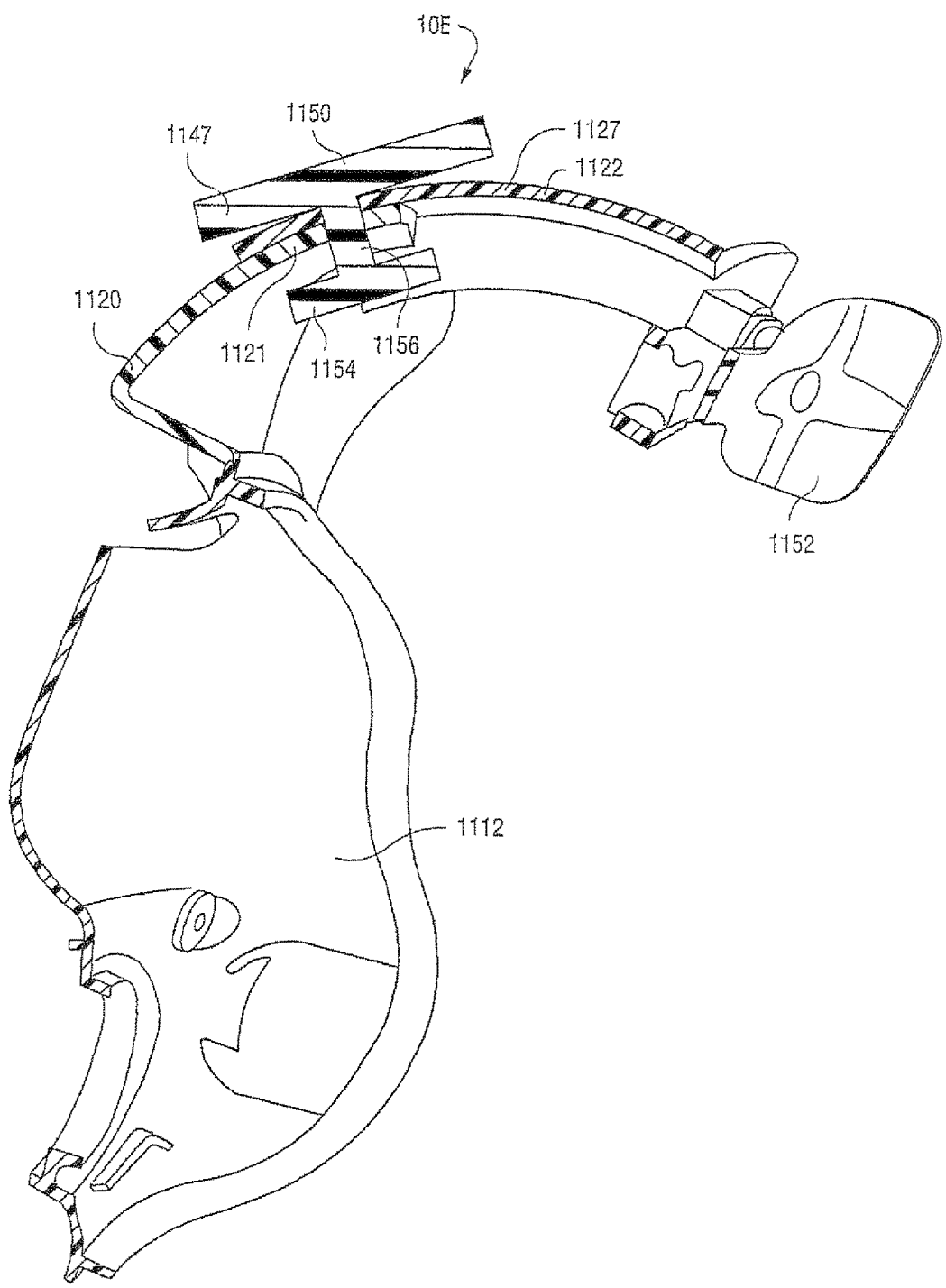
Figures 4, 26:
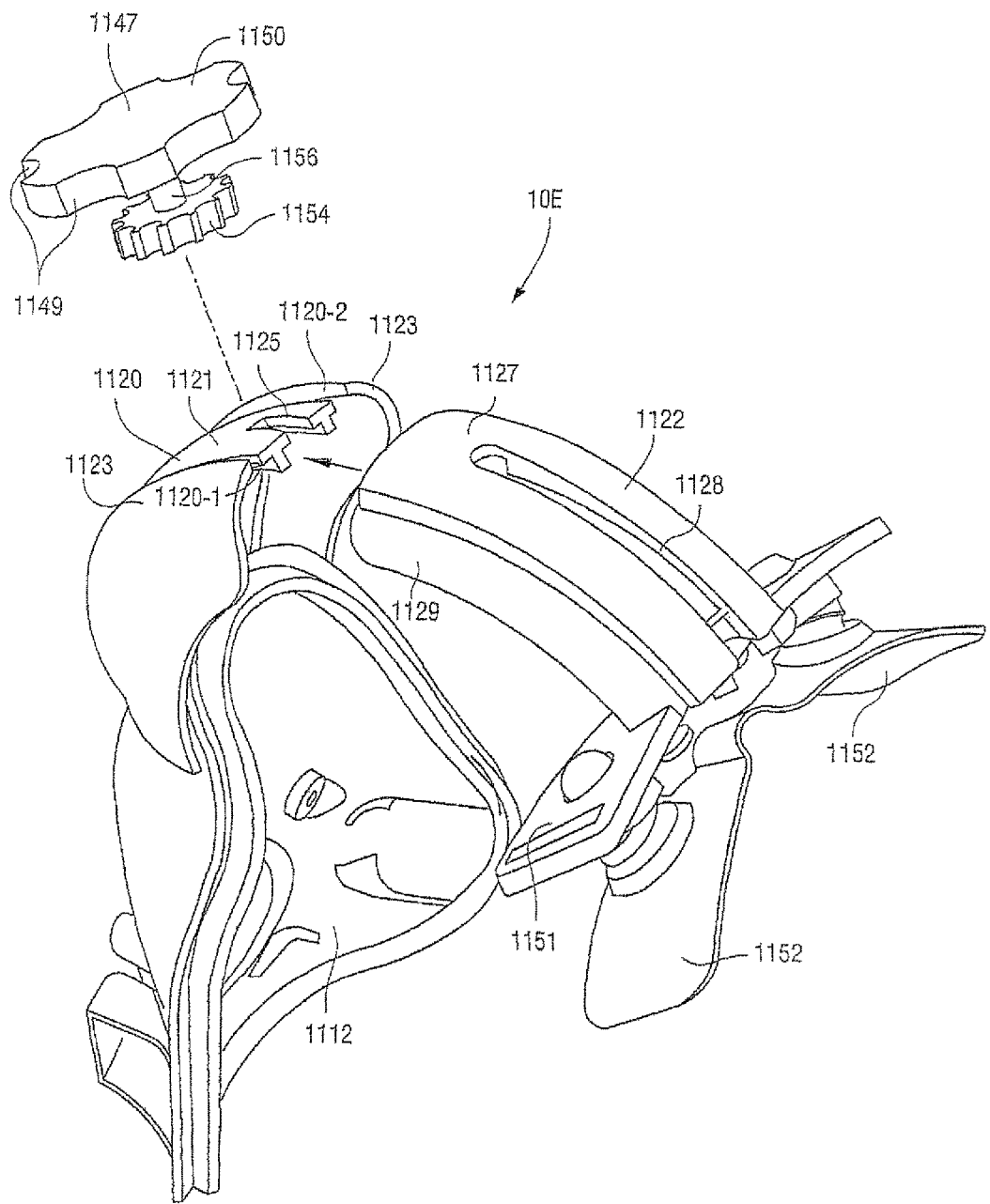

FIGS. 26-1 to 26-4 illustrate a FMA including a forehead support 10E according to another embodiment of the present invention. The forehead support 10E includes a receiver 1120 provided to the mask frame 1112 for receiving a slider bar 1122. The slider bar 1122 is joined to forehead cushion support plates 1151 that carry forehead cushions 1152.

The receiver 1120 has a split track including spaced-apart arcuately shaped channels 1120-1 and 1120-2 (FIG. 26-4) that define an elongated central finger 1121 and outer guide rails 1123 (see FIGS. 26-2 and 26-4). The central finger 1121 includes a slot 1125 (FIG. 26-4) that retains an adjustment knob 1150. In the illustrated embodiment, the split track is molded into the mask frame 1112 and is designed so as to be molded in a single line of draw (without complex sliding cores).

The slider bar 1122 (FIG. 26-4) is fed into the receiver 1120 so that the upper wall 1127 is supported on the central finger 1121 and the side walls 1129 are guided by the outer guide rails 1123 (see FIGS. 26-2, 26-3, and 26-4). Thus, the central finger 1121 provides restraint against downward movement of the slider bar 1122.

The slider bar 1122 defines a central elongate slot 1128. The adjustment knob 1150 is fed into the slider bar 1122 via a void at one end of the slot 1128 adjacent the forehead end. The post member 1156 of the adjustment knob 1150 then clips into the slot 1125 of the central finger 1121 (FIG. 26-4). When coupled, the gear 1154 provided on the adjustment knob 1150 engages gear teeth positioned on the underside of the slider bar 1122. Thus, turning of the adjustment knob 1150 causes adjustable movement of the slider bar 1122. As illustrated, the head 1147 of the adjustment knob 1150 includes grooves or finger grips 1149, e.g., 2, 4, or 6, that make the knob 1150 easier to operate (see FIGS. 26-1 and 26-4).

Advantages of the forehead support 10E include ease of manufacture and strength. Also, the decoupling of the central finger 1121 from the outer guide rails 1123 enables the mechanism to flex and come apart under abuse loads instead of fracturing. Further, the forehead support 10E has good overall aesthetics.

Figures 2, 27:
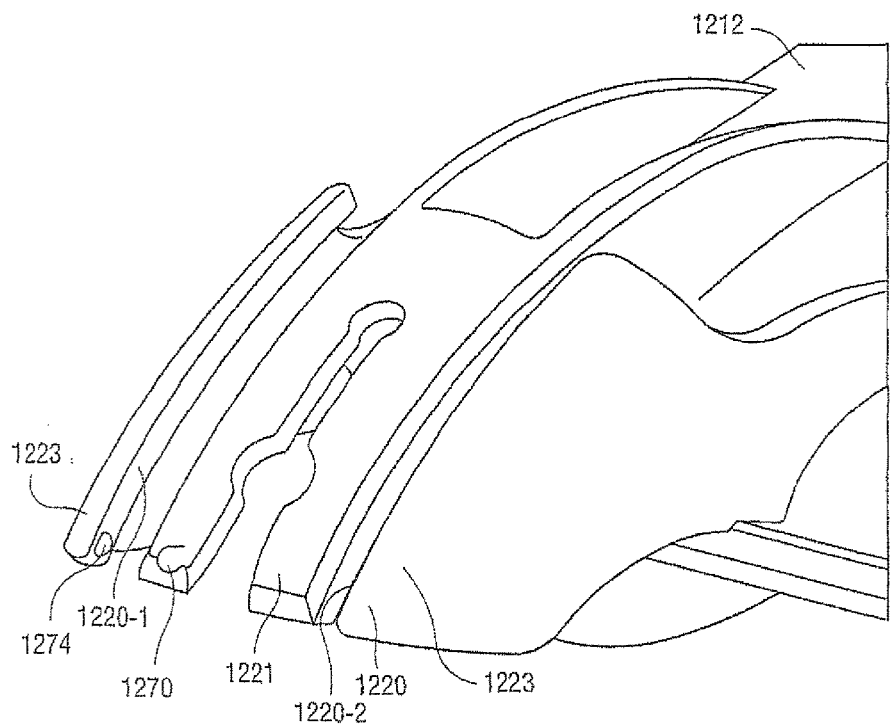
Figures 3, 27:
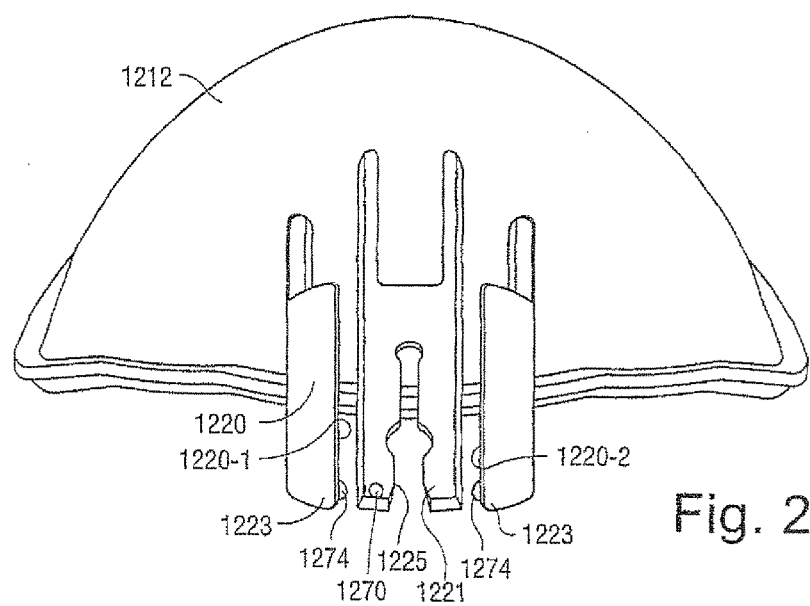
Figures 4, 27:
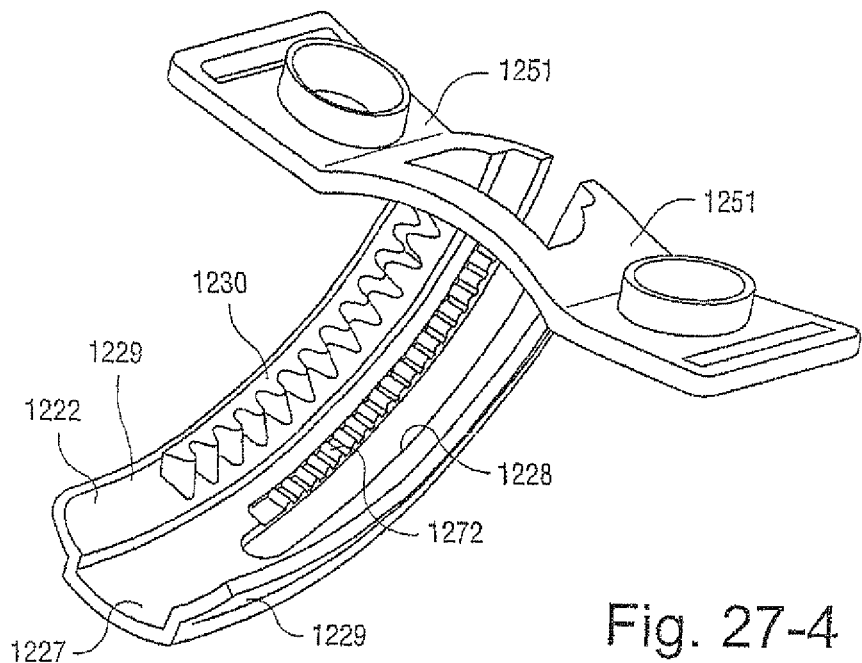
Figures 5, 27:
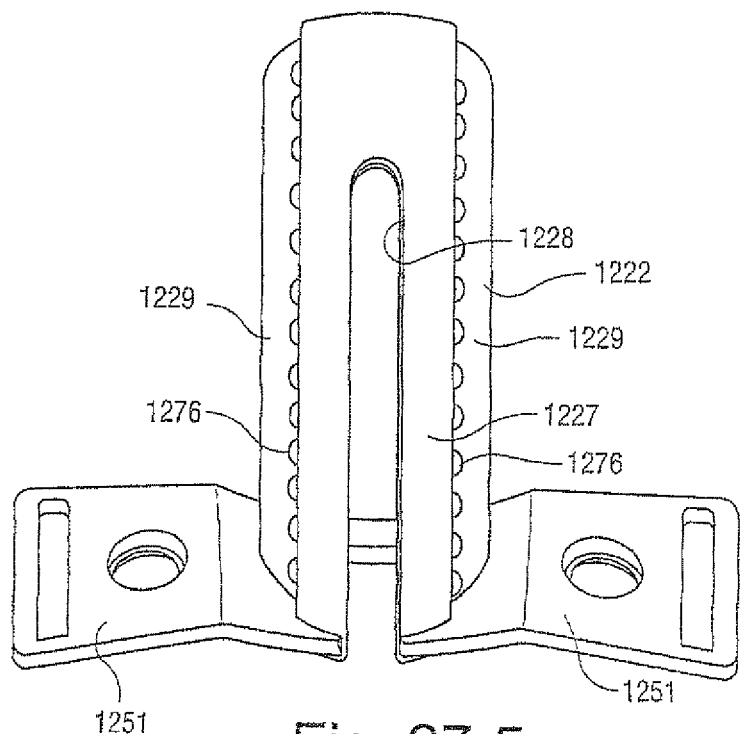
Figures 6, 27:
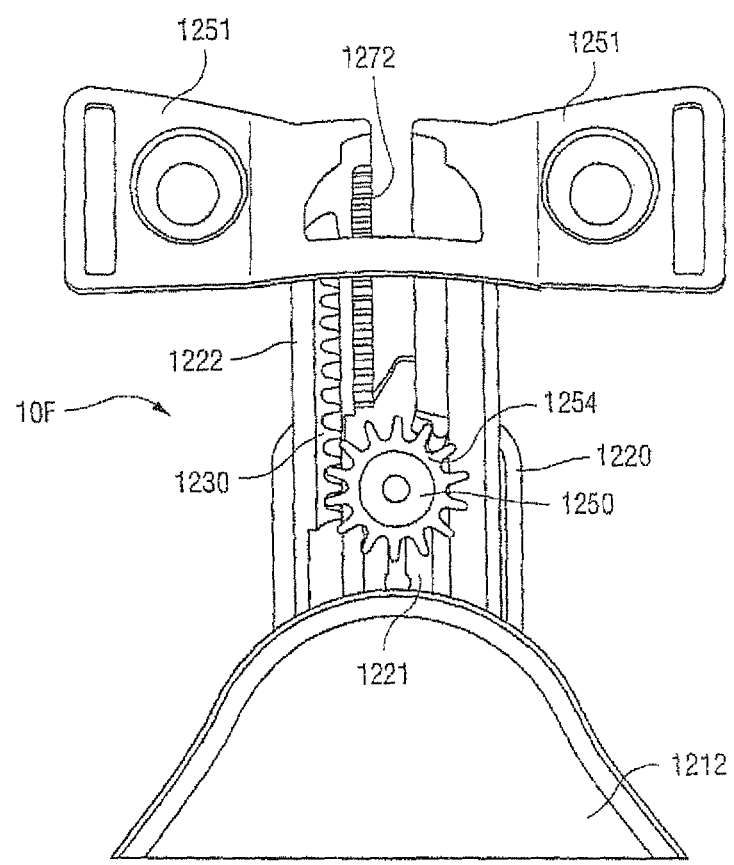

FIGS. 27-1 to 27-6 illustrate a FMA including a forehead support 10F according to another embodiment of the present invention. The forehead support 10F includes a receiver 1220 provided to the mask frame 1212 for receiving a slider bar 1222. The slider bar 1222 is joined to forehead cushion support plates 1251 (see FIG. 27-1) that carry forehead cushions.

Similar to the receiver 1120, the receiver 1220 has a split track including spaced-apart arcuately shaped channels 1220-1 and 1220-2 that define an elongated central finger 1221 and outer guide rails 1223 (see FIGS. 27-2 and 27-3). The central finger 1221 includes a slot 1225 that retains an adjustment knob 1250 (see FIG. 27-1). In the illustrated embodiment, the split track is molded into the mask frame 1212 and is designed so as to be molded in a single line of draw (without complex sliding cores).

The slider bar 1222 is fed into the receiver 1220 so that the upper wall 1227 is supported on the central finger 1221 and the side walls 1229 are guided by the outer guide rails 1223. Thus, the central finger 1221 provides restraint against downward movement of the slider bar 1222.

The slider bar 1222 defines a central elongate slot 1228 (see FIGS. 27-4 and 27-5). The adjustment knob 1250 is fed into the slider bar 1222 via a void at one end of the slot 1228 adjacent the forehead end. The post member of the adjustment knob 1250 then clips into the slot 1225 of the central finger 1221. When coupled, the gear 1254 provided on the adjustment knob 1250 engages gear teeth 1230 positioned on the underside of the slider bar 1222 (see FIG. 27-6). Thus, turning of the adjustment knob 1250 causes adjustable movement of the slider bar 1222. As illustrated, the head 1247 of the adjustment knob 1250 includes grooves or finger grips 1249, e.g., 2, 4, or 6, that make the knob 1250 easier to operate (see FIG. 27-1).

Also, the forehead support 10F includes a detent assembly or ratchet arrangement that is self-locking to lock the forehead support 10F in position. Specifically, the central finger 1221 may include a protrusion or detent button 1270 (see FIGS. 27-2 and 27-3) that is adapted to interact with a series of teeth or ribs 1272 provided on the underside of the slider bar 1222 (see FIG. 27-4). Alternatively, each guide rail 1223 may include a protrusion or detent button 1274 (see FIGS. 27-2 and 27-3) that is adapted to interact with a series of teeth or ribs 1276 provided on sides of the slider bar 1222 (see FIGS. 27-1 and 27-5). Thus, the ratchet arrangement may include either one of the protrusion 1270/teeth 1272 or the protrusion 1274/teeth 1276. As the adjustment knob 1250 is turned to extend or retract the slider bar 1222, the protrusion 1270 will move into and out of engagement with the teeth 1272 on the underside of the slider bar 1222, or the protrusions 1274 will move into and out of engagement with the teeth 1276 on sides of the slider bar 1222. As such, the protrusions 1270, 1274 will be seated within respective teeth 1272, 1276 (FIGS. 27-4 and 27-5) to assist in restraining the slider bar 1222 at the desired position. However, turning movement applied to the adjustment knob 1250 will cause the protrusions 1270, 1274 to be resiliently unseated from respective teeth 1272, 1276 to allow sliding movement of the slider bar 1222 until the next teeth 1272, 1276 are aligned with respective protrusions 1270, 1274, whereby the protrusions 1270, 1274 are again seated therewithin. The guide rails 1223 may flex outwardly during the ratcheting movement. This ratchet arrangement provides the user with a means of measuring the amount of adjustment one makes to the forehead support position. The teeth 1272, 1276 may be evenly spaced or may be graduated.

Advantages of the forehead support 10F include ease of manufacture and strength. Also, the decoupling of the central finger 1221 from the outer guide rails 1223 enables the mechanism to flex and come apart under abuse loads instead of fracturing. Further, the forehead support 10F has good overall aesthetics.

XIII. Seventh Illustrated Embodiment of Forehead Support

Figures 1, 28:
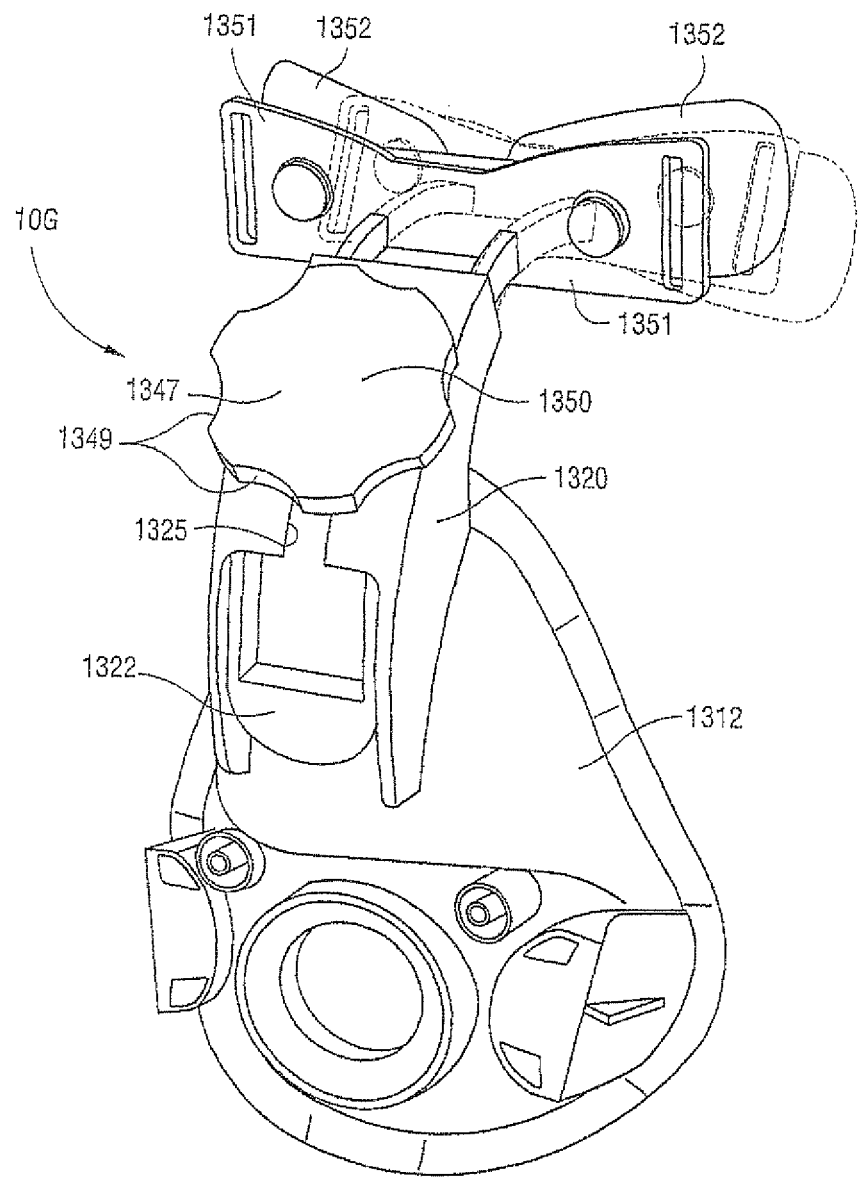
Figures 2, 28:
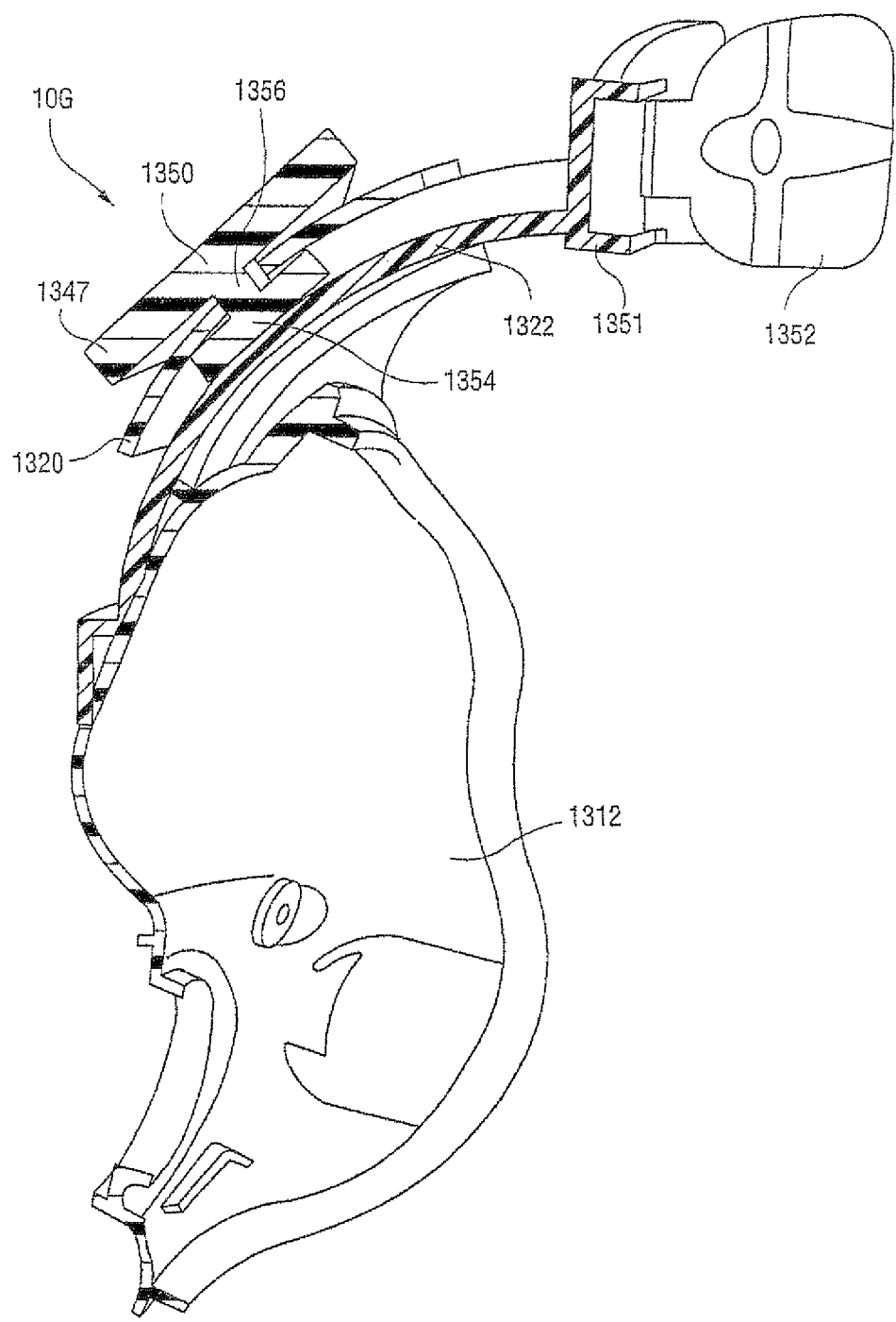
Figures 3, 28:
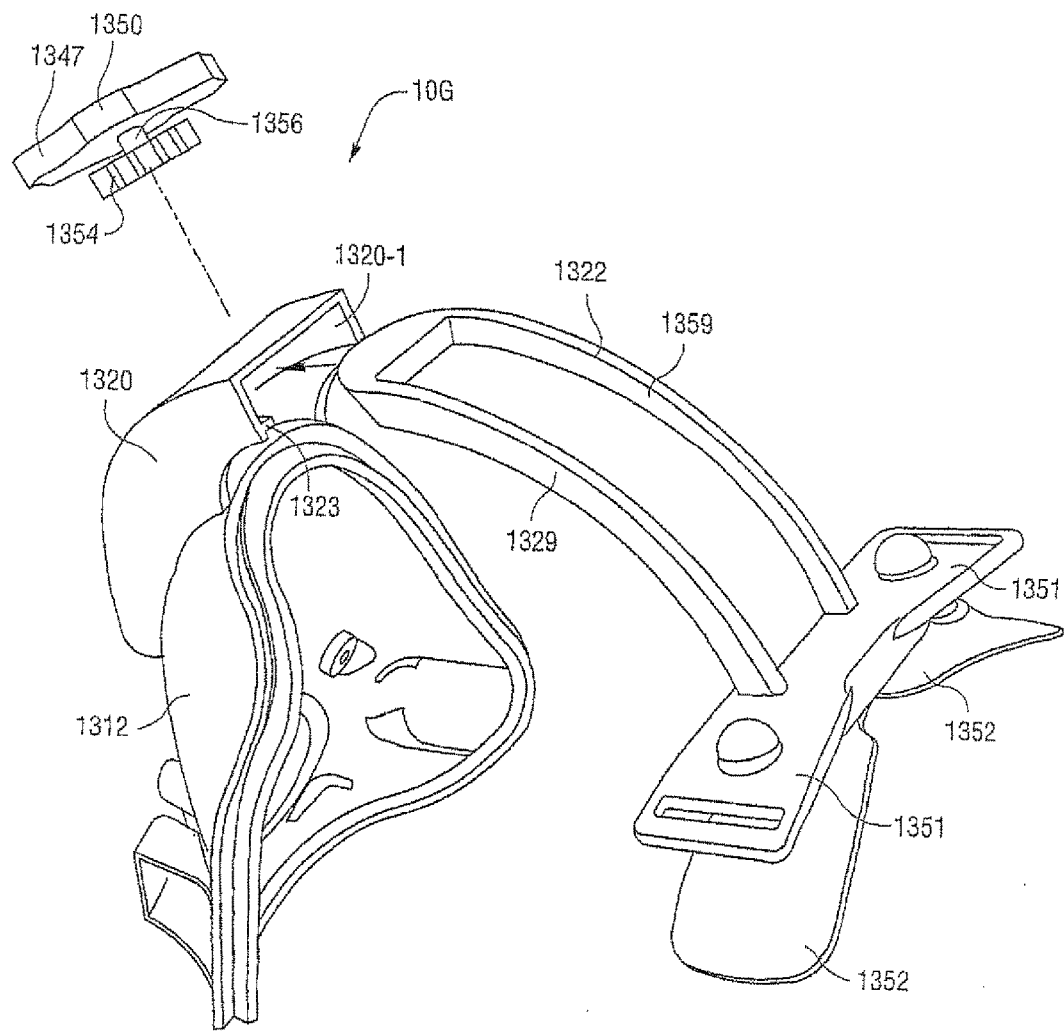

FIGS. 28-1 to 28-3 illustrate a FMA including a forehead support 10G according to another embodiment of the present invention. The forehead support 10G includes a receiver 1320 provided to the mask frame 1312 for receiving a slider bar 1322. The slider bar 1322 is joined to forehead cushion support plates 1351 that carry forehead cushions 1352.

The receiver 1320 defines an arcuately shaped channel 1320-1 for receiving the correspondingly arcuately shaped slider bar 1322 (see FIG. 28-3). The receiver also includes a slot 1325 that retains an adjustment knob 1350. In the illustrated embodiment, the receiver 1320 is molded into the mask frame 1312 and is designed so as to be molded with a pivoting core and provide sufficient space for cooling of the core.

The slider bar 1322 is fed into the channel 1320-1 of the receiver 1320, and the adjustment knob 1350 is fed into the receiver 1320 via a void at a bottom end of the slot 1325 opposite the forehead end. The post member 1356 of the adjustment knob 1350 then clips into a top end of the slot 1325. The adjustment knob 1350 clips into place from the bottom rather than the top to prevent the knob 1350 from being directed towards the user if it detaches. Also, the knob 1350 is self-contained.

When coupled, the gear 1354 provided on the adjustment knob 1350 engages gear teeth positioned on the top side of the slider bar 1322. Thus, turning of the adjustment knob 1350 causes adjustable movement of the slider bar 1322. As illustrated, the head 1347 of the adjustment knob 1350 includes grooves or finger grips 1349, e.g., 2, 4, or 6, that make the knob 1350 easier to operate (see FIG. 28-1).

As illustrated, the slider bar 1322 has generally c-shaped cross-section configuration, and the side walls 1329 of the slider bar 1322 are supported on outer guide flanges 1323 that provide restraint against downward movement of the slider bar 1322.

Advantages of the forehead support 10G include ease of molding and good overall aesthetics.

XIV. Eighth Illustrated Embodiment of Forehead Support

Figures 1, 29:
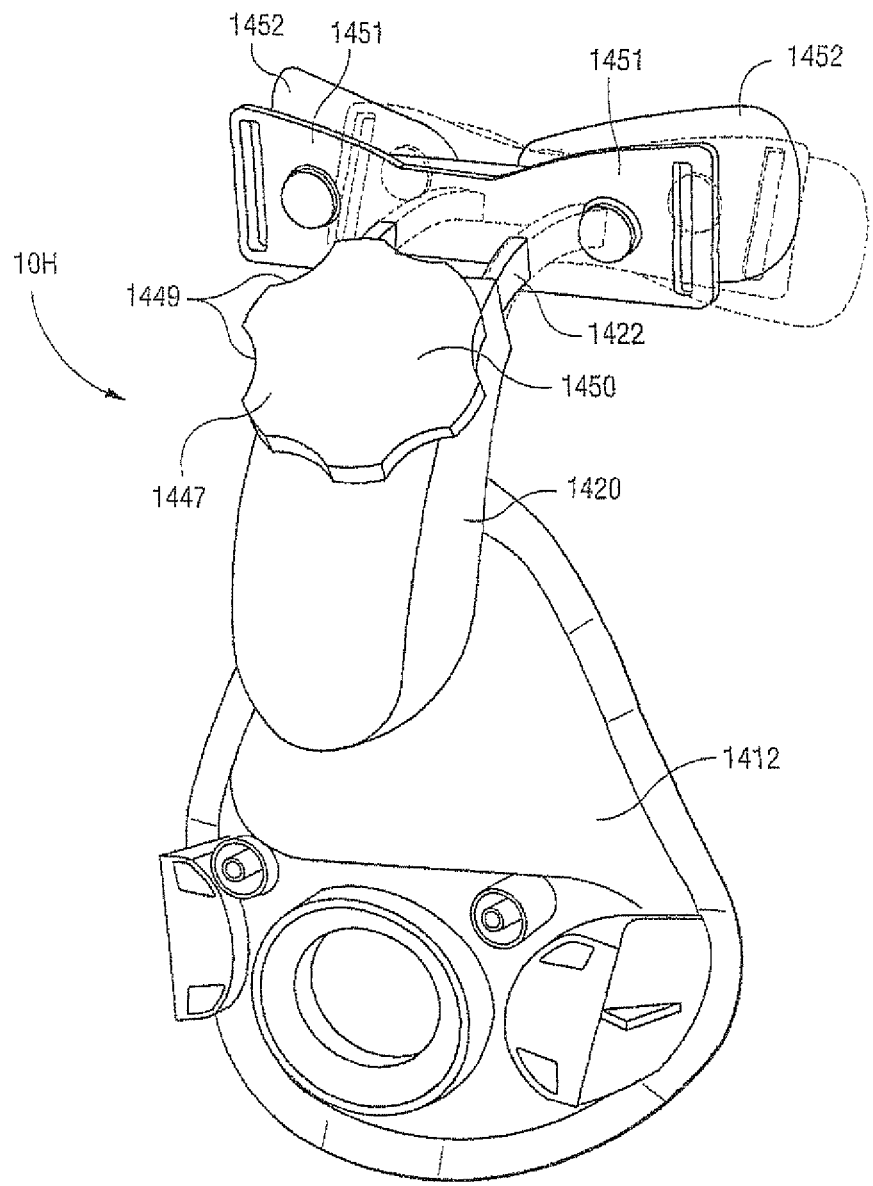
Figures 2, 29:
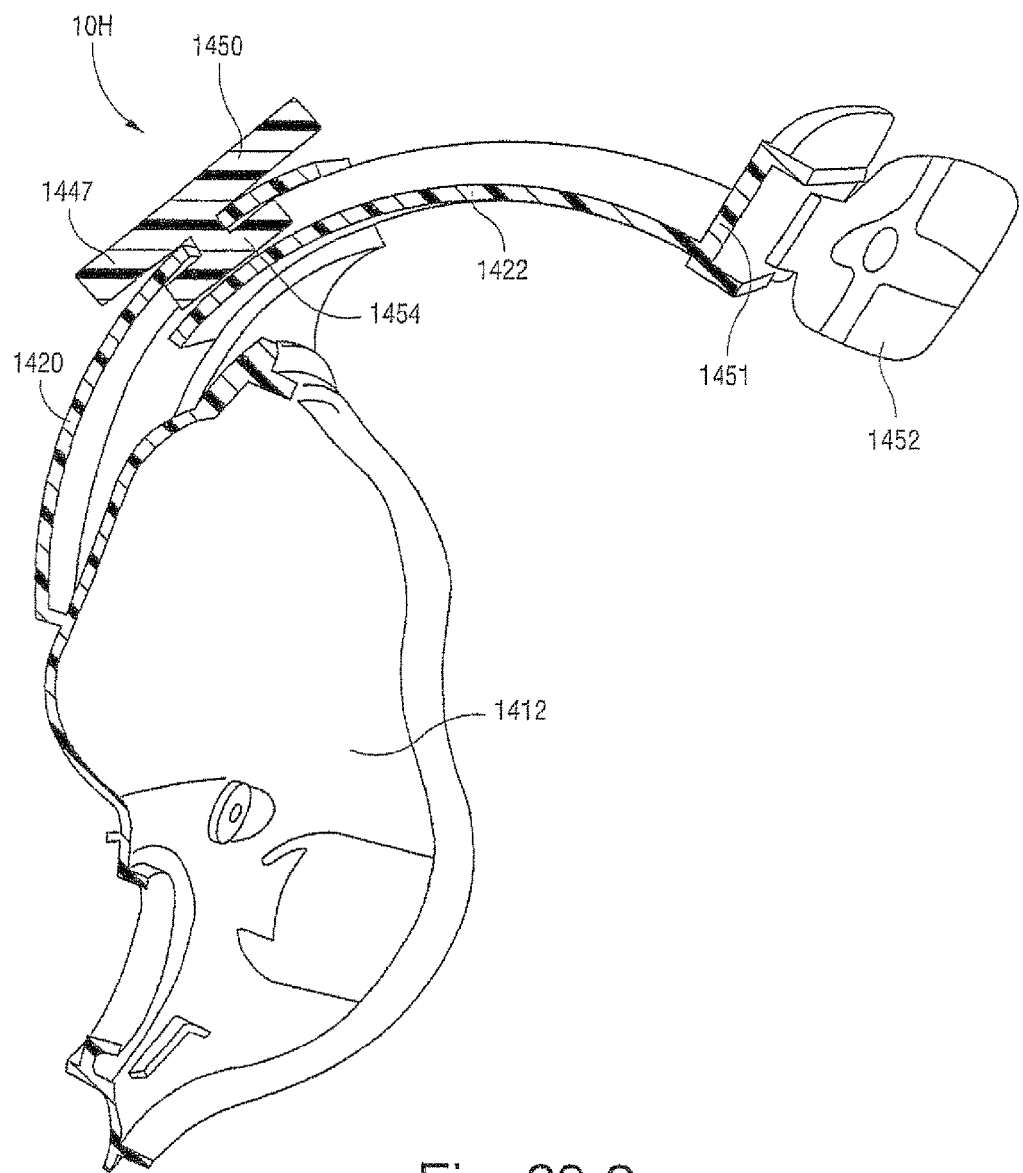
Figures 3, 29:
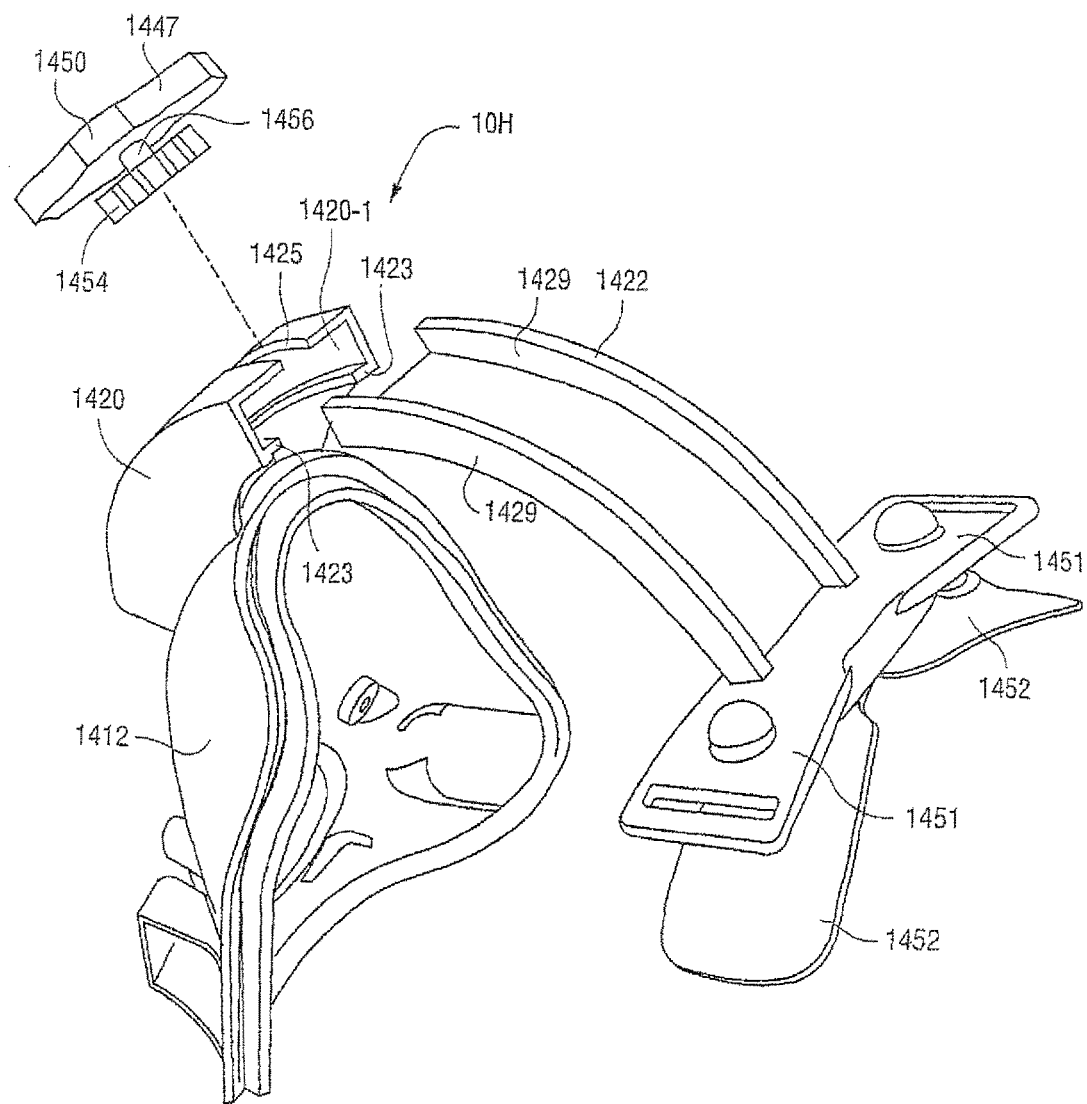

FIGS. 29-1 to 29-3 illustrate a FMA including a forehead support 10H according to another embodiment of the present invention. The forehead support 10H includes a receiver 1420 provided to the mask frame 1412 for receiving a slider bar 1422. The slider bar 1422 is joined to forehead cushion support plates 1451 that carry forehead cushions 1452.

The receiver 1420 defines an arcuately shaped channel 1420-1 for receiving the correspondingly arcuately shaped slider bar 1422 (see FIG. 29-3). The receiver also includes a slot 1425 that retains an adjustment knob 1450.

The slider bar 1422 is fed into the channel 1420-1 of the receiver 1420, and the adjustment knob 1450 is fed into the receiver 1420 via a void at a top end of the slot 1425 adjacent the forehead end. The post member 1456 of the adjustment knob 1450 then clips into the slot 1425. In contrast to the forehead support 10G, the adjustment knob 1450 clips into place from the top of the receiver 1420 rather than the bottom. Also, the receiver 1420 is fully enclosed at its bottom, whereas the receiver 1320 described above had an open configuration at its bottom.

When coupled, the gear 1454 provided on the adjustment knob 1450 engages gear teeth positioned on the topside of the slider bar 1422. Thus, turning of the adjustment knob 1450 causes adjustable movement of the slider bar 1422. As illustrated, the head 1447 of the adjustment knob 1450 includes grooves or finger grips 1449, e.g., 2, 4, or 6, that make the knob 1450 easier to operate (see FIG. 29-1).

As illustrated, the slider bar 1422 has generally c-shaped cross-section configuration, and the side walls 1429 of the slider bar 1422 are supported on outer guide flanges 1423 that provide restraint against downward movement of the slider bar 1422.

Advantages of the forehead support 10H include ease of molding and good overall aesthetics.

XV. Ninth Illustrated Embodiment of Forehead Support

Figures 1, 30:
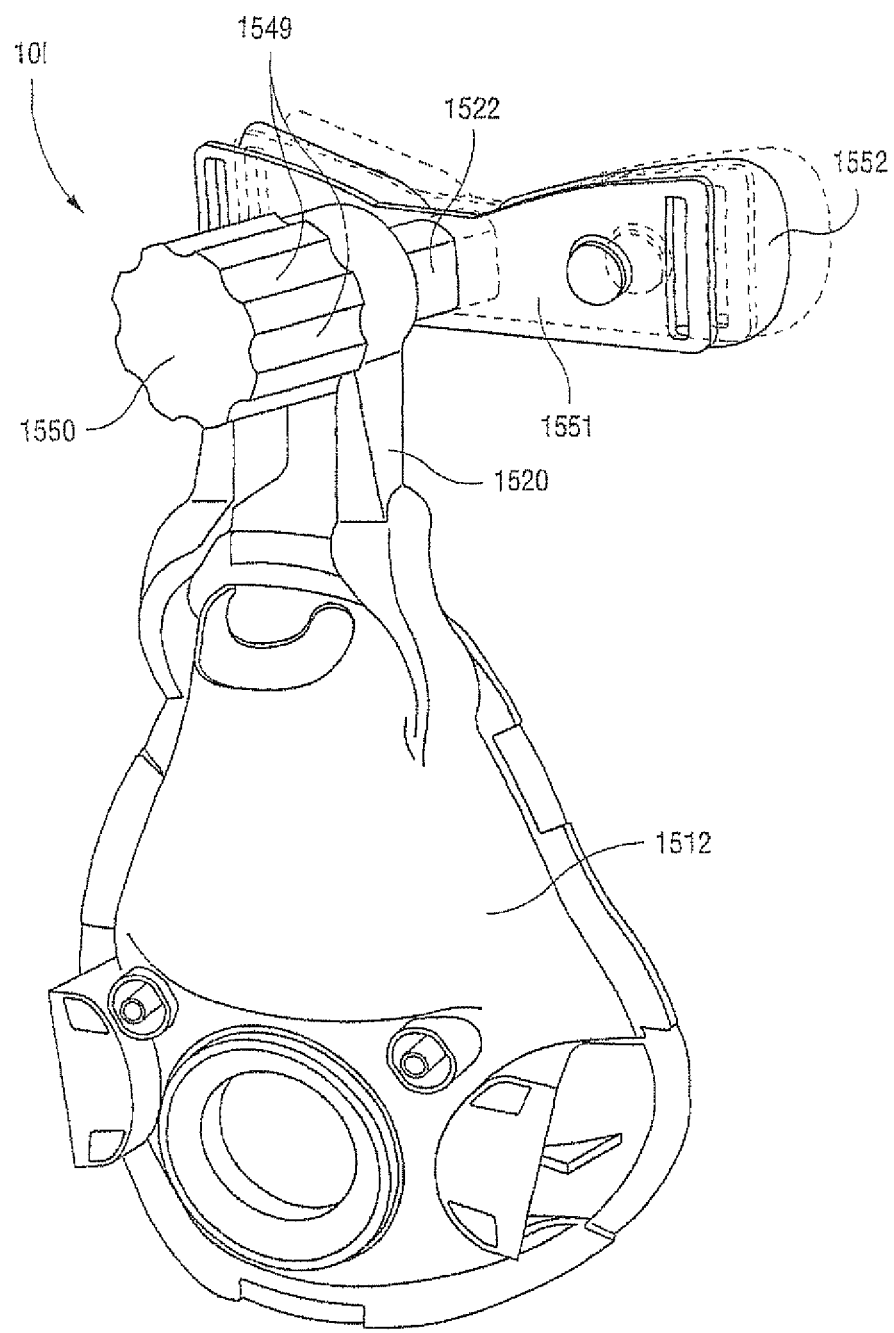
Figures 2, 30:
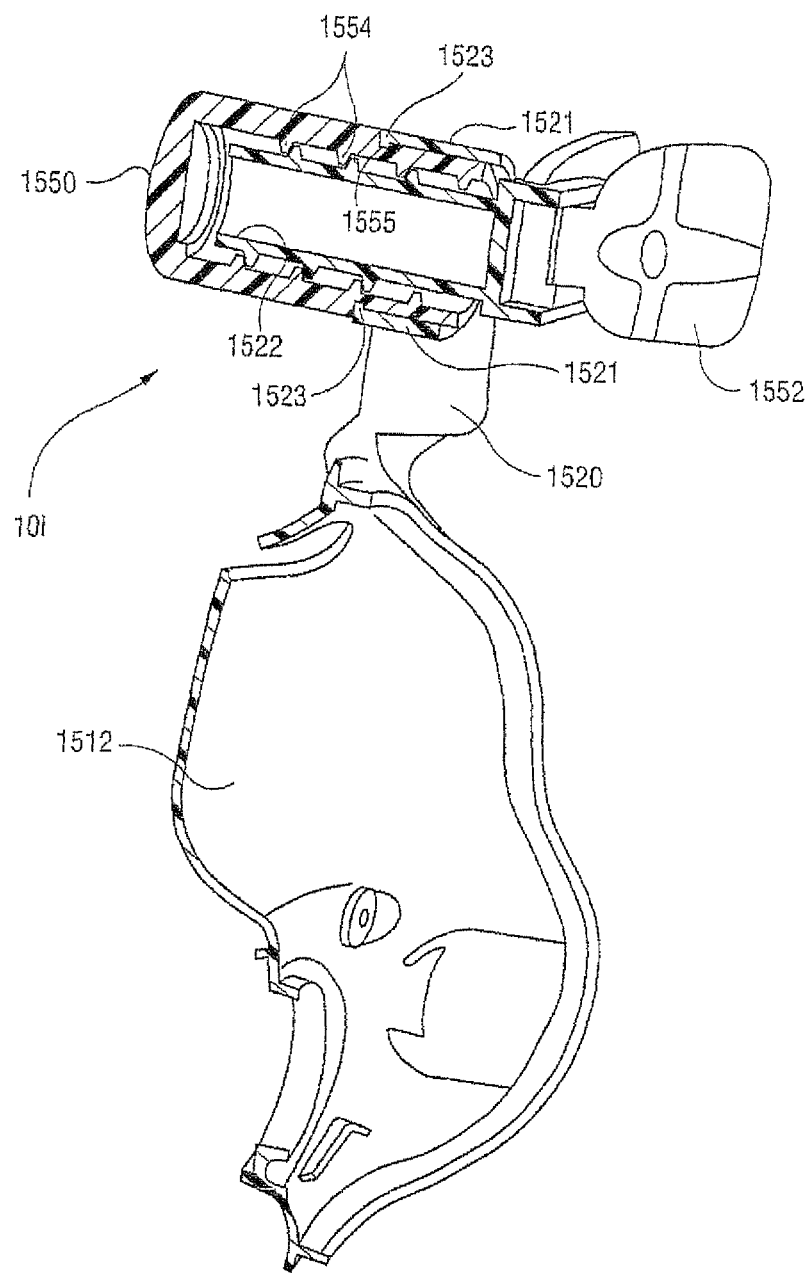
Figures 3, 30:
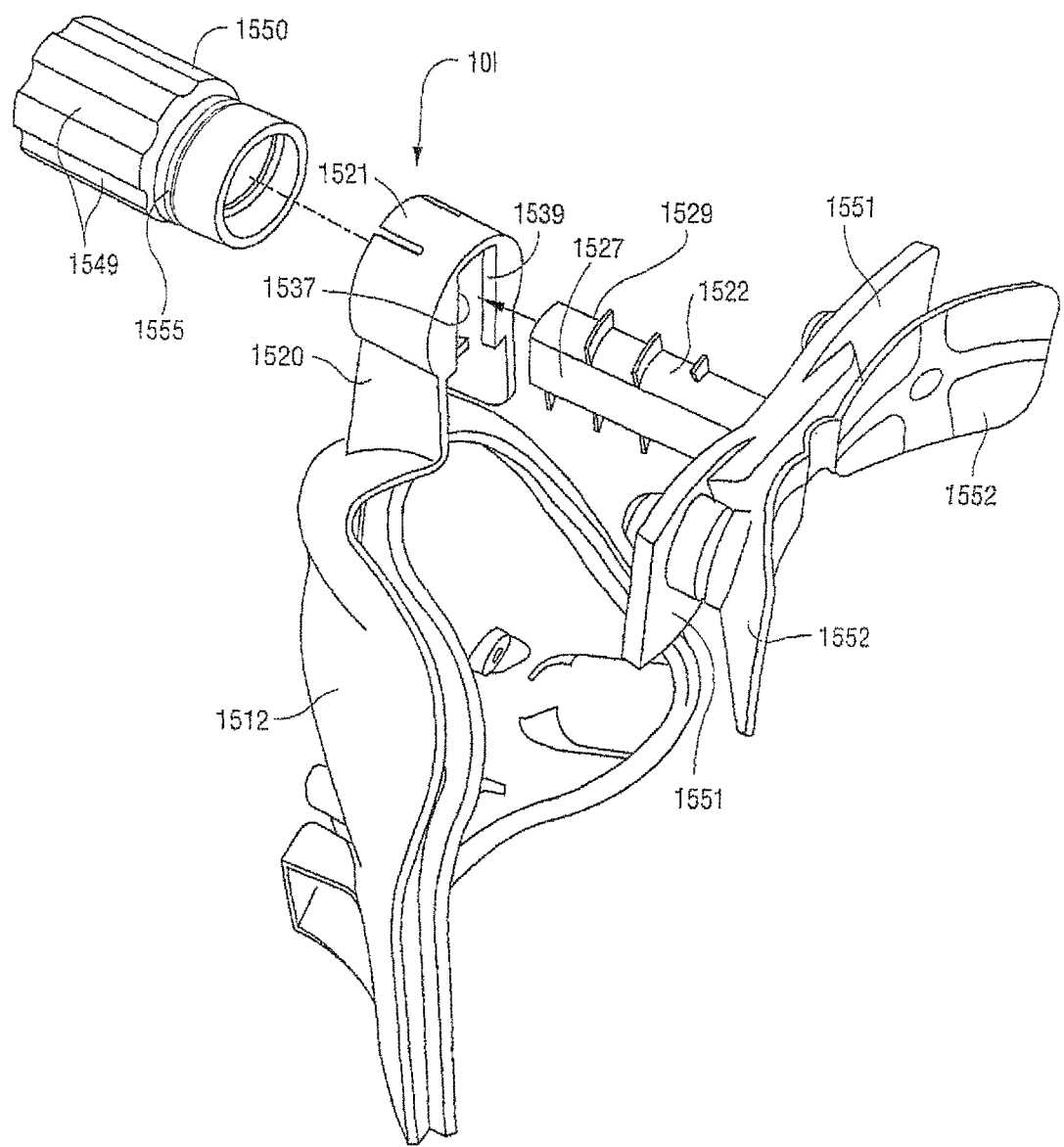

FIGS. 30-1 to 30-3 illustrate a FMA including a forehead support 10I according to another embodiment of the present invention. In this embodiment, the forehead support 10I uses a screw-type actuator to move the forehead support along a generally linear path.

As illustrated, the forehead support 10I includes a support 1520 provided to the mask frame 1512 for supporting an adjustment knob 1550. The adjustment knob 1550 includes internal threads 1554 and clips onto the support 1520 with a snap-fit. Specifically, the support 1520 includes opposing resilient arm members 1521 that each provide a protrusion 1523 on a free end thereof. The adjustment knob 1550 includes an annular groove 1555. When the adjustment knob 1550 is assembled to the support 1520, the resilient arm members 1521 deflect outwardly until the protrusions 1523 snap into the groove 1555 (see FIGS. 30-2 and 30-3). The adjustment knob 1550 receives a threaded shaft 1522 therein such that the internal threads 1554 are intermeshed with the threaded shaft 1522. The threaded shaft 1522 is joined to forehead cushion support plates 1551 that carry forehead cushions 1552. In the illustrated embodiment, the threaded shaft 1522 has a tubular cross-section with D-shaped ends. This arrangement of the shaft 1522 provides flat surfaces 1527, 1529 that engage flat surfaces 1537, 1539 provided on the support 1520. The flat surfaces 1537, 1539 of the support 1520 guide the flat surfaces 1527, 1529 of the shaft 1522 in use and also prevent rotation of the support plates 1551 as the adjustment knob 1550 is rotated. However, other cross-sectional configurations are possible, e.g., circular.

When the knob 1550 is rotated, the threaded shaft 1522 extends from or retracts into the knob 1550 which causes adjustable movement of the forehead cushions 1552. As illustrated, the adjustment knob 1550 includes grooves or finger grips 1549 that make the knob 1550 easier to operate (see FIGS. 30-1 and 30-3). In the illustrated embodiment, the forehead support 10I has a straight line of motion. However, the forehead support 10I may include a worm drive with slight curvature as an alternative embodiment.

Advantages of the forehead support 10I include ease of molding, strength, a straightforward adjustment mechanism, and good overall aesthetics.

XVI. Tenth Illustrated Embodiment of Forehead Support

Figures 1, 31:
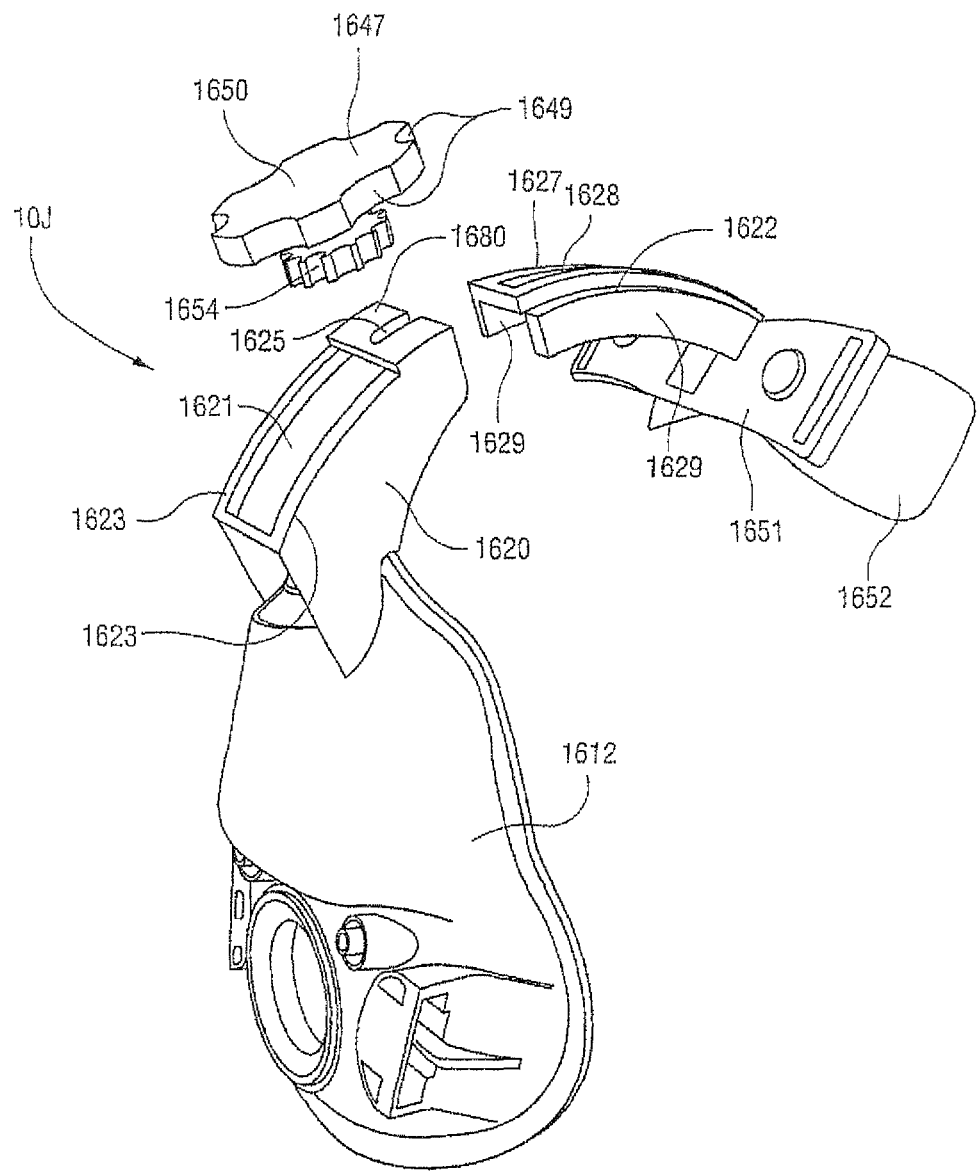
Figures 2, 31:
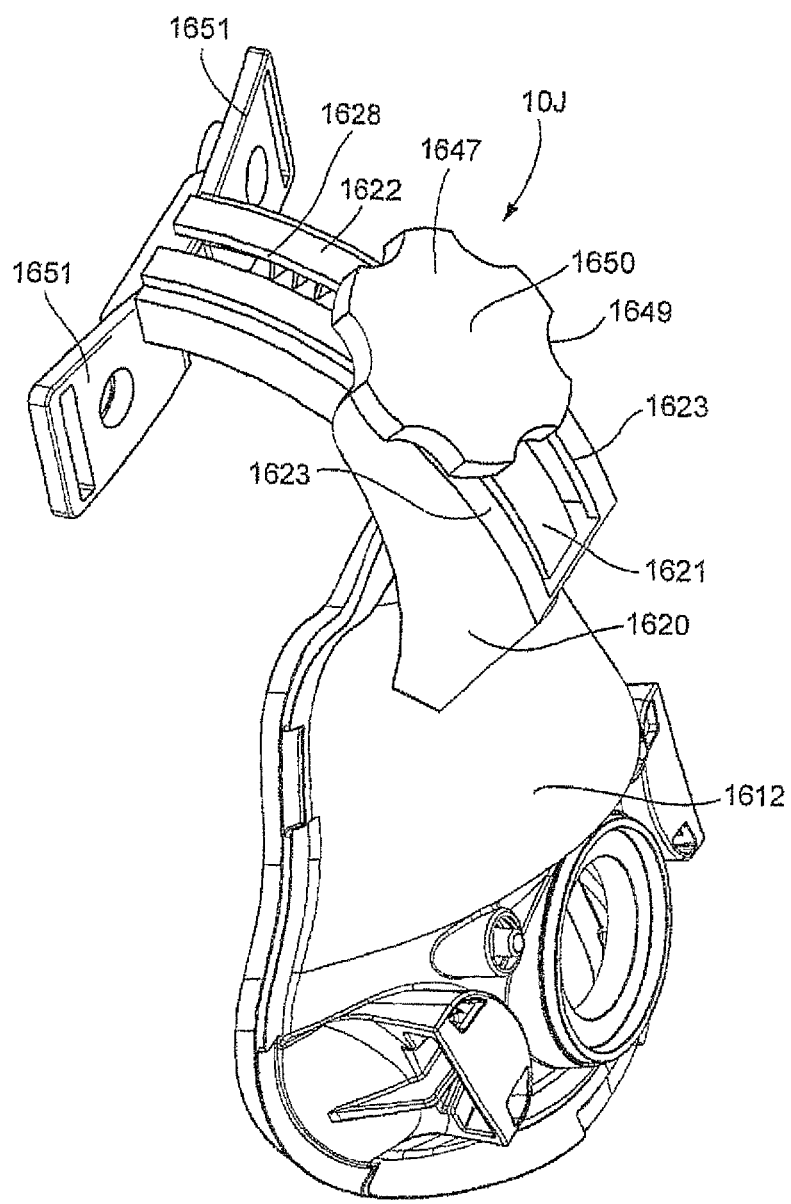
Figures 3, 31:
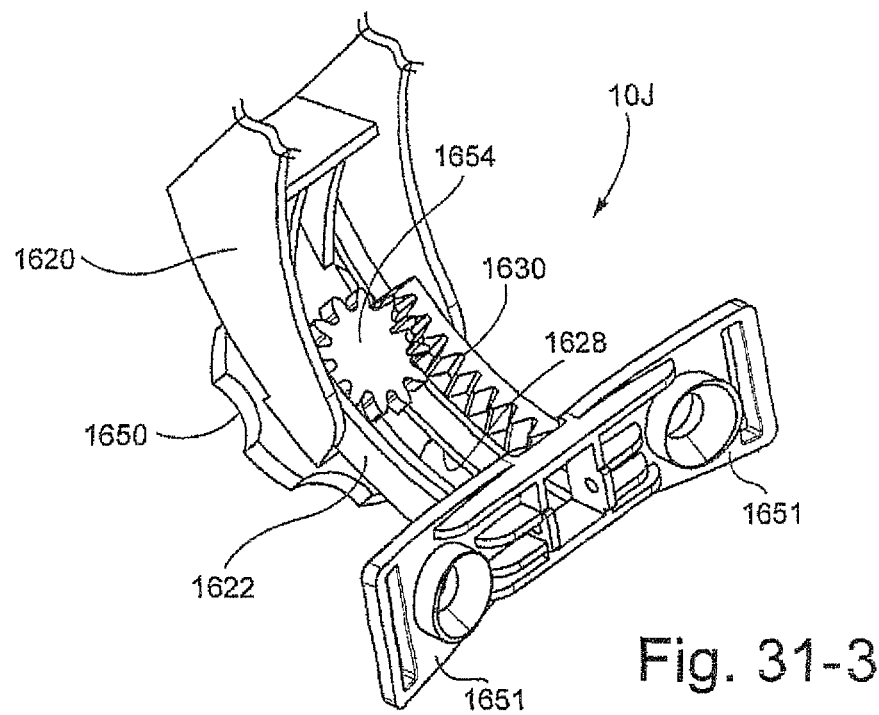
Figures 4, 31:
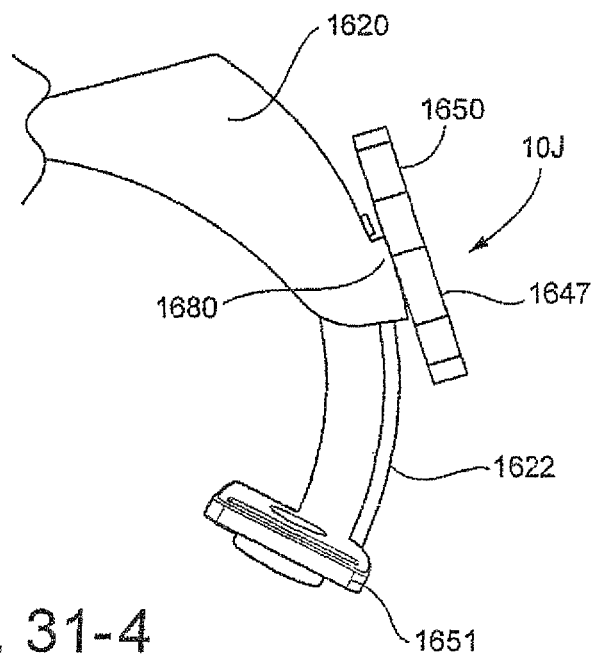
Figures 5, 31:
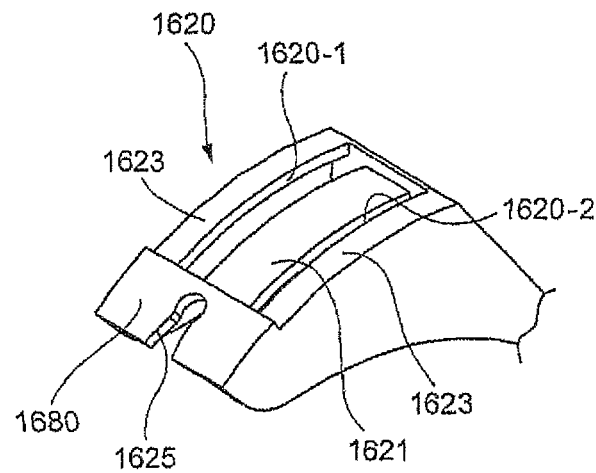
Figures 6, 31:
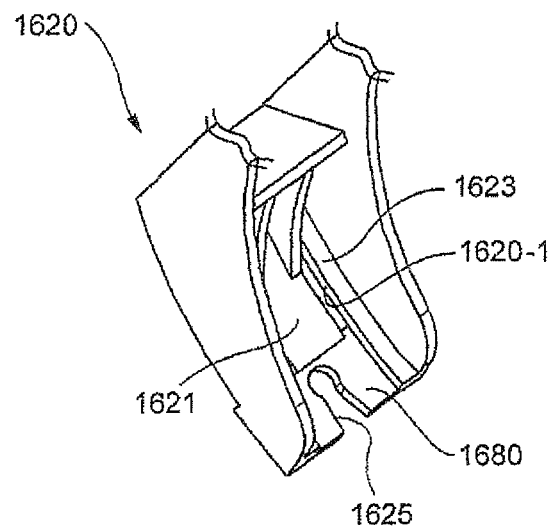
Figures 7, 31:
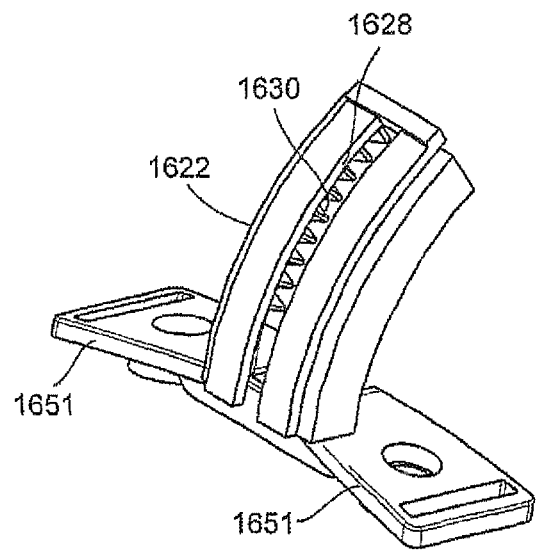
Figures 8, 31:
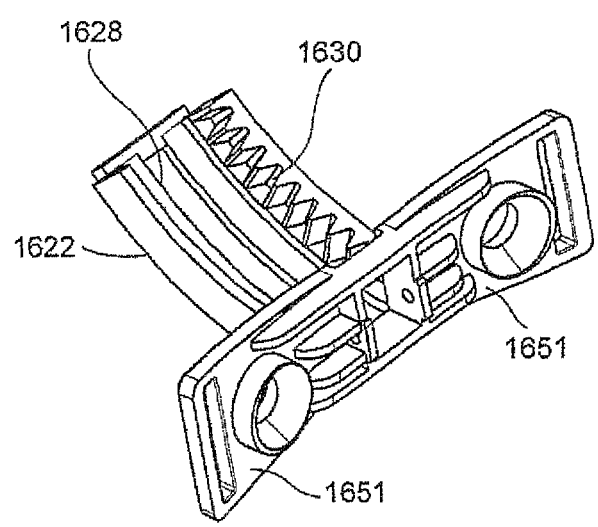

FIGS. 31-1 to 31-8 illustrates a FMA including a forehead support 10J according to another embodiment of the present invention. The forehead support 10J includes a receiver 1620 provided to the mask frame 1612 for receiving a slider bar 1622. The slider bar 1622 is joined to forehead cushion support plates 1651 that carry forehead cushions 1652.

Similar to the forehead support 10E, the receiver 1620 has a split track including spaced-apart arcuately shaped channels 1620-1 and 1620-2 that define an elongated central finger 1621 and outer guide rails 1623 (see FIGS. 31-5 and 31-6). In contrast, the receiver 1620 is squarer in shape and includes a bridge 1680 between the outer guide rails 1623 that provides a slot 1625 for retaining an adjustment knob 1650. The bridge 1680 may improve the strength of the receiver 1620. In the illustrated embodiment, the split track is molded into the mask frame 1612 and may be molded in a single line of draw.

The slider bar 1622 is fed into the receiver 1620 so that the upper wall 1627 is supported on the central finger 1621 and the side walls 1629 are guided by the outer guide rails 1623. Thus, the central finger 1621 provides restraint against downward movement of the slider bar 1622.

The slider bar 1622 defines a central elongate slot 1628 (see FIGS. 31-7 and 31-8). The adjustment knob 1650 is fed into the slider bar 1622 via a void at one end of the slot 1628 adjacent the forehead end. The post member of the adjustment knob 1650 then clips into the slot 1625 of the bridge 1680. When coupled, the gear 1654 provided on the adjustment knob 1650 engages gear teeth 1630 positioned on the underside of the slider bar 1622 (see FIG. 31-3). Thus, turning of the adjustment knob 1650 causes adjustable movement of the slider bar 1622. As illustrated, the head 1647 of the adjustment knob 1650 includes grooves or finger grips 1649, e.g., 2, 4, or 6, that make the knob 1650 easier to operate.

XVII. Eleventh Illustrated Embodiment of Forehead Support

Figures 1, 32:
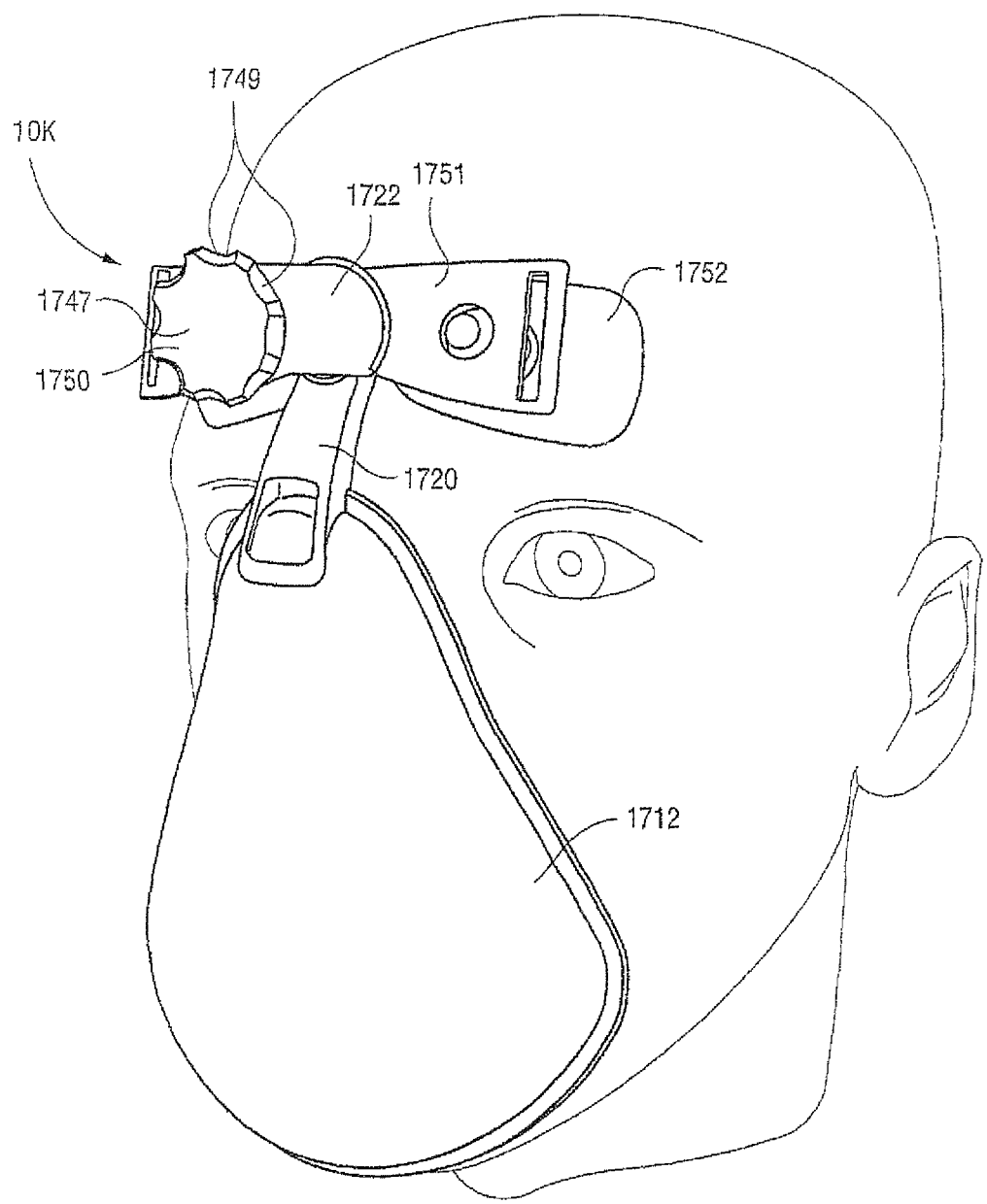
Figures 2, 32:
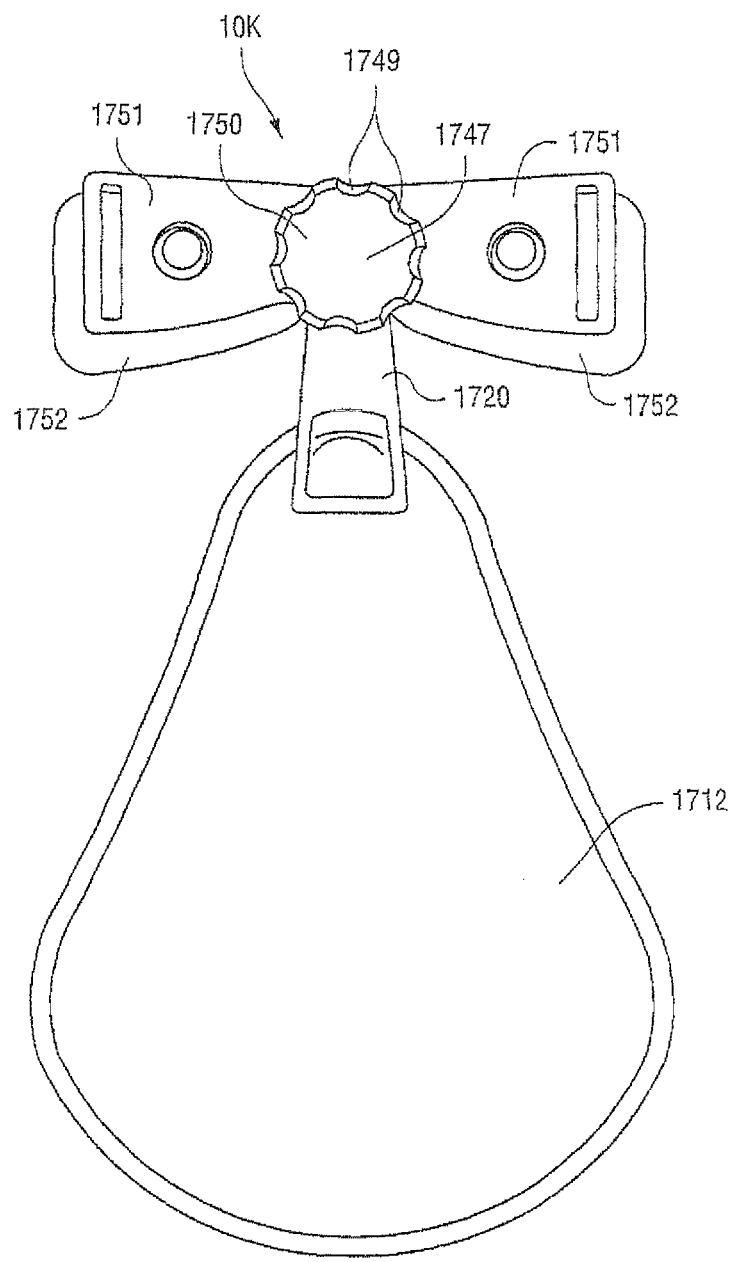
Figures 3, 32:
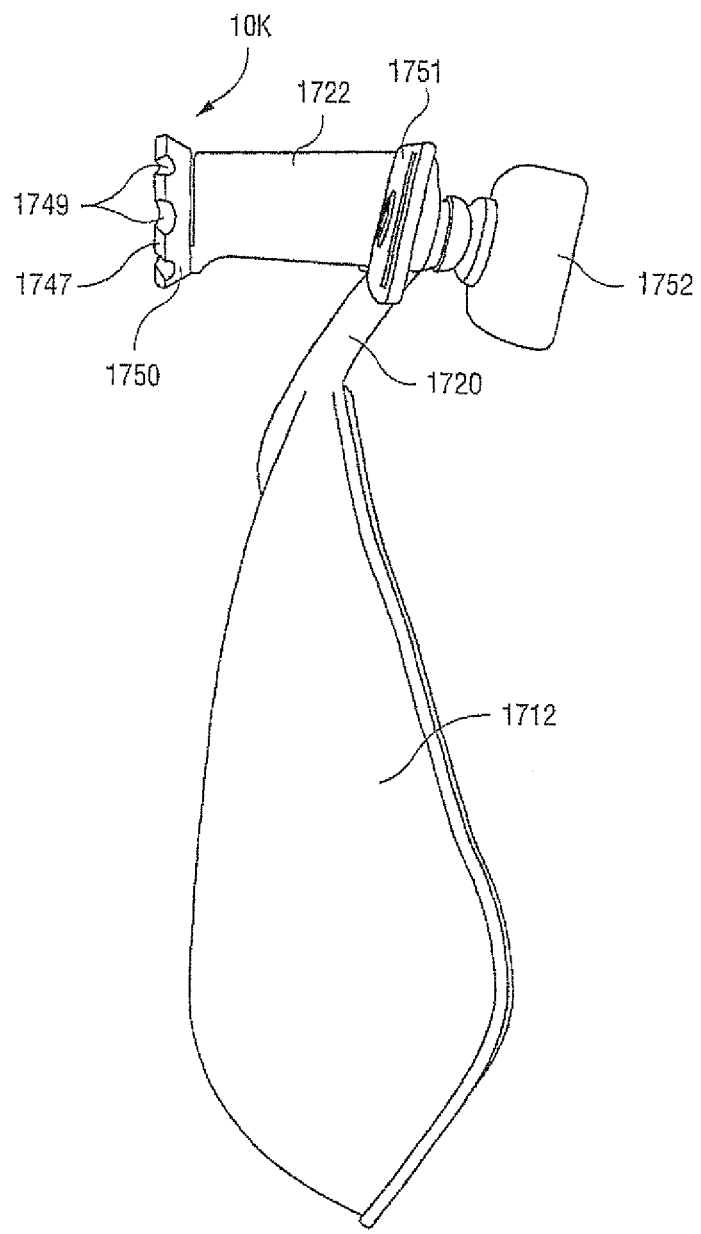
Figures 4, 32:
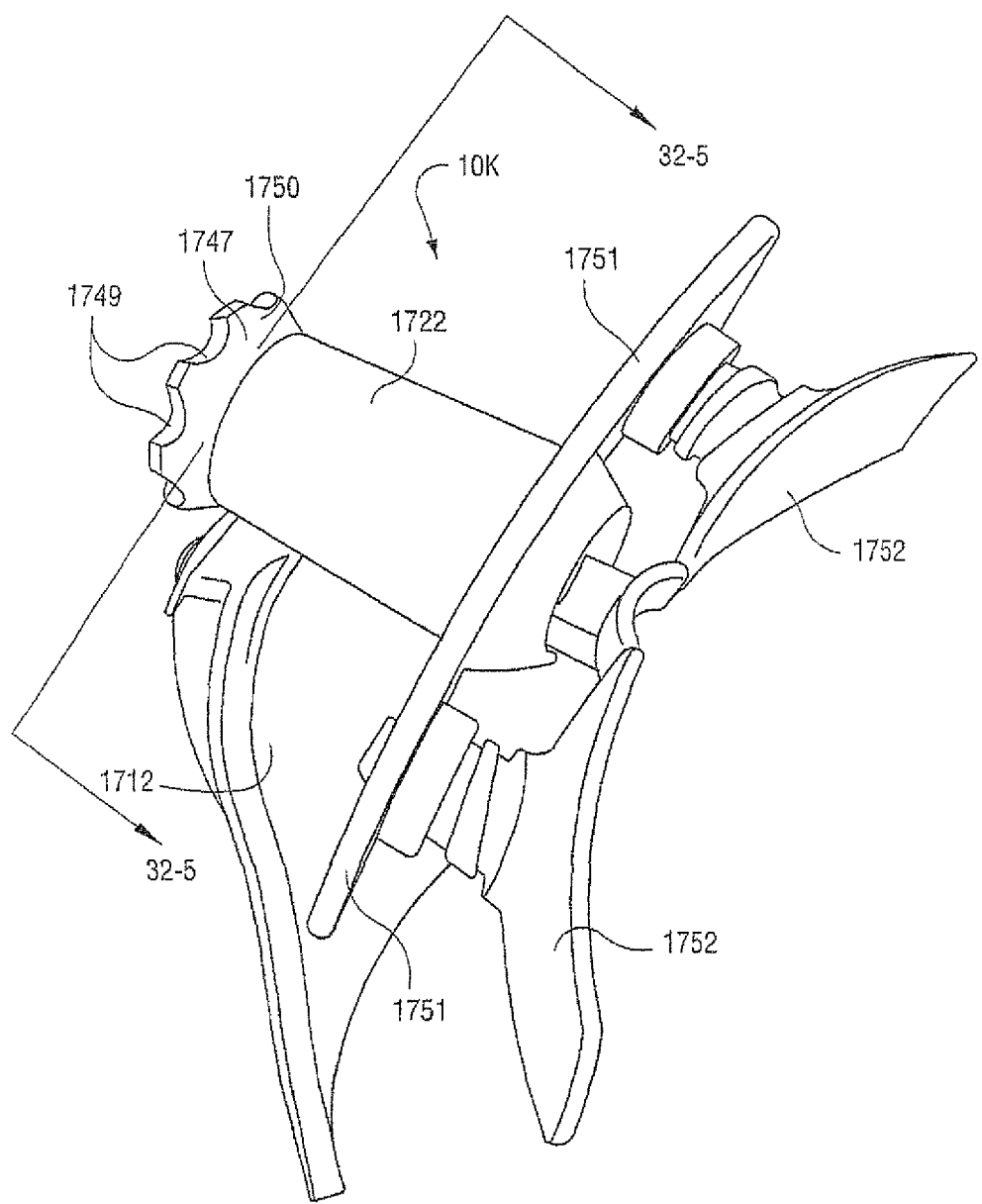
Figures 5, 32:
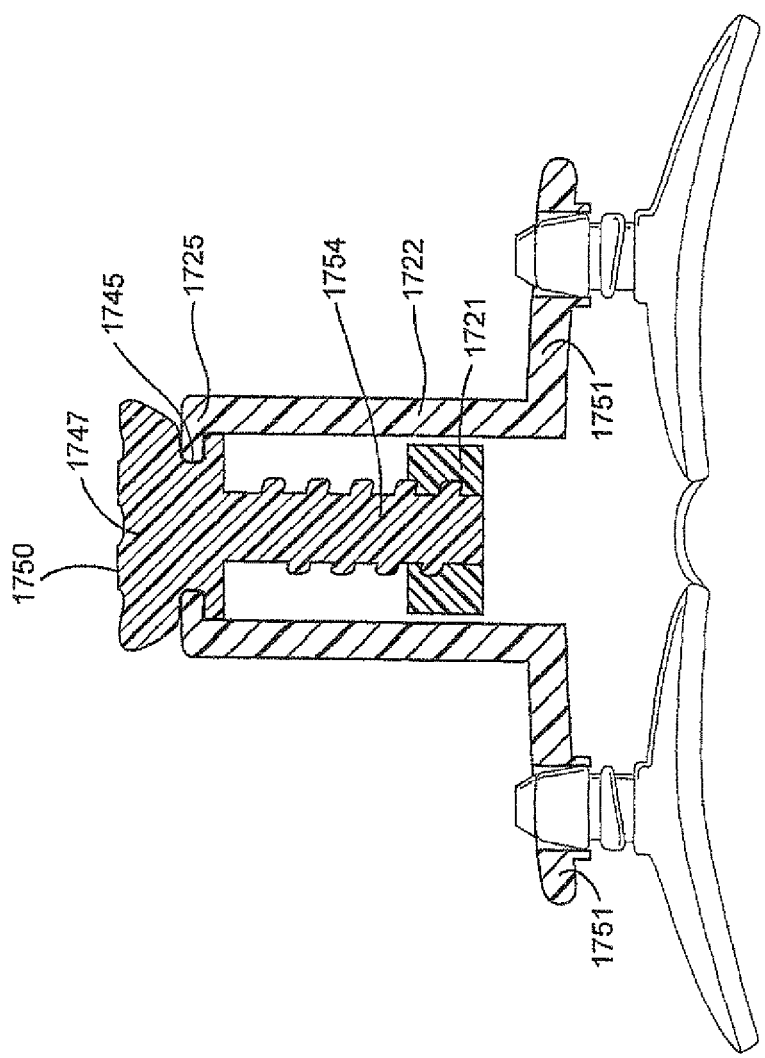

FIGS. 32-1 to 32-6 illustrate a FMA including a forehead support 10K according to another embodiment of the present invention. In this embodiment, the forehead support 10K uses a screw-type actuator to move the forehead support along a generally linear path.

As illustrated, the forehead support 10K includes a support 1720 provided to the mask frame 1712. The support 1720 includes an internally threaded tube portion 1721. The adjustment knob 1750 includes a threaded shaft 1754 that engages within the internally threaded tube portion 1721 such that the threaded shaft 1754 is intermeshed with the internally threaded tube portion 1721 (see FIG. 32-5). The adjustment knob 1750 also engages a tube 1722 joined to forehead cushion support plates 1751 that carry forehead cushions 1752. Specifically, the tube 1722 has a lower open portion 1723 that allows the tube 1722 to fit around the internally threaded tube portion 1721 (see FIG. 32-6). In addition, the end of the tube 1722 has an annular flange 1725 that engages within an annular groove 1745 provided in the head 1747 of the adjustment knob 1750 (see FIGS. 32-5 and 32-6).

When the knob 1750 is rotated, the knob 1750 and the tube 1722 extend or retract from the internally threaded tube portion 1721 of the support 1720 which allows adjustment of the forehead cushions 1752 relative to the frame 1712. Thus, the knob 1750 doesn't move relative to the patient in use. Rather, the frame 1712 is moved relative to the forehead support. As illustrated, the head 1747 of the adjustment knob 1750 includes grooves or finger grips 1749 that make the knob 1750 easier to operate.

XVIII. Twelfth Illustrated Embodiment of Forehead Support

Figures 1, 33:
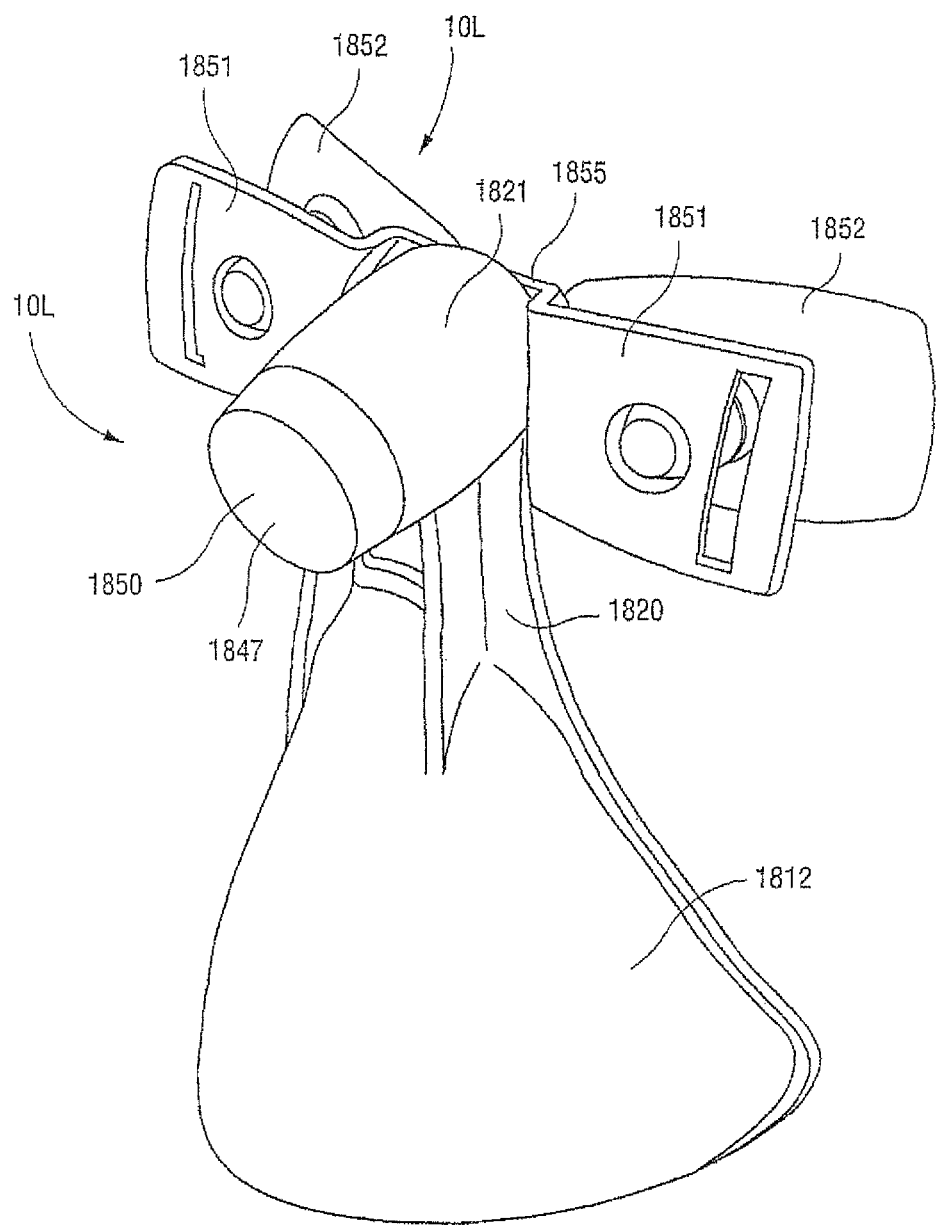
Figures 2, 33:
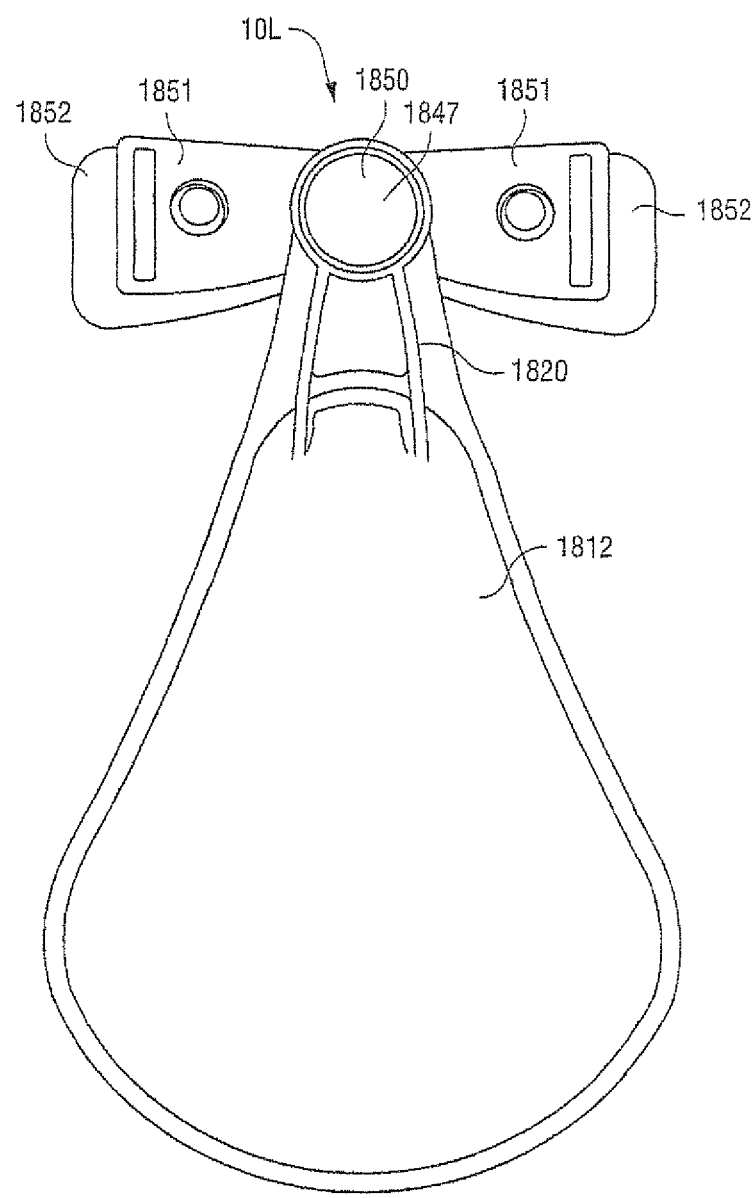
Figures 3, 33:
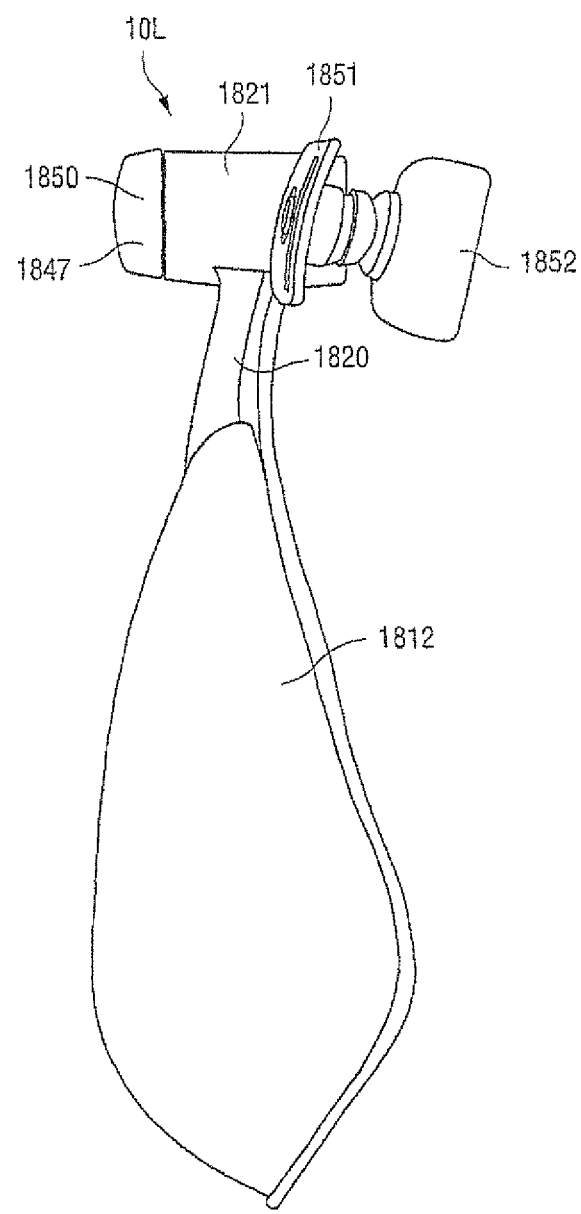
Figures 4, 33:
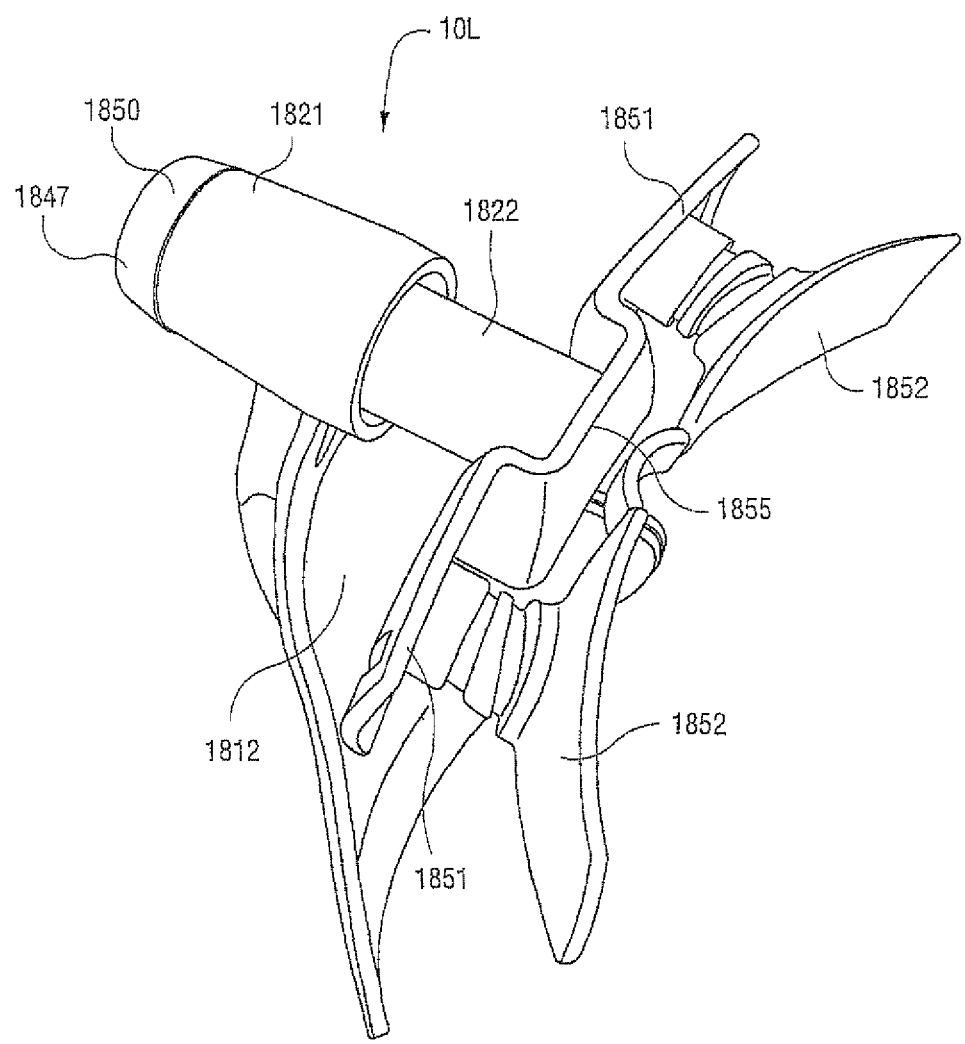
Figures 5, 33:
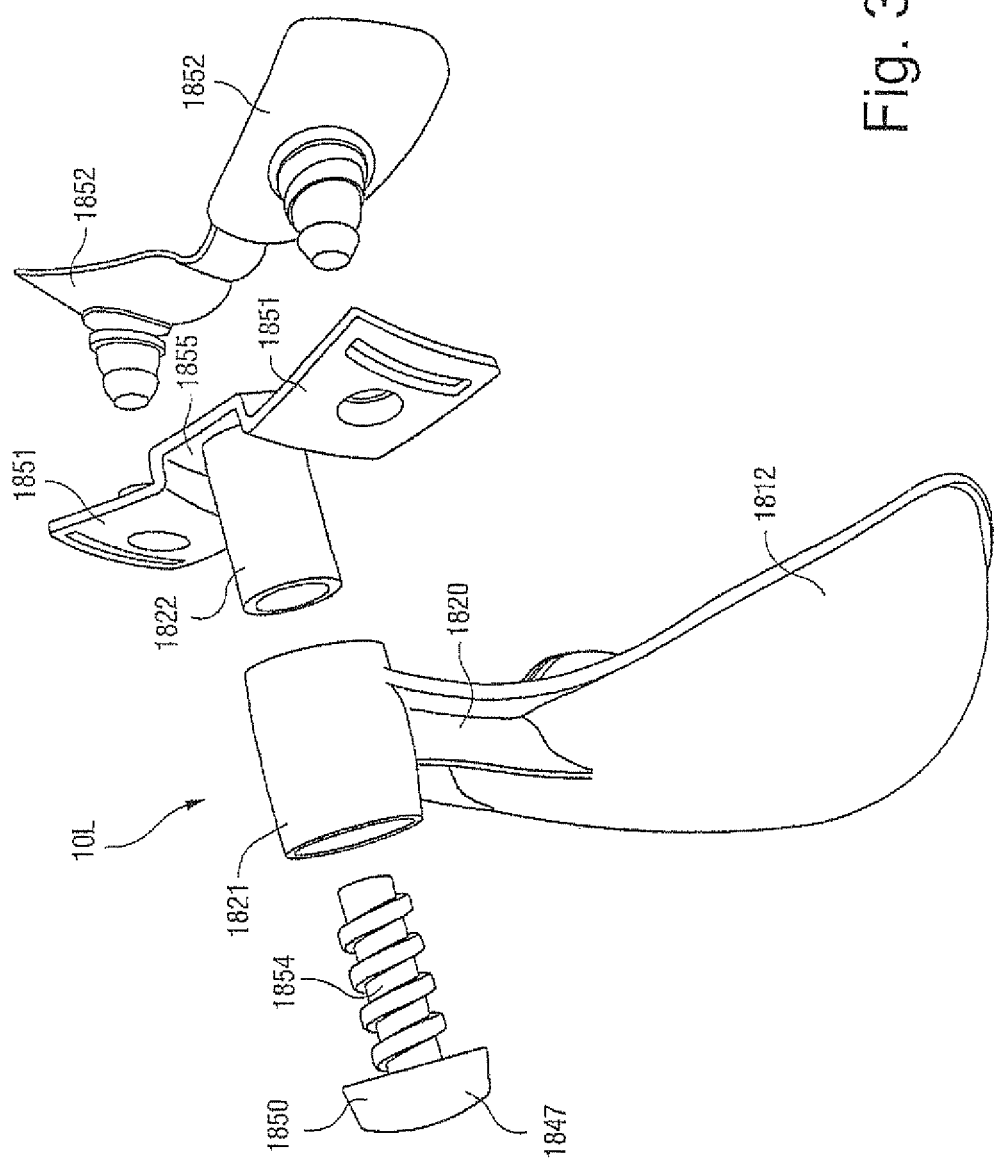
Figures 6, 33:
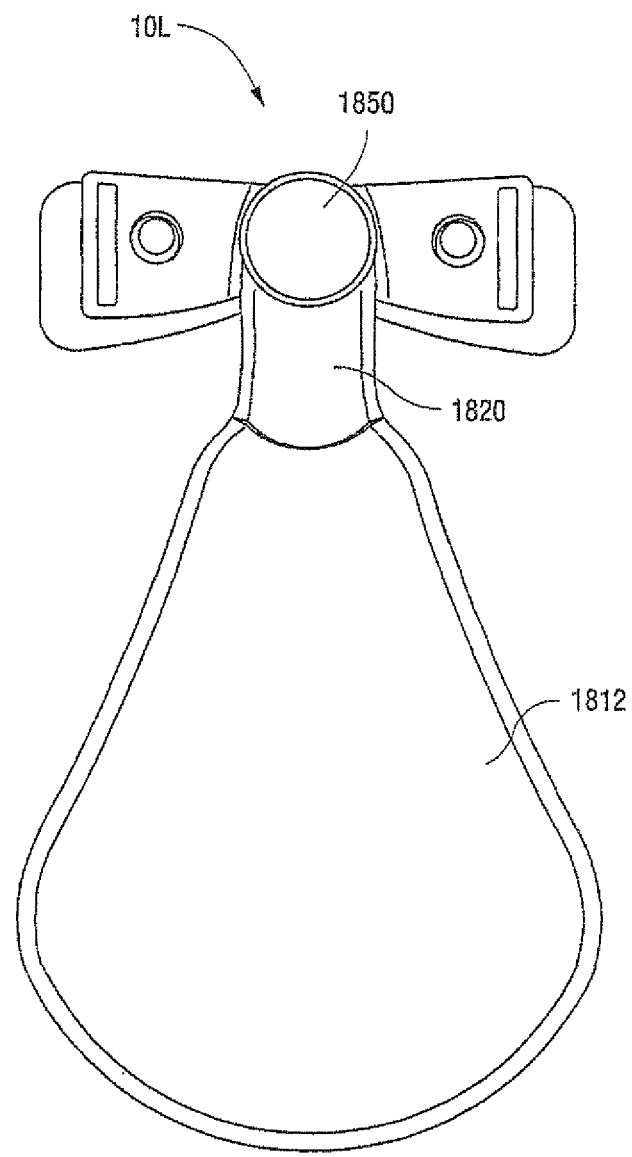

FIGS. 33-1 to 33-6 illustrate a FMA including a forehead support 10L according to another embodiment of the present invention. In this embodiment, the forehead support 10L uses a screw-type actuator to move the forehead support along a generally linear path.

As illustrated, the forehead support 10L includes a support 1820 provided to the mask frame 1812 for supporting an adjustment knob 1850. The adjustment knob 1850 includes a threaded shaft 1854 that extends through a tube portion 1821 of the support 1820. The threaded shaft 1854 also engages within an internally threaded tube 1822 such that the threaded shaft 1854 is intermeshed with the internally threaded tube 1822. The internally threaded tube 1822 is joined to forehead cushion support plates 1851 that carry forehead cushions 1852.

When the knob 1850 is rotated, the internally threaded tube 1822 extends or retracts from the threaded shaft 1854 of the knob 1850 which causes adjustable movement of the forehead cushions 1852. Thus, the knob 1850 does not move relative to the frame 1812 but does move relative to the patient. In an embodiment, the head 1847 of the adjustment knob 1850 may include one or more markings, e.g., company name.

As illustrated, the support plates 1851 may include a recessed central support 1855 to conserve space. Also, the nut and bolt type assembly allows easy cleaning and assembly/disassembly. In an embodiment, the support 1820 may include a more enclosed configuration (such as the support 1820 shown in FIG. 33-6) to facilitate cleaning of the support 1820.

XIX. Thirteenth Illustrated Embodiment of Forehead Support

Figures 1, 34:
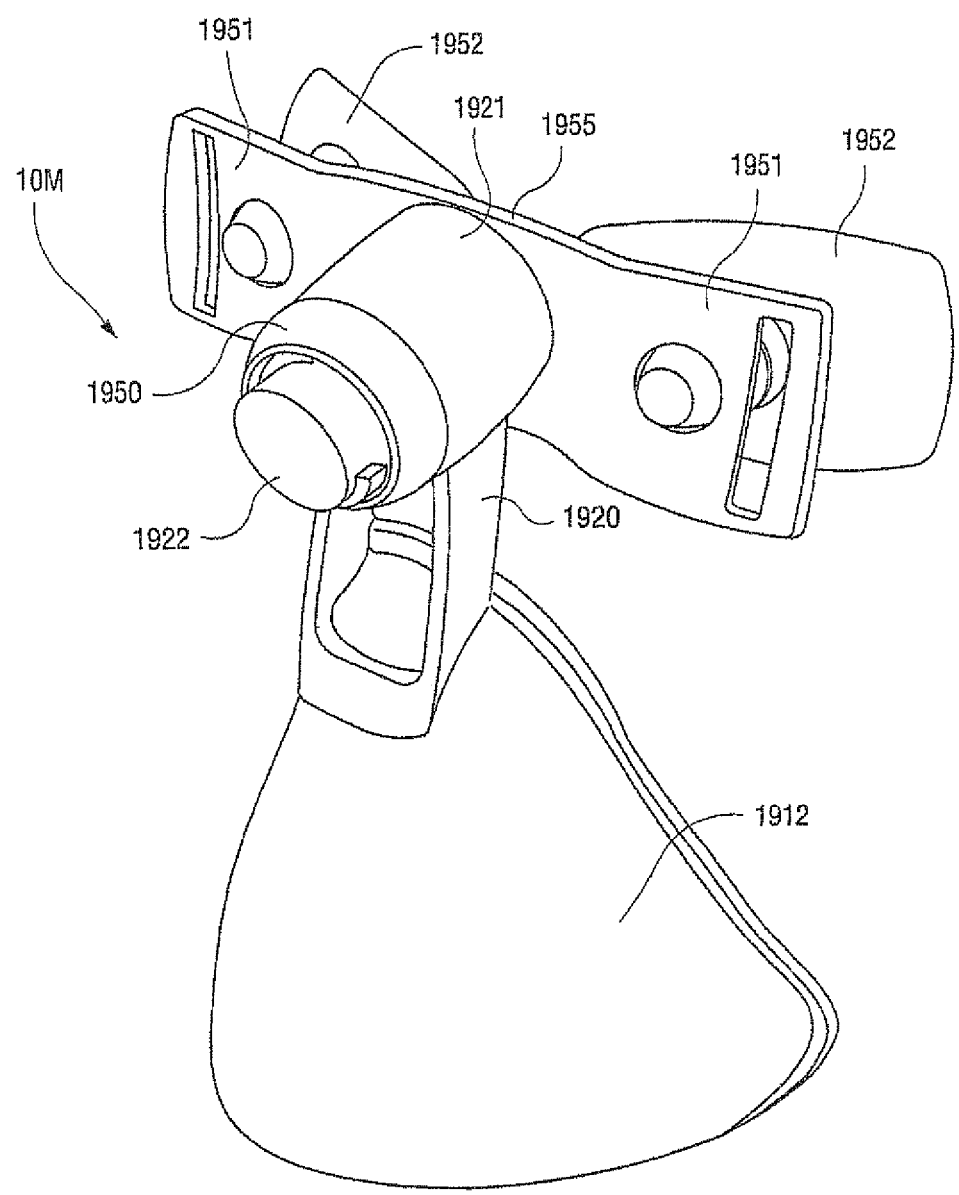
Figures 2, 34:
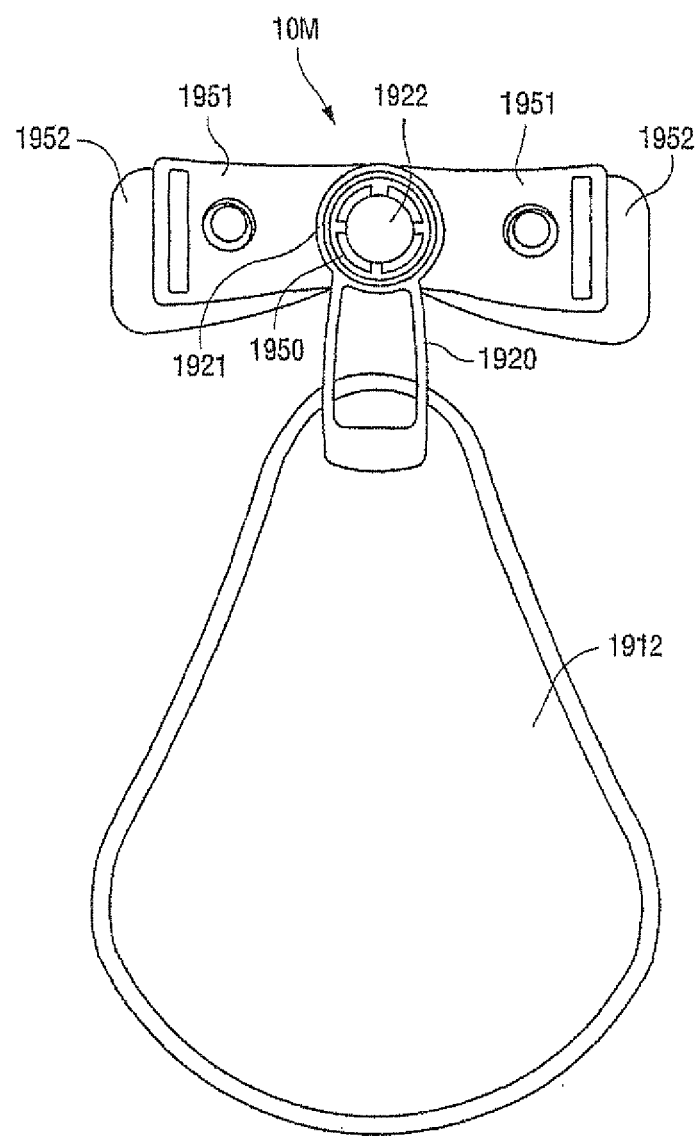
Figures 3, 34:
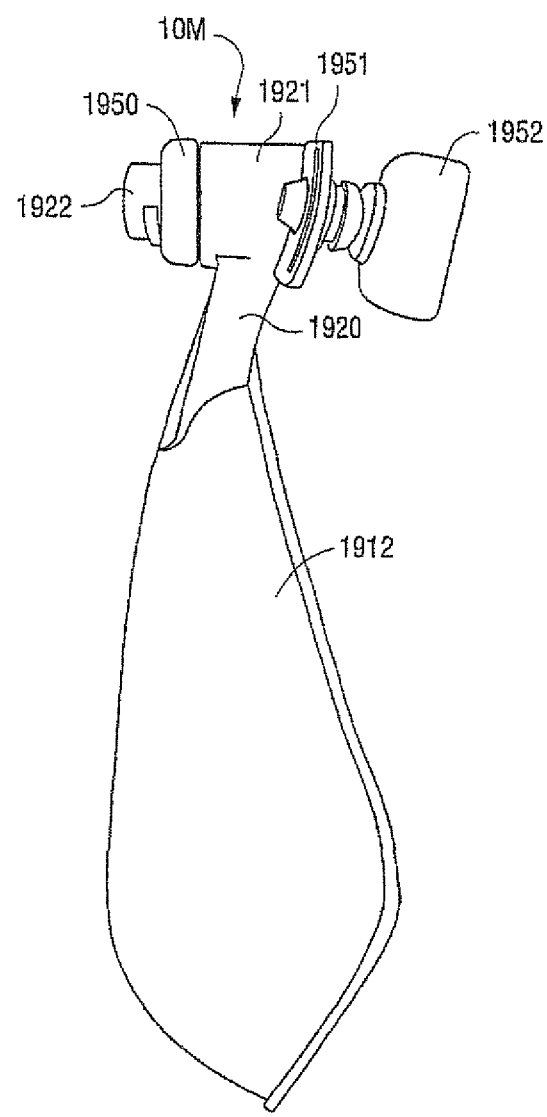
Figures 4, 34:
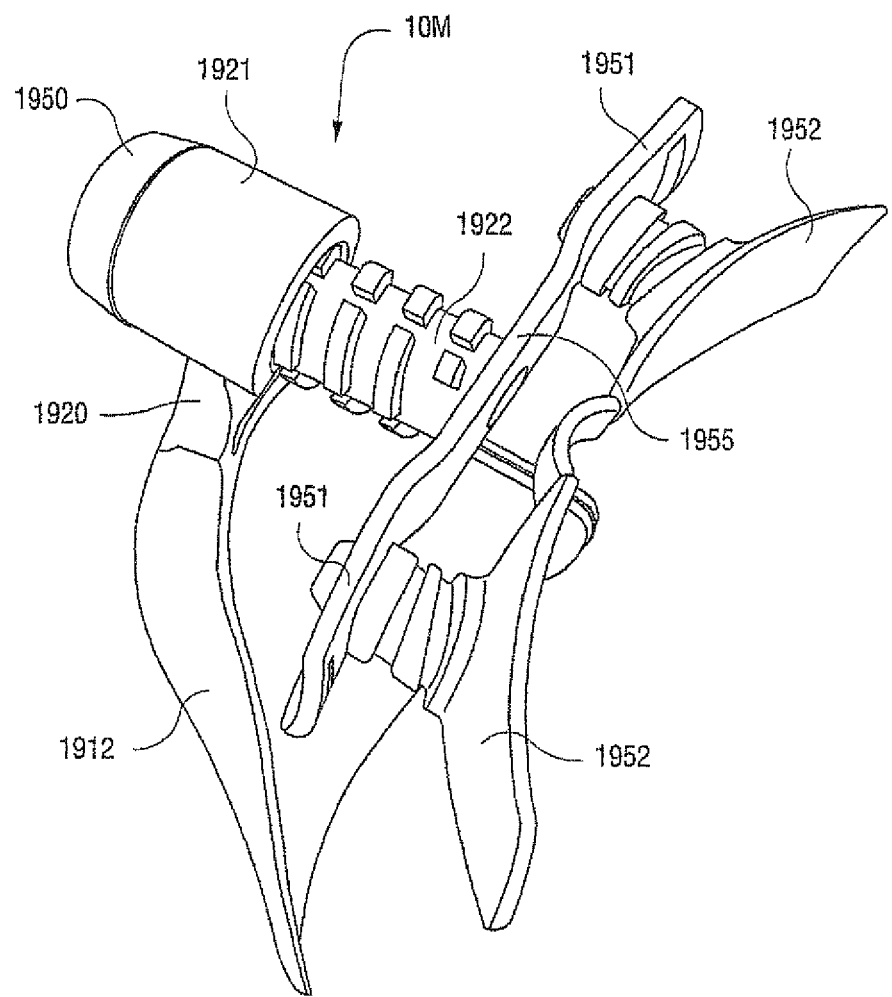
Figures 5, 34:
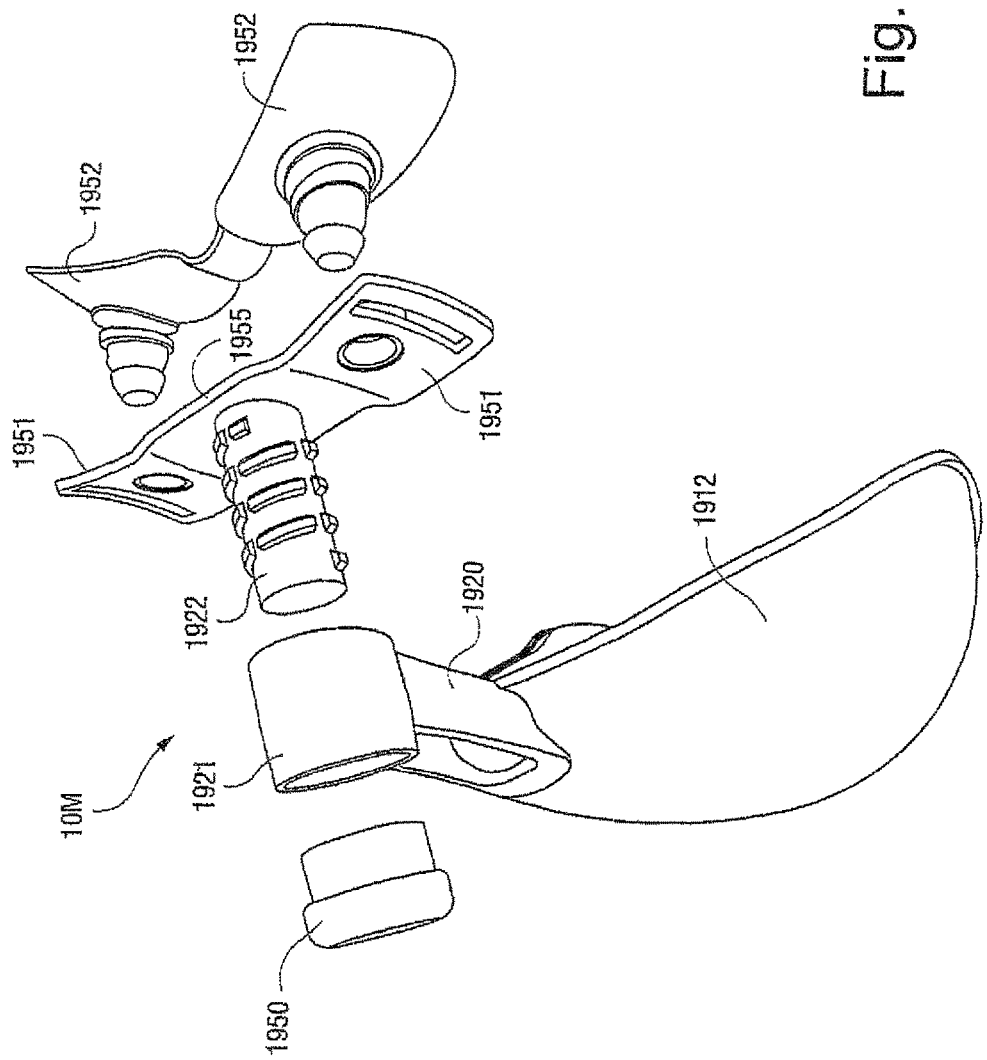

FIGS. 34-1 to 34-5 illustrate a FMA including a forehead support 10M according to another embodiment of the present invention. In this embodiment, the forehead support 10M uses a screw-type actuator to move the forehead support along a generally linear path.

As illustrated, the forehead support 10M includes a support 1920 provided to the mask frame 1912 for supporting an adjustment ring 1950. The adjustment ring 1950 includes internal threads and has a reduced diameter that extends into a tube portion 1921 of the support 1920. A threaded shaft 1922 (FIG. 34-4) extends through the tube portion 1921 and the adjustment ring 1950 such that the internal threads of the adjustment ring 1950 are intermeshed with the threaded shaft 1922. The threaded shaft 1922 is joined to forehead cushion support plates 1951 that carry forehead cushions 1952.

When the adjustment ring 1950 is rotated, the threaded shaft 1922 extends or retracts from the adjustment ring 1950 which causes adjustable movement of the forehead cushions 1952. Thus, the ring 1950 does not move relative to the frame 1912. As shown in FIGS. 34-1 and 34-3, the threaded shaft 1922 may emerge at the front.

As illustrated, the support plates 1951 may include a recessed central support 1955 to conserve space. Also, this nut and bolt type arrangement makes the assembly compact and reduces the actual and visual bulk.

XX. Fourteenth Illustrated Embodiment of Forehead Support

FIG. 35 illustrates a FMA including a forehead support 10N according to another embodiment of the present invention. In this embodiment, the forehead support 10N uses a screw-type actuator to move the forehead support along a generally linear path.

As illustrated, the forehead support 10N includes a support 2020 provided to the mask frame 2012 for supporting an adjustment knob 2050. The adjustment knob 2050 includes a threaded shaft 2054 that extends through a tube portion 2021 of the support 2020. The threaded shaft 2054 also engages within an internally threaded tube 2022 such that the threaded shaft 2054 is intermeshed with the internally threaded tube 2022. The internally threaded tube 2022 is joined to forehead cushion support plates 2051 that carry forehead cushions 2052.

When the knob 2050 is rotated, the internally threaded tube 2022 extends or retracts from the threaded shaft 2054 of the knob 2050 which causes adjustable movement of the forehead cushions 2052. Thus, the knob 2050 does not move relative to the frame 2012.

As illustrated, the support plates 2051 include a contoured central support 2055 that matches the contour of the tube portion 2021 of the support 2020. Also, the head 2047 of the knob 2050 includes a contour that matches the contour of the tube portion 2021. This arrangement allows the assembly to be retracted into a compact position.

In an embodiment, portions of the knob 2050 may be opaque. Also, the head 2047 of the knob 2050 and the threaded shaft 2054 may be constructed in two parts and permanently or semi-permanently assembled.

XXI. Fifteenth Illustrated Embodiment of Forehead Support

Figures 1, 36:
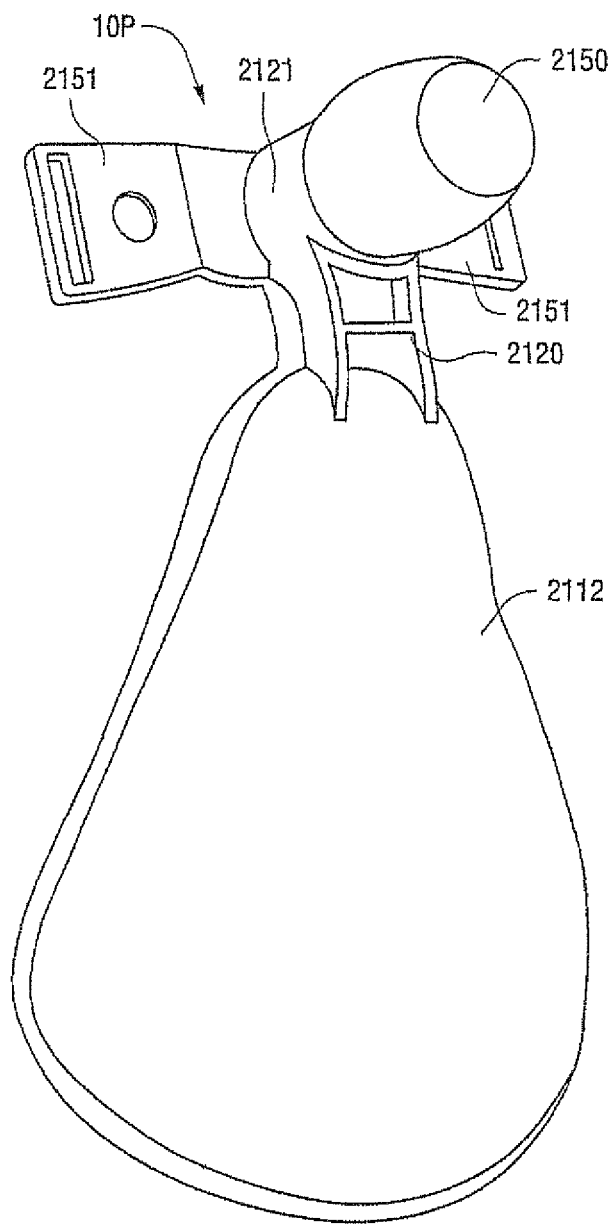
Figures 3, 36:
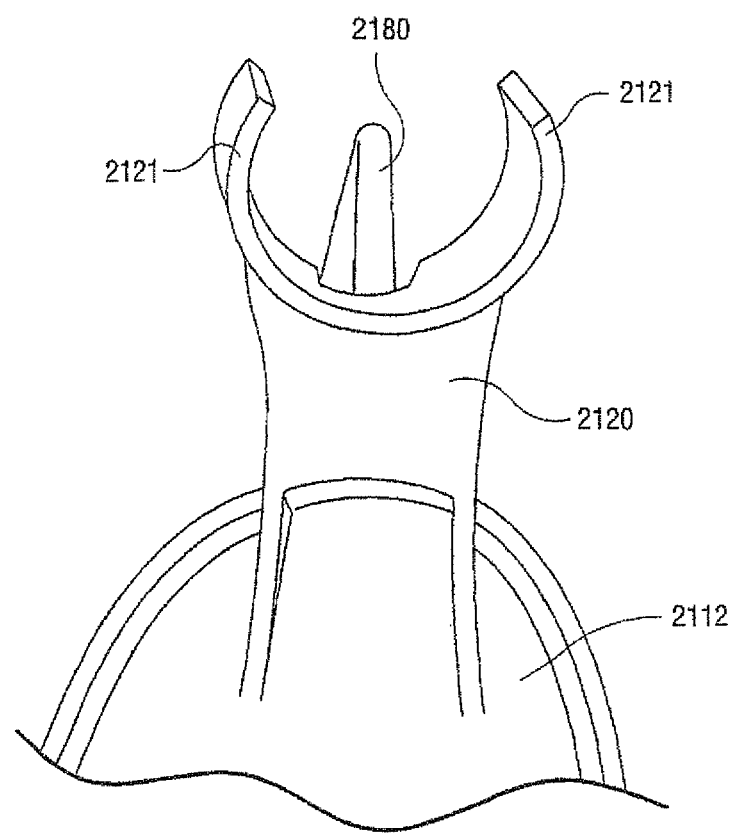
Figures 4, 36:
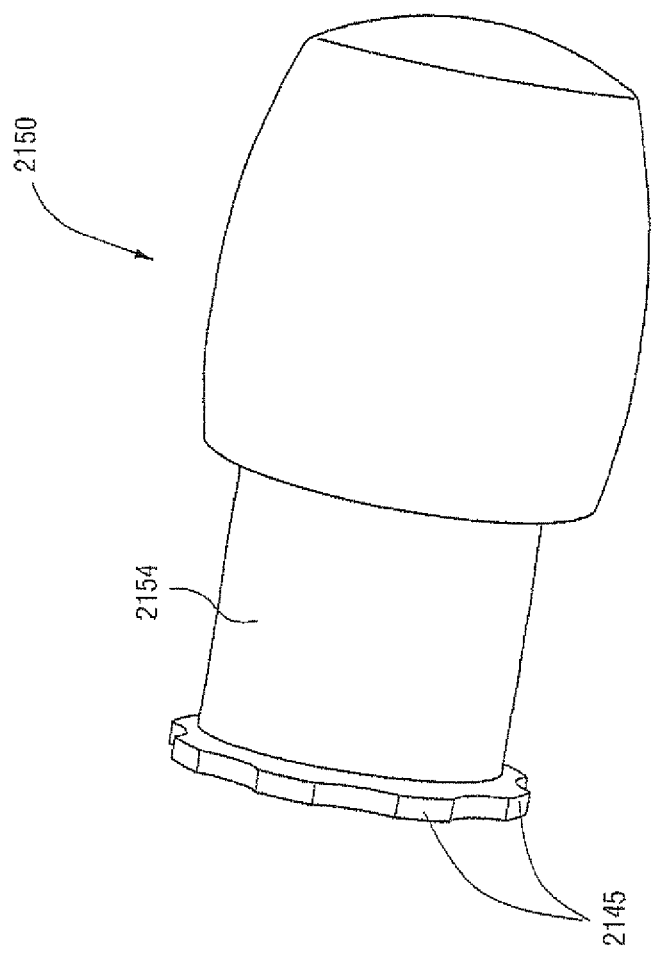
Figures 5, 36:
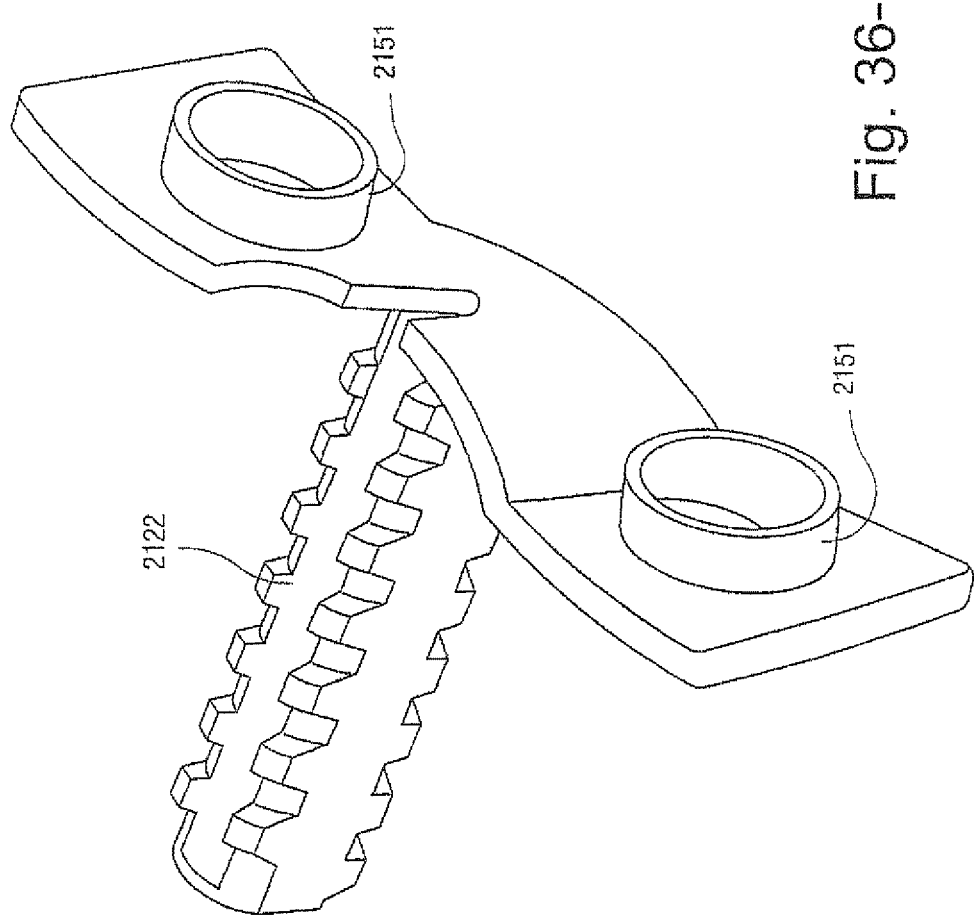

FIGS. 36-1 to 36-5 illustrate a FMA including a forehead support 10P according to another embodiment of the present invention. In this embodiment, the forehead support 10P uses a screw-type actuator to move the forehead support along a generally linear path.

As illustrated, the forehead support 10P includes a support 2120 provided to the mask frame 2112 for supporting an adjustment knob 2150. The adjustment knob 2150 includes internal threads and has a reduced diameter portion 2154 that clips onto retaining arms 2121 of the support 2120 with a snap-fit. The adjustment knob 2150 receives a threaded shaft 2122 therein such that the internal threads of the knob 2150 are intermeshed with the threaded shaft 2122. The threaded shaft 2122 is joined to forehead cushion support plates 2151 that carry forehead cushions.

When the knob 2150 is rotated, the threaded shaft 2122 extends from or retracts into the knob 2150 which causes adjustable movement of the forehead cushions. As illustrated, a prong 2180 may be positioned into a keyway of the threaded shaft 2122 to prevent spinning and hence lock the threaded shaft 2122 in place. Also, the end of the adjustment knob 2150 includes a series of teeth 2145 that engage a base 2147 of the prong 2180 (see FIGS. 36-2 and 36-4). As the knob 2150 is rotated, the teeth 2145 ratchet or click against the base 2147 which provides tactile feedback during rotation.

The knob 2150/threaded shaft 2122 subassembly may be easily assembled/disassembled to the support 2120 with a snap-fit. This allows for easy cleaning. Also, since the knob 2150/threaded shaft 2122 subassembly may be easily disassembled without movement of the threads, the original forehead position may be maintained even when the knob 2150/threaded shaft 2122 subassembly is disassembled from the support 2120.

XXII. Sixteenth Illustrated Embodiment of Forehead Support

Figures 1, 37:
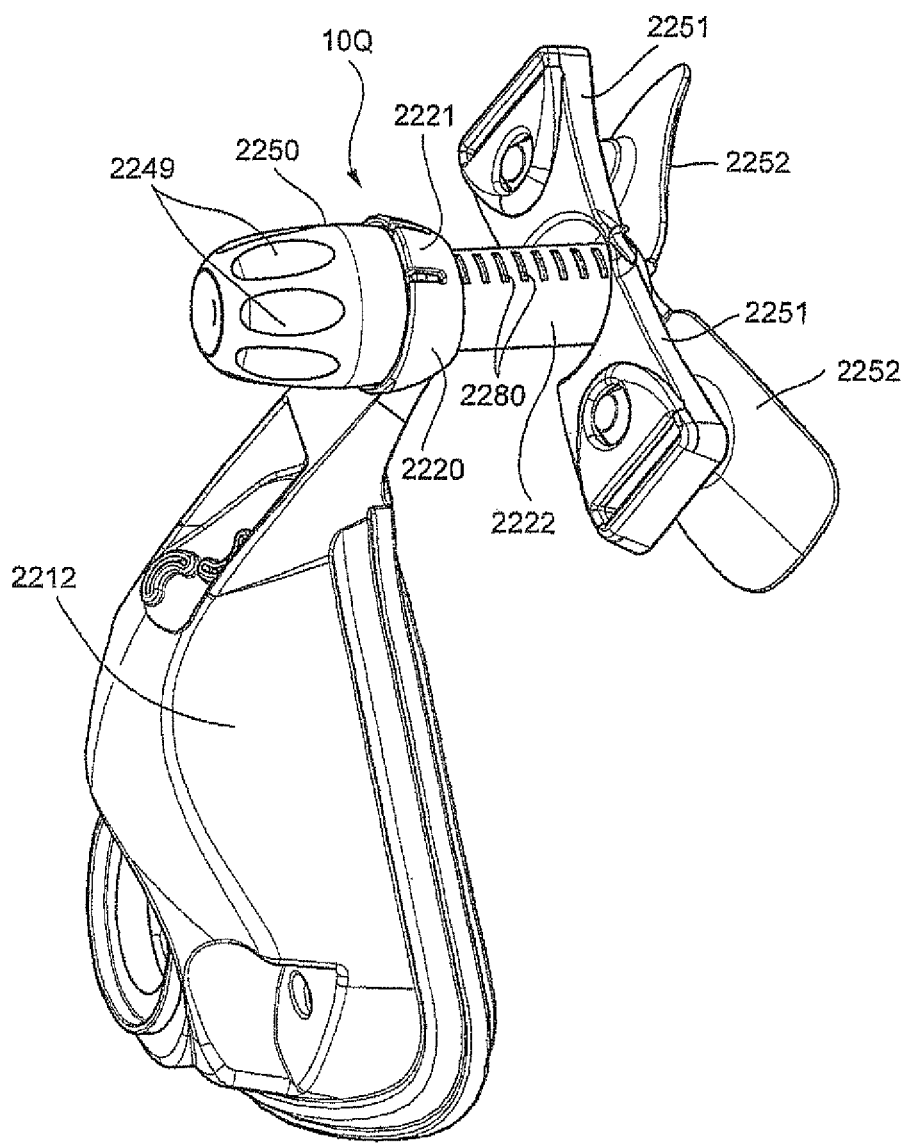
Figures 2, 37:
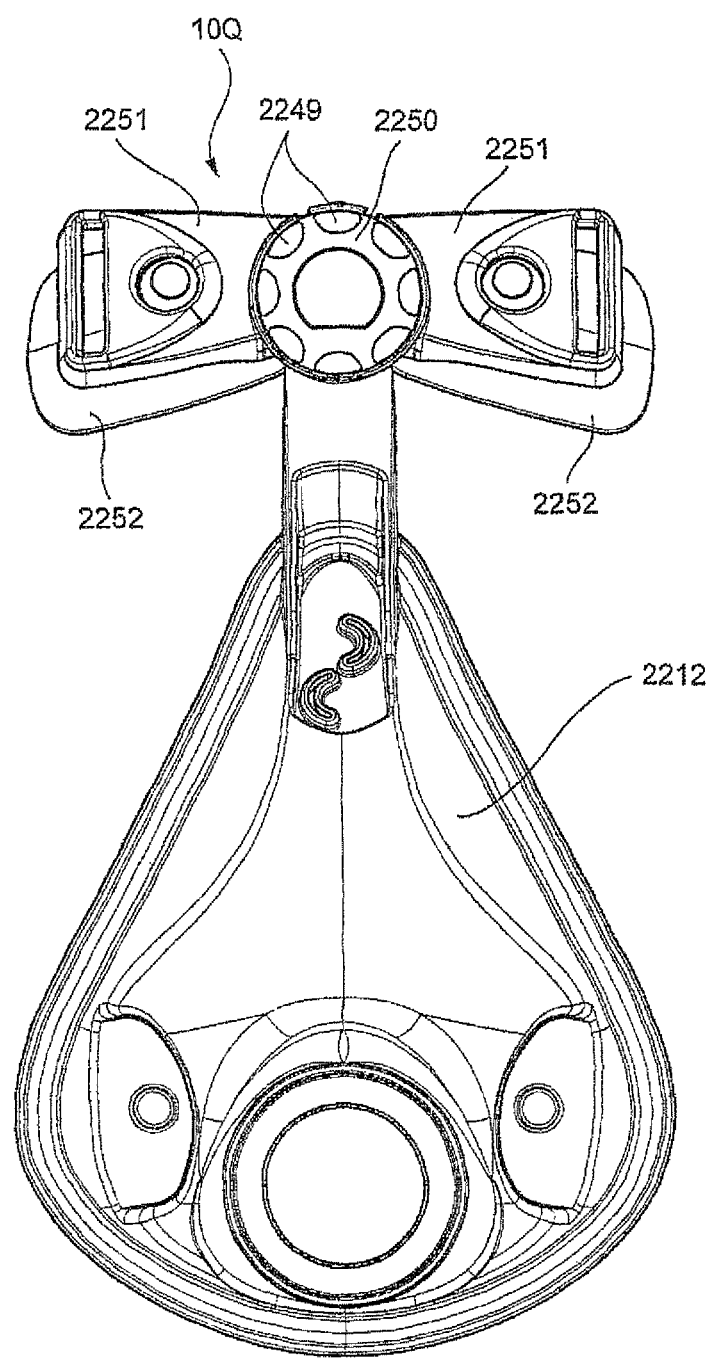
Figures 3, 37:
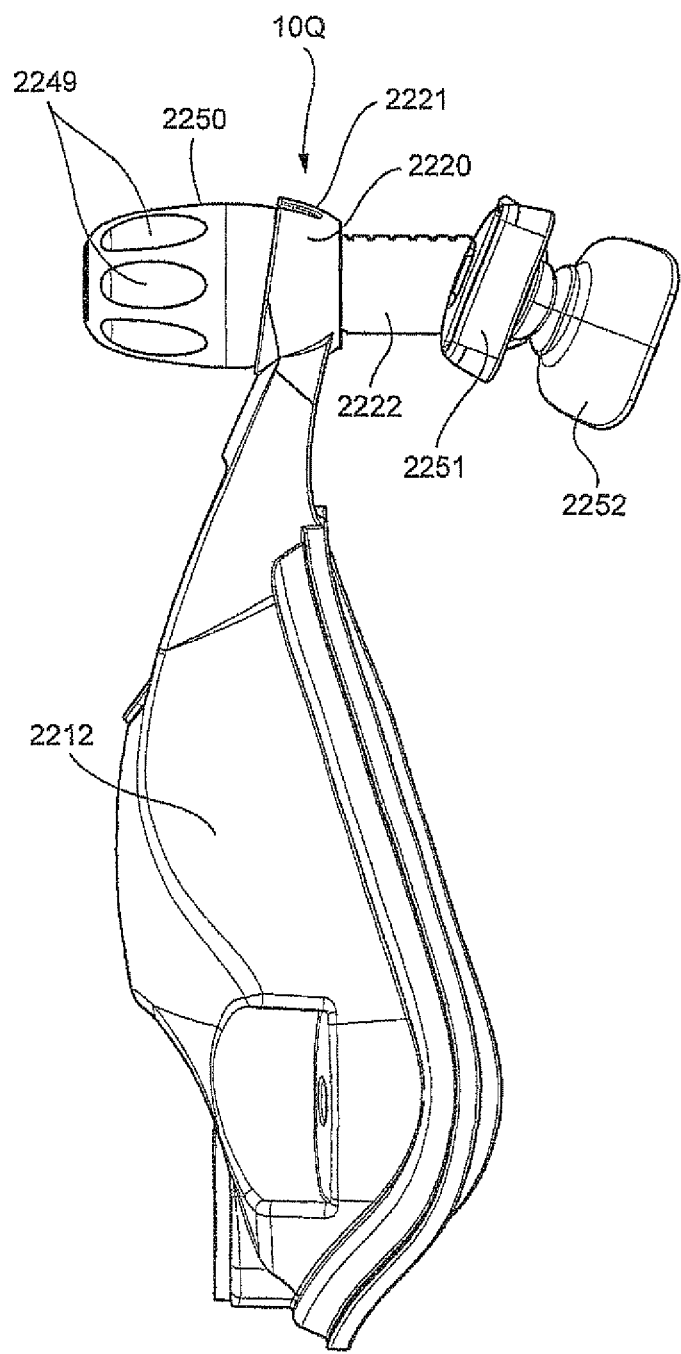
Figures 4, 37:
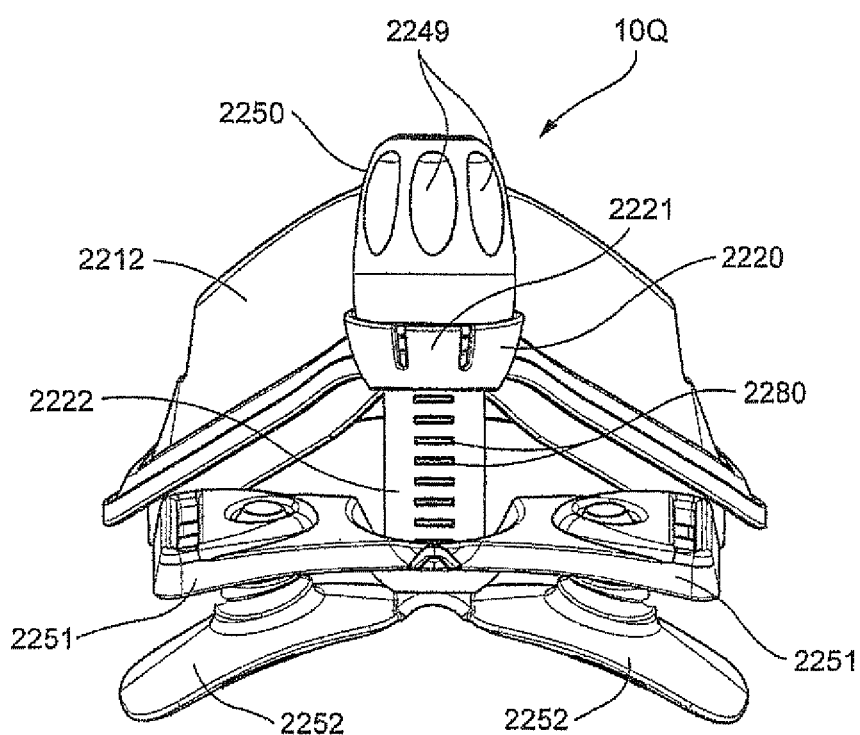
Figures 5, 37:
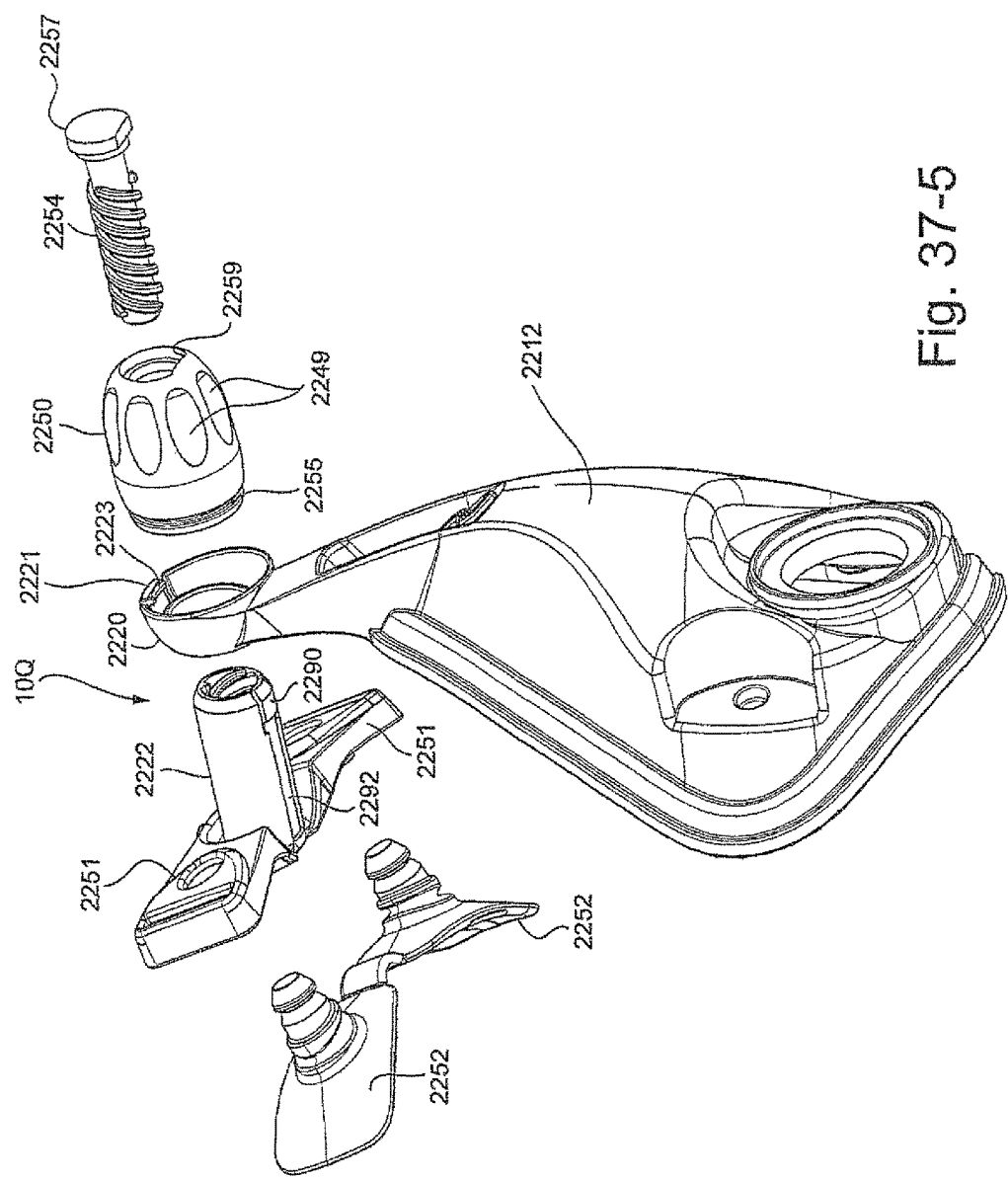
Figures 12, 37:
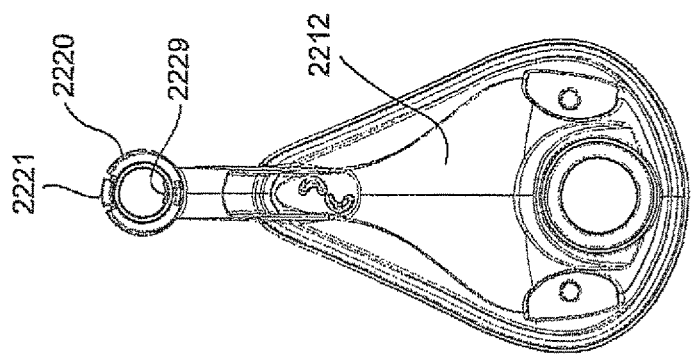
Figures 13, 37:
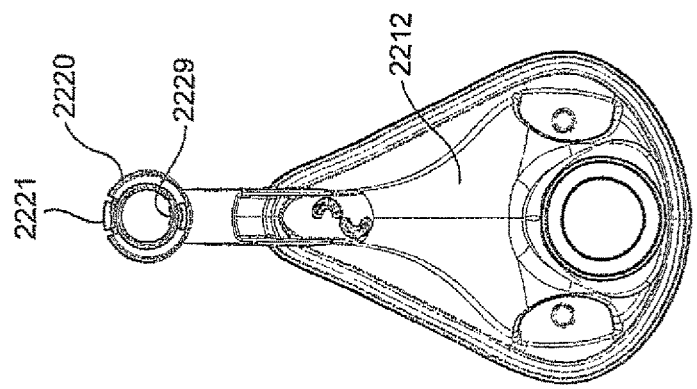
Figures 14, 37:
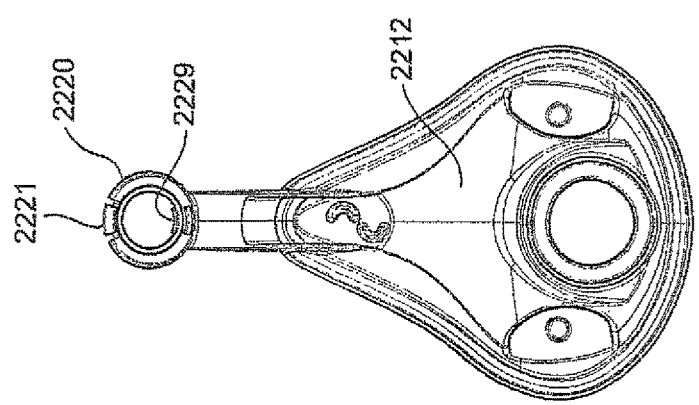
Figures 15, 37:
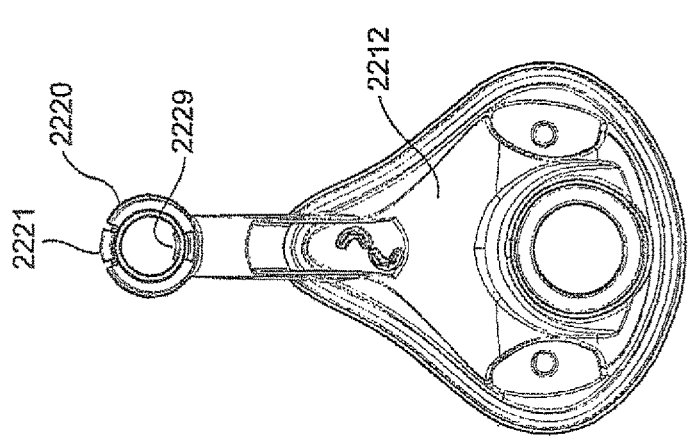

FIGS. 37-1 to 37-15 illustrate a FMA including a forehead support 10Q according to another embodiment of the present invention. In this embodiment, the forehead support 10Q uses a screw-type actuator to move the forehead support along a generally linear path.

As illustrated, the forehead support 10Q includes a support 2220 provided to the mask frame 2212 for supporting an adjustment knob 2250. The adjustment knob 2250 clips onto the support 2220 with a snap-fit. Specifically, the support 2220 includes a resilient arm member 2221 that provides a protrusion 2223 on a free end thereof. The adjustment knob 2250 includes an annular groove 2255. When the adjustment knob 2250 is assembled to the support 2220, the resilient arm member 2221 deflects outwardly until the protrusion 2223 snaps into the groove 2255 (see FIGS. 37-1 and 37-4 to 37-7).

A threaded shaft 2254 is provided to the adjustment knob 2250. In the illustrated embodiment, the threaded shaft 2254 and the adjustment knob 2250 are constructed in two parts and permanently or semi-permanently assembled. Specifically, the head 2257 of the threaded shaft 2254 includes a non-circular outer perimeter, e.g., head 2257 has at least one flat edge, that engages within a corresponding non-circular opening 2259 provided in the adjustment knob 2250. This mechanically interlocks the adjustment knob 2250 and the threaded shaft 2254. The knob 2250 and shaft 2254 may be further secured with an adhesive. However, the adjustment knob 2250 and the threaded shaft 2254 may be integrally formed as a one-piece structure.

The threaded shaft 2254 engages within an internally threaded tube 2222 such that the threaded shaft 2254 is intermeshed with the internally threaded tube 2222. The internally threaded tube 2222 is joined to forehead cushion support plates 2251 that carry forehead cushions 2252. The internally threaded tube 2222 includes a resilient arm 2290 that engages the support 2220 with a snap-fit to prevent disassembly. Also, the internally threaded tube 2222 includes a keyway 2292 that engages a protrusion 2229 (e.g., see FIGS. 37-12 to 37-15) provided to the support 2220 to prevent the tube 2222 and hence the forehead cushions 2252 from twisting relative to the frame 2212.

When the knob 2250 is rotated, the internally threaded tube 2222 extends or retracts from the threaded shaft 2254 provided to the knob 2250 which causes adjustable movement of the forehead cushions 2252.

As illustrated, the knob 2250 includes grooves or finger grips 2249 that make the knob 2250 easier to operate. The grips 2249 are relatively large to assist patients with relatively large hands. Preferably, the knob 2050 is opaque to hide the inner mechanisms and provide a sense of simple design reflecting ease of use. The knob 2250 may be manufactured from TPE (thermoplastic elastomer) which is tactile for the patient. However, other suitable materials may be used.

In the illustrated embodiment, the forehead cushion support plates 2251 include slots for attaching headgear straps. However, the forehead cushion support plates 2251 may include clip receiving structures for engaging headgear clips. Also, the tube 2222 is recessed into the support plates 2251 which allows maximum extension with minimum protrusion from the forehead, thereby reducing actual and visual bulk. Further, as best shown in FIGS. 37-1 and 37-4, the tube 2222 may be labeled, e.g., spaced apart grooves 2280, to allow the forehead support position to be remembered. Moreover, the tube 2222 may be frosted so that the internal threads are less visible, thereby reducing the technological/mechanical look of the forehead support and making it appear more user friendly and simple.

In an embodiment, the forehead support provides movement of about 24 mm+/−10 mm. This range of movement may vary, e.g., depending on the characteristics and structure of the mask cushion.

The threads for the threaded shaft 2254 and the internally threaded tube 2222 are preferably designed such that sufficient extension is provided for a particular rotation. In addition, the threads may be designed to be self-locking. In an embodiment, the threads may have a pitch of about 12 mm. However, the pitch may be in the range of 4-15 mm. It is noted that a lower thread size may be better for self-locking but may require more turns to set the desired forehead support distance. Also, in an embodiment, the threads may be 3 start LH threads. However, the threads may be RH threads. It is noted that a LH thread may feel more intuitively correct for the patient in that as they tighten the thread, the forehead support moves towards their face. Also, the threads may have any suitable number of starts and may be chosen for strength, moldability and friction characteristics. Further, in an embodiment, the threads have a 29 degree ACME thread angle. However, the thread angle may be in the range of 10-60 degrees. Also, other thread profiles may be used. Additionally, in an embodiment, the threads may have a 1.3 mm thread height. However, the thread height may be in the range of 0.5-2 mm and may be chosen for strength and moldability.

As shown in FIGS. 37-12 to 37-15, the mask frame 2212 may be provided in various sizes, e.g., extra small, small, medium, and large, to accommodate a wide range of patients. Any suitable number of sizes may be provided.

XXIII. Seventeenth Illustrated Embodiment of Forehead Support

Figures 1, 18:
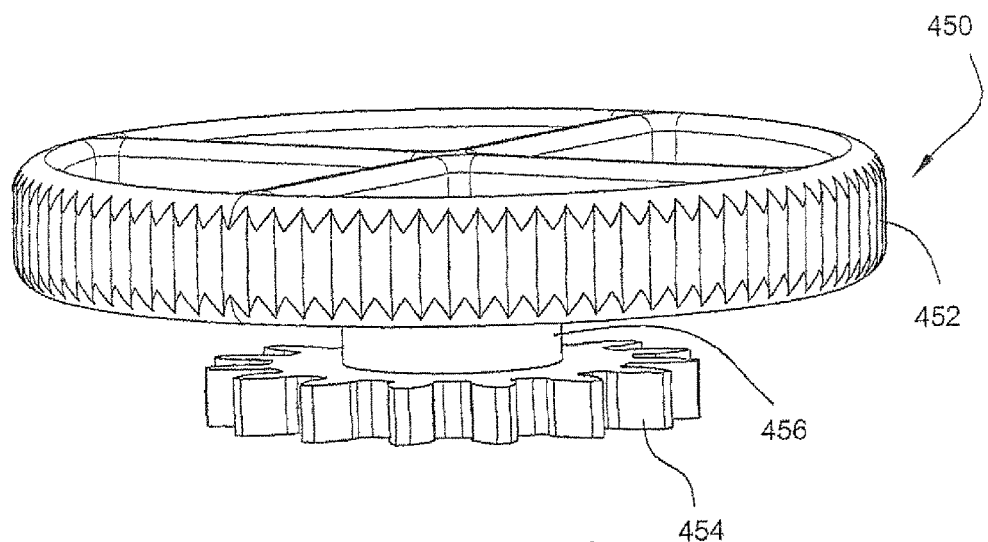
Figures 2, 18:
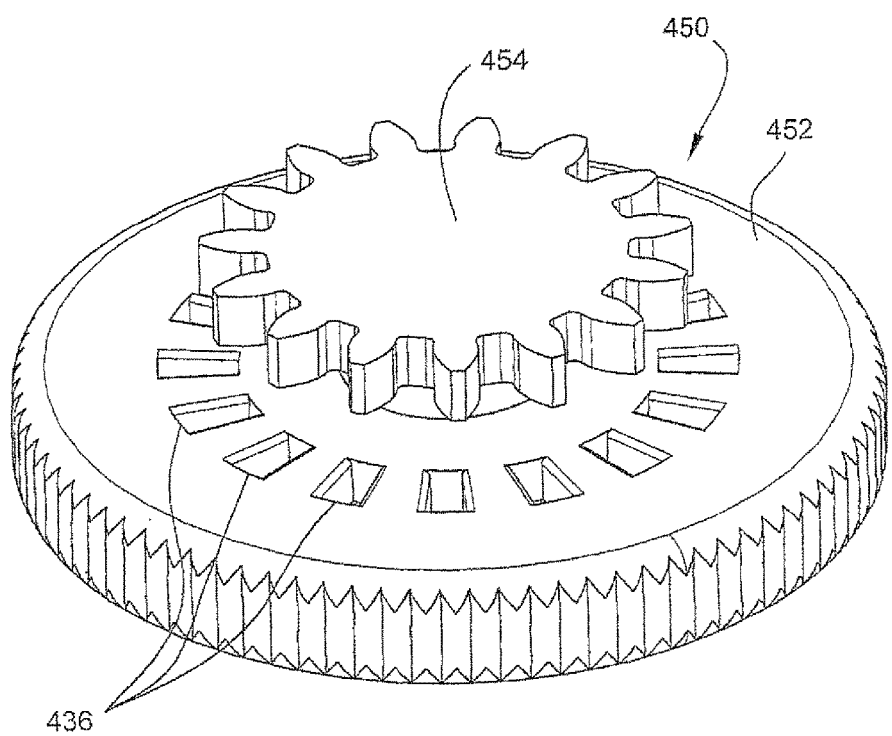
Figures 3, 18:
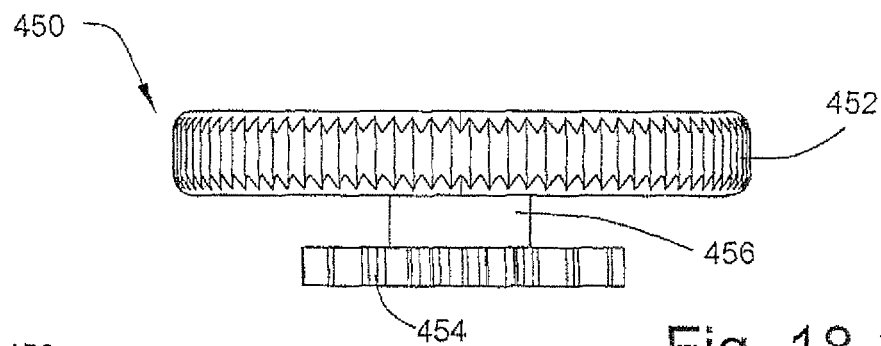
Figures 4, 18:
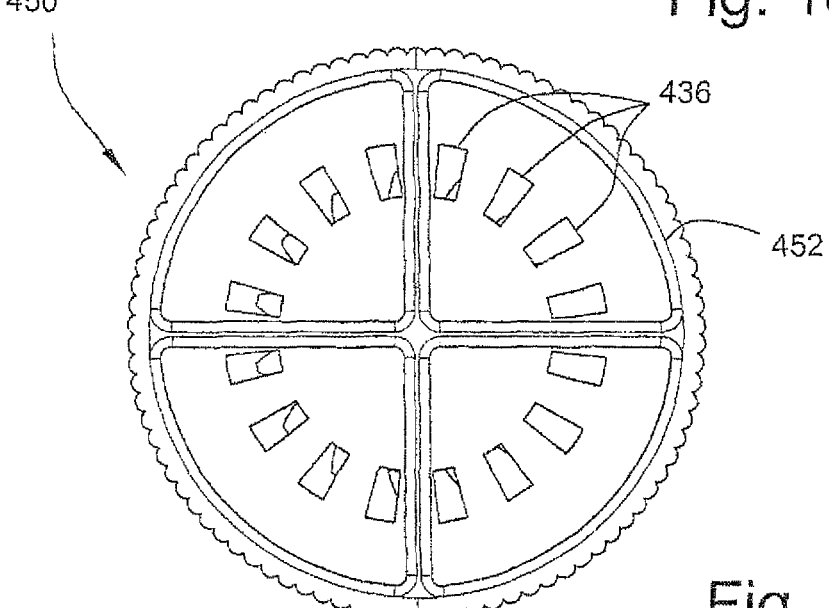
Figures 5, 18:
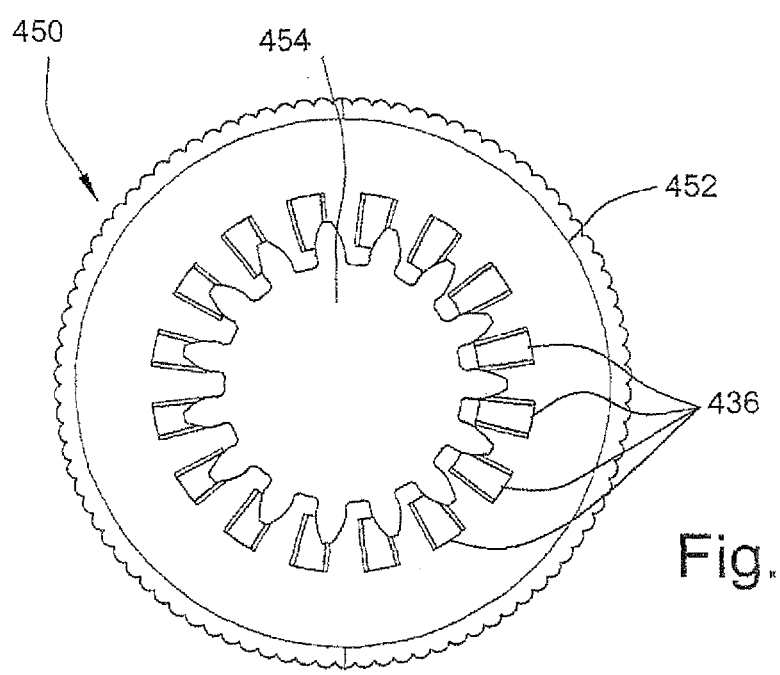
Figures 1, 38:
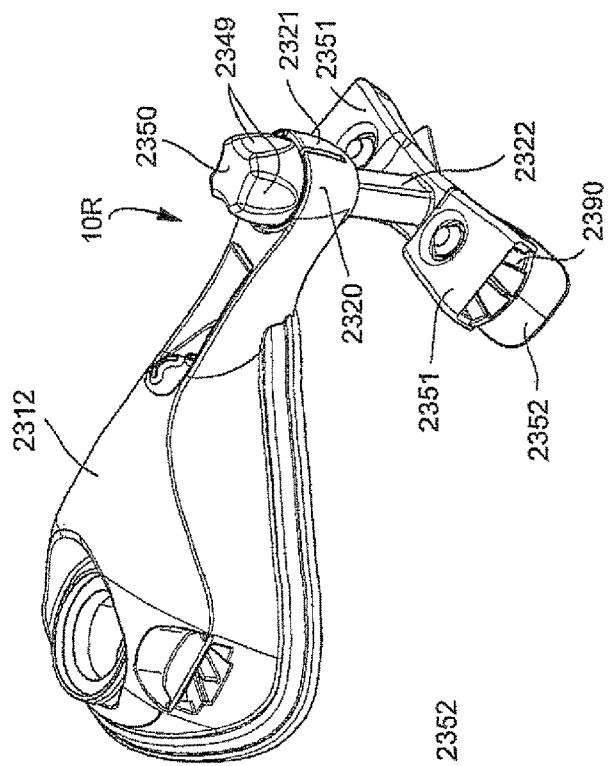
Figures 3, 38:
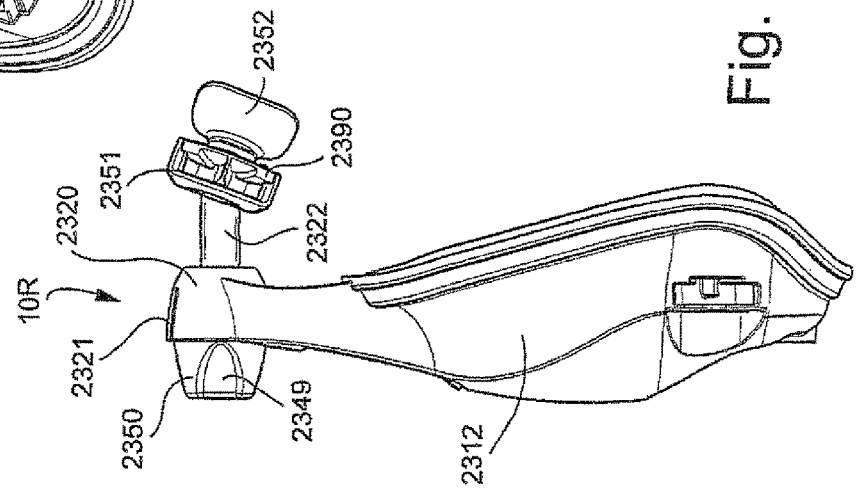
Figures 2, 38:
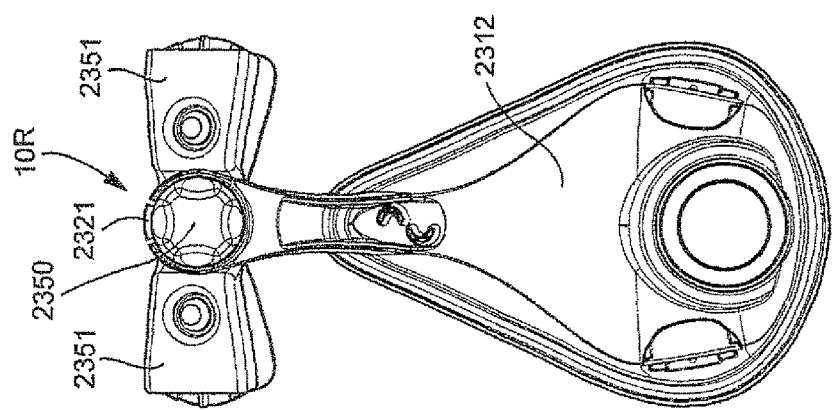
Figures 5, 38:
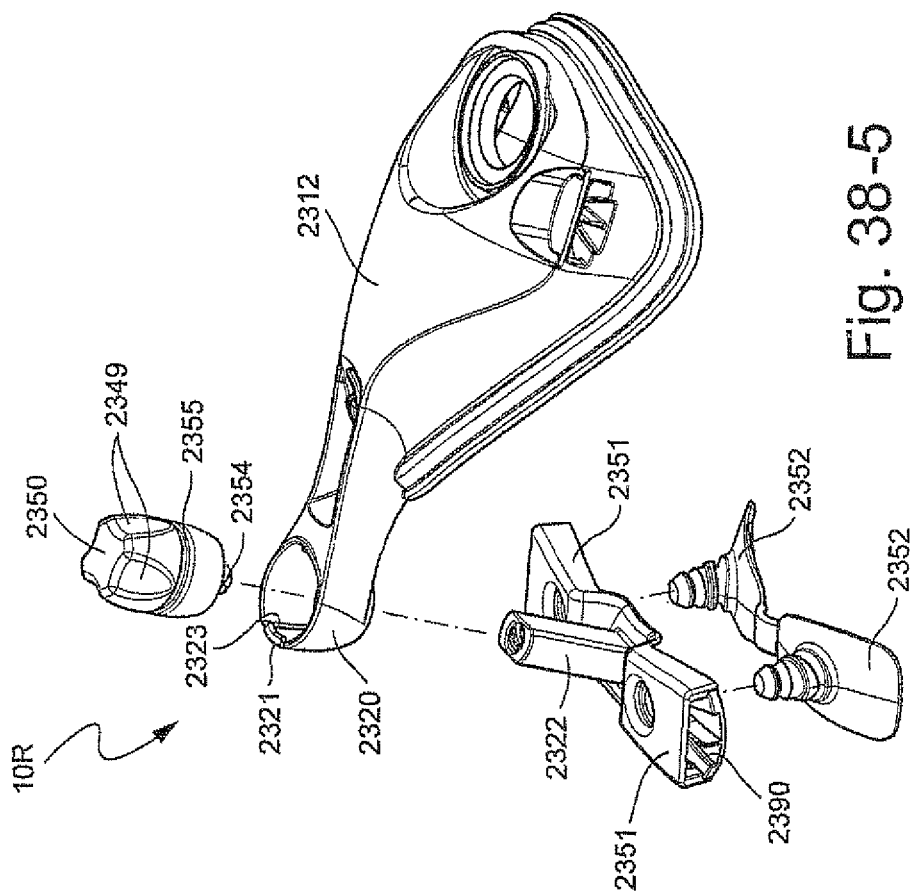
Figures 4, 38:
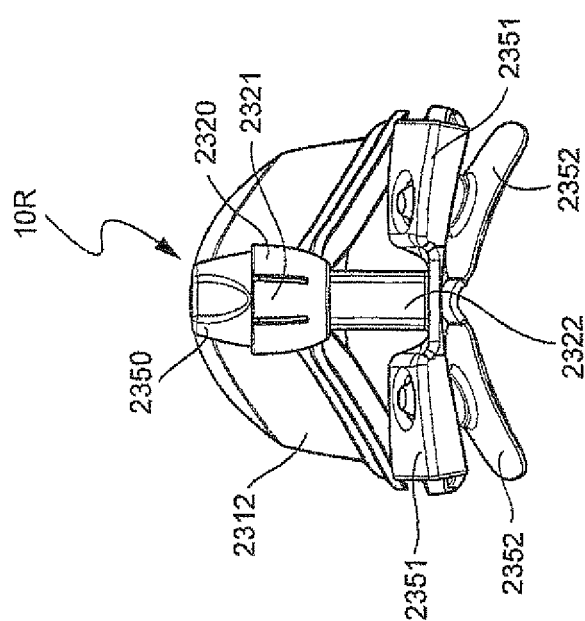
Figures 6, 38:
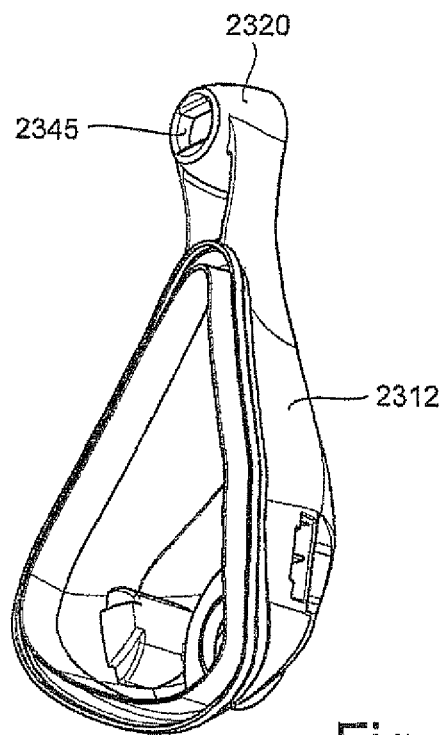
Figures 7, 38:
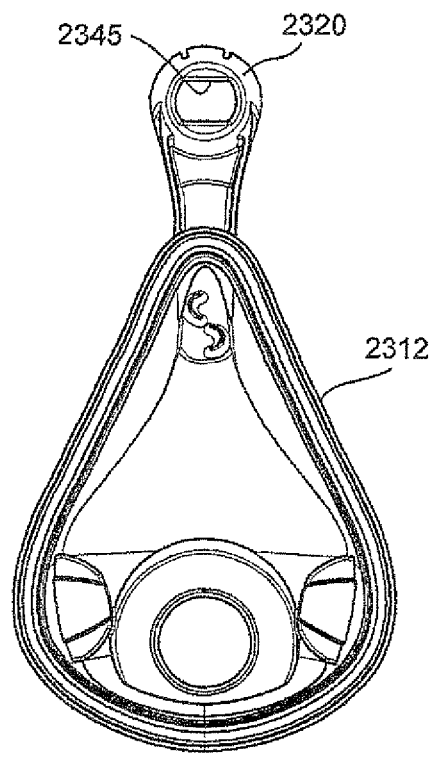
Figures 13, 38:
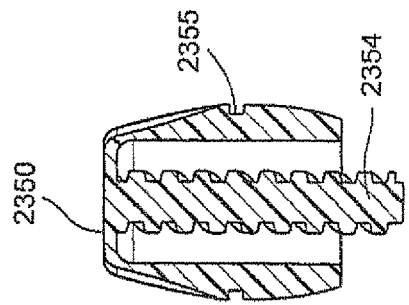
Figures 11, 38:
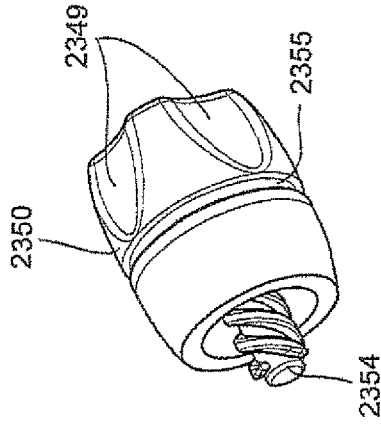
Figures 10, 38:
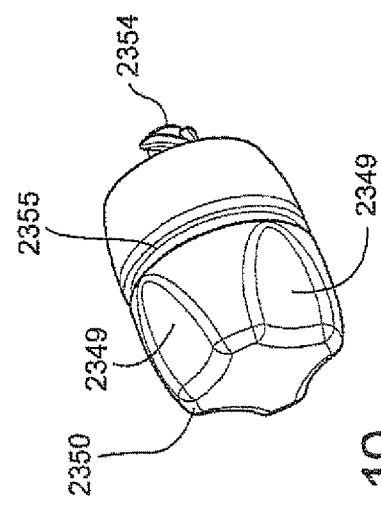
Figures 12, 38:
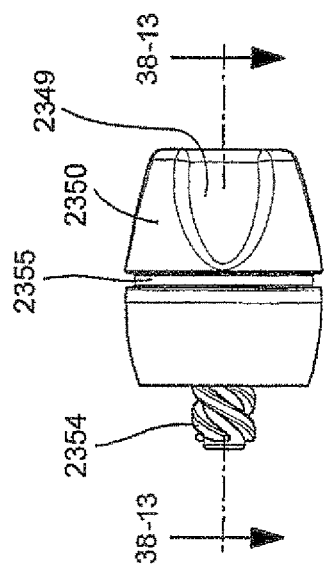
Figures 18, 38:
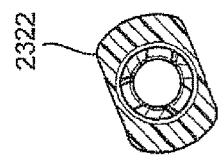
Figures 17, 38:
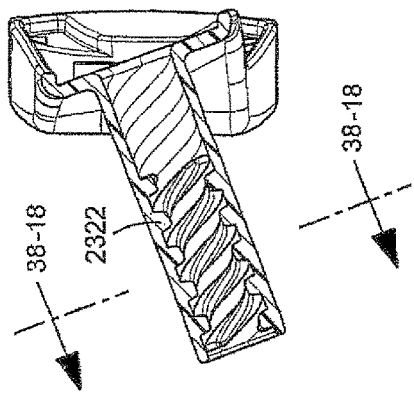
Figures 16, 38:
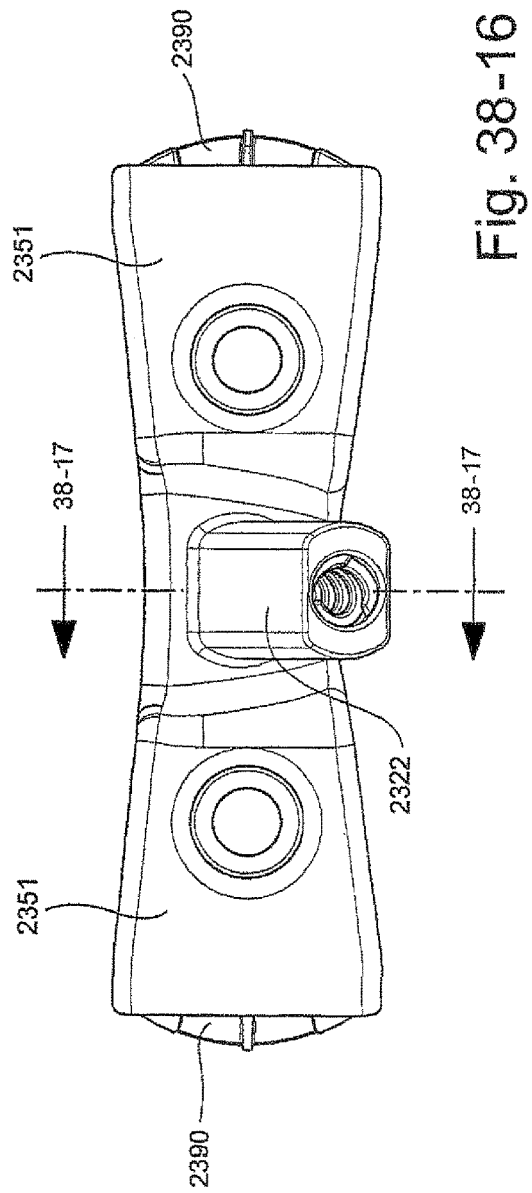

FIGS. 38-1 to 38-18 illustrate a FMA including a forehead support 10R according to another embodiment of the present invention. In this embodiment, the forehead support 10R uses a screw-type actuator to move the forehead support along a generally linear path.

As illustrated, the forehead support 10R includes a support 2320 provided to the mask frame 2312 for supporting an adjustment knob 2350. The adjustment knob 2350 clips onto the support 2320 with a snap-fit. Specifically, the support 2320 includes a first protrusion 2325 and a resilient arm member 2321 that provides a second protrusion 2323 on a free end thereof. The adjustment knob 2350 includes an annular groove 2355. When the adjustment knob 2350 is assembled to the support 2320, the resilient arm member 2321 deflects outwardly until the first and second protrusions 2325 and 2323 snap into the groove 2355 (see FIGS. 38-1, 38-4, 38-5, 38-9, and 38-10 to 38-13). As illustrated, the support 2320 is relatively wide and covers or shrouds a portion of the knob 2350, e.g., about half of the knob 2350, to reduce the visual bulk of the knob 2250 and improve the aesthetics of the design.

As best shown in FIGS. 38-5 and 38-10 to 38-13, a threaded shaft 2354 is provided to the adjustment knob 2350. In the illustrated embodiment, the threaded shaft 2354 and the adjustment knob 2350 are integrally formed, e.g., integrally molded, as a one-piece structure. However, the adjustment knob 2350 and the threaded shaft 2354 may be constructed in two parts and permanently or semi-permanently assembled, e.g., by an adhesive.

The threaded shaft 2354 engages within an internally threaded tube 2322 such that the threaded shaft 2354 is intermeshed with the internally threaded tube 2322. The internally threaded tube 2322 is joined to forehead cushion support plates 2351 that carry forehead cushions 2352 as shown in FIGS. 38-1, 38-3, 38-4, 38-5, and 38-14 to 38-18. As best shown in FIGS. 38-6, 38-7, 38-9, 38-16, and 38-18, the internally threaded tube 2322 includes a non-circular outer profile or exterior surface that is adapted to extend through a non-circular opening 2345 provided to the support 2320 to prevent the tube 2322 and hence the forehead cushions 2352 from twisting or rotating relative to the frame 2312.

When the knob 2350 is rotated, the internally threaded tube 2322 extends or retracts from the threaded shaft 2354 provided to the knob 2350 which causes adjustable movement of the forehead cushions 2352.

As illustrated, the knob 2350 includes scallops or finger grips 2349, e.g., four finger grips 2349, that reduce the visual and actual bulk of the knob 2350. In addition, the finger grips 2349 make the knob 2350 easier to operate.

In the illustrated embodiment, the forehead cushion support plates 2351 include clip receiving structures or clip receptacles 2390 for engaging headgear clips associated with headgear straps. The headgear clips may be structured like those disclosed in U.S. Pat. No. 6,374,826 and/or PCT Application No. PCT/AU04/01834, filed Dec. 24, 2004, the entireties of both being incorporated herein by reference. However, the forehead cushion support plates 2351 may include other suitable structures for engaging headgear straps, e.g., slots. Also, the tube 2322 is recessed into the support plates 2351 which allows maximum extension with minimum protrusion from the forehead, thereby reducing actual and visual bulk.

XXIV. Embodiment of Thread Form

Figures 4, 39:
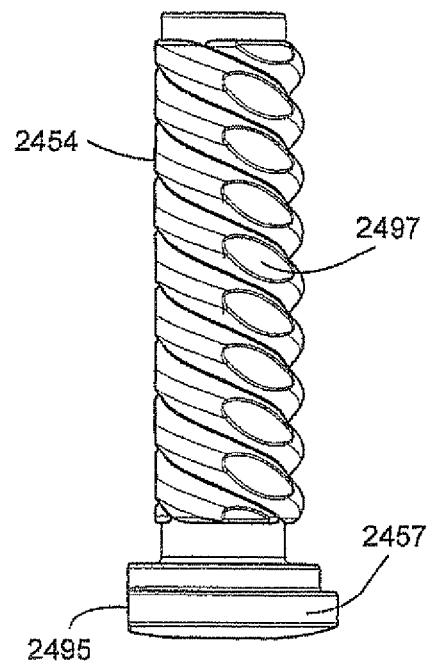
Figures 5, 39:
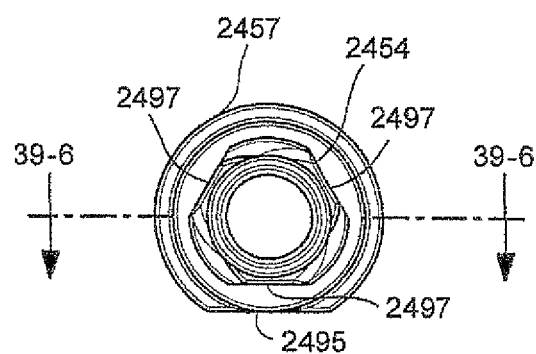
Figures 6, 39:
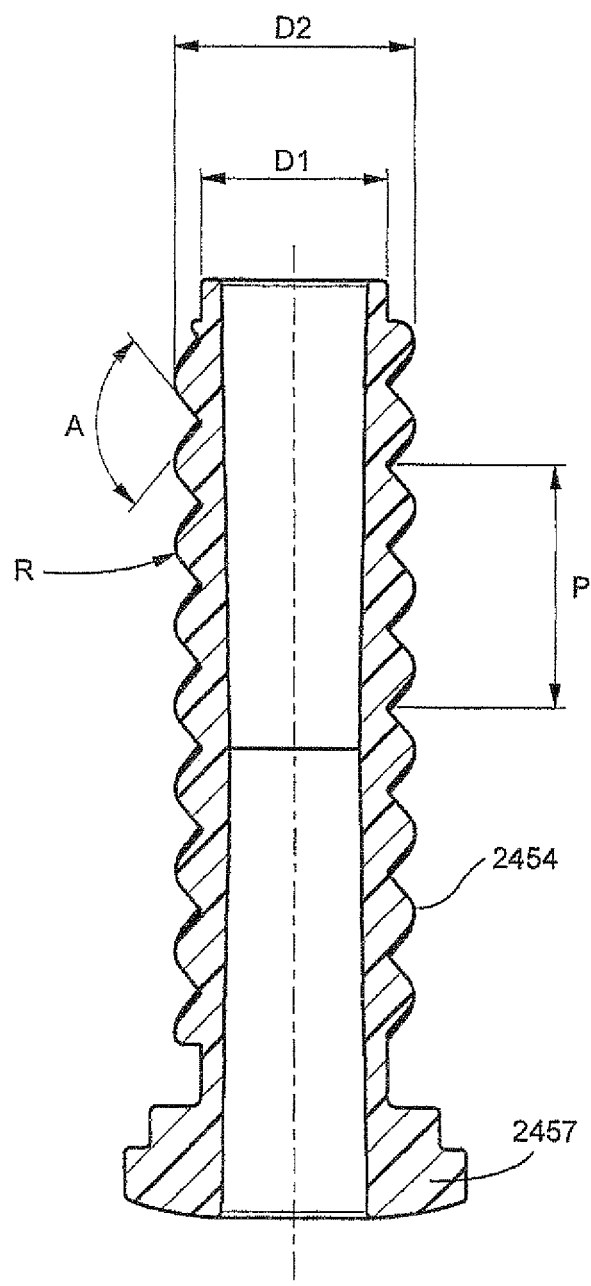
Figures 8, 39:
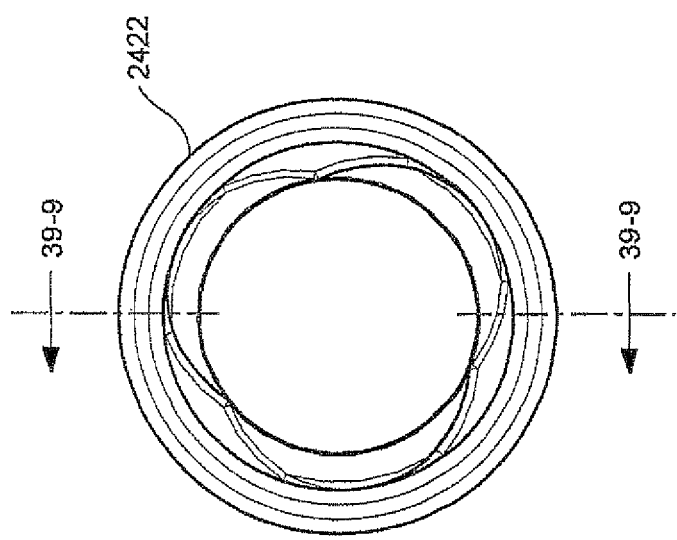
Figures 7, 39:
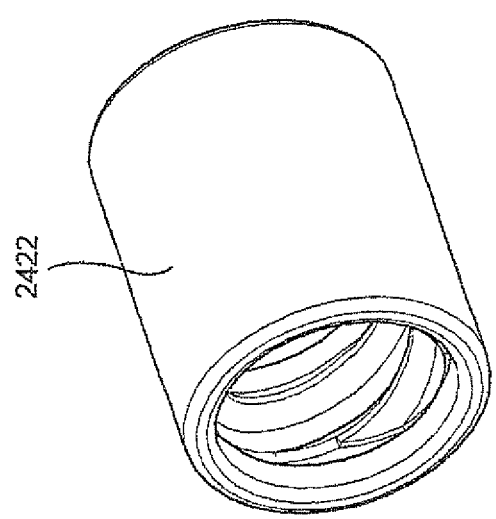

FIGS. 39-1 to 39-9 illustrate a thread form for a forehead support according to an embodiment of the present invention. The thread form may be implemented or employed in a forehead support of a FMA such as those discussed above.

FIGS. 39-1 to 39-6 illustrate a threaded shaft or bolt 2454 and FIGS. 39-7 to 39-9 illustrate an internally threaded tube 2422 that is adapted to be intermeshed with the threaded shaft 2454. The threaded shaft 2454 may be permanently or semi-permanently assembled to an adjustment knob such as those discussed above (e.g., see FIG. 37-5), and the internally threaded tube 2422 may be joined to forehead cushion support plates that carry forehead cushions or form a portion of the support provided to the mask frame for supporting the adjustment knob and shaft 2454.

As illustrated, the head 2457 of the threaded shaft 2454 includes a non-circular outer perimeter that provides a flat edge 2495. The non-circular head 2457 may be engaged within a corresponding non-circular opening provided in the adjustment knob to mechanically interlock the adjustment knob and the threaded shaft 2454 (e.g., see FIG. 37-5). However, threaded shaft 2454 may be interlocked with an adjustment knob in other suitable manners. For example, the head 2457 may include more than one flat edge, e.g., hexagon-shaped.

The threads for the threaded shaft 2454 and the internally threaded tube 2422 may be designed to provide sufficient extension for a particular rotation, to be self-locking, and/or to facilitate manufacturing. In an embodiment, the threads may have a pitch P of about 12 mm. However, the pitch may be in the range of 4-15 mm. It is noted that a lower thread size may be better for self-locking but may require more turns to set the desired forehead support distance. Also, in an embodiment, the threads may be 3 start threads and may be LH or RH threads. However, the threads may have any suitable number of starts and may be chosen for strength, moldability and friction characteristics. Further, in an embodiment, the threads have an included angle A of 90-110°, preferably 100°, and a radius R of 0.8-1.5 mm, preferably 1.1 mm. However, other suitable angles and radiuses are possible depending on application. Additionally, in an embodiment, the threads of the shaft 2454 may have a diameter D1 of 8-10 mm, preferably 9 mm, and a diameter D2 of 10-13 mm, preferably 11.6 mm. In an embodiment, the threads of the tube 2422 may have a diameter D1 of 8-11 mm, preferably 9.7 mm, and a diameter D2 of 11-13 mm, preferably 12 mm.

Further, the threads of the threaded shaft 2454 may include three flat edges 2497 that may be molded with a three-way split block. However, the threads may be devoid of flat edges or may include other suitable numbers of flat edges.

XXV. Embodiment of Forehead Cushion

Figures 1, 40:
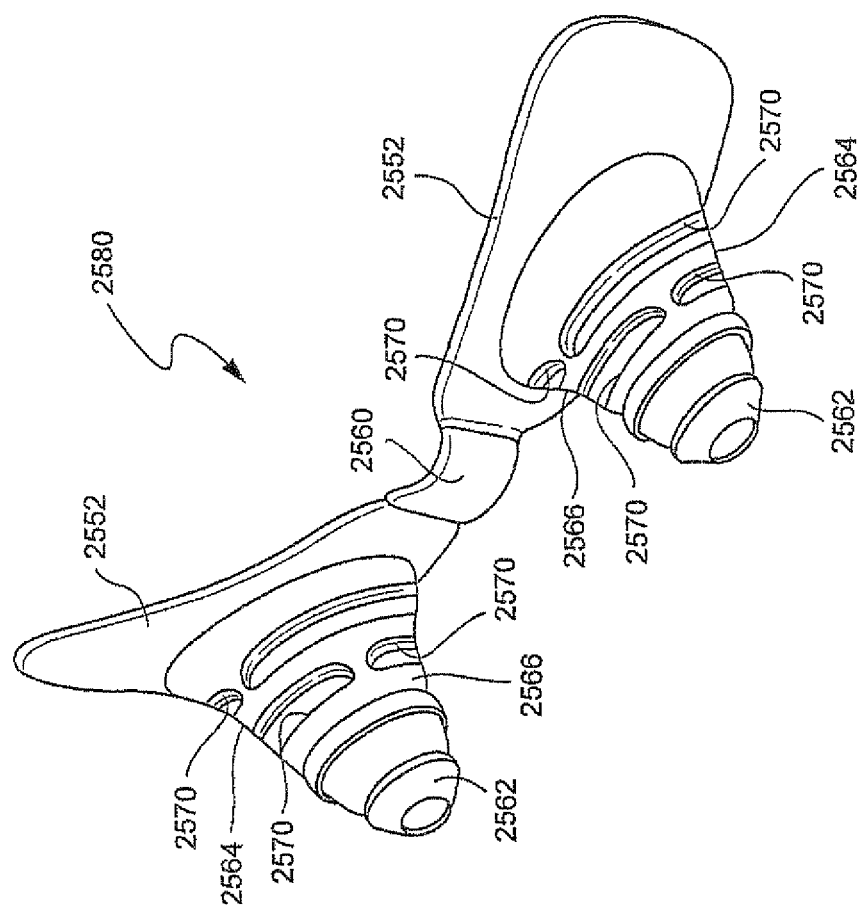
Figures 9, 39:
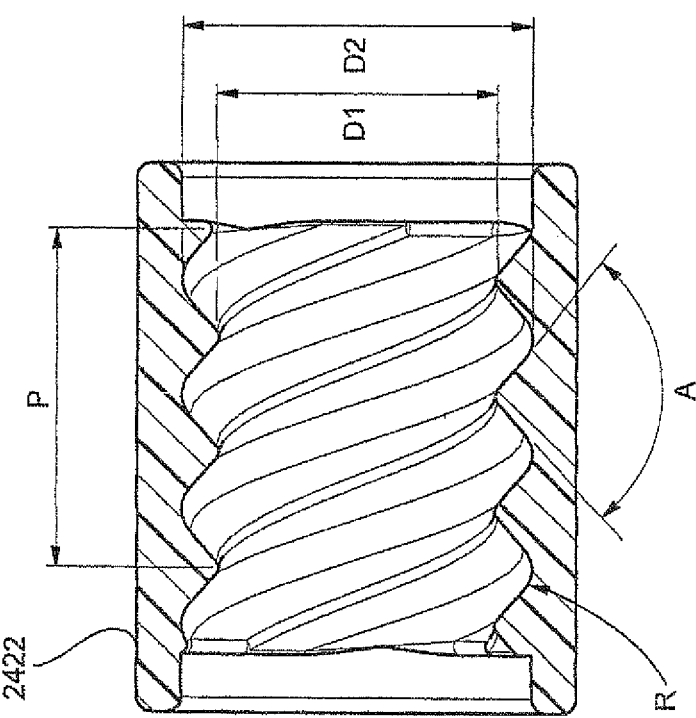
Figures 2, 40:
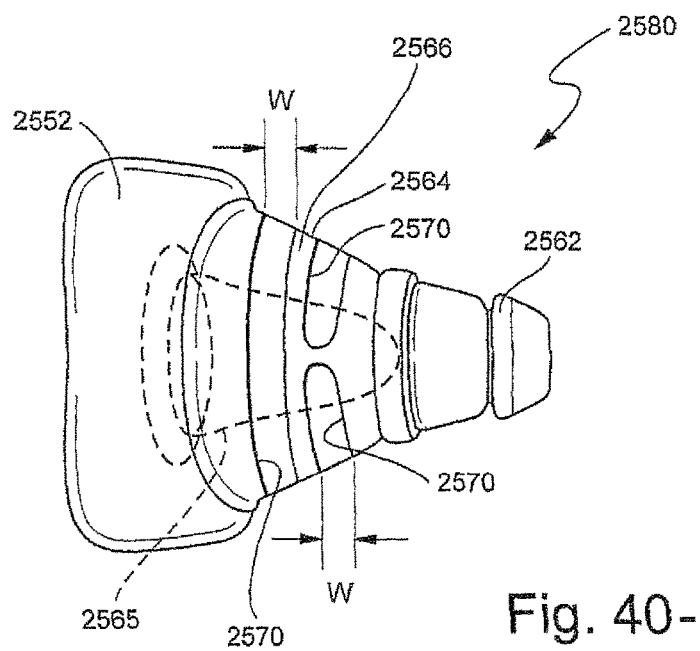
Figures 3, 40:
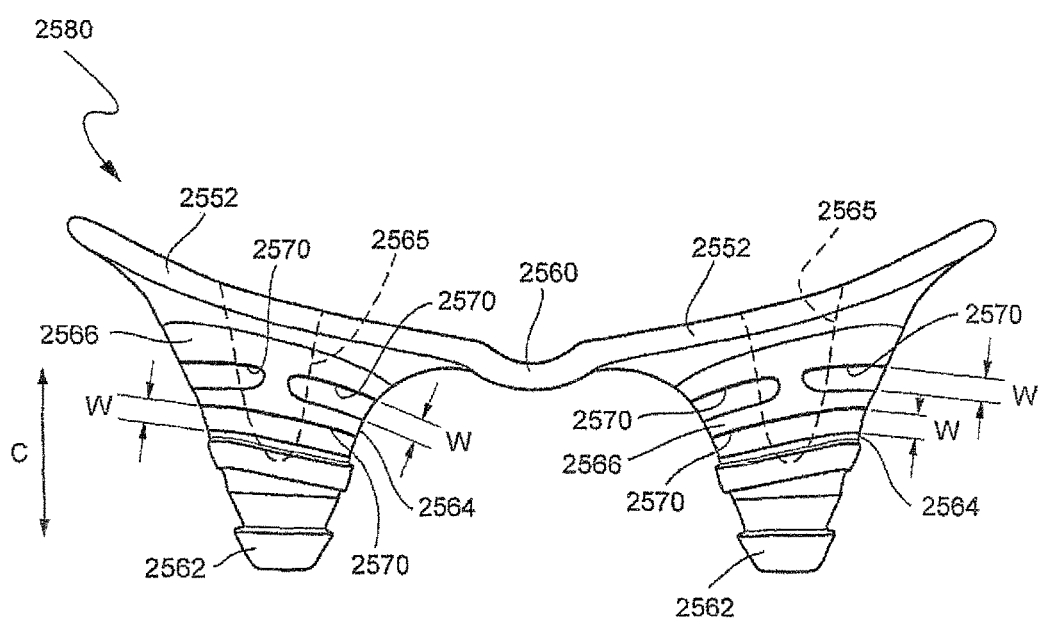

FIGS. 40-1 to 40-3 illustrate a forehead cushion 2580 for a forehead support according to an embodiment of the present invention. The forehead cushion 2580 may be implemented or employed in a forehead support of a FMA such as those discussed above. In addition, the forehead cushion 2580 may be employed in a forehead support including attachment members with one or more slots such as the forehead support shown and described below in FIGS. 41-1 to 41-3.

The forehead cushion 2580 is formed of an elastomeric material, e.g., silicone, and includes a pair of cushions 2552 that are joined to one another with a one-piece bridge 2560. The interior surfaces or forehead contacting surfaces of the cushions 2552 may have a general "concave" contour and thus be adapted for conformable shaping relative to a patient's forehead profile.

Each cushion 2552 has an attachment head 2562 protruding rearwardly therefrom which is inserted into and through a respective aperture formed in support plates of a forehead cushion support so as to physically attach the cushions 2552 to the support plates.

The attachment head 2562 is joined to the back of each cushion 2552 by a flexible connector 2564 which serves to allow compliant movement of the cushions 2552 so they may be comfortably positioned in contact with the patient's forehead. As illustrated, the connector 2564 has a cored-out or hollow interior 2565 to provide a cylindrical connector side wall 2566. The connector side wall 2564 has a plurality of slots 2570 therethrough that allow the connector wall 2564 and hence the cushions 2552 to compress, and thus provide additional adjustment that may be required for some users to extend the range of the forehead cushion 2580.

In the illustrated embodiment, the slots 2570 are provided in two rows with each row including two spaced-apart slots. Each slot 2570 has an elongated, generally rectangular configuration with a longitudinal axis that extends generally transverse to a longitudinal axis of the connector 2564. The slots 2570 each have a width W of 1-5 mm, preferably 3 mm, which allows the forehead cushion 2580 to compress, e.g., in folds like those of a concertina. In the illustrated embodiment, the length of compression C may be 2-10 mm, preferably 6 mm. However, the slots may be arranged, configured, and/or dimensioned in other suitable manners to adjust the range or manner of compression. In addition, the slots may be provided in other cushion arrangements in a similar manner in order to provide additional adjustment or compression in such cushion arrangements.

XXVI. Embodiment of Forehead Cushion Support

Figures 1, 41:
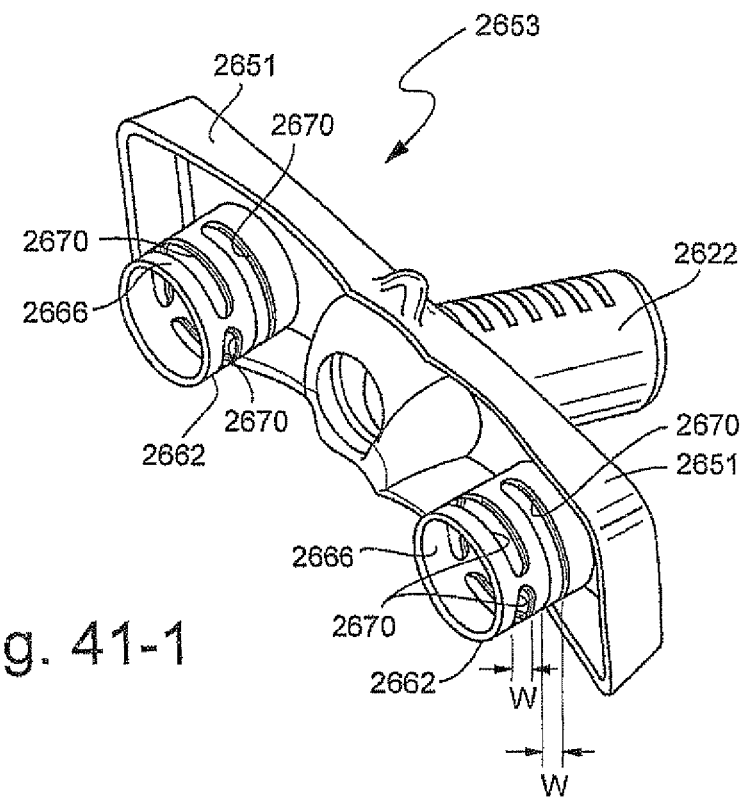
Figures 2, 41:
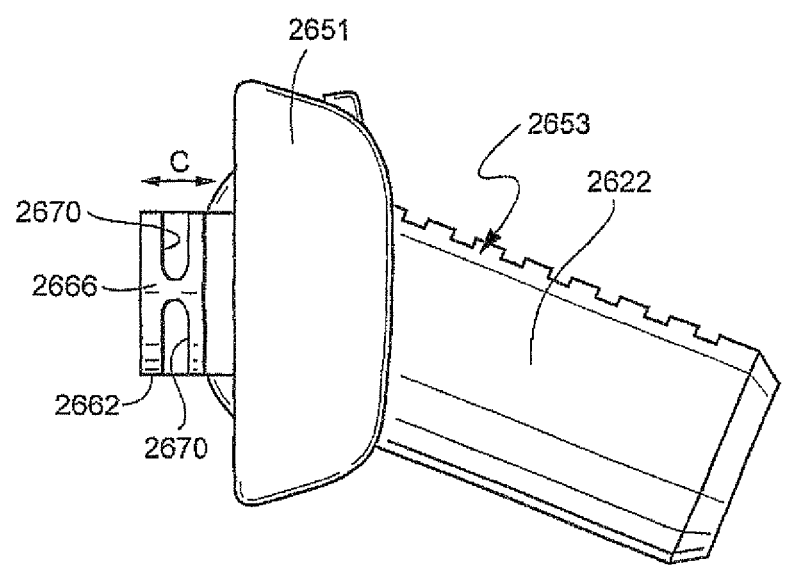
Figures 3, 41:
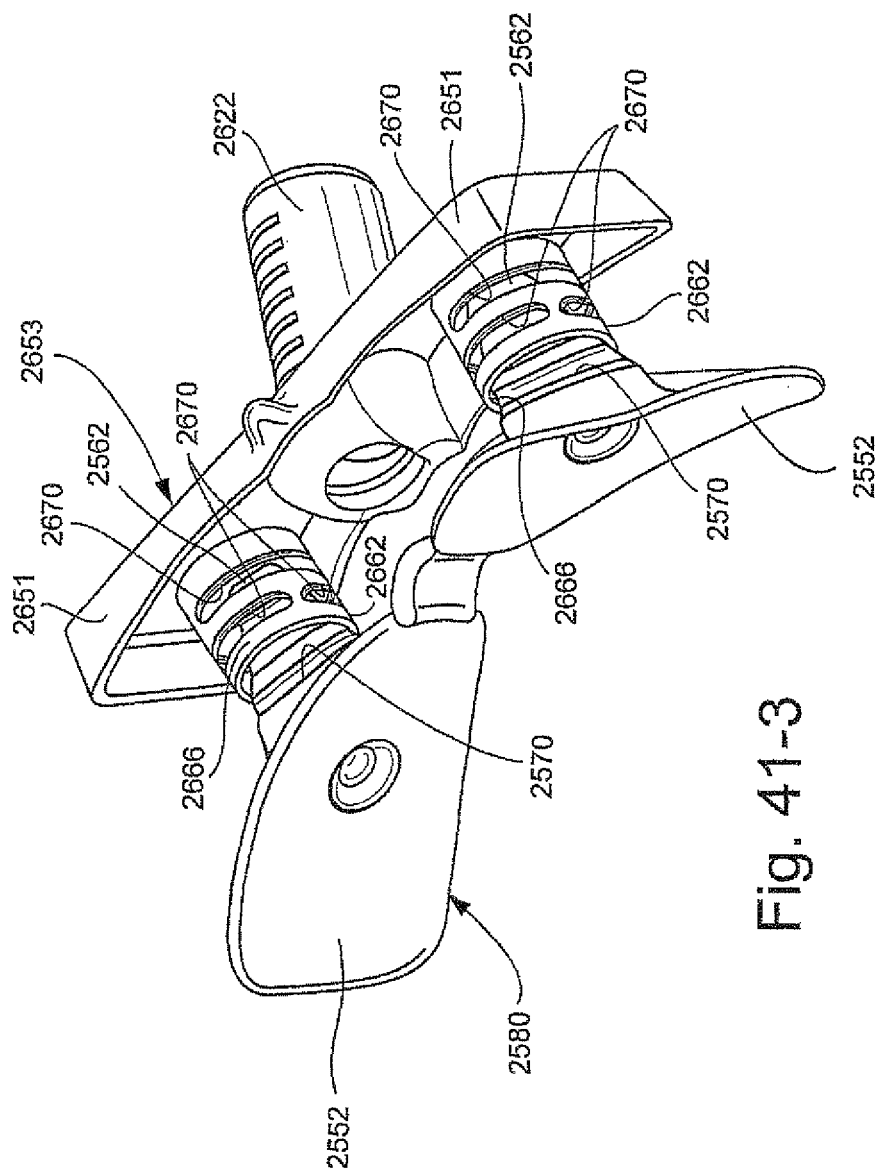

FIGS. 41-1 to 41-3 illustrate a forehead cushion support 2653 for a forehead support according to an embodiment of the present invention. The forehead cushion support 2653 is adapted for use with a forehead cushion 2580 as described above.

As illustrated, the forehead cushion support 2653 includes forehead cushion support plates 2651 and a tube or slider 2622 joined to the support plates 2651, e.g., formed of a rigid polymer material. The support plates 2651 extend generally transversely relative to the slider 2622 and thus define a general T-shaped support.

Each support plate 2651 has an attachment member 2662 protruding rearwardly therefrom which is adapted to receive a respective attachment head 2562 of the forehead cushion 2580 so as to physically attach the forehead cushion 2580 to the support plates 2651 (see FIG. 41-3). In use, the slider 2622 is extended or retracted with respect to the mask frame which causes adjustable movement of the forehead cushions 2552.

As illustrated, each attachment member 2662 has a cylindrical connector side wall 2666. The side wall 2666 has a plurality of slots 2670 therethrough that allow the side wall 2666 and hence the forehead cushion support 2653 to compress, and thus extend the range of movement of the forehead cushion support 2653 to provide additional adjustment. The attachment members 2662 may be made from polycarbonate, polypropylene, or silicone, for example. Also, the attachment members 2662 may be integrally formed in one-piece with the support plates 2651 and slider 2622, or formed separately and attached thereto. The attachment members 2662 may be manufactured from any suitable flexible material and the slots or apertures 2670 in the attachment members 2662 allow compression of the attachment members 2662.

In the illustrated embodiment, the slots 2670 are provided in two rows with each row including two spaced-apart slots. Each slot 2670 has an elongated, generally rectangular configuration with a longitudinal axis that extends generally transverse to a longitudinal axis of the attachment member 2662. As illustrated, the slots 2670 each have a width W of 1-5 mm, preferably 3 mm, which allows the forehead cushion support 2653 to compress, e.g., in folds like those of a concertina. In the illustrated embodiment, the length of compression C may be 2-10 mm, preferably 6 mm. However, the slots may be arranged, configured, and/or dimensioned in other suitable manners to adjust the range or manner of compression. In addition, the slots may be provided in other cushion support arrangements in a similar manner in order to provide additional adjustment or compression in such cushion support arrangements.

When the forehead cushion 2580 is attached to the forehead cushion support 2653, the slots 2570 of the forehead cushion 2580 may align with corresponding slots 2670 of the forehead cushion support 2653. However, one or more slots 2570 may be offset from the slots 2670. In addition, the slot arrangement, configuration, and/or dimension of one or more of the slots 2570 may be similar to and/or different than the slot arrangement, configuration, and/or dimension of one or more of the slots 2670.

XXVII. Embodiment of Forehead Cushion Support

Figures 1, 42:
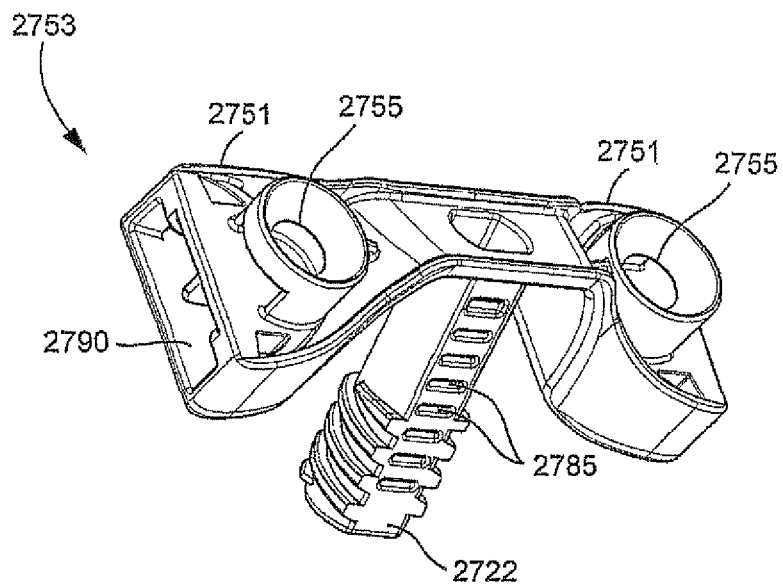
Figures 2, 42:
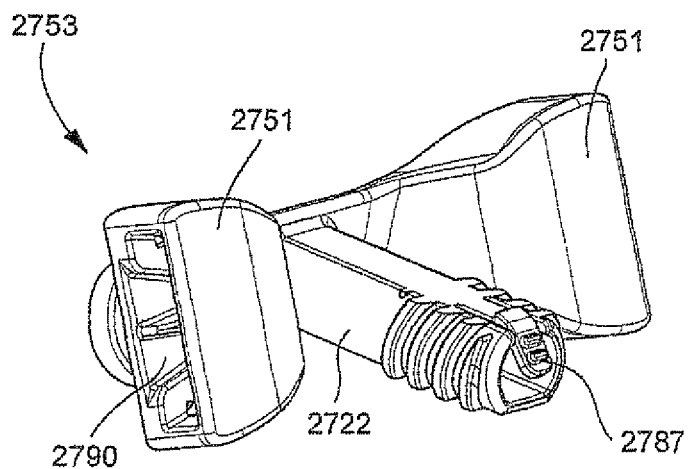
Figures 3, 42:
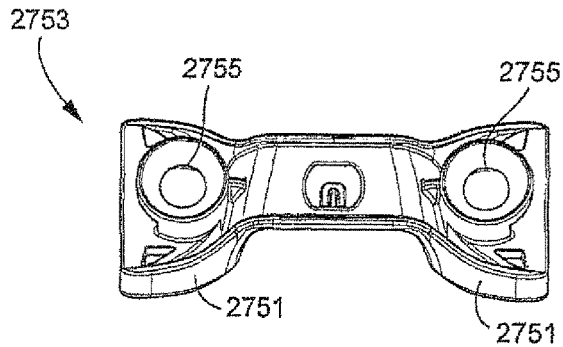
Figures 4, 42:
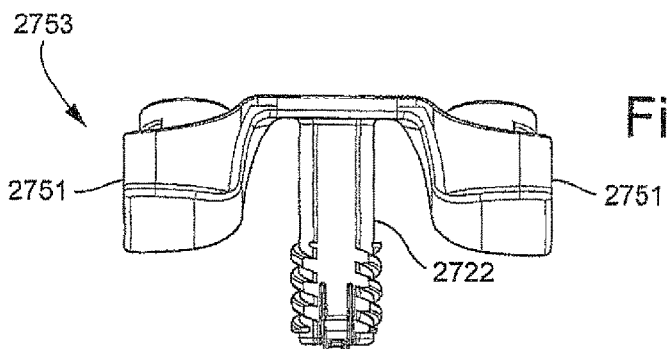
Figures 5, 6, 7, 42:
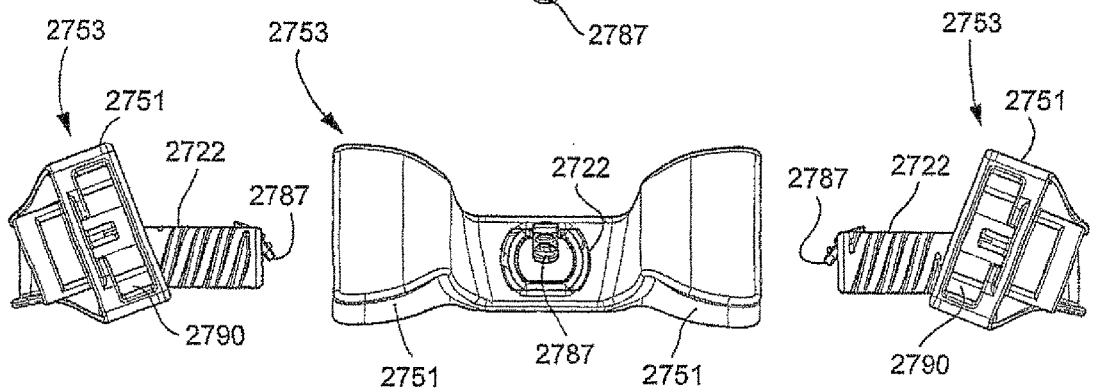
Figures 8, 42:
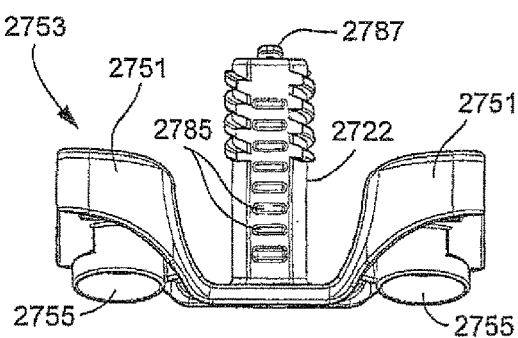

FIGS. 42-1 to 42-8 illustrate a forehead cushion support 2753 for a forehead support according to an embodiment of the present invention. The forehead cushion support 2753 is adapted for use with a forehead cushion such as those described above, e.g. see forehead cushion 1752 in FIG. 32-6.

As illustrated, the forehead cushion support 2753 includes forehead cushion support plates 2751 and a tube or slider 2722 joined to the support plates 2751. The support plates 2751 extend generally transversely relative to the slider 2722 and thus define a general T-shaped support.

The slider 2722 includes integrally molded male threads (used for forehead support depth adjustment). The male threaded slider 2722 has flats at the top and bottom thereof (see FIG. 42-6) to improve moldability and to provide keyed assembly with the mask frame (to prevent rotation). Also, recessed slots 2785 are provided at the bottom of the slider 2722 to provide indexed tactile feedback on adjustment position. In addition, a resilient tab 2787 is provided to the slider 2722 to provide quick-release assembly to the mask frame.

Each support plate 2751 has a generally circular attachment recess 2755 to receive a respective attachment head of the forehead cushion, e.g., formed of flexible silicone, so as to physically attach the forehead cushion to the support plates 2751. In use, the slider 2722 is extended or retracted with respect to the mask frame which causes adjustable movement of the forehead cushion.

The forehead cushion support plates 2751 include clip receiving structures or clip receptacles 2790 for engaging headgear clips associated with headgear straps. The headgear clips may be structured like those disclosed in U.S. Pat. No. 6,374,826 and/or PCT Application No. PCT/AU04/01834, filed Dec. 24, 2004, the entireties of both being incorporated herein by reference. However, the forehead cushion support plates 2751 may include other suitable structures for engaging headgear straps, e.g., slots. Also, the tube 2722 is recessed into the support plates 2751 which allows maximum extension with minimum protrusion from the forehead, thereby reducing actual and visual bulk.

In the illustrated embodiment, the clip receptacles 2790 are integrally molded with the plates 2751 and slider 2722. Also, the clip receptacles 2790 are molded in front of the attachment recesses 2755, thereby reducing the overall width of the T-shaped forehead cushion support 2753.

XXVIII. Eighteenth Illustrated Embodiment of Forehead Support

Figures 3, 43:
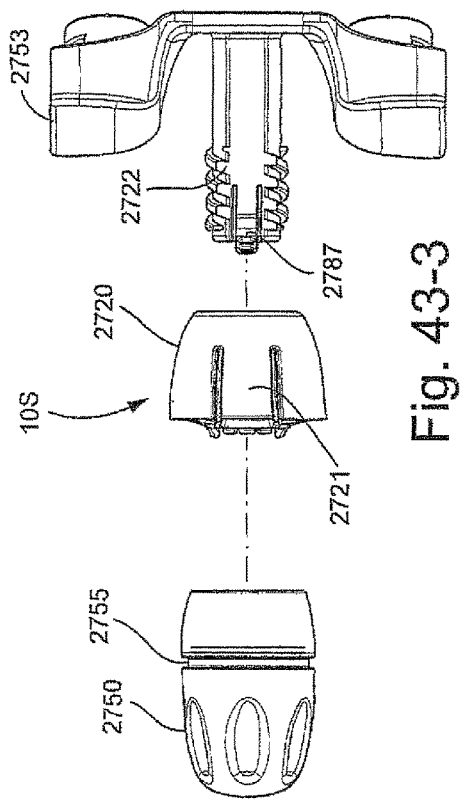
Figures 5, 43:
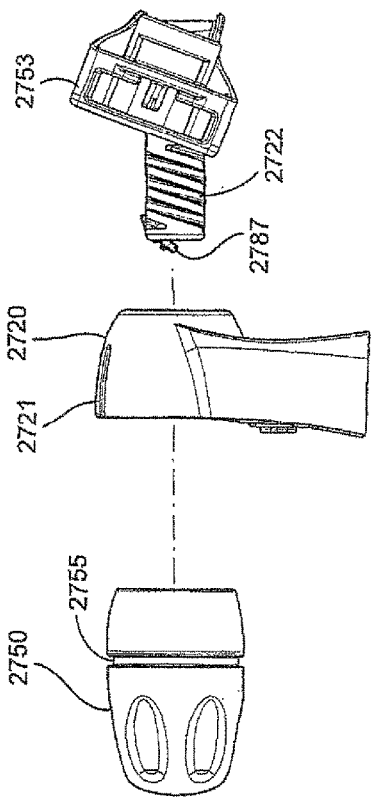
Figures 6, 43:
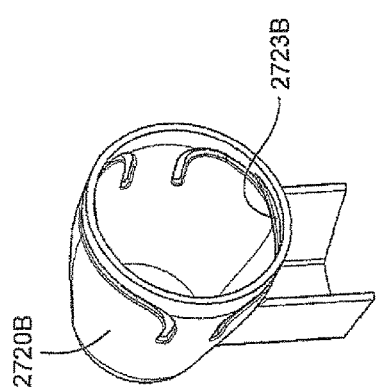
Figures 4, 43:
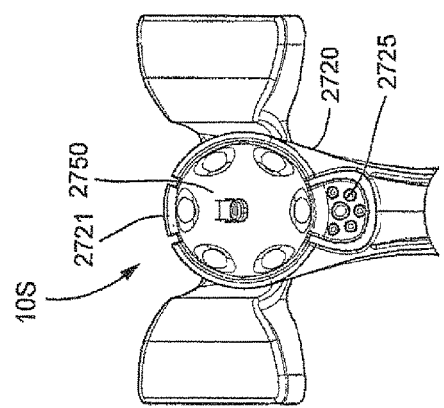
Figures 8, 43:
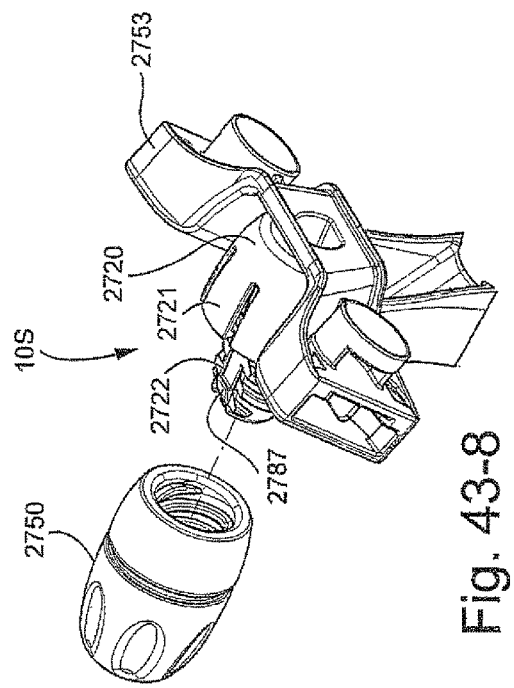
Figures 10, 43:
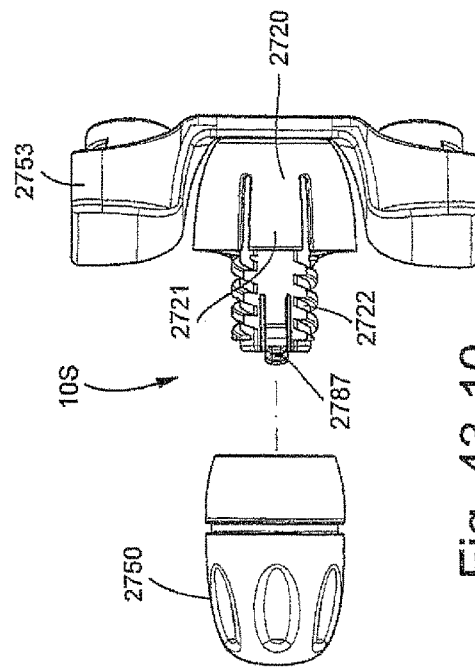
Figures 7, 43:
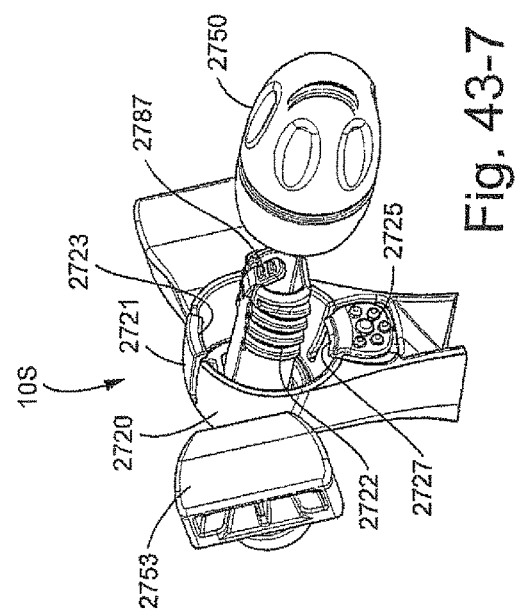
Figures 9, 43:
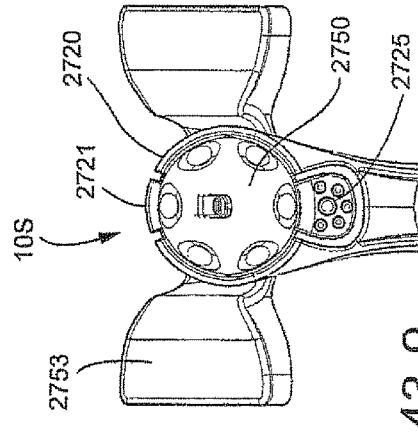
Figures 11, 43:
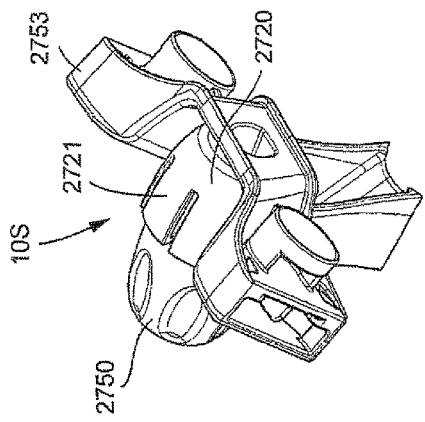
Figures 13, 43:
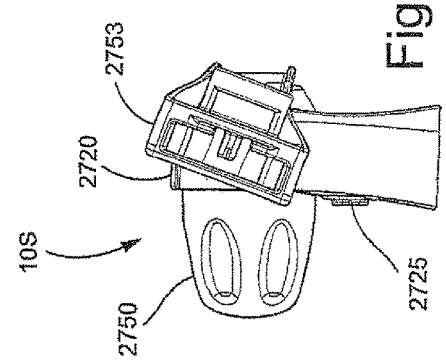
Figures 12, 43:
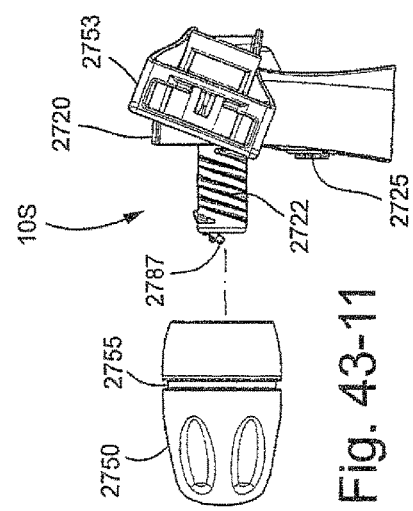
Figures 15, 43:
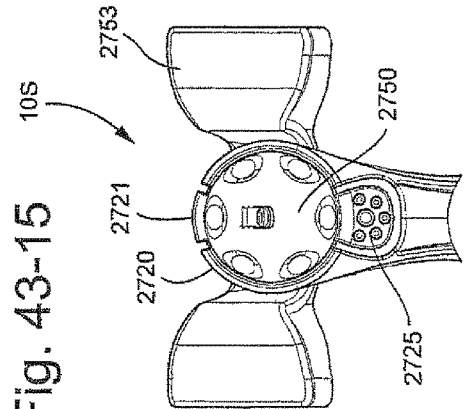
Figures 14, 16, 43:
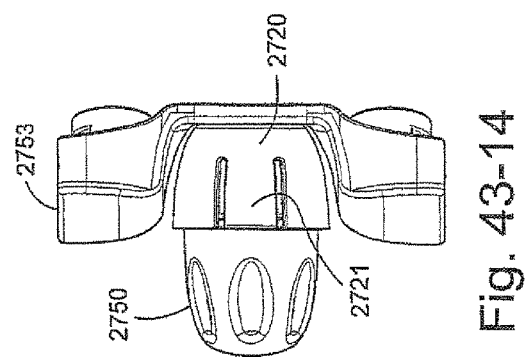

FIGS. 43-1 to 43-21 illustrate a FMA including a forehead support 10S according to another embodiment of the present invention. In this embodiment, the forehead support 10S incorporates the forehead cushion support 2753 described above in FIGS. 42-1 to 42-8, and uses a screw-type actuator to move the forehead cushion support 2753 along a generally linear path.

As illustrated, the forehead support 10S includes a support 2720 provided to the mask frame 2712 for supporting an adjustment knob 2750. The adjustment knob 2750 clips onto the support 2720 with a snap-fit. Specifically, the front of the support 2720 includes a resilient arm member 2721 that provides a first protrusion 2723 on a free end thereof, and a resilient quick-release button 2725 that provides a second protrusion 2727 on a free end thereof. The adjustment knob 2750 includes an annular groove 2755. When the adjustment knob 2750 is assembled to the support 2720, the resilient arm member 2721 and button 2725 deflect outwardly until the first and second protrusions 2723 and 2727 snap into the groove 2755 (see FIGS. 43-12 to 43-16). The knob 2750 may be quickly released from the support 2720 by depressing the quick-release button 2725.

FIG. 43-6 illustrates an alternative embodiment of a support 2720B provided to the mask frame. As illustrated, a quick-release detail is integrally molded with the frame to retain the knob 2750. Specifically, upper and lower protrusions 2723B (only lower protrusions visible) are provided to engage the knob 2750, and the knob 2750 may be released by squeezing the sides of the support 2720B.

The adjustment knob 2750 includes internal threads and receives the threaded slider 2722 of the forehead cushion support 2753 therein such that the internal threads of the knob 2750 are intermeshed with the threaded slider 2722.

As best shown in FIGS. 43-1, 43-2, 43-17, 43-18, and 43-20, the threaded slider 2722 includes a non-circular outer profile or exterior surface (i.e., flats at the top and bottom thereof) that is adapted to extend through a non-circular opening 2745 provided to the support 2720 to prevent the slider 2722 and hence the forehead cushion support 2753 from twisting or rotating relative to the frame 2712. Also, the resilient tab 2787 of the forehead cushion support 2753 engages the opening 2745 with a snap-fit, and may be quickly released from the support 2720 by depressing the tab 2787.

When the knob 2750 is rotated, the threaded slider 2722 extends or retracts from the internally threaded knob 2750 which causes adjustable movement of the forehead cushions.

As shown in FIG. 43-2, a ridge 2792 is integrally molded inside the opening 2745 of the support 2720. The ridge 2792 engages the recessed slots 2785 provided at the bottom of the slider 2722 (see FIGS. 42-1 and 42-8) to provide indexed tactile feedback on adjustment position. As the knob 2750 is rotated, the ridge 2792 ratchets or clicks against the slots 2785.

Figures 1, 11:
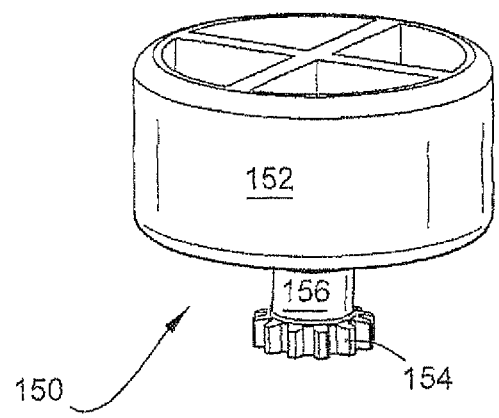
Figures 2, 11:
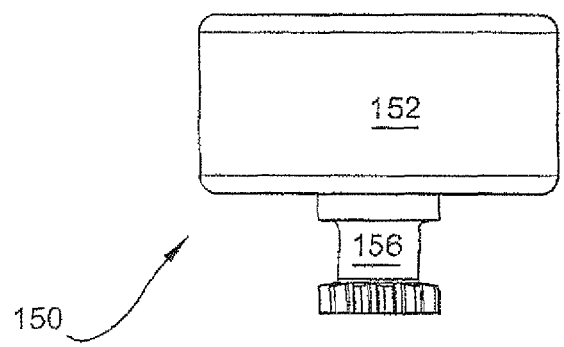
Figures 3, 11:
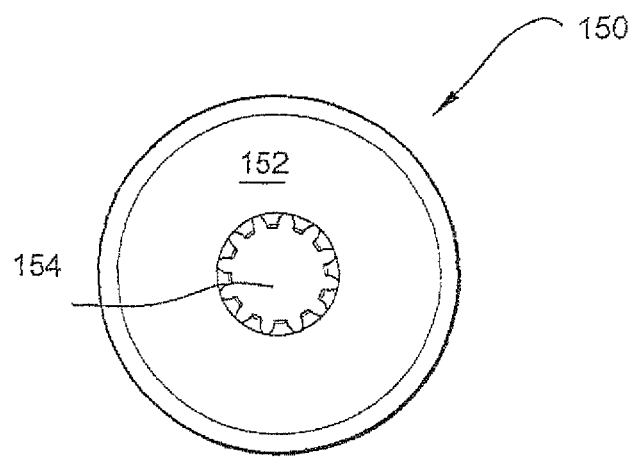
Figures 1, 17:
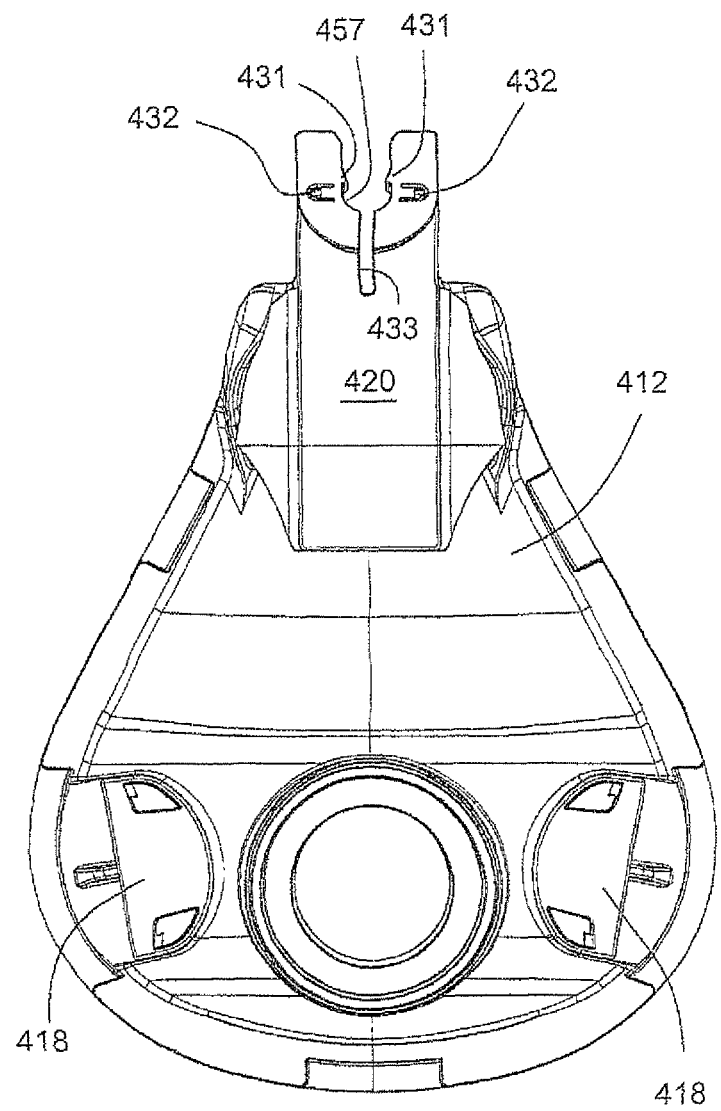
Figures 2, 17:
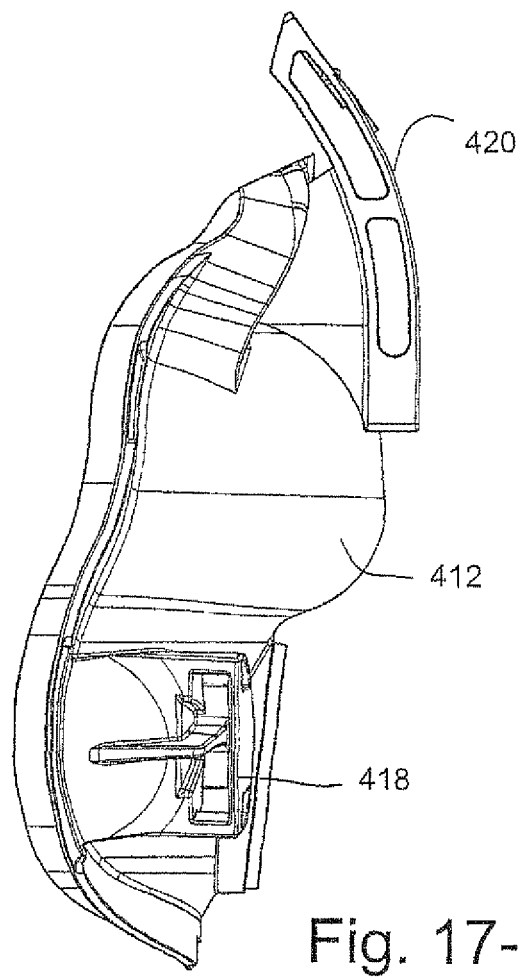
Figures 3, 17:
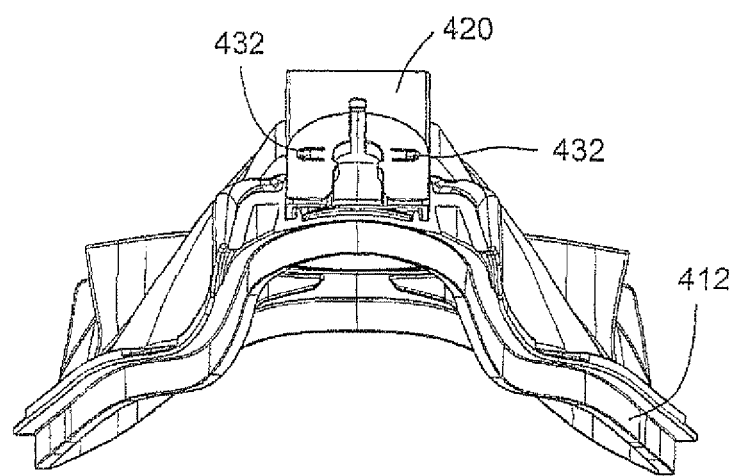
Figures 4, 17:
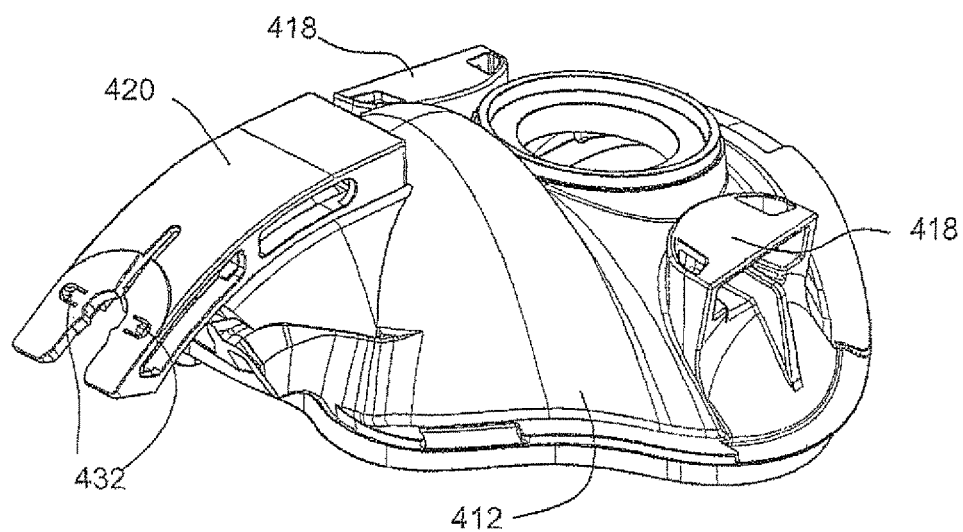
Figures 5, 17:
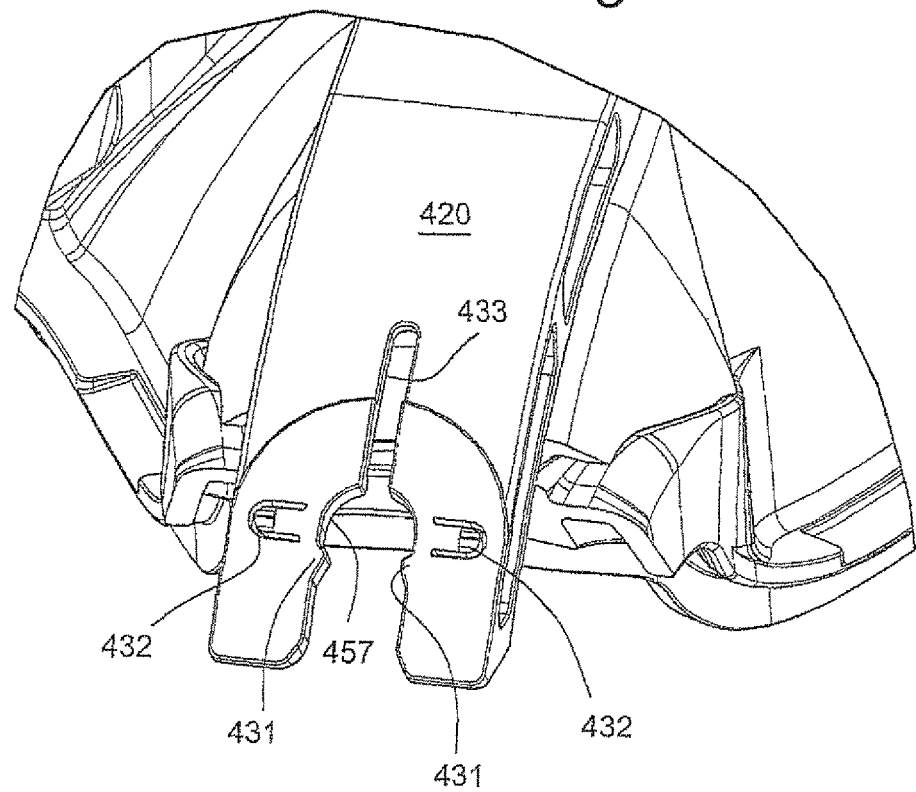
Figures 6, 17:
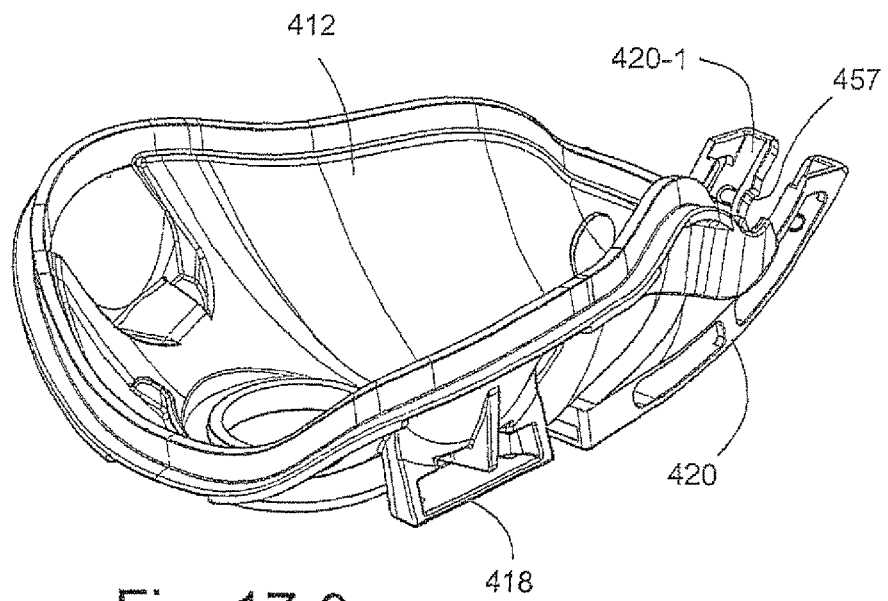
Figures 7, 17:
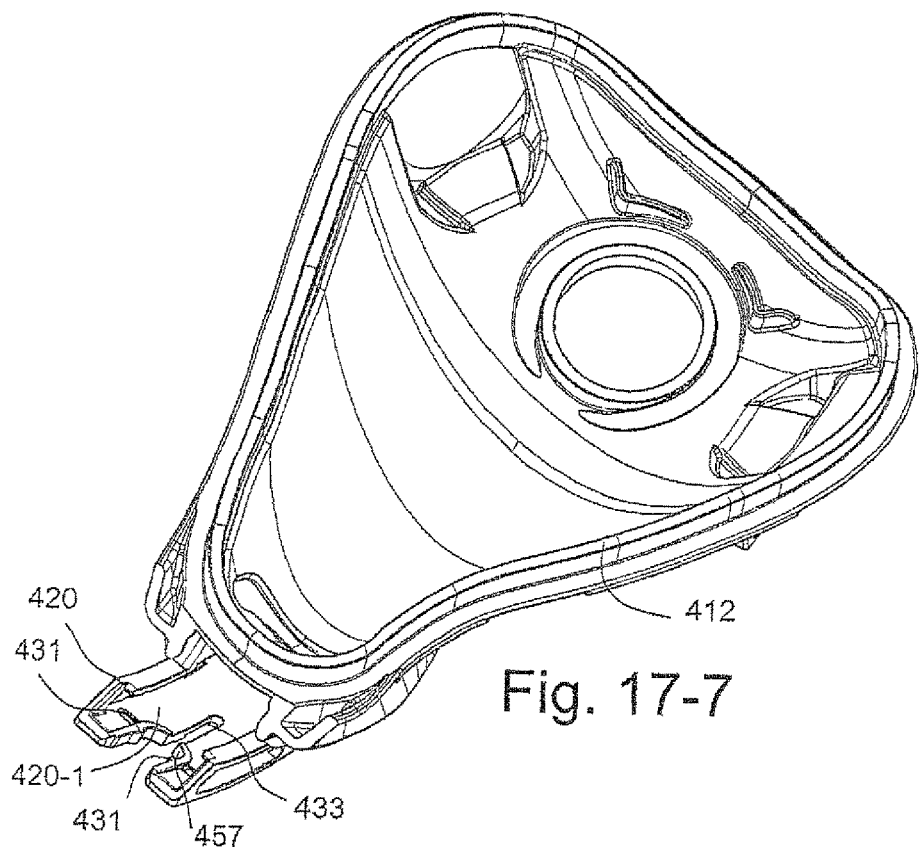

FIGS. 43-1 to 43-5 are exploded views of the forehead support 10S, FIGS. 43-7 to 43-11 are partial assembled views of the forehead cushion support 2753 engaged with the support 2720, FIGS. 43-12 to 43-16 are assembled views of the forehead support 10S, and FIGS. 43-17 to 43-21 are isolated views of the frame 2712.

XXIX. Embodiment of Forehead Cushion Support

Figures 1, 44:
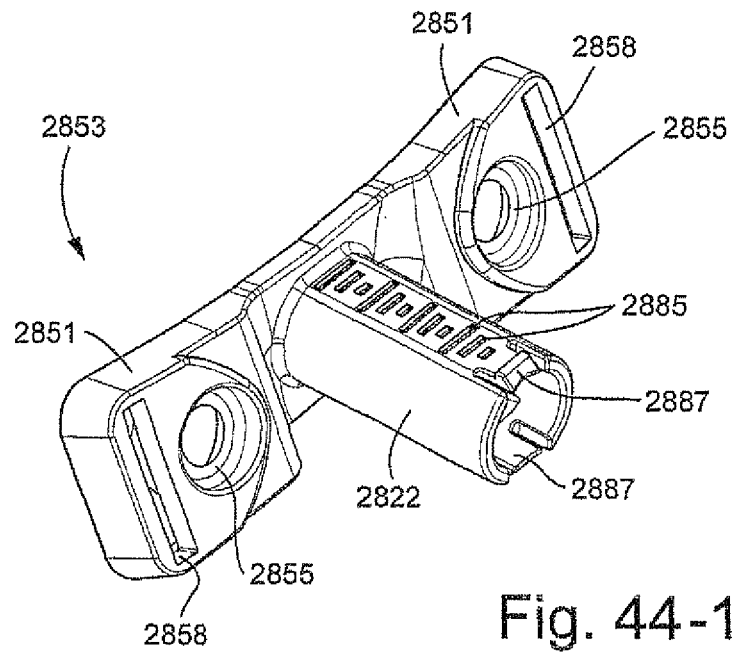
Figures 2, 44:
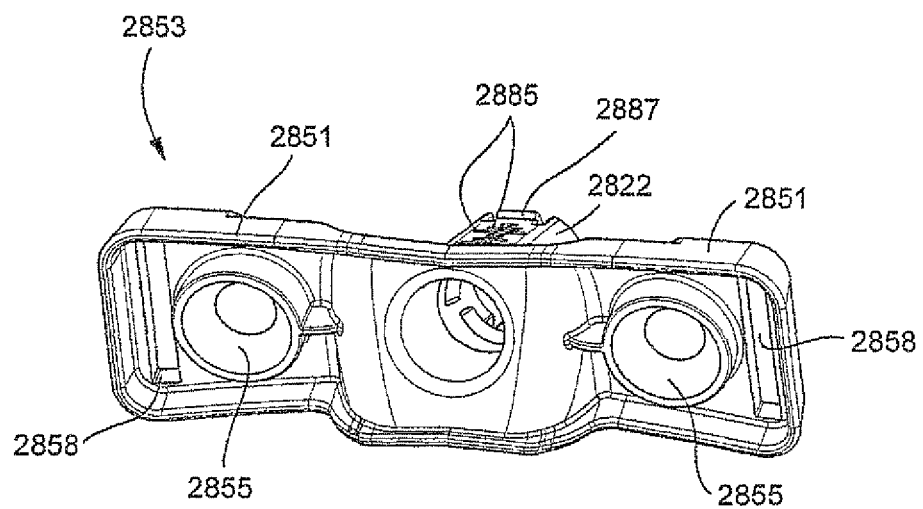
Figures 3, 44:
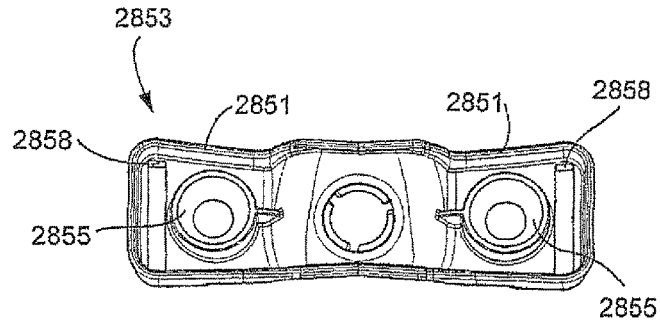
Figures 4, 44:
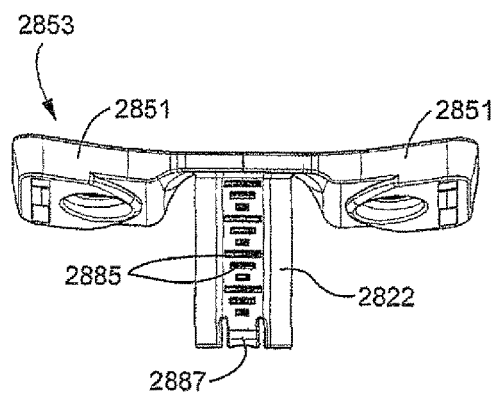
Figures 5, 6, 7, 44:
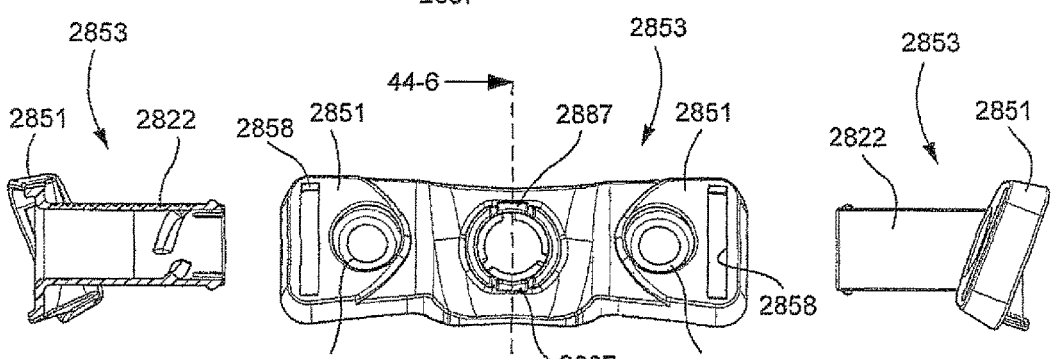
Figures 8, 44:
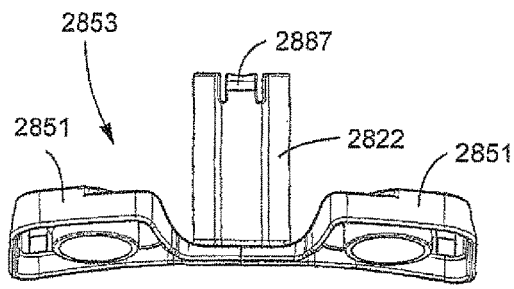

FIGS. 44-1 to 44-8 illustrate a forehead cushion support 2853 for a forehead support according to an embodiment of the present invention. The forehead cushion support 2853 is adapted for use with a forehead cushion such as those described above, e.g. see forehead cushion 1752 in FIG. 32-6.

As illustrated, the forehead cushion support 2853 includes forehead cushion support plates 2851 and a tube or slider 2822 joined to the support plates 2851. The support plates 2851 extend generally transversely relative to the slider 2822 and thus define a general T-shaped support.

The slider 2822 includes integrally molded 3-lug female threads (for better moldability). Only a 3-lug thread form is needed to engage the mating male thread provided on the adjustment knob (described below). However, other thread forms are possible. The female or internally threaded slider 2822 has flats at the top and bottom thereof (see FIGS. 44-1 and 44-5) to improve moldability and to provide keyed assembly with the mask frame (to prevent rotation). Also, recessed slots 2885 (of varying width and depth) are provided at the top of the slider 2822 to provide indexed and visual feedback on adjustment position. In addition, resilient tabs 2887 are provided to the top and bottom of the slider 2822 to provide quick-release assembly to the mask frame. The resilient tabs 2887 prevent the forehead cushion support 2853 from falling out of the frame when fully extended. The presence of the threaded shaft 2854 of the adjustment knob 2850 (see FIGS. 4501 to 45-19 below) prevents the resilient tabs 2887 from deflecting.

Each support plate 2851 has a generally circular attachment recess 2855 to receive a respective attachment head of the forehead cushion, e.g., formed of flexible silicone, so as to physically attach the forehead cushion to the support plates 2851. In use, the slider 2822 is extended or retracted with respect to the mask frame which causes adjustable movement of the forehead cushion.

The forehead cushion support plates 2851 include integrally molded slots 2858 for engaging headgear straps.

XXX. Nineteenth Illustrated Embodiment of Forehead Support

Figures 12, 45:
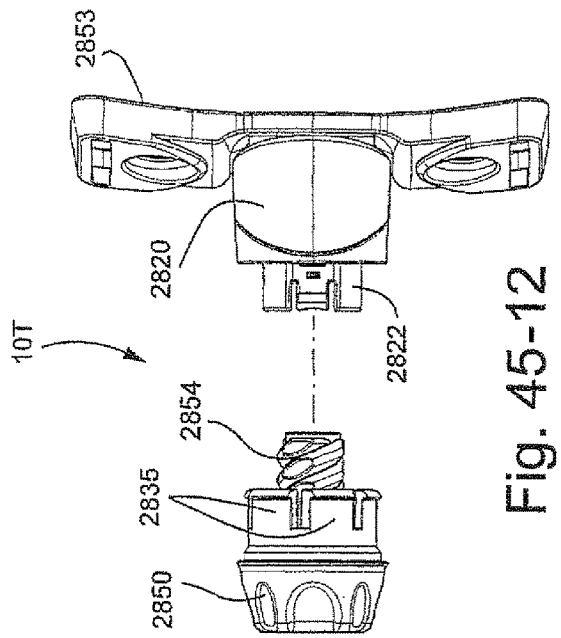
Figures 14, 45:
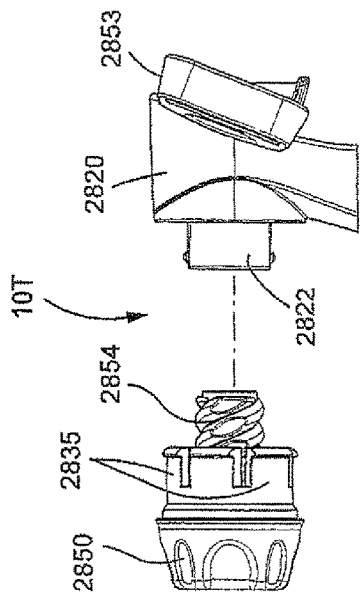
Figures 11, 45:
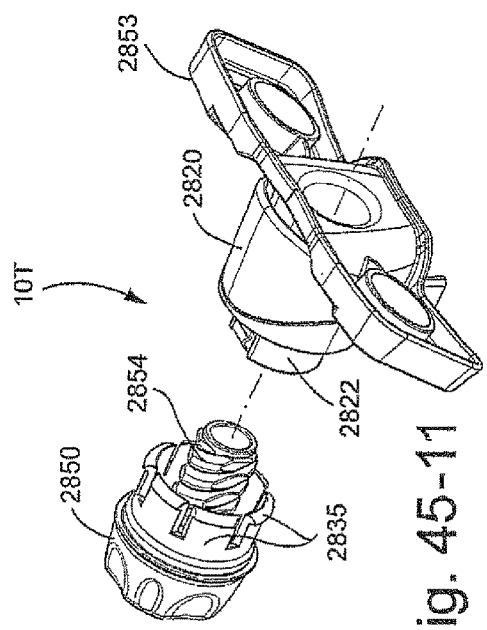
Figures 13, 45:
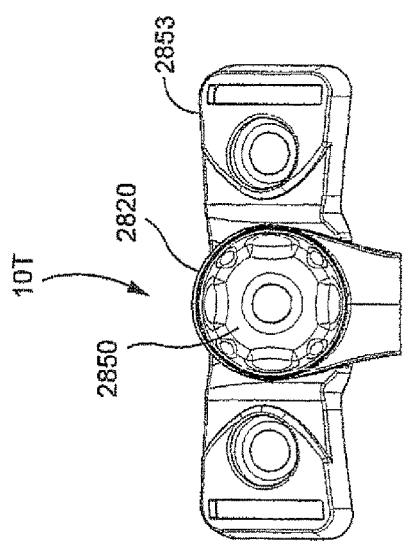

FIGS. 45-1 to 45-19 illustrate a forehead support 10T according to another embodiment of the present invention. In this embodiment, the forehead support 10T incorporates the forehead cushion support 2853 described above in FIGS. 44-1 to 44-8, and uses a screw-type actuator to move the forehead cushion support 2853 along a generally linear path.

As illustrated, the forehead support 10T includes a support 2820 provided to the mask frame 2812 for supporting an adjustment knob 2850. The adjustment knob 2850 clips onto the support 2820 with a snap-fit. Specifically, the adjustment knob 2850 includes multiple resilient arm members 2835, e.g., six finger quick-release feature, integrally molded therewith. When the adjustment knob 2850 is assembled to the support 2820, the resilient arm members 2835 snap into the support 2820 (see FIGS. 45-15 to 45-19).

As illustrated, a threaded shaft 2854 is provided to the adjustment knob 2850. In the illustrated embodiment, the threaded shaft 2854 and the adjustment knob 2850 are integrally formed, e.g., integrally molded, as a one-piece structure. However, the adjustment knob 2850 and the threaded shaft 2854 may be constructed in two parts and permanently or semi-permanently assembled, e.g., by an adhesive. For example, FIGS. 45-4 to 45-6 illustrate a two part knob 2850 and threaded shaft 2854 for improved moldability. As shown in FIG. 45-6, the male threaded shaft 2854 includes a three-start design and features three flats (i.e., trilobial cross-section) for improved moldability.

The threaded shaft 2854 engages within the internally threaded slider 2822 of the forehead cushion support 2853 such that the threaded shaft 2854 is intermeshed with the internally threaded slider 2822.

The internally threaded slider 2822 includes a non-circular outer profile or exterior surface (i.e., flats at the top and bottom thereof) that is adapted to extend through a non-circular opening 2845 or key feature (see FIG. 45-2) provided to the support 2820 to prevent the slider 2822 and hence the forehead cushion support 2853 from twisting or rotating relative to the frame 2812. Also, the resilient tabs 2887 of the forehead cushion support 2853 engage the opening 2845 with a snap-fit to provide quick-release assembly.

When the knob 2850 is rotated, the internally threaded tube 2822 extends or retracts from the threaded shaft 2854 provided to the knob 2850 which causes adjustable movement of the forehead cushions.

FIG. 45-3 illustrates an alternative embodiment of a support 2820B provided to the mask frame. As illustrated, ridges 2823B are integrally molded inside the opening 2845B to retain the arm members 2835 of the adjustment knob 2850. Also, a ridge 2823C is integrally molded inside the opening 2845B to provide indexed incremental adjustment of the forehead support and to provide tactile feedback. The ridge or ratchet 2823C will act against the grooves 2827 between the resilient arm members 2835 of the adjustment knob 2850 to provide indexed incremental adjustment of the forehead support and to provide tactile feedback.

Figures 1, 14:
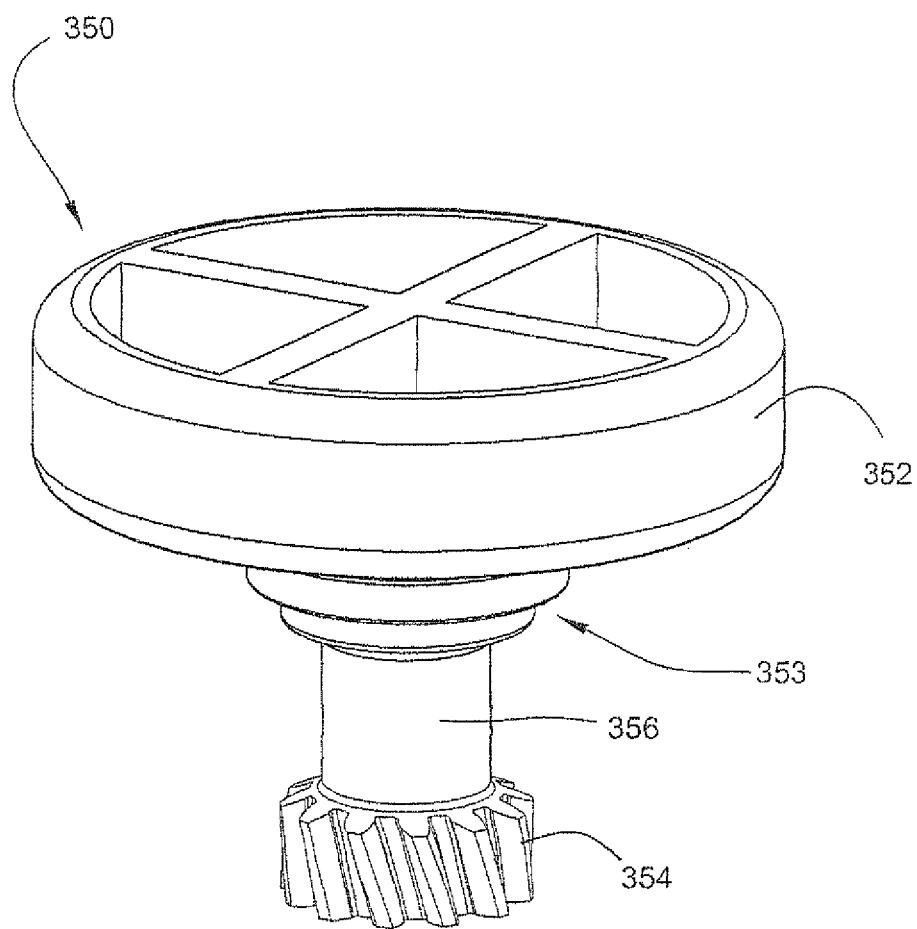
Figures 2, 14:
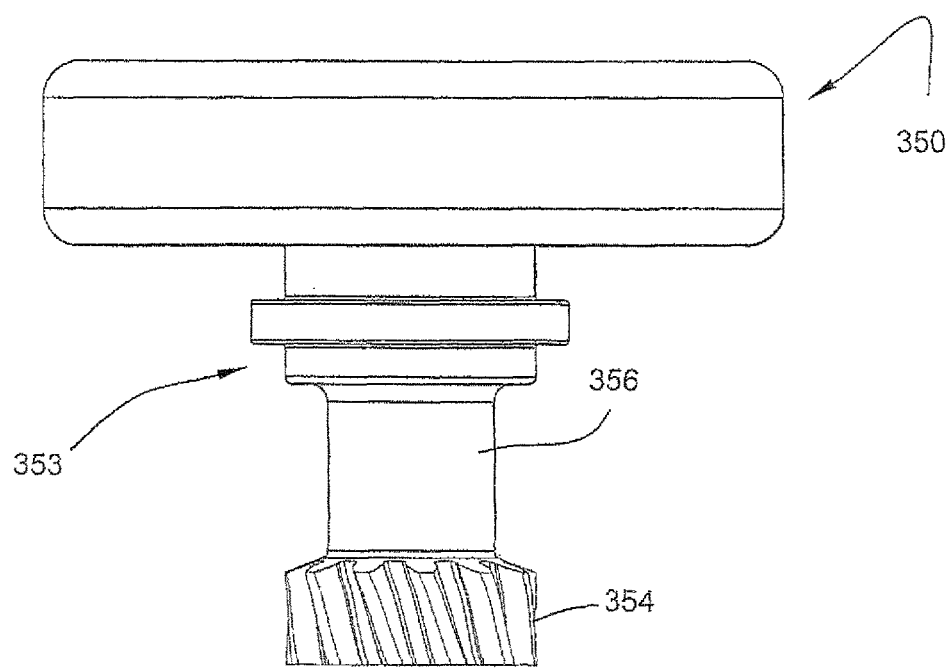
Figures 3, 14:
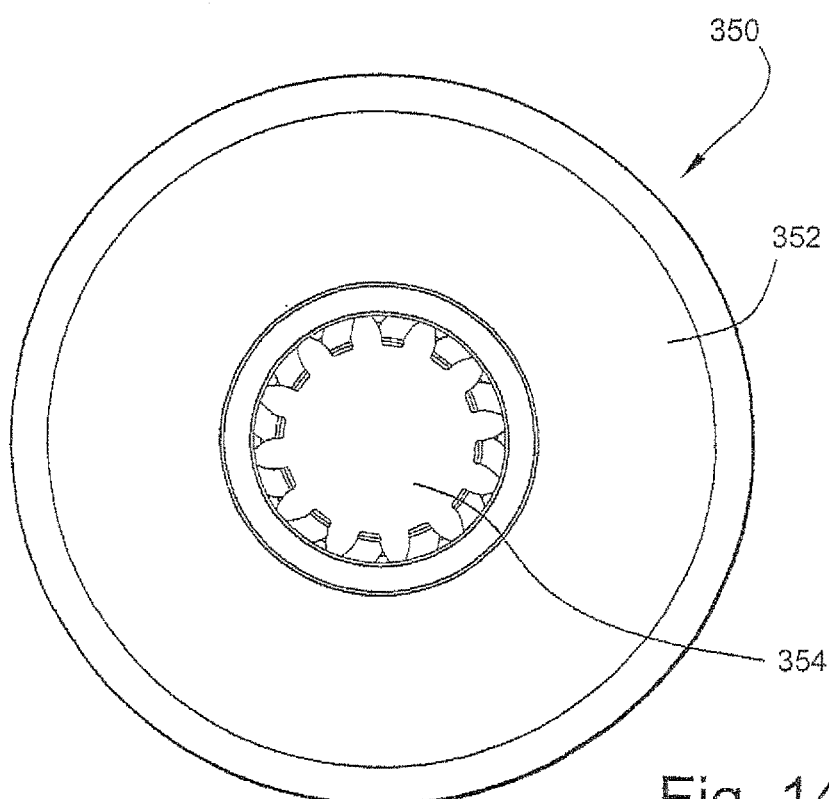

FIGS. 45-1, 45-2, and 45-7 to 45-9 are exploded views of the forehead support 10T, FIGS. 45-10 to 45-14 are partial assembled views of the forehead cushion support 2853 engaged with the support 2820, and FIGS. 45-15 to 45-19 are assembled views of the forehead support 10T.

XXXI. Twentieth Illustrated Embodiment of Forehead Support

FIGS. 46-1 to 46-16 illustrate a forehead support 10U according to another embodiment of the present invention. In this embodiment, the forehead support 10U uses a screw-type actuator to move the forehead support along a generally linear path.

As illustrated, the forehead support 10U includes a support 2920 provided to the mask frame 2912 for supporting an adjustment knob 2950. The adjustment knob 2950 includes a threaded shaft 2954 that extends through the support 2920. The threaded shaft 2954 engages within an internally threaded tube 2922 such that the threaded shaft 2954 is intermeshed with the internally threaded tube 2922. The internally threaded tube 2922 is joined to forehead cushion support plates 2951 that carry forehead cushions.

When the knob 2950 is rotated, the internally threaded tube 2922 extends or retracts from the threaded shaft 2954 which causes adjustable movement of the forehead cushions.

The internally threaded tube 2922 has flats at the top and bottom thereof to improve moldability and to provide keyed assembly with the mask frame (to prevent rotation). The internally threaded tube 2922 is adapted to extend through a non-circular opening 2945 or key feature (see FIG. 46-1) provided to the support 2920 to prevent the tube 2922 and hence the forehead cushions from twisting or rotating relative to the frame 2912. In addition, resilient tabs 2987 (see FIGS. 46-1 and 46-2) are provided to the top and bottom of the tube 2922 to provide quick-release assembly to the mask frame.

In the illustrated embodiment, the knob 2950 has a male threaded shaft 2954 with a three-start design and features three flats (i.e., trilobial cross-section) for improved moldability (see FIG. 46-6). In an embodiment, the head 2947 and shaft 2954 of the knob 2950 are integrally molded in one piece to simplify tooling.

The head 2947 of the knob 2950 clips onto the support 2920 with a snap-fit. As shown in FIG. 46-5, the head 2947 of the knob 2950 is slotted so it can be squeezed for disassembly from the support 2920.

FIGS. 46-1 to 46-5 are exploded views of the forehead support 10U, FIGS. 46-7 to 46-11 are partial assembled views of the forehead cushion support engaged with the support 2920, and FIGS. 46-12 to 46-16 are assembled views of the forehead support 10U.

XXXII. Twenty-First Illustrated Embodiment of Forehead Support

Figures 4, 47:
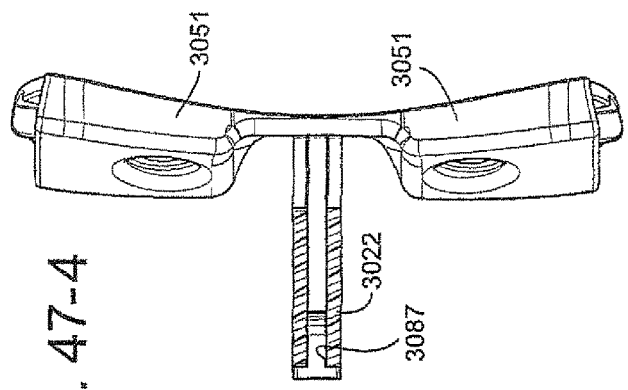
Figures 5, 47:
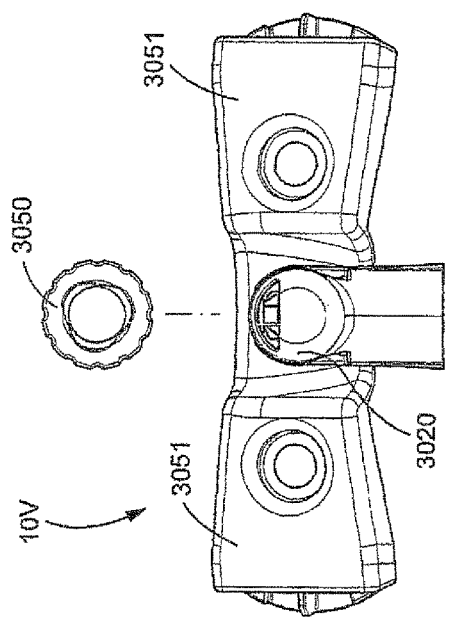
Figures 6, 47:
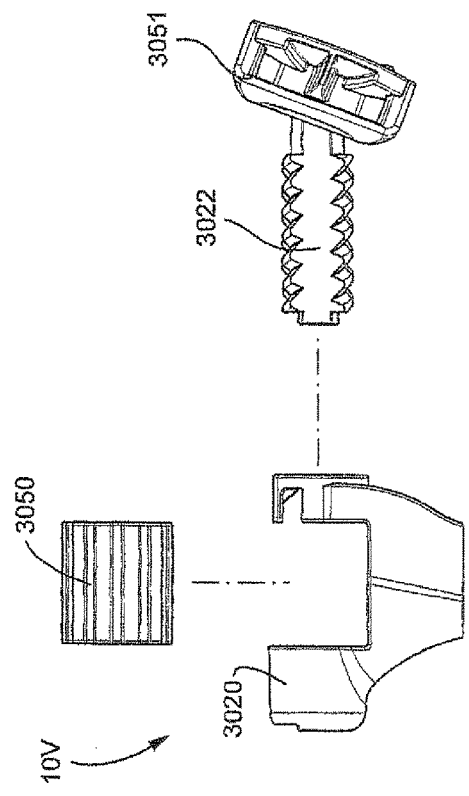
Figures 13, 47:
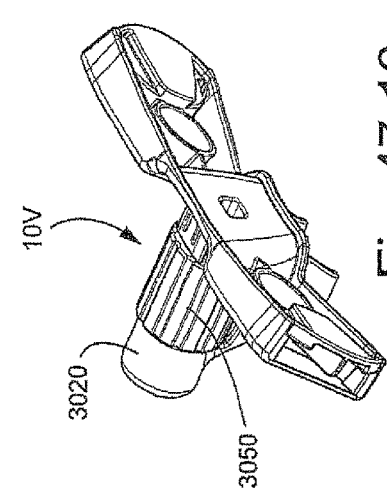
Figures 16, 47:
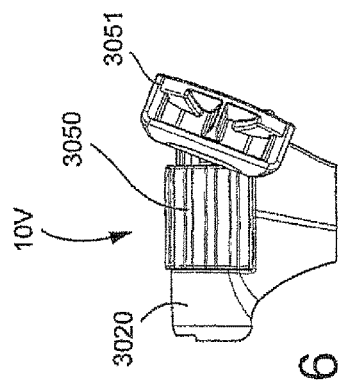
Figures 14, 47:
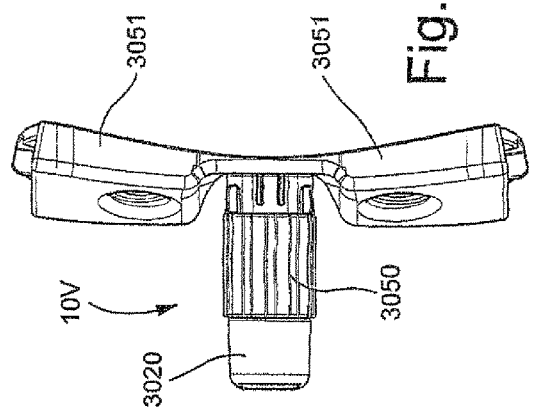
Figures 12, 47:
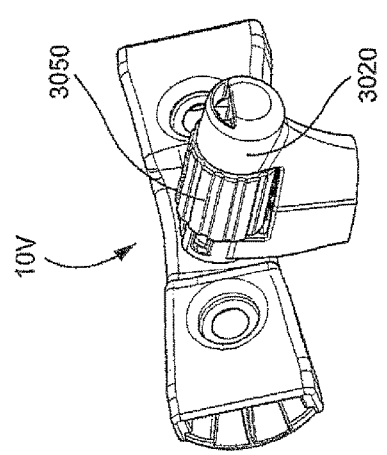
Figures 15, 47:
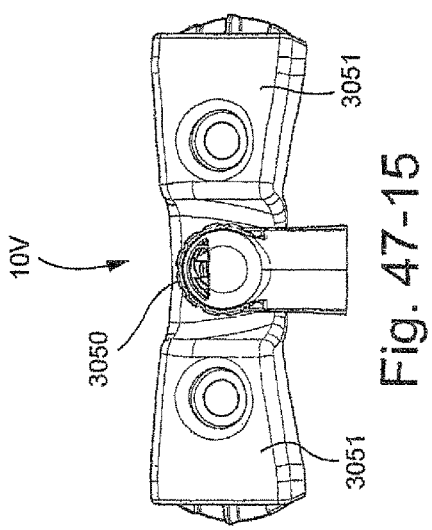

FIGS. 47-1 to 47-16 illustrate a forehead support 10V according to another embodiment of the present invention. In this embodiment, the forehead support 10V uses a screw-type actuator to move the forehead support along a generally linear path.

As illustrated, the forehead support 10V includes a support 3020 provided to the mask frame 3012 for supporting an adjustment knob or dial 3050. The adjustment dial 3050 includes internal threads (female threads) and is trapped between the frame geometry. A threaded shaft 3022 extends through the support 3020 and the adjustment dial 3050 such that the internal threads of the adjustment dial 3050 are intermeshed with the threaded shaft 3022. The threaded shaft 3022 is joined to forehead cushion support plates 3051 that carry forehead cushions.

When the adjustment dial 3050 is rotated, the threaded shaft 3022 extends or retracts from the adjustment dial 3050 which causes adjustable movement of the forehead cushions.

The threaded shaft 3022 has flats on both sides thereof to improve moldability and to provide keyed assembly with the mask frame (to prevent rotation). The threaded shaft 3022 includes elongated slots 3087 that receive respective protrusions 3089 provided to the support 3020. The protrusions 3089 are integrally molded with the support 3020 and provide a key feature to prevent rotation of the forehead cushion support.

In the illustrated embodiment, the threaded shaft 3022 has a three-start design and features two flats for improved moldability (see FIG. 47-3).

FIGS. 47-1, 47-2, and 47-4 to 47-6 are exploded views of the forehead support 10V, FIGS. 47-7 to 47-11 are partial assembled views of the adjustment dial 3050 engaged with the support 3020, and FIGS. 47-12 to 47-16 are assembled views of the forehead support 10V.

XXXIII. Twenty-Second Illustrated Embodiment of Forehead Support

Figures 8, 48:
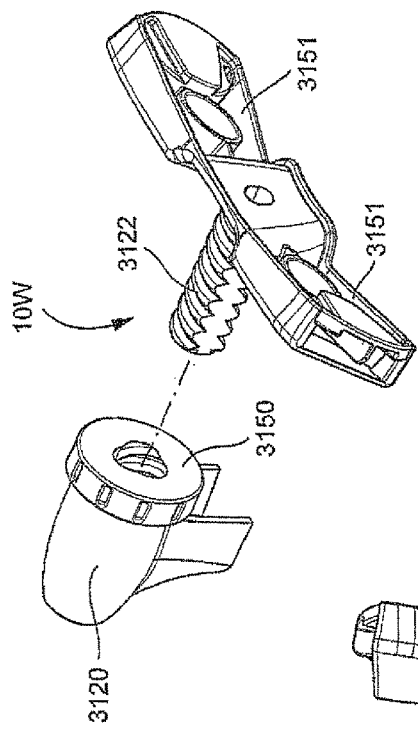
Figures 7, 48:
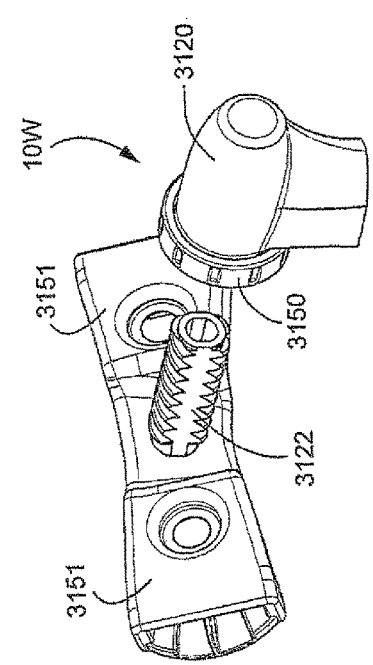
Figures 9, 48:
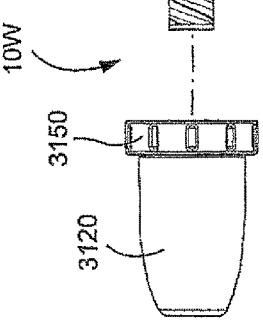
Figures 11, 48:
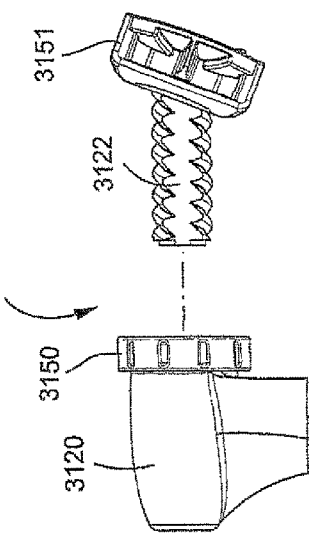
Figures 10, 48:
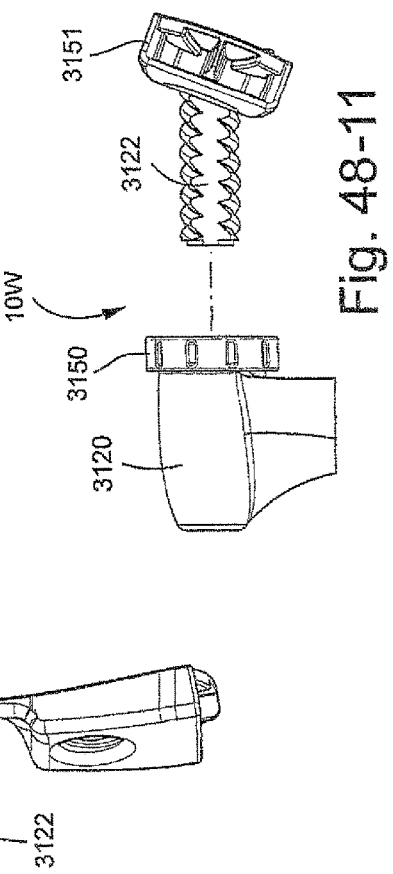
Figures 13, 48:
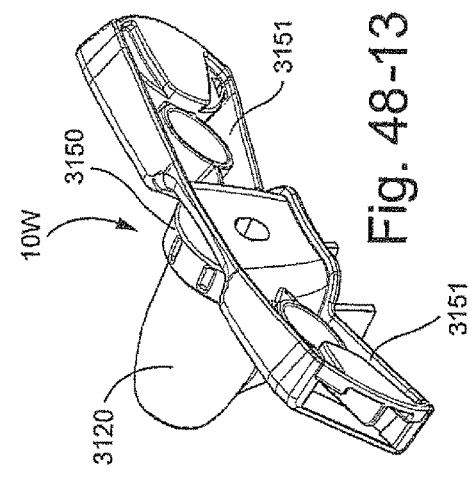
Figures 16, 48:
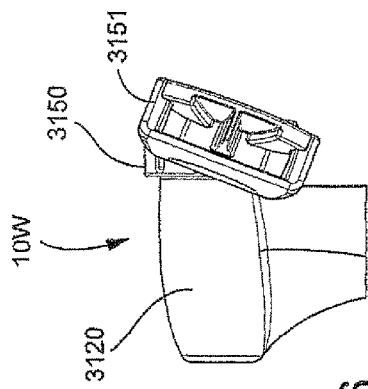
Figures 14, 48:
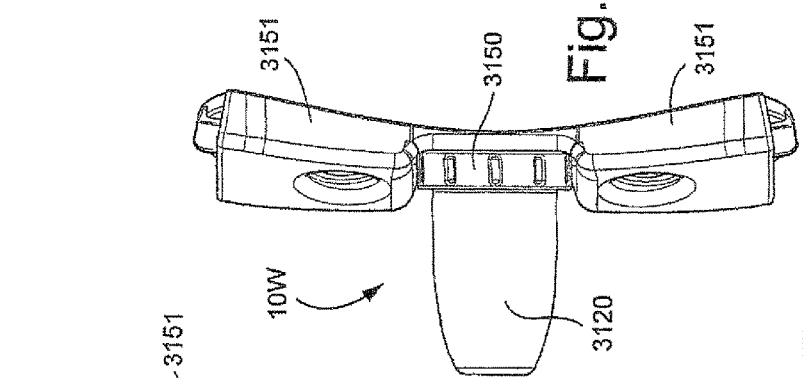
Figures 12, 48:
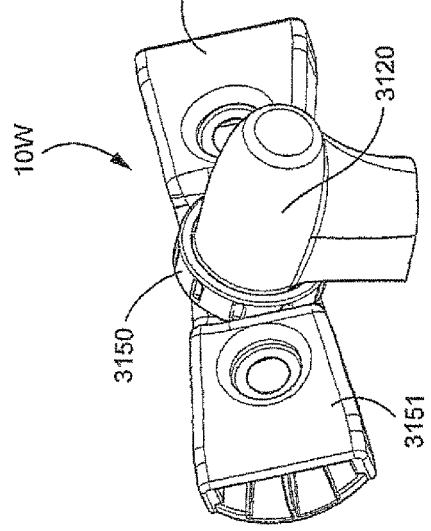
Figures 15, 48:
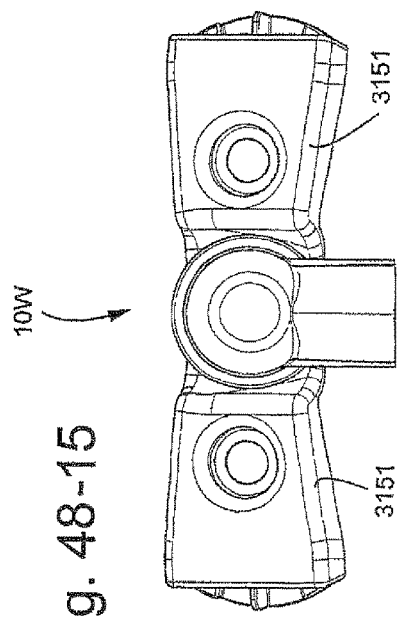

FIGS. 48-1 to 48-16 illustrate a forehead support 10W according to another embodiment of the present invention. In this embodiment, the forehead support 10W uses a screw-type actuator to move the forehead support along a generally linear path.

As illustrated, the forehead support 10W includes a support 3120 provided to the mask frame 3112 for supporting an adjustment knob or dial 3150. The adjustment dial 3150 includes internal threads (female threads) and is attached to the front of the support 3120, e.g., with a snap-fit. A threaded shaft 3122 extends through the adjustment dial 3150 and into the support 3120 such that the internal threads of the adjustment dial 3150 are intermeshed with the threaded shaft 3122. The threaded shaft 3122 is joined to forehead cushion support plates 3151 that carry forehead cushions.

When the adjustment dial 3150 is rotated, the threaded shaft 3122 extends or retracts from the adjustment dial 3150 which causes adjustable movement of the forehead cushions.

The threaded shaft 3122 has flats on both sides thereof to improve moldability and to provide keyed assembly with the mask frame (to prevent rotation). The interior of the support 3120 may include integrally molded key features to prevent rotation of the forehead cushion support in use.

In the illustrated embodiment, the threaded shaft 3122 has a three-start design and features two flats for improved moldability (see FIG. 48-3).

FIGS. 48-1, 48-2, and 48-4 to 48-6 are exploded views of the forehead support 10W, FIGS. 48-7 to 48-11 are partial assembled views of the adjustment dial 3150 engaged with the support 3120, and FIGS. 48-12 to 48-16 are assembled views of the forehead support 10W.

XXXIV. Twenty-Third Illustrated Embodiment of Forehead Support

Figures 4, 49:
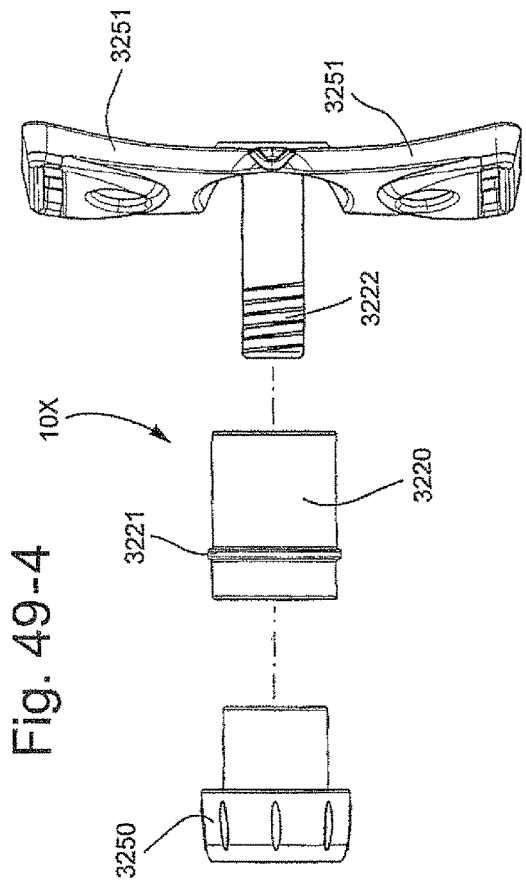
Figures 6, 49:
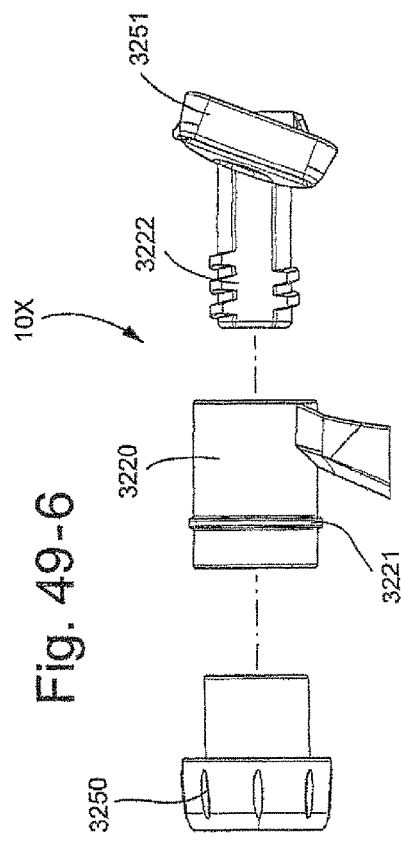
Figures 5, 49:
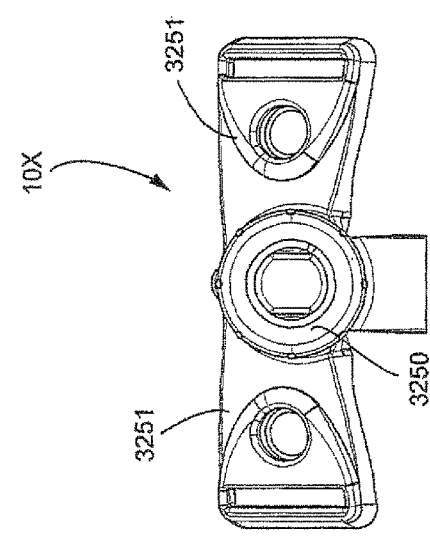

FIGS. 49-1 to 49-16 illustrate a forehead support 10X according to another embodiment of the present invention. In this embodiment, the forehead support 10X uses a screw-type actuator to move the forehead support along a generally linear path.

As illustrated, the forehead support 10X includes a support 3220 provided to the mask frame 3212 for supporting an adjustment knob or dial 3250. The adjustment dial 3250 includes internal threads (female threads) and is attached to a front of the support 3220. In the illustrated embodiment, the support 3220 includes an annular ring 3221 that engages an annular channel 3223 integrally molded with the dial 3250 to retain the dial 3250 on the support 3220.

A threaded shaft 3222 extends through the support 3220 and adjustment dial 3250 such that the internal threads of the adjustment dial 3250 are intermeshed with the threaded shaft 3222. The threaded shaft 3222 is joined to forehead cushion support plates 3251 that carry forehead cushions.

When the adjustment dial 3250 is rotated, the threaded shaft 3222 extends or retracts from the adjustment dial 3250 which causes adjustable movement of the forehead cushions.

The threaded shaft 3222 has flats on both sides thereof to improve moldability and to provide keyed assembly with the mask frame (to prevent rotation). The threaded shaft 3222 is adapted to extend through a non-circular opening 3245 or key feature (see FIG. 49-1) provided to the support 3220 to prevent the tube 3222 and hence the forehead cushions from twisting or rotating relative to the frame 3212.

In the illustrated embodiment, the threaded shaft 3222 has a single-start design and features two flats for improved moldability (see FIG. 49-3).

FIGS. 49-1, 49-2, and 49-4 to 49-6 are exploded views of the forehead support 10X, FIGS. 49-7 to 49-11 are partial assembled views of the forehead cushion support engaged with the support 3220, and FIGS. 49-12 to 49-16 are assembled views of the forehead support 10X.

XXXV. Twenty-Fourth Illustrated Embodiment of Forehead Support

Figures 7, 50:
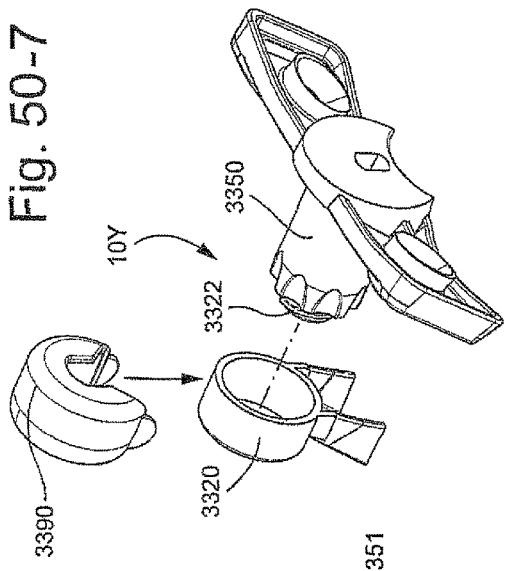
Figures 10, 50:
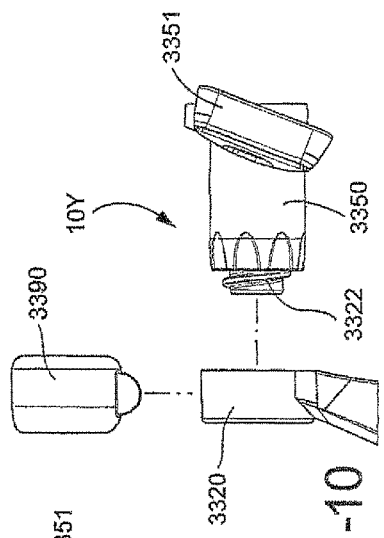
Figures 8, 50:
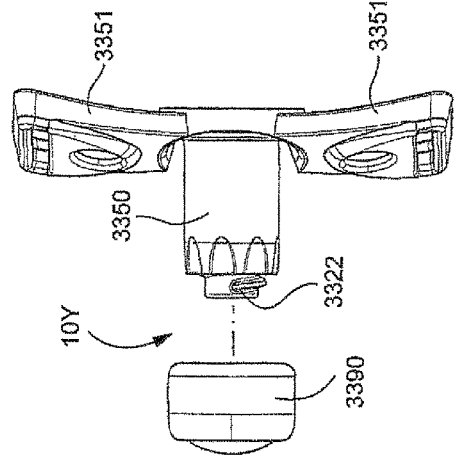
Figures 6, 50:
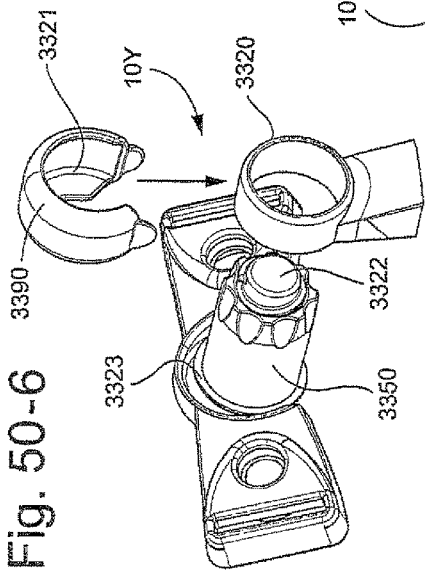
Figures 9, 50:
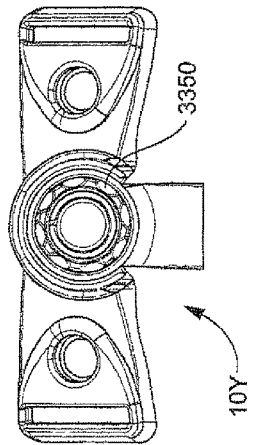

FIGS. 50-1 to 50-15 illustrate a forehead support 10Y according to another embodiment of the present invention. In this embodiment, the forehead support 10Y uses a screw-type actuator to move the forehead support along a generally linear path.

As illustrated, the forehead support 10Y includes a support 3320 provided to the mask frame 3312 for supporting an adjustment knob or dial 3350. The adjustment dial 3350 includes internal threads (female threads) and is retained to the support 3320 by a removable locking ring 3390. In the illustrated embodiment, the locking ring 3390 engages the support 3320 with a snap-fit and includes an annular channel 3321 that engages an annular ring 3323 integrally molded with the dial 3350 to retain the dial 3350 on the support 3320.

A threaded shaft 3322 extends through the adjustment dial 3350 such that the internal threads of the adjustment dial 3350 are intermeshed with the threaded shaft 3322. The threaded shaft 3322 is joined to forehead cushion support plates 3351 that carry forehead cushions.

When the adjustment dial 3350 is rotated, the threaded shaft 3322 extends or retracts from the adjustment dial 3350 which causes adjustable movement of the forehead cushions.

The threaded shaft 3322 has flats on both sides thereof to improve moldability and to provide keyed assembly with the mask frame (to prevent rotation). The threaded shaft 3322 is adapted to extend through a non-circular opening 3345 or key feature (see FIG. 50-2) provided to the locking ring 3390 to prevent the tube 3322 and hence the forehead cushions from twisting or rotating relative to the frame 3312. This embodiment has similar benefits to the fifteenth illustrated embodiment of the forehead support 10P. That is, forehead support 10Y maintains the forehead support position as the subassembly may be removed as one piece once the locking ring 3390 is removed.

In the illustrated embodiment, the threaded shaft 3322 passes through the adjustment dial 3350 to reduce the overall visual length and bulk of the assembly (see FIGS. 50-11 to 50-15).

FIGS. 50-1 to 50-5 are exploded views of the forehead support 10Y, FIGS. 50-6 to 50-10 are partial assembled views of the forehead cushion support engaged with the adjustment dial 3350, and FIGS. 50-11 to 50-15 are assembled views of the forehead support 10Y.

XXXVI. Twenty-Fifth Illustrated Embodiment of Forehead Support

Figures 1, 24:
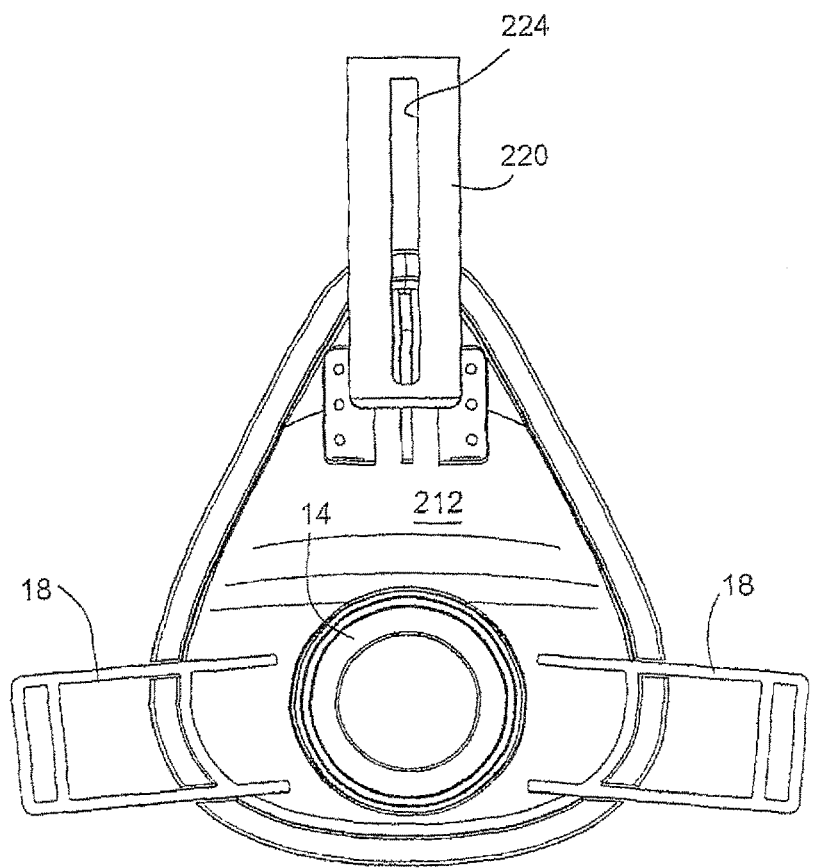
Figures 3, 24:
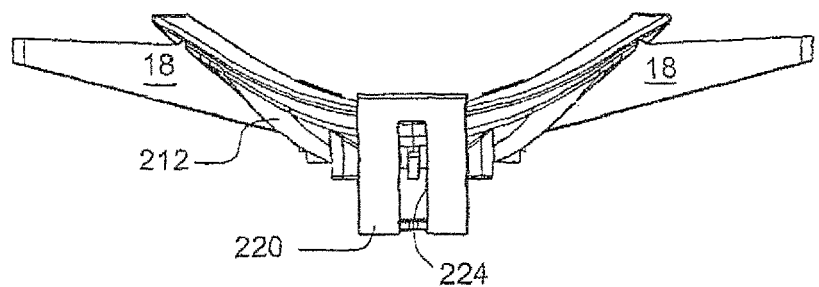
Figures 2, 24:
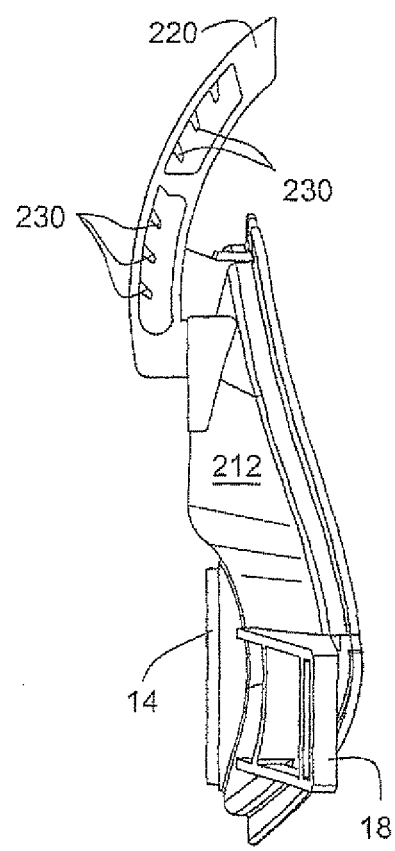
Figures 4, 24:
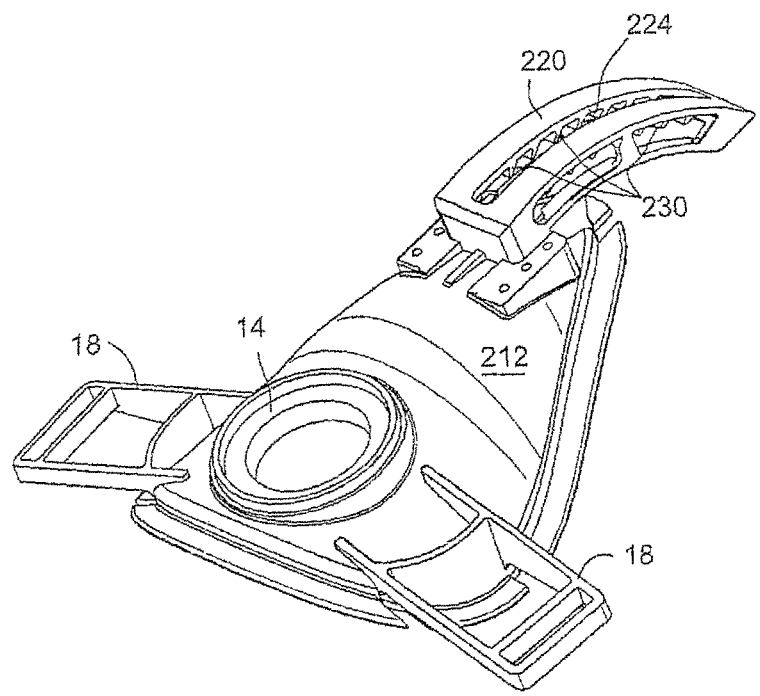
Figures 5, 24:
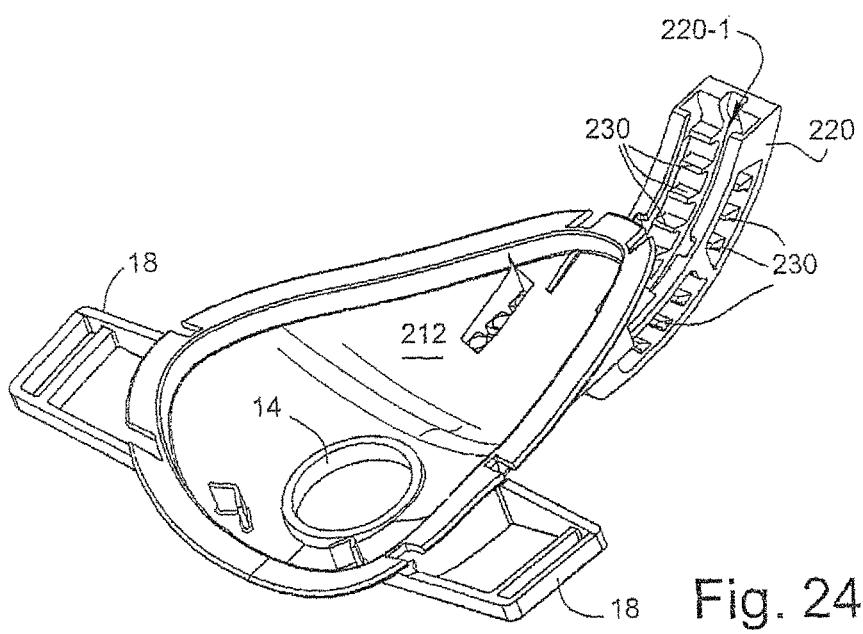
Figures 12, 51:
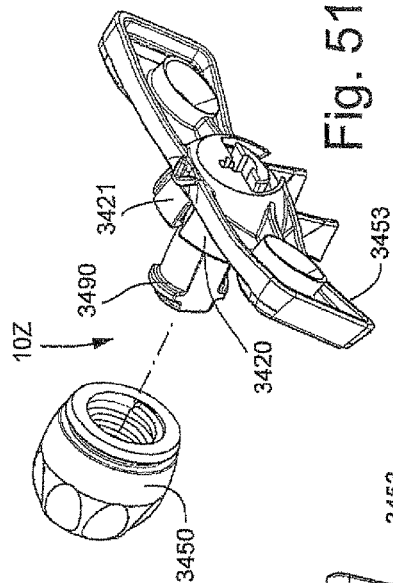
Figures 14, 51:
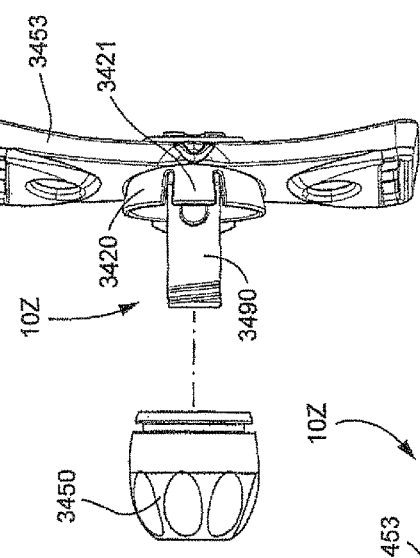
Figures 15, 51:
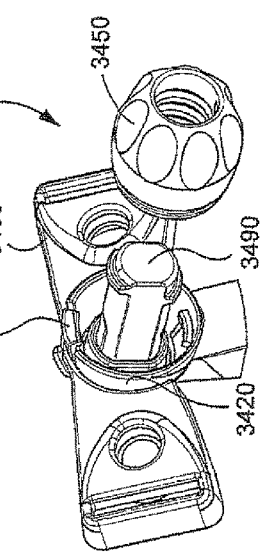
Figures 13, 51:
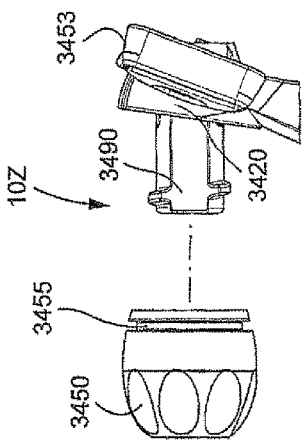
Figures 16, 51:
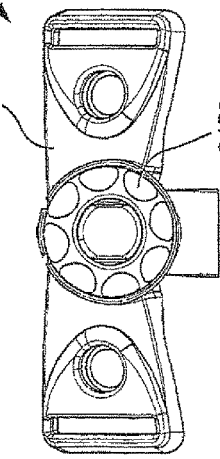
Figures 18, 51:
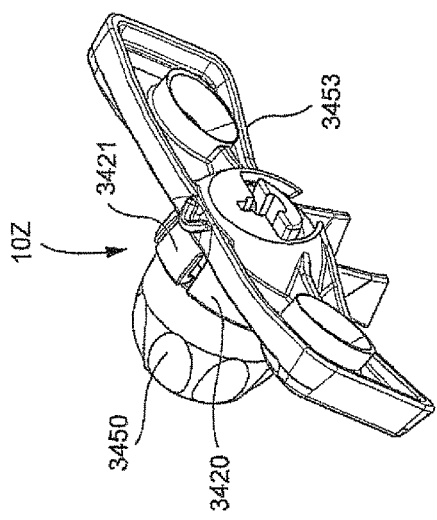
Figures 17, 51:
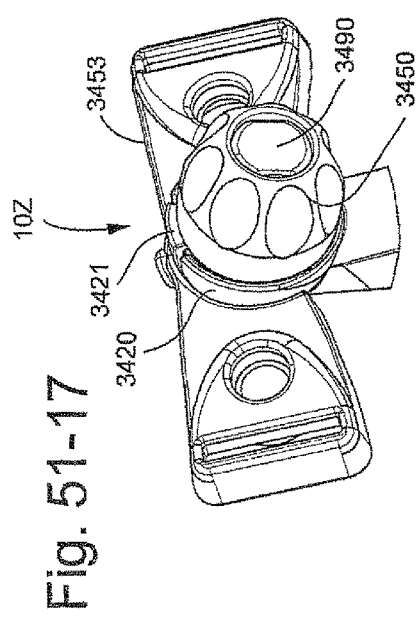
Figures 19, 51:
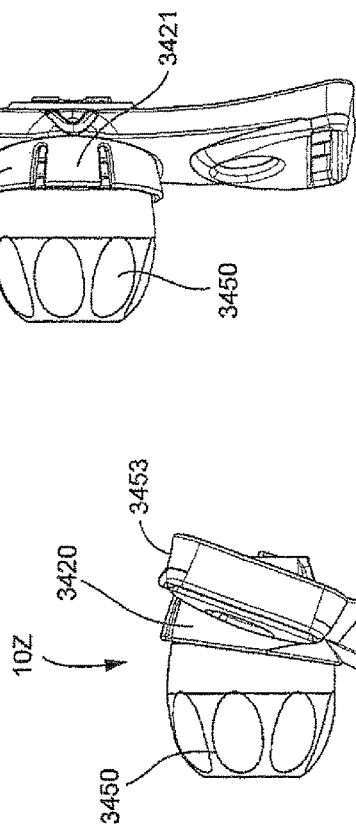
Figures 21, 51:
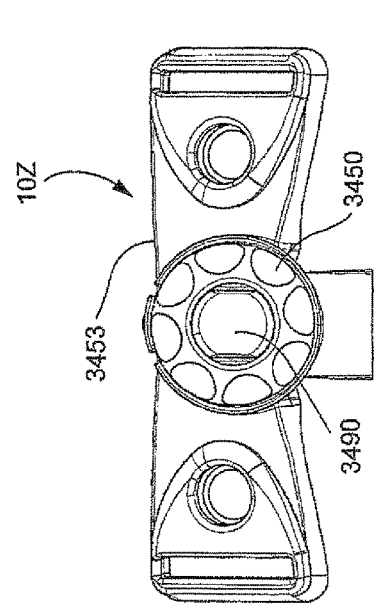
Figures 20, 51:
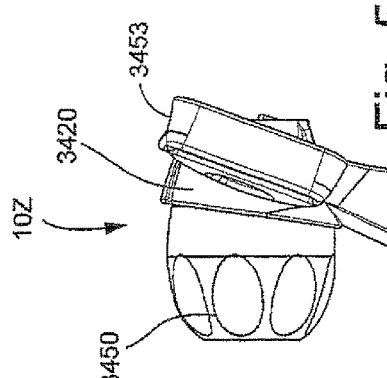

FIGS. 51-1 to 51-24 illustrate a forehead support 10Z according to another embodiment of the present invention. In this embodiment, the forehead support 10Z uses a screw-type actuator to move the forehead support along a generally linear path.

As illustrated, the forehead support 10Z includes a support 3420 provided to the mask frame 3412 for supporting an adjustment knob 3450. The adjustment knob 3450 clips onto the support 3420 with a snap-fit. Specifically, the front of the support 3420 includes a resilient arm member 3421 that provides a first protrusion 3423 on a free end thereof, and a second protrusion 3427 opposite the first protrusion 3423. The adjustment knob 3450 includes an annular groove 3455. When the adjustment knob 3450 is assembled to the support 3420, the resilient arm member 3421 deflects outwardly until the first and second protrusions 3423 and 3427 snap into the groove 3455.

The adjustment knob 3450 includes internal threads and receives a threaded insert 3490 provided to the forehead cushion support 3453 such that the internal threads of the knob 3450 are intermeshed with the threaded insert 3490. Specifically, the forehead cushion support 3453 includes a shaft 3422 that is joined to forehead cushion support plates 3451 that carry forehead cushions. The threaded insert 3490 is attached to the shaft 3422, e.g., with a snap-fit. When the adjustment knob 3450 is rotated, the threaded insert 3490 extends or retracts from the adjustment knob 3450 which causes adjustable movement of the forehead cushions.

The threaded insert 3490 has flats on both sides thereof to improve moldability and to provide keyed assembly with the mask frame (to prevent rotation). The threaded insert 3490 is adapted to extend through a non-circular opening 3445 or key feature (see FIGS. 51-1 and 51-2) integrally molded with the support 3420 to prevent the insert 3490 and hence the forehead cushion support 3453 from twisting or rotating relative to the frame 3412.

In the illustrated embodiment, the threaded insert 3490 has a single-start design and features two flats for improved moldability (see FIG. 51-3).

As shown in FIG. 51-22, the threaded insert 3490 may be rotated for positioning in two ways, i.e., orientation 1 or orientation 2, onto the shaft 3422 of the forehead cushion support 3453 to change the limit of travel of the forehead cushion support 3453. Orientation 1 provides a lower limit of travel L1 (see FIG. 51-23), and orientation 2 provides an upper limit of travel L2 (see FIG. 51-24). In an embodiment, orientation 1 may be designed to cater to the majority of the patient population, and may be minimal in its aesthetic bulk.

FIGS. 51-1, 51-2, and 51-4 to 51-6 are exploded views of the forehead support 10Z, FIGS. 51-7 to 51-11 are partial assembled views of the forehead cushion support engaged with the threaded insert 3490, FIGS. 51-12 to 51-16 are partial assembled views of the forehead cushion support and insert 3490 engaged with the support 3420, and FIGS. 51-17 to 51-21 are assembled views of the forehead support 10Z.

XXXVII. Embodiment of Forehead Cushion Support

FIGS. 52-1 and 52-2 illustrate forehead cushion supports 3553A and 3553B for a forehead support according to alternative embodiments of the present invention. The forehead cushion supports 3553A and 3553B are adapted for use with a forehead cushion such as those described above, e.g., see forehead cushion 1752 in FIG. 32-6.

As illustrated, each forehead cushion support 3553A and 3553B includes forehead cushion support plates 3551 and a tube or slider 3522 joined to the support plates 3551. The support plates 3551 extend generally transversely relative to the slider 3522 and thus define a general T-shaped support.

The forehead cushion support plates 3551 of the forehead cushion support 3553A include integrally molded slots 3558 for engaging headgear straps, and the forehead cushion support plates 3551 of the forehead cushion support 3553B include clip receiving structures or clip receptacles 3590 for engaging headgear clips associated with headgear straps.

Also, each forehead cushion support 3553A and 3553B includes one or more ribs 3580 on the slider 3522 to ensure correct orientation on assembly and to prevent rotation of each forehead cushion support in use, especially at maximum extension. As illustrated, the slider 3522 of the forehead cushion support 3553A includes two ribs 3580 on a bottom thereof, and the slider 3522 of the forehead cushion support 3553B includes a rib 3580 on at least one side thereof. However, other rib arrangements are possible.

XXXVIII. Embodiment of Forehead Cushion Support

FIGS. 53-1 to 53-5 illustrate forehead cushion supports 3653 for a forehead support according to another embodiment of the present invention. The forehead cushion support 3653 is adapted for use with a forehead cushion such as those described above, e.g. see forehead cushion 1752 in FIG. 32-6.

As illustrated, the forehead cushion support 3653 includes forehead cushion support plates 3651 and a tube or slider 3622 joined to the support plates 3651. The support plates 3651 extend generally transversely relative to the slider 3622 and thus define a general T-shaped support.

The forehead cushion support plates 3651 include integrally molded slots 3658 for engaging headgear straps. As illustrated, the bottom of the slots 3658 are open. This arrangement allows headgear straps to be inserted and removed via the open end of the slots 3658 without the need for releasing or undoing an attachment structure, e.g., Velcro® tabs, at the end of the headgear straps. Therefore, it is not necessary to adjust headgear fit each time the mask is worn. The open slots or slotted holes 3658 negate the need for quick-release headgear clips on the forehead cushion support 3653, thereby minimizing the overall width of the forehead cushion support 3653.

XXXIX. Embodiment of Forehead Cushion Support

FIGS. 54-1 to 54-5 illustrate forehead cushion supports 3753 for a forehead support according to another embodiment of the present invention. The forehead cushion support 3753 is adapted for use with a forehead cushion such as those described above, e.g. see forehead cushion 1752 in FIG. 32-6.

As illustrated, the forehead cushion support 3753 includes forehead cushion support plates 3751 and a tube or slider 3722 joined to the support plates 3751. The support plates 3751 extend generally transversely relative to the slider 3722 and thus define a general T-shaped support.

The forehead cushion support plates 3751 include integrally molded slots 3758 with cross-bars 3759 for engaging headgear straps. As illustrated, the top of the slots 3758 are open. This arrangement allows headgear straps to be inserted onto and removed off the cross-bars 3759 via the open end of the slots 3758 without the need for releasing or undoing an attachment structure, e.g., Velcro® tabs, at the end of the headgear straps. Therefore, it is not necessary to adjust headgear fit each time the mask is worn. The open slots or slotted holes 3758 negate the need for quick-release headgear clips on the forehead cushion support 3753, thereby minimizing the overall width of the forehead cushion support 3753.

XL. Twenty-Sixth Illustrated Embodiment of Forehead Support

FIGS. 55-1 and 55-2 illustrate a forehead support 10AA according to another embodiment of the present invention. In this embodiment, the forehead support 10AA uses a rack and pinion type actuator to move or adjust the forehead support along a generally linear path.

As illustrated, the forehead support 10AA includes a support 3820 provided to the mask frame 3812 for supporting an adjustment knob or dial 3850. The adjustment dial 3850 is removably positioned into an opening provided on top of the support 3820 with a snap-fit. The adjustment dial 3850 includes a gear 3854 and adjustment heads 3856 on both sides of the gear 3854. This arrangement allows adjustment of the gear 3854 from both sides of the support 3820 to cater to both left and right hand use.

The forehead cushion support 3853 includes a gear rack 3830 that extends through the support 3820 such that the gear 3854 of the dial 3850 is intermeshed with the gear rack 3830. The gear rack 3830 is joined to forehead cushion support plates 3851 that carry forehead cushions. When the adjustment dial 3850 is rotated, the gear rack 3830 extends or retracts from the adjustment dial 3850 which causes adjustable movement of the forehead cushions.

Locking of the forehead cushion support 3853 into a desired position may be achieved by friction between the gear 3854 and the gear rack 3830 and/or by other mechanical means.

XLI. Twenty-Seventh Illustrated Embodiment of Forehead Support

FIGS. 56-1 to 56-3 illustrate a forehead support 10BB according to another embodiment of the present invention. In this embodiment, the forehead support 10BB uses a screw-type actuator to move the forehead support along a generally linear path.

As illustrated, the forehead support 10BB includes a support 3920 provided to the mask frame 3912 for supporting an adjustment dial 3950. The adjustment dial 3950 includes a threaded shaft 3954 that extends through the support 3920. The threaded shaft 3954 threadably engages an intermediate threaded tube or screw nut 3956. The intermediate tube 3956 is internally and externally threaded. The threaded shaft 3954 engages the internal threads of the intermediate tube 3956. The external threads of the intermediate tube 3956 engage an internally threaded tube 3922 that is joined to forehead cushion support plates 3951 that carry forehead cushions.

This arrangement provides telescopic forehead support adjustment. Specifically, the threaded tube 3922 and intermediate tube 3956 provide a linear two-stage screw mechanism. In use, the threaded shaft 3954 of the adjustment dial 3950 drives the intermediate tube 3956 which when fully extended will in turn engage the threaded tube 3922 of the forehead cushion support 3953. The telescopic design allows the overall length of the forehead support mechanism (and hence the visual bulk) to be further reduced.

Although a two-stage telescopic arrangement is illustrated, other multiple stage, e.g., greater than two-stage, telescopic arrangements are possible.

XLII. Twenty-Eighth Illustrated Embodiment of Forehead Support

Figures 1, 57:
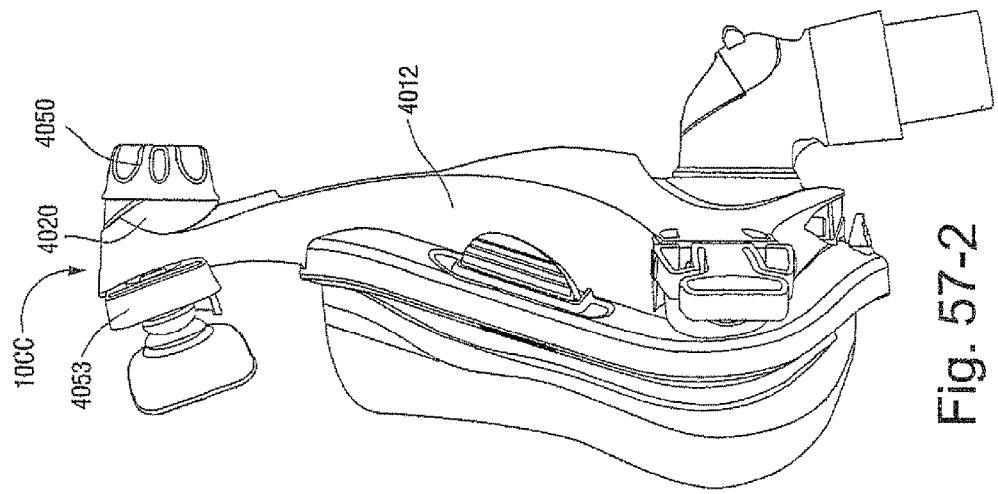
Figures 2, 57:
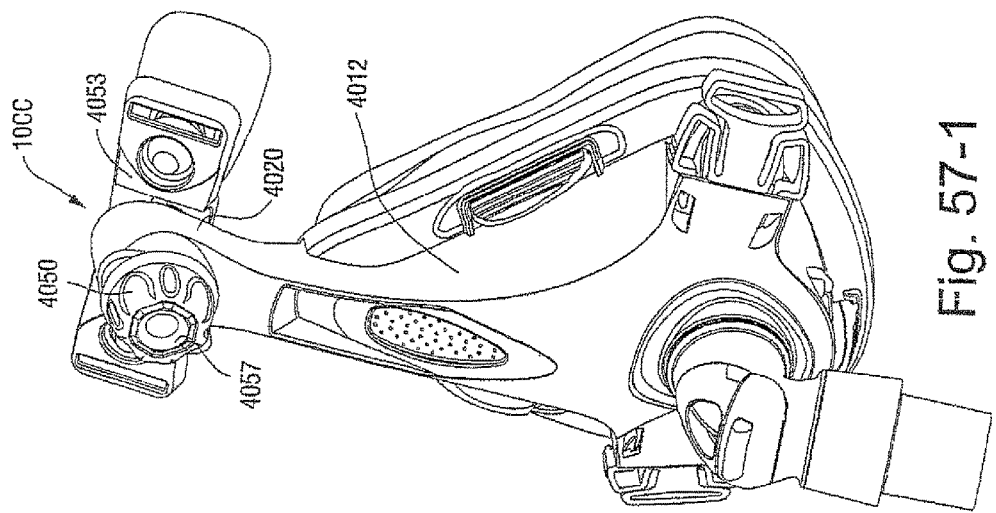
Figures 4, 57:
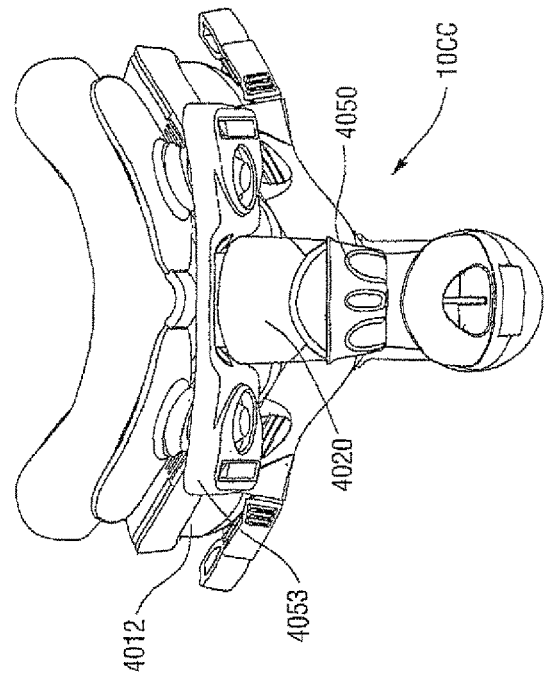
Figures 3, 57:
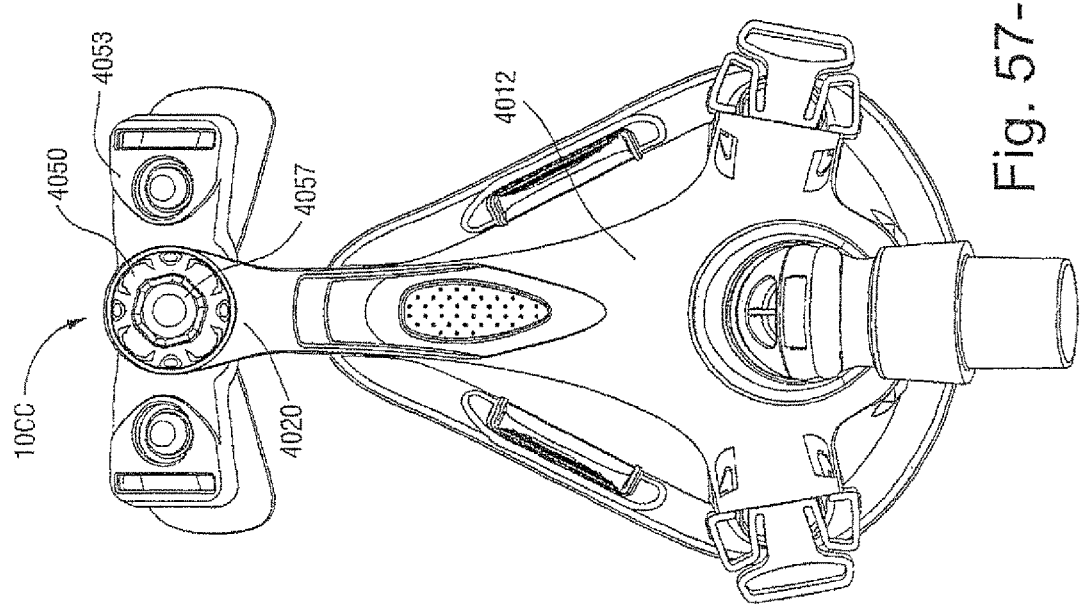
Figures 8, 57:
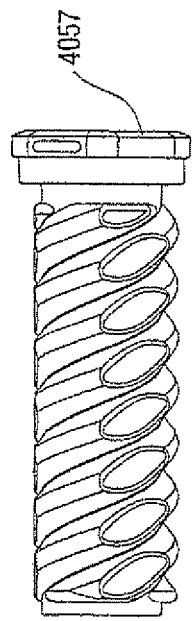
Figures 5, 57:
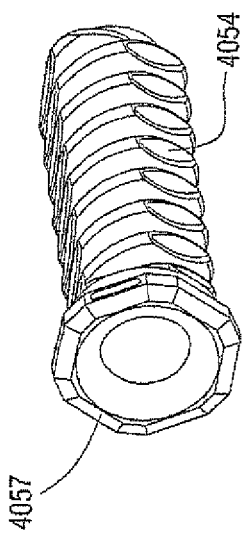
Figures 6, 57:
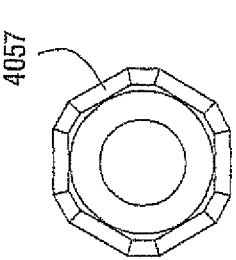
Figures 7, 57:
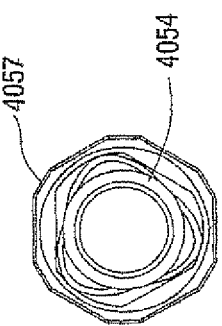
Figures 9, 57:
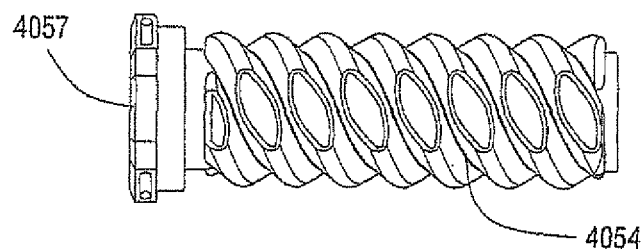
Figures 10, 57:
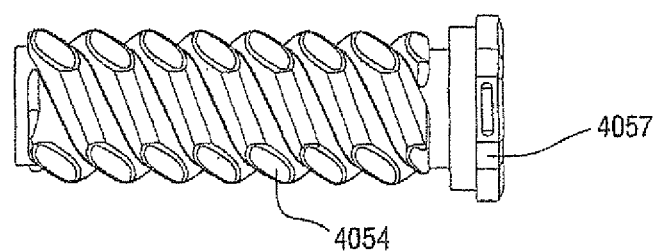
Figures 11, 57:
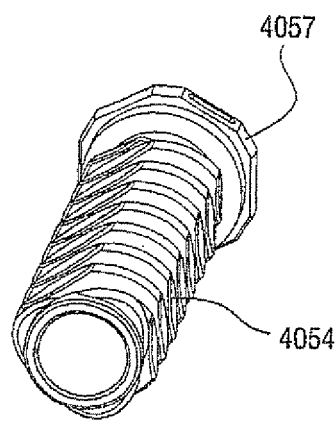
Figures 12, 57:
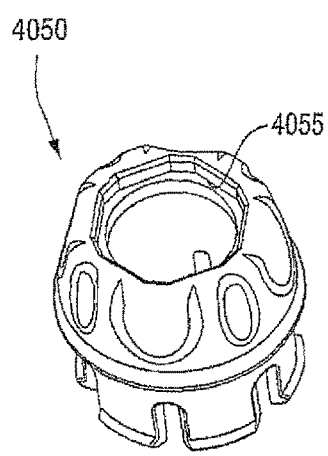
Figures 13, 57:
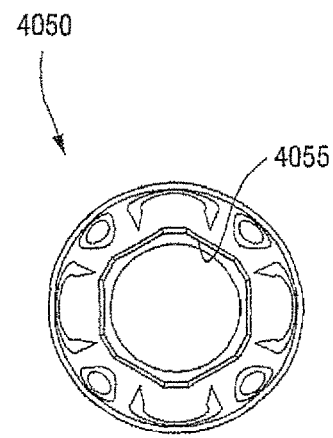
Figures 14, 57:
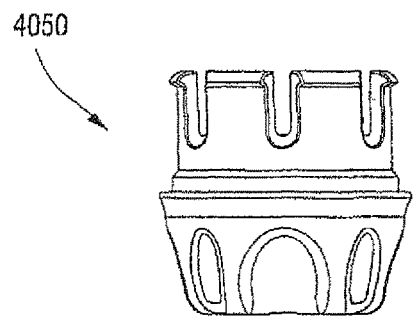
Figures 15, 57:
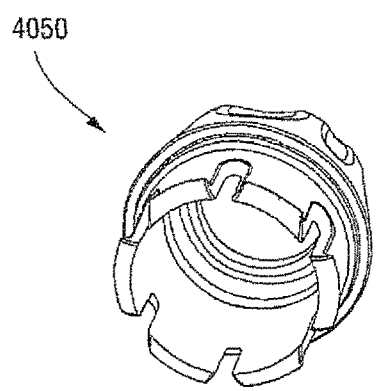

FIGS. 57-1 to 57-15 illustrate a forehead support 10CC according to another embodiment of the present invention. In this embodiment, the forehead support 10CC uses a screw-type actuator to move the forehead support along a generally linear path.

Similar to the embodiment of FIGS. 37-1 to 37-15, the forehead support 10CC includes an adjustment knob 4050 (see FIGS. 57-12 to 57-15) with a non-circular opening 4055, e.g., generally hexagonal, that engages a non-circular head 4057, e.g., generally hexagonal, provided to a threaded shaft 4054 (see FIGS. 57-5 to 57-11). This interlocks the knob 4050 and threaded shaft 4054 and prevents relative movement. The adjustment knob 4050 clips onto the support 4020 of frame 4012 with a snap-fit, and the threaded shaft 4054 engages within an internally threaded tube of a forehead cushion support 4053. When the knob 4050 is rotated, the forehead cushion support 4053 extends or retracts with respect to the frame 4012.

In each of the above embodiments, the forehead support may or may not include headgear clip receptacles for engaging headgear clips associated with headgear straps. The forehead supports may include other suitable structures for engaging headgear straps, e.g., slots.

The forehead supports and/or forehead support cushions described above may be used on different masks, and accordingly the amount of travel of the adjustment mechanism may be altered depending on the mask configuration.

In each of the above embodiments, one method of fitting the FMA to a patient may include starting with the forehead support "tightened", i.e., forehead cushions compressed against the patient, and then moving the forehead support outwardly from the patient to achieve patient comfort while maintaining a seal. However, the FMA may be fit to a patient in other suitable manners.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike.

What is claimed is:

1. A mask assembly to provide pressurized gas to a patient, the mask assembly comprising:

a mask frame having a support extending from an upper portion of the mask frame, said mask frame adapted to receive a mask cushion;

a forehead cushion support plate having a front face and a rear face;

a forehead cushion to be positioned against a plane of the patient's forehead and joined to the forehead cushion support plate at the rear face, said forehead cushion configured to be movably compliant relative to the forehead cushion support plate;

an extension attached to the forehead cushion support plate at the front face, said extension comprising a substantially hollow tube;

a plurality of position markings located longitudinally on an upper side of the extension;

a plurality of teeth positioned on a bottom side of the extension and opposite the upper side;

a receiver having a top side, said receiver attached to the support opposite the mask frame, said receiver comprising a tube receiver housing and an internal ring supported within said tube receiver housing, said internal ring structured to slidably receive said tube, said tube extending through said internal ring such that said internal ring defines a linear adjustment path of said tube for adjustment between an extended position toward the patient's forehead and a retracted position away from the patient's forehead, and a distal end of said tube comprises a tab to engage the internal ring in the extended position to prevent disassembly; and
a push button disposed on the top side of the receiver, said push button adapted to be depressed to disengage the push button from the plurality of teeth to allow for sliding adjustment of said tube within said internal ring along said linear adjustment path.

2. The mask assembly of claim 1, wherein said forehead cushion, together with the forehead cushion support plate, is slidably adjustable along the linear adjustment path to adjust depth and the forehead cushion is flexibly adjustable by compliant movement relative to the forehead cushion support plate to substantially match the plane of the patient's forehead.

3. The mask assembly of claim 1, wherein said forehead cushion support plate is positioned at an oblique angle relative to the linear adjustment path or structured to be angled toward the forehead of the patient with respect to the linear adjustment path.

4. The mask assembly of claim 1, wherein said tube comprises a frosted portion, said plurality of position markings being positioned on said frosted portion, and
wherein said plurality of position markings comprise a plurality of numbered position markings to indicate at least eight adjustment positions.

5. The mask assembly of claim 1, wherein the distal end of said tube is enclosed within the tube receiver housing in the retracted position and the extended position, and
wherein said tube receiver housing comprises an opening through which said push button extends.

6. The mask assembly of claim 1, wherein said forehead cushion, together with the forehead cushion support plate, is slidably adjustable along the linear adjustment path to adjust depth and the forehead cushion is flexibly adjustable by compliant movement relative to the forehead cushion support plate to substantially match the plane of the patient's forehead,
wherein said forehead cushion support plate is positioned at an oblique angle relative to the linear adjustment path or structured to be angled toward the forehead of the patient with respect to the linear adjustment path,
wherein said tube comprises a frosted portion, said plurality of position markings being positioned on said frosted portion,
wherein said plurality of position markings comprise a plurality of numbered position markings to indicate at least eight adjustment positions,
wherein the distal end of said tube is enclosed within the tube receiver housing in the retracted position and the extended position, and
wherein said tube receiver housing comprises an opening through which said push button extends.

7. A mask assembly to provide pressurized gas to a patient, the mask assembly comprising:
a mask cushion to form a seal with the patient's airways;
a forehead support including a forehead cushion support plate having a front face and a rear face;
a forehead cushion to be positioned against a plane of the patient's forehead and joined to the forehead cushion support plate at the rear face, said forehead cushion configured to be movably compliant relative to the forehead cushion support plate;
an extension in the form of a tube attached to the forehead cushion support plate at the front face, the tube being hollow along the entire length of the tube;
a plurality of position markings located longitudinally on an upper side of the tube;
a plurality of teeth positioned on a bottom side of the tube;
a receiver defining a linear adjustment path to slidably receive said extension along said linear adjustment path; and
a push button disposed on the receiver and associated with a pawl, said push button being depressible to disengage the pawl from the plurality of teeth of the tube, and said push button being adapted to allow for adjustment of said extension within said receiver along said linear adjustment path toward and away from the forehead of the patient.

8. The mask assembly of claim 7, wherein said forehead cushion, together with the forehead cushion support plate, is linearly adjustable along the adjustment path and flexibly adjustable to substantially conform to the plane of the patient's forehead by compliant movement relative to the forehead cushion support plate.

9. The mask assembly of claim 7, wherein said receiver comprises a tube receiver housing and an internal ring supported within said tube receiver housing, said tube extending through said internal ring such that said internal ring defines said linear adjustment path of said tube for adjustment between an extended position towards the patient's forehead and a refracted position away from the patient's forehead.

10. The mask assembly of claim 9, wherein a distal end of said tube comprises a tab to engage the internal ring in the extended position to prevent disassembly, and
wherein the distal end of said tube is enclosed within the tube receiver housing in the retracted position and the extended position.

11. The mask assembly of claim 7, wherein said forehead cushion support plate is positioned at an oblique angle relative to the linear adjustment path or structured to be angled toward the forehead of the patient with respect to the linear adjustment path.

12. The mask assembly of claim 7, wherein said plurality of position markings comprise a plurality of numbered position markings.

13. The mask assembly of claim 12, wherein said tube comprises a frosted portion and the plurality of numbered position markings are located on the frosted portion.

14. The mask assembly of claim 7, wherein said forehead cushion, together with the forehead cushion support plate, is linearly adjustable along the adjustment path and flexibly adjustable to substantially conform to the plane of the patient's forehead by compliant movement relative to the forehead cushion support plate,
wherein said receiver comprises a tube receiver housing and an internal ring supported within said tube receiver housing, said tube extending through said internal ring such that said internal ring defines said linear adjustment path of said tube for adjustment between an extended position towards the patient's forehead and a retracted position away from the patient's forehead,
wherein a distal end of said tube comprises a tab to engage the internal ring in the extended position to prevent disassembly,
wherein the distal end of said tube is enclosed within the tube receiver housing in the retracted position and the extended position
wherein said forehead cushion support plate is positioned at an oblique angle relative to the linear adjustment path or structured to be angled toward the forehead of the patient with respect to the linear adjustment path, wherein said plurality of position markings comprise a plurality of numbered position markings, and
wherein said tube comprises a frosted portion and the plurality of numbered position markings are located on the frosted portion.

15. A mask assembly to provide pressurized gas to a patient, the mask assembly comprising:
a mask frame and a mask cushion to form a seal with the patient's airways, said mask frame adapted to receive the mask cushion;
a forehead support including a support, a forehead cushion support plate, and a forehead cushion to be positioned against a plane of the patient's forehead and joined to the forehead cushion support plate, said forehead cushion configured to be movably compliant relative to the forehead cushion support plate;
an extension attached to the forehead cushion support plate;
a plurality of position markings located longitudinally on the extension;
a plurality of teeth positioned on the extension;
a receiver attached to the support opposite the mask frame, and said receiver defining a linear adjustment path to slidably receive said extension along said linear adjustment path; and
a push button disposed on the receiver, said push button adapted to be depressed to allow adjustment of said extension within said receiver along said linear adjustment path toward and away from the forehead of the patient by disengagement of the push button with the plurality of teeth of the extension,
wherein said forehead cushion, together with the forehead cushion support plate, is linearly adjustable along the linear adjustment path and flexibly adjustable to substantially match the plane of the patient's forehead by compliant movement relative to the forehead cushion support plate.

16. The mask assembly of claim 15, wherein said extension comprises a substantially hollow tube having a frosted portion.

17. The mask assembly of claim 16, wherein said plurality of position markings comprise a plurality of numbered position markings located on the frosted portion.

18. The mask assembly of claim 16, wherein said receiver comprises a tube receiver housing and an internal ring supported within said tube receiver housing, said tube extending through said internal ring such that said internal ring defines said linear adjustment path of said tube for adjustment between an extended position toward the patient's forehead and a refracted position away from the patient's forehead.

19. The mask assembly of claim 18, wherein a distal end of said tube comprises a tab to engage the internal ring in the extended position to prevent disassembly, and
wherein said tube receiver housing comprises an opening through which said push button extends.

20. The mask assembly of claim 19, wherein the distal end of said tube is enclosed within the tube receiver housing in the retracted position and the extended position.

21. The mask assembly of claim 15, wherein said forehead cushion support plate is positioned at an oblique angle relative to the linear adjustment path or structured to be angled toward the forehead of the patient with respect to the linear adjustment path.

22. The mask assembly of claim 15, wherein said extension comprises a substantially hollow tube having a frosted portion,
wherein said plurality of position markings comprise a plurality of numbered position markings located on the frosted portion,
wherein said receiver comprises a tube receiver housing and an internal ring supported within said tube receiver housing, said tube extending through said internal ring such that said internal ring defines said linear adjustment path of said tube for adjustment between an extended position toward the patient's forehead and a retracted position away from the patient's forehead
wherein a distal end of said tube comprises a tab to engage the internal ring in the extended position to prevent disassembly,
wherein said tube receiver housing comprises an opening through which said push button extends,
wherein the distal end of said tube is enclosed within the tube receiver housing in the retracted position and the extended position, and
wherein said forehead cushion support plate is positioned at an oblique angle relative to the linear adjustment path or structured to be angled toward the forehead of the patient with respect to the linear adjustment path.

23. A mask assembly to provide pressurized gas to a patient, the mask assembly comprising:
a mask frame having and a receiver attached to the mask frame by a support, said mask frame adapted to receive a mask cushion, the mask cushion adapted to form a seal with the patient's airways;
a forehead cushion support plate;
a forehead cushion to be positioned against a plane of the patient's forehead and joined to the forehead cushion support plate, said forehead cushion configured to be movably compliant relative to the forehead cushion support plate;
a tube attached to the forehead cushion support plate opposite the forehead cushion;
a plurality of position markings located longitudinally on the tube;
a plurality of teeth on the tube opposite the plurality of position markings; and
a push button disposed on the receiver, said push button having a depressed position wherein the push button is disengaged from the plurality of teeth of the tube, the tube being slidable along an adjustment path when the push button is in the depressed position,
wherein said receiver comprises a tube receiver housing and an internal ring supported within said tube receiver housing, said ring being substantially circular in shape and fully surrounding said tube, said tube extending through said internal ring such that said internal ring defines said adjustment path of said tube for adjustment between an extended position towards the patient's forehead and a retracted position away from the patient's forehead.

24. The mask assembly of claim 23, wherein said tube comprises a frosted portion, and
wherein said plurality of position markings comprise a plurality of numbered position markings on the frosted portion.

25. The mask assembly of claim 23, wherein said adjustment path comprises a linear adjustment path.

26. The mask assembly of claim 25, wherein said forehead cushion, together with the forehead cushion support plate, is linearly adjustable along the linear adjustment path and flexibly adjustable by compliant movement relative to the forehead cushion support plate.

27. The mask assembly of claim 23, wherein said forehead cushion support plate is positioned at an oblique angle relative to a longitudinal axis of the tube or structured to be angled toward the forehead of the patient with respect to the longitudinal axis of the tube.

28. The mask assembly of claim 23, wherein a distal end of said tube is enclosed within the tube receiver housing in the retracted position and the extended position.

29. The mask assembly of claim 23, wherein a distal end of said tube comprises a tab to engage the internal ring in the extended position to prevent disassembly.

30. The mask assembly of claim 23, wherein said tube comprises a frosted portion,
- wherein said plurality of position markings comprise a plurality of numbered position markings on the frosted portion,
- wherein said adjustment path comprises a linear adjustment path,
- wherein said forehead cushion, together with the forehead cushion support plate, is linearly adjustable along the linear adjustment path and flexibly adjustable by compliant movement relative to the forehead cushion support plate,
- wherein said forehead cushion support plate is positioned at an oblique angle relative to a longitudinal axis of the tube or structured to be angled toward the forehead of the patient with respect to the longitudinal axis of the tube,
- wherein a distal end of said tube is enclosed within the tube receiver housing in the retracted position and the extended position, and
- wherein the distal end of said tube comprises a tab to engage the internal ring in the extended position to prevent disassembly.

* * * * *